US007230242B2

(12) United States Patent
Behar et al.

(10) Patent No.: US 7,230,242 B2
(45) Date of Patent: Jun. 12, 2007

(54) METHODS FOR SEM INSPECTION OF FLUID CONTAINING SAMPLES

(75) Inventors: Vered Behar, Moshav Bait Zait (IL); Amotz Nechushtan, Aseret (IL); Yossef Kliger, Rishon Lezion (IL); Opher Gileadi, Oxford (GB); David Sprinzak, Pasadena, CA (US); Ory Zik, Rehovot (IL); Yiftah Karni, Rehovot (IL)

(73) Assignee: Quantomix Ltd, Nes-Ziona (IL)

( * ) Notice: Subject to any disclaimer, the term of this patent is extended or adjusted under 35 U.S.C. 154(b) by 242 days.

(21) Appl. No.: 10/516,411

(22) PCT Filed: Jun. 1, 2003

(86) PCT No.: PCT/IL03/00457

§ 371 (c)(1),
(2), (4) Date: Dec. 2, 2004

(87) PCT Pub. No.: WO03/104848

PCT Pub. Date: Dec. 18, 2003

(65) Prior Publication Data

US 2005/0173632 A1  Aug. 11, 2005

Related U.S. Application Data

(60) Provisional application No. 60/448,808, filed on Feb. 20, 2003, provisional application No. 60/393,747, filed on Jul. 8, 2002.

(30) Foreign Application Priority Data

Jun. 5, 2002  (IL) .................................... 150054
Jun. 5, 2002  (IL) .................................... 150055

(51) Int. Cl.
*G01N 23/00* (2006.01)

(52) U.S. Cl. .................................................. 250/310
(58) Field of Classification Search ................ 250/310, 250/440.11, 442.11
See application file for complete search history.

(56) References Cited

U.S. PATENT DOCUMENTS

| | | | |
|---|---|---|---|
| 3,218,459 A | 11/1965 | Bens | |
| 3,378,684 A | 4/1968 | Mentink et al. | |
| 3,657,596 A | 4/1972 | Goetze et al. | |
| 4,037,109 A | 7/1977 | Hosokawa et al. | |

(Continued)

FOREIGN PATENT DOCUMENTS

WO  WO 02/14830  2/2002

(Continued)

OTHER PUBLICATIONS

Angulo P., "Nonalcoholic Fatty Liver Disease", N. Engl J. Med, vol. 346, No. 16, 1221-31, 2002.

(Continued)

*Primary Examiner*—Kiet T. Nguyen
(74) *Attorney, Agent, or Firm*—Pearl, Cohen Zedek Latzer, LLP

(57) ABSTRACT

A method of visualizing a sample in a wet environment including introducing a sample into a specimen enclosure in a wet environment and scanning the sample in the specimen enclosure in a scanning electron microscope, thereby visualizing the sample.

22 Claims, 168 Drawing Sheets

U.S. PATENT DOCUMENTS

| | | | |
|---|---|---|---|
| 4,071,766 | A | 1/1978 | Kalman et al. |
| 4,115,689 | A | 9/1978 | Won |
| 4,308,457 | A | 12/1981 | Reimer |
| 4,448,311 | A | 5/1984 | Houser |
| 4,587,666 | A | 5/1986 | Torrisi et al. |
| 4,596,928 | A | 6/1986 | Dantilatos |
| 4,609,809 | A | 9/1986 | Yamaguchi et al. |
| 4,618,938 | A | 10/1986 | Sandland et al. |
| 4,705,949 | A | 11/1987 | Grimes, II et al. |
| 4,720,622 | A | 1/1988 | Iwata et al. |
| 4,720,633 | A | 1/1988 | Nelson |
| 4,880,976 | A | 11/1989 | Mancuso et al. |
| 4,929,041 | A | 5/1990 | Vahala et al. |
| 4,992,662 | A | 2/1991 | Danilatos |
| 5,097,134 | A | 3/1992 | Kimoto et al. |
| 5,103,102 | A | 4/1992 | Economou et al. |
| 5,122,663 | A | 6/1992 | Chang et al. |
| 5,250,808 | A | 10/1993 | Danilatos et al. |
| 5,323,441 | A | 6/1994 | Torrisi et al. |
| 5,326,971 | A | 7/1994 | Theodore et al. |
| 5,362,964 | A | 11/1994 | Knowles et al. |
| 5,406,087 | A | 4/1995 | Fujiyoshi et al. |
| 5,412,211 | A | 5/1995 | Knowles |
| 5,466,940 | A | 11/1995 | Litman et al. |
| 5,502,306 | A | 3/1996 | Meisburger et al. |
| 5,644,132 | A | 7/1997 | Litman et al. |
| 5,667,791 | A | 9/1997 | Hersh et al. |
| 5,789,748 | A | 8/1998 | Liu et al. |
| 5,811,803 | A | 9/1998 | Komatsu et al. |
| 5,859,699 | A | 1/1999 | Baer et al. |
| 5,898,261 | A | 4/1999 | Barker |
| 5,945,672 | A | 8/1999 | Knowles et al. |
| 6,025,592 | A | 2/2000 | Knowles et al. |
| 6,072,178 | A | 6/2000 | Mizuno |
| 6,114,695 | A | 9/2000 | Todokoro et al. |
| 6,130,434 | A | 10/2000 | Mitchell et al. |
| 6,157,446 | A | 12/2000 | Baer et al. |
| 2004/0046120 | A1 | 3/2004 | Moses et al. |
| 2004/0217297 | A1 | 11/2004 | Moses et al. |
| 2005/0279938 | A1* | 12/2005 | Moses et al. ............... 250/311 |

FOREIGN PATENT DOCUMENTS

| | | |
|---|---|---|
| WO | WO 02/45125 | 6/2002 |
| WO | WO 03/104848 | 1/2003 |
| WO | WO/2004/075209 | 2/2004 |

OTHER PUBLICATIONS

Ault K.A, et al. "In-Vivo Biotinylation Demonstrates that Reticulated Platelets are the Youngest Platelets in Circulation", Exp hematology, 23, 996-1001, 1995.

Becker, R.P. and Sogard, M., "Visualization of Subsurface Structures in Cells and Tissues by Backscattered Electron Imaging", Scanning Electron Microscopy (II), 835-870, 1979.

Birks, J.B., "The Theory and Practice of Scintillation Counting", Pergamon Press, 1964.

Bozza P. T. et al., "Pathways for Eosinophil Lipid Body Induction: Differing Signal Transduction in cells from Normal and Hypereosinophilic Subjects", Journal of Leukocyte Biology, vol. 64, 563-569, 1998.

Brocker W. and Pfefferkorn G., "Applications of the Cathodoluminescence Method in Biology and Medicine", Scanning Electron Microscopy vol. II, 125-132, 1979.

Burns W.A. et al., "The Clinician's View of Diagnostic Electron Microscopy", Human Pathology, 6, 467-78, 1975.

Carlen, B. and Englund, E., "Diagnostic Value of Electron Microscopy in a Case of Juvenile Neuronal Ceroid Lipofuscinosis", Ultrastructural Pathology 25, 285-288, 2001.

Davison E. & Colquhoun W., "Ultrathin Formvar Support Films for Transmission Electron Microscopy", J. Elec. Microsc. Tech. vol. 2, 35-43, 1985.

Cook G.S. & Costreton J.W., "Foley Catheter Biofilm Formation Comparison Study in an in-Vitro Assay", unknown publication date, http://www.bacterin.com/pdf/whitepaper.pdf.

de Assis E. F. et al., "Synergism Between Platelet-Activating Factor-Like Phospholipids and Perxisome Proliferator-Activated Receptor Gamma Agonists Generated During Low Density Lipoprotein Oxidation that induces Lipid Body Formation in Leukocytes", The Journal of Immunology, 171, 2090-2098, 2003.

De Mets M. and Lagasse A., "An Investigation of Some Organic Chemicals as Cathodoluminescent Dyes using the Scanning Electron Microscope" Journal of Microscopy vol. 94, 151-156, 1971.

De Rijk Eveline P.C.T. et al, "A Fast Histochemical Staining Method to Identify Hyaline Droplets in the Rat Kidney", Toxicologic Pathology, vol. XXXI, 462-464, 2003.

Dykstra M.J. et al, "Suggested Standard Operating Procedures (SOPs) for the Preparation of Electron Microscopy Samples for Toxicology/Pathology Studies in a GLP Environment", Toxicologic Pathology, vol. XXX, 735-743, 2002.

Feinerman & Crewe, "Miniature Electron Optics", Advances in Imaging and Electron Physics, vol. 102, 187, 1998.

Fisher C. et al., "An Assessment of the Value of Electron Microscopy in Tumor Diagnosis", Journal Clinical Pathology 38, 403-408, 1985.

Garman R. H. et al., "Method to Identify and Characterize Developmental Neurotoxicity for Human Health Risk Assessment II: Neuropathology", Environmental Health Perspective, vol. 109, 93-100, 2001.

Gileadi O. et al, "Squid Sperm to Clam Eggs: Imaging Wet Samples in a Scanning Electron Microscope", Biol. Bull., 205, 177-179, 2003.

Goldstein, et al., Scanning Electron Microscopy and X-ray Microanalysis, Pleneum Press, New York, London, 1992.

Goodpaster B. H. et al., "Skeletal Muscle Lipid Content and Insulin Resistance: Evidence for a paradox in Endurance-Trained Athletes", The Journal of Clinical Endocrinology & Metabolism 86 (12), 5755-5761, 2001.

Grande JP et al., "Renal Biopsy in Lupus Nephritis", Lupus 7, 611-617, 1998.

Green E.D.H "Atmospheric Scanning Electron Microscopy" Ph. D Dissertation, Department of Electronic Engineering, Stanford University, 1992.

Griffiths "Trends in Cell Biology", V. 11 :153-154, 2001.

Gu Xin et al, "The Value of Electron Microscopy in the Diagnosis of IgA Nephropathy", Ultrastructural Pathology 26, 203-210, 2002.

Gyorkey F. et al., "The Usefulness of Electron Microscopy in the Diagnosis of Human Tumors", Human Pathology 6,421-441, 1975.

Handley & Olsen, "Butvar B-98 As a Thin Support Film", Ultramicroscopy vol. 4, 479-480, 1979.

Hard G. C. et al., "Risk Assessment of d-Limonene: An Example of Male Rat-Specific Renal Tumorigens", Critical Reviews in Toxicology, 24 (3), 231-254, 1994.

Harris L.G. et al., "Contrast Optimisation for Backscattered Electron Imaging of Resin Embedded Cells", Scanning Microscopy, vol. 13, No. 1, 71-81, 1999.

Hayat, M.A., "Principles and Techniques of Electron Microscopy - Biological Applications", Fourth edition, Cambridge University Press, 2000.

Hermann, R., Walther, P. and Müller, M., "Immunogold-labeling in Scanning Electron Microscopy", Histochem. Cell. Biol., 106,31-39, 1996.

Herrera G. A., "The Value of Electron Microscopy in the Diagnosis and Clinical Management of Lupus Nephritis", Ultrastructural Pathology 23, 63-77, 1999.

Hoffman-Fezer et al., "Preclinical Evaluation of Biotin Labeling for Red Cell Survival Testing" Annals of Hematology, vol. 74, 231-238, 1997.

Hollinshead M. et al., "Anti-biotin Antibodies Offer Superior Organelle-specific Labeling of Mitochondria over Avidin or Streptavidin", The Journal of Histochemistry & Cytochemistry, 45 (8), 1053-7, 1997.

Hough P.V.C. et al., "Identification Of Biological Molecules in situ at High Resolution via the Fluorescence Excited by a Scanning Electron Beam", Proceedings of the National Academy of Sciences of the United States of America, vol. 73, No. 2, 317-321, 1976.

J.B. Steyn, et al, "An Efficient Spectroscopic Detection System for Cathodoluminescence Mode Scanning Electron Microscopy (SEM)", Journal of Microscopy, vol. 107, Pt 2, Jul. 1976, pp. 107-128.

Kelley D. E. et al, "Dysfunction of Mitochondria in Human Skeletal Muscle in Type 2 Diabetes", Diabetes vol. 51, 2944-2950, 2002.

Kelley D. E. et al, "Muscle Triglyceride and Insulin Resistance", Annu. Rev. Nutr. 22, 325-46, 2002.

Kirkpatrick P., "High-Throughput Screening Birds of a Feather...", Nature Reviews Drug Discovery v. 1, 330, 2002.

Kristiansen, E. and Madsen, C., "Induction of Protein Droplet (alpha-2 microglobulin) Nephropathy in Male Rats After Short-Term Dosage with 1,8-cineole and l-limonene", Toxicology Letters 80, 147-152, 1995.

Lehning E. J. et al, "Gamma-Diketone Peripheral Neuropathy", Toxicology and Applied Pharmacology 165, 127-140, 2000.

Levit-Binnun N. et al, "Quantitative Detection of Protein Arrays", Anal. Chem. 75, 1436-1441, 2003.

LoPachin R. M. et al, "Gamma-Diketone Central Neuropathy: Quantitative Morphometric Analysis of Axons in Rat Spinal Cord White Matter Regions and Nerve Roots", Toxicology and Applied Pharmacology, 193, 29-46, 2003.

Mathews R.G., "Conditions for Imaging Emulsions in the Environment Scanning Electron Microscope", Scanning, v. 24, 75-85, 2002.

McGovern S. L. et al, "A Common Mechanism Underlying Promiscuous Inhibitors from Virtual and High-Throughput Screening", J. Med. Chem, 45, 1712-1722, 2002.

McIntosh R. J., "Electron Microscopy of Cells: A New Beginning for a New Century", The Journal of Cell Biology, vol. 153, No. 6, F25-F32, 2001.

McKinney W. and Hough Paul V.C., "A New Detector System for Cathodoluminescence Microscopy", Scanning Electron Microscopy, vol. I, 251-256, 1977.

Mittler, M.A., Walters, B.C. and Stopa, E.G., "Observer Reliability in Histological Grading of Astrocytoma Stereotactic Biopsies", J. Neurosurg 85, 1091-1094, 1996.

Moriki T. et al., "Activation of Preformed EGF Receptor Dimers by Ligand-induced Rotation of the Transmembrane Domain", J. Mol. Biol. 311, 1011-1026, 2001.

Muskhelishvili L. et al, "An Immunohistochemical Label to Facilitate Counting of Ovarian Follicles", Toxicologic Pathology, vol. XXX, 400-402, 2002.

Nyska A. et al, "Biocompatibility of the Ex-PRESS Miniature Glaucoma Drainage Implant", Journal of Glaucoma, vol. XII, 275-280, 2003.

Pacheco P. et al, "Lipopolysaccaride-Induced Leukocyte Lipid Body Formation In Vivo: Innate Immunity Elicited Intracellular Loci involved in Eicosanoid Metabolism", The Journal of Immunology, 169, 6498-6506, 2002.

Petersen K. F. et al, "Mitochondrial Dysfunction in the Elderly: Possible Role in Insulin Resistance", Science, vol. 300, 1140-1142, 2003.

Prescott-Matthews J.S., et al., "Methyl tert-Butyl Ehter Causes alpha2u-Globulin Nephropathy and Enhanced Renal Cell Proliferation on Male Fischer-344 Rats", Toxicology and Applied Pharmacology, vol. 143, 301-314, 1997.

Robinson V.N.E., "The Examination of Hydrated Specimens in Electron Microscopes", Analysis of organic and biological surfaces, P. Echlin, 191-207, John Wiley and Sons, New York, 1984.

Sedar, A.W., Silver, M.J. and Ingerman-Wojenski, C.M., "Backscattered Electron Imaging to Visualize Arterial Endothelial Detachment in the Scanning Electron Microscope", Scanning Electron Microscopy, vol. II, 969-74, 1983.

Shulman G. I., "Cellular Mechanisms of Insulin Resistance", The Journal of Clinical Investigation, vol. 106, No. 2, 171-176, 2000.

Singer I. I. et al. "CCR5, CXCR4 and CD4 Are Clustered and Closely Apposed on Microvilli of Human Macrophages and T Cells", Journal of Virology, vol. 75, No. 8, 3779-3790, 2001.

Spargo, B. H., "Practical use of Electron Microsscopy for the Diagnosis of Glomerular Disease", Human Pathology vol. 6, 405-420, 1975.

Swift & Brown, J. Phys. E: Sci. Instrum. 3, 924-926, 1970.

Thornley, "New Applications of the Scanning Electron Microscope", Ph. D Dissertation 3886, Corpus Christi College, Cambridge, 1960.

Tucker, J.A., "The Continuing Value of Electron Microscopy in Surgical Pathology", Ultrastructural Pathology, vol. 24,383-9, 2000.

Weisberg S. P et al, "Obesity is Associated with Macrophage Accumulation in Adipose Tissue", Journal of Clinical Investigation, vol. 112 No. 12, 1796-1808, 2003.

Wellen K. E. et al, "Obesity-Induced Inflammatory Changes in Adipose Tissue", The Journal of Clinical Investigation, vol. 112 No. 12, 1785-88, 2003.

Weller P.F. et al., "Cytoplasmic Lipid Bodies of Neutrophils: Formation Induced by cis-Unsaturated Fatty Acids and Mediated by Protein Kinase C", The Journal of Cell Biology, vol. 113, No. 1, 137-146, 1991.

Xu H. et al "Chronic Inflammation in Fat Plays a Crucial Role in the Development of Obesity-Related Insulin Resistance", Journal of Clinical Investigation, vol. 112, No. 12, 1821-30, 2003.

Schlessinger J., "Ligand-Induces, Receptor-Mediated Dimerization and Activation of EGF Receptor", Cell vol. 110, 669-672, 2002.

* cited by examiner

FIG. 1A
FIG. 1B
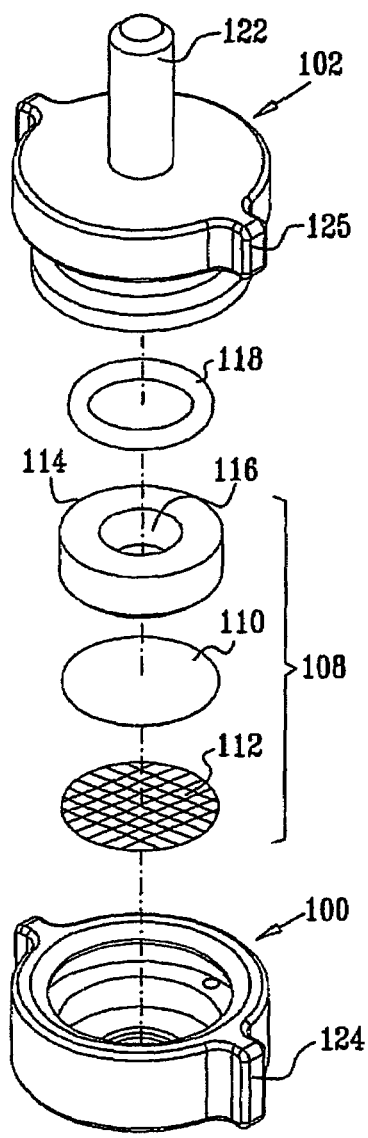
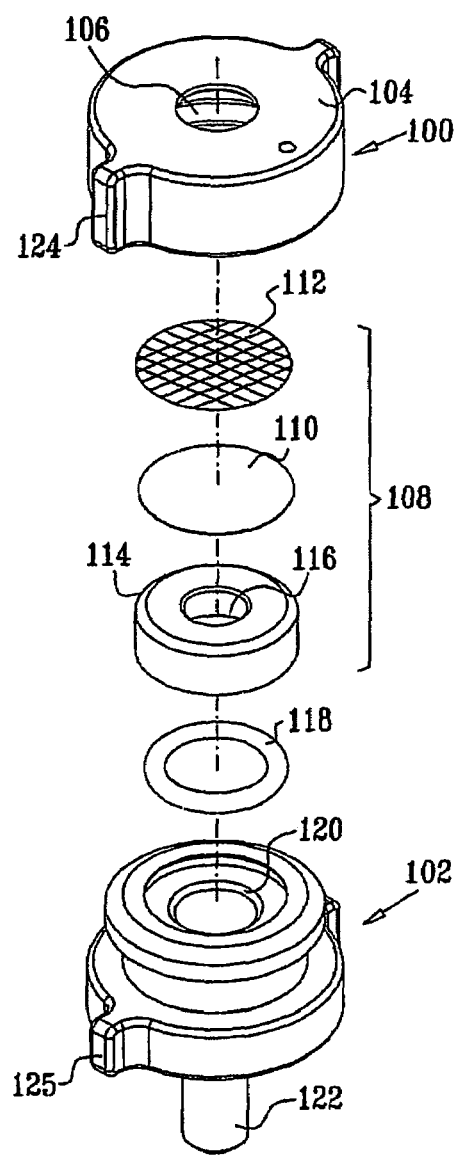

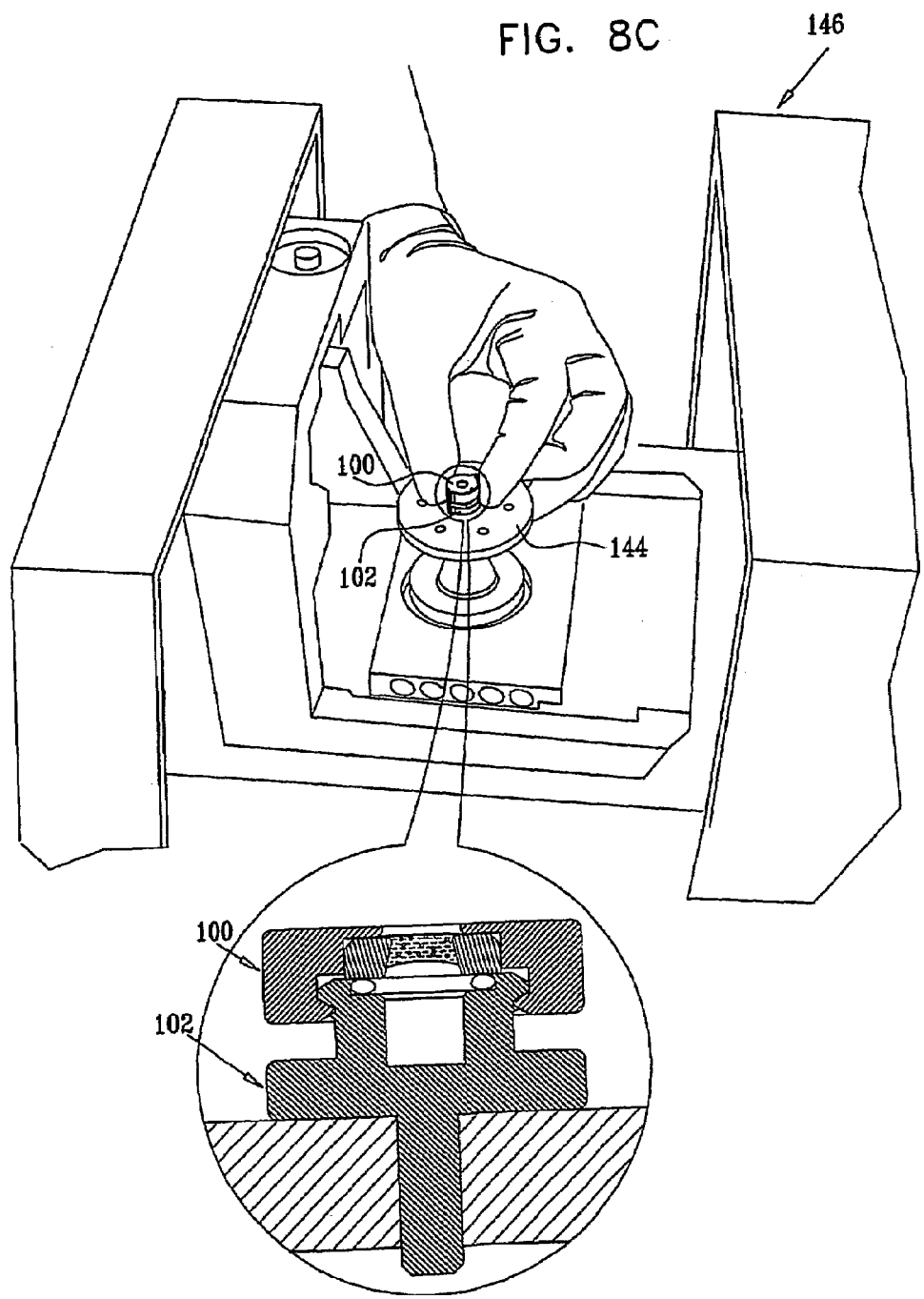

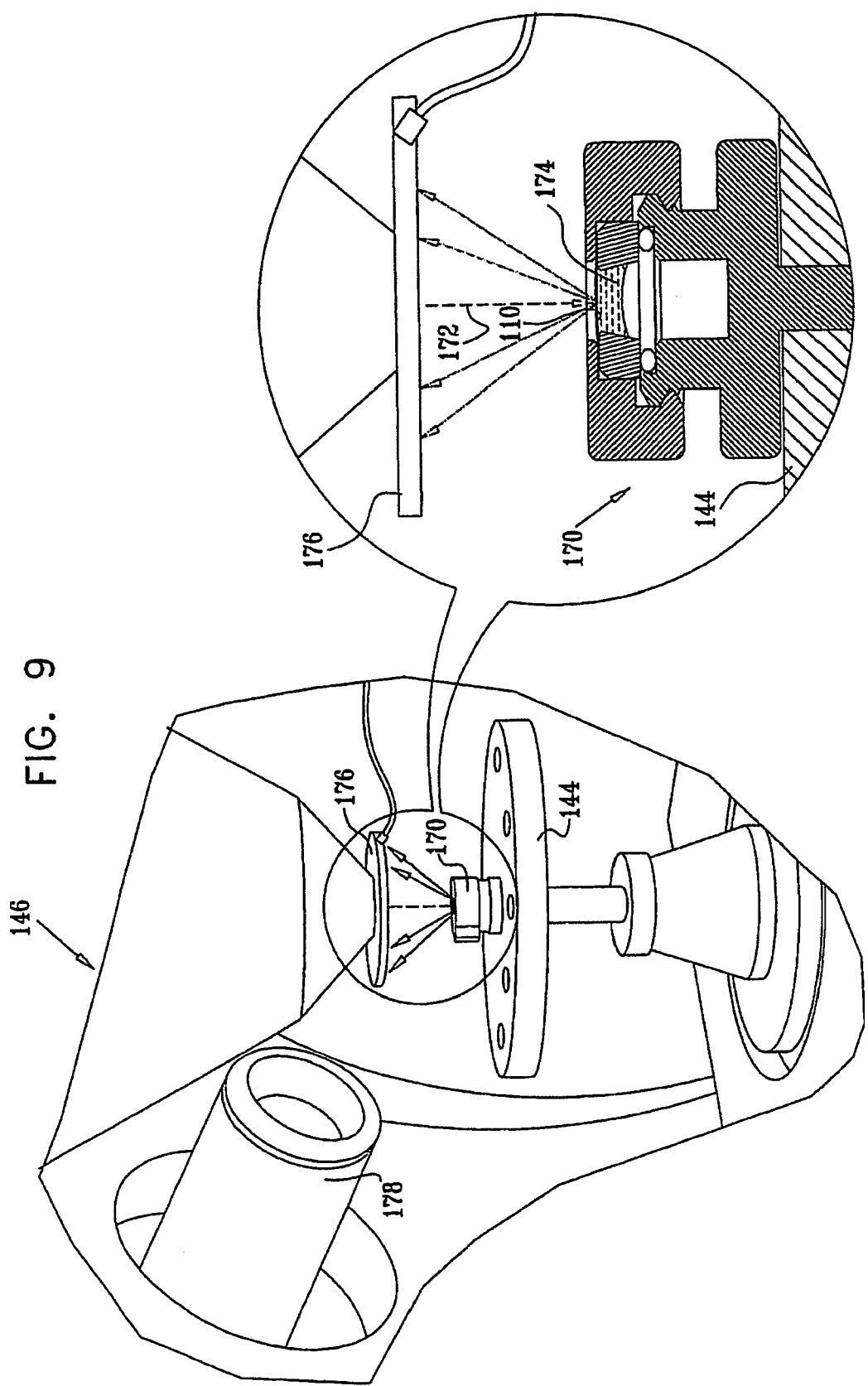

FIG. 11A
FIG. 11B
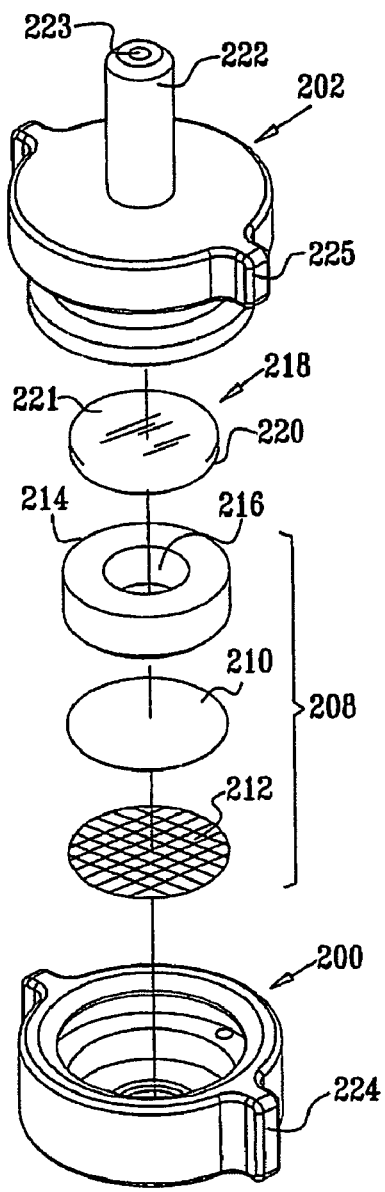
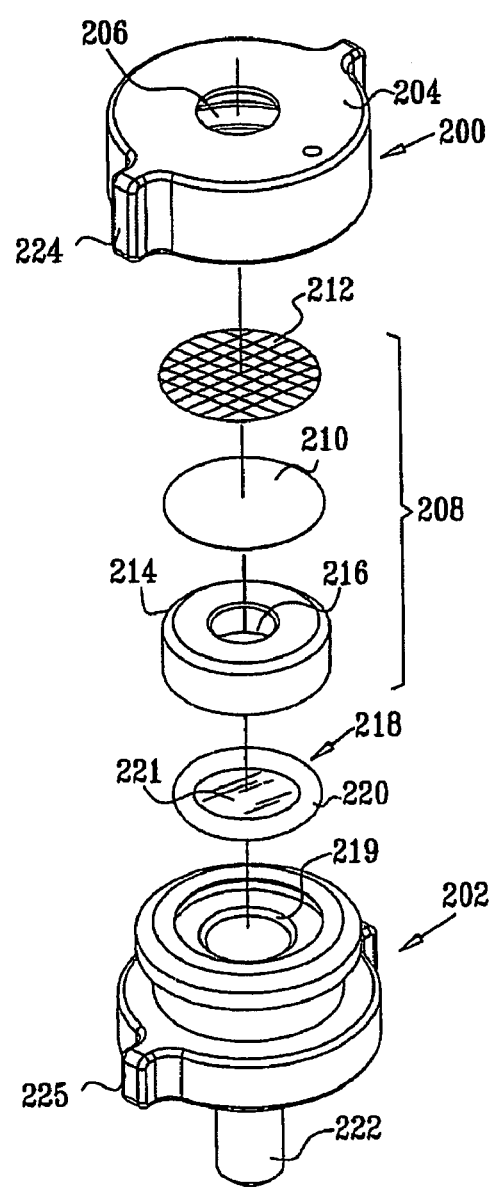

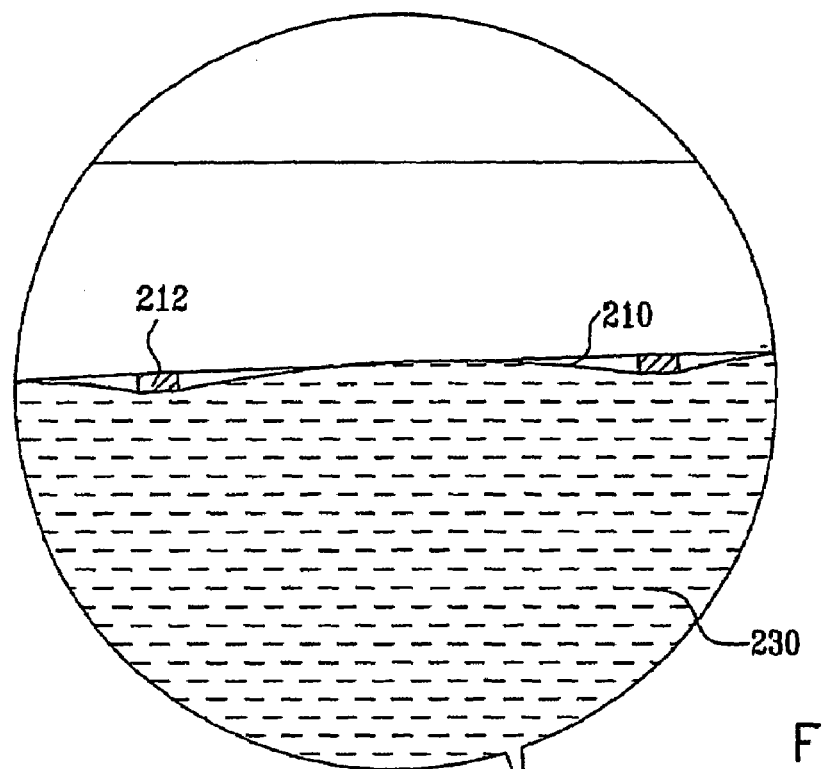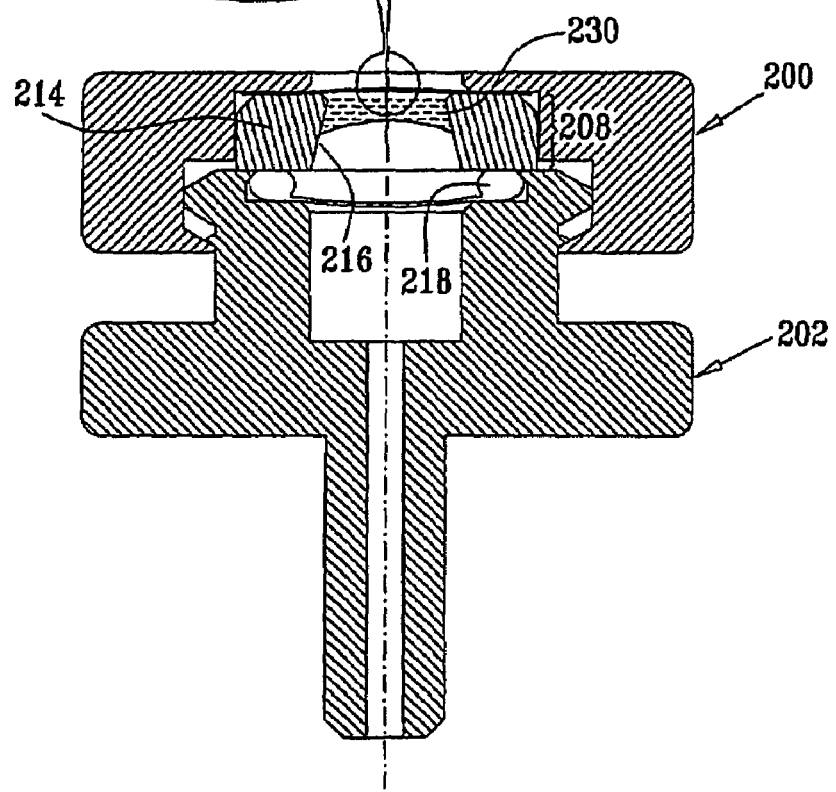
FIG. 16B

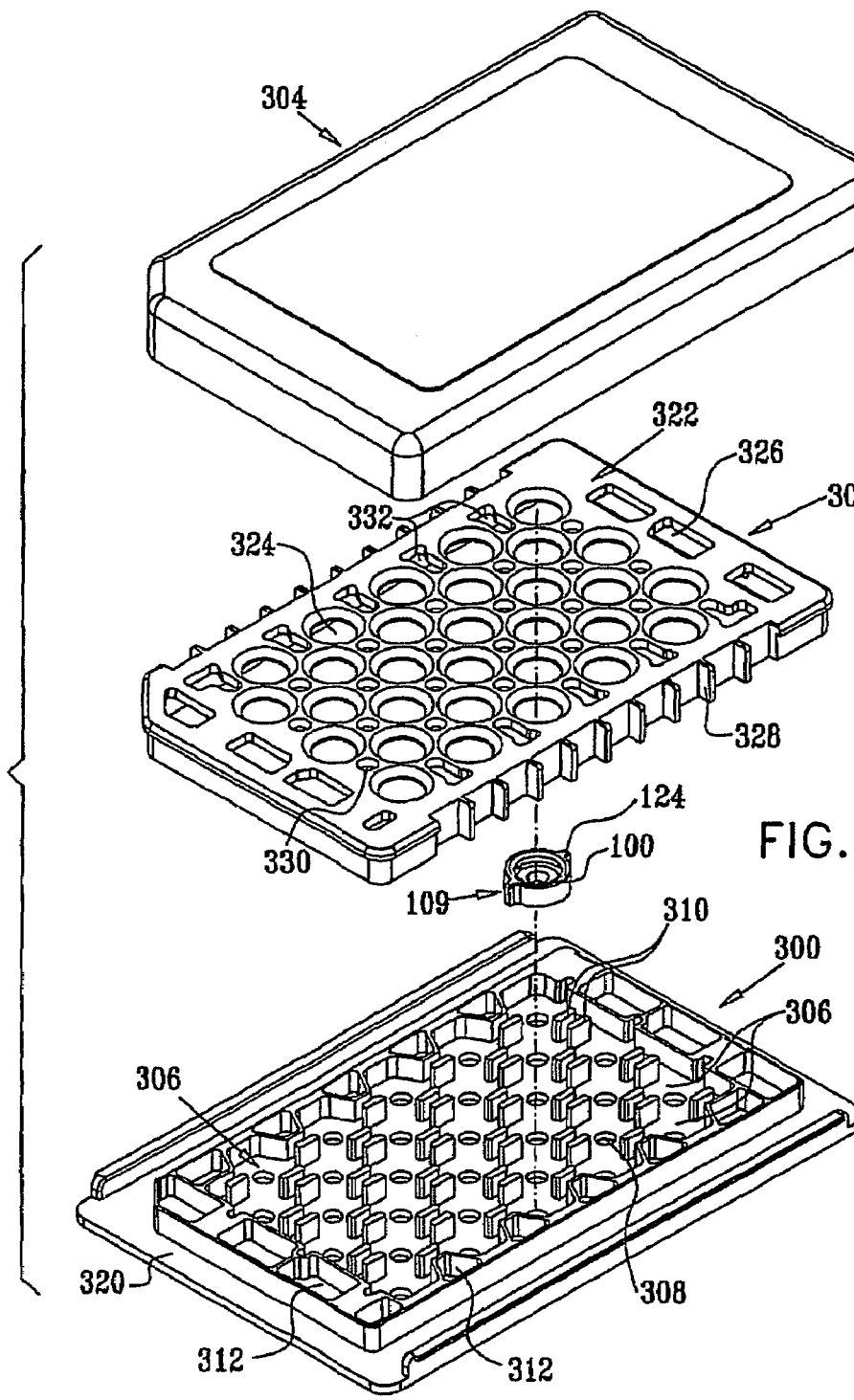

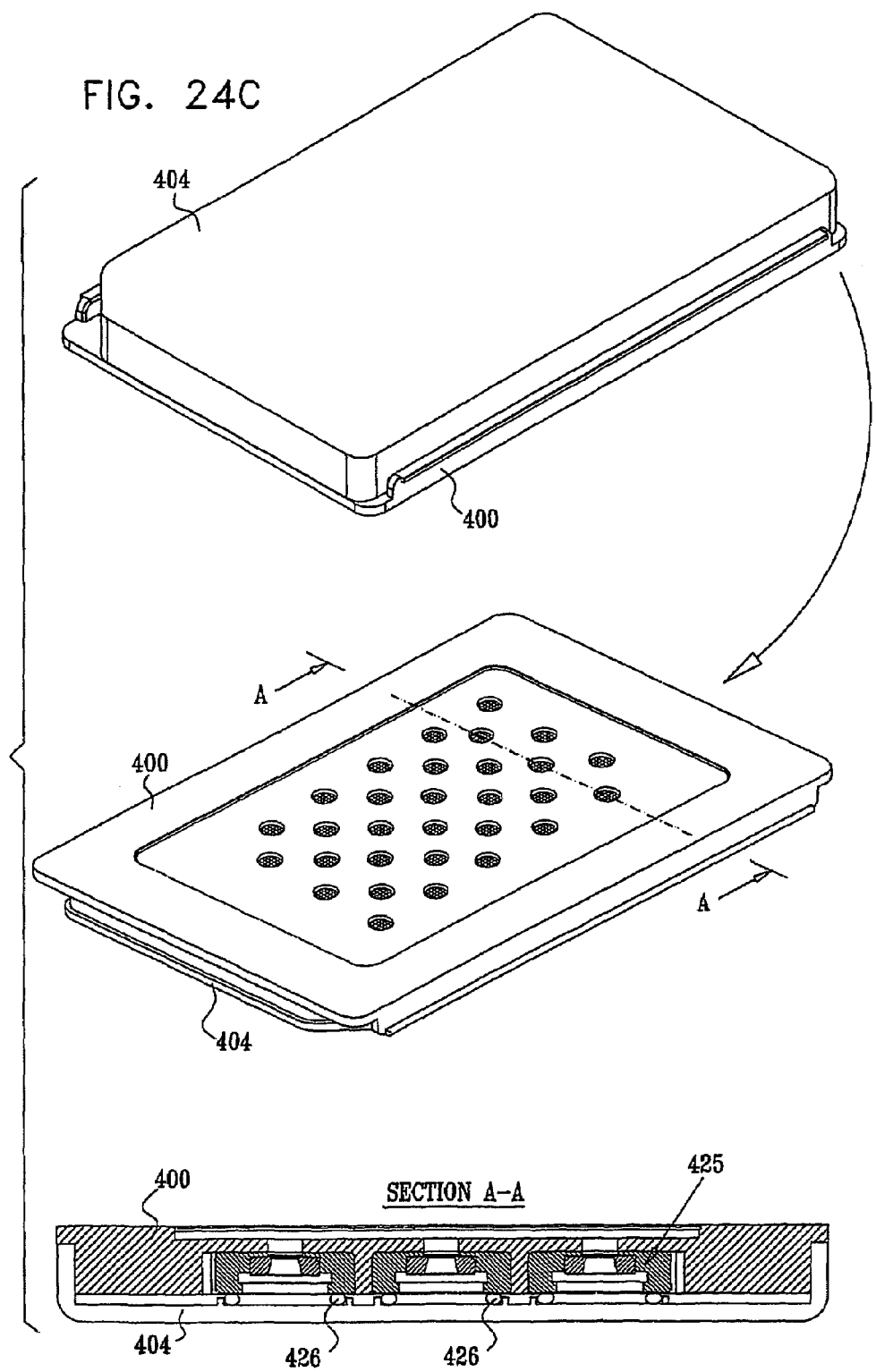

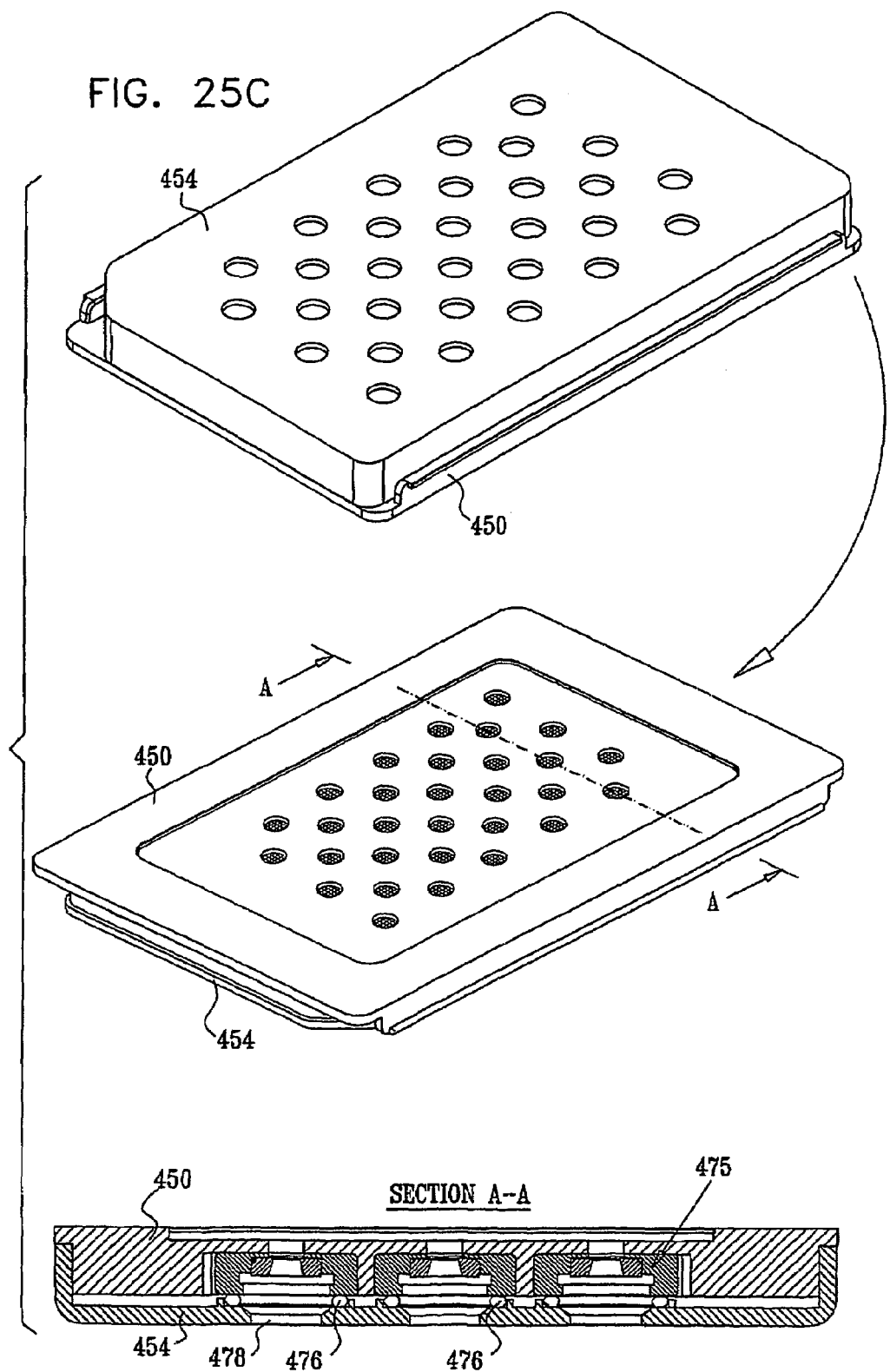

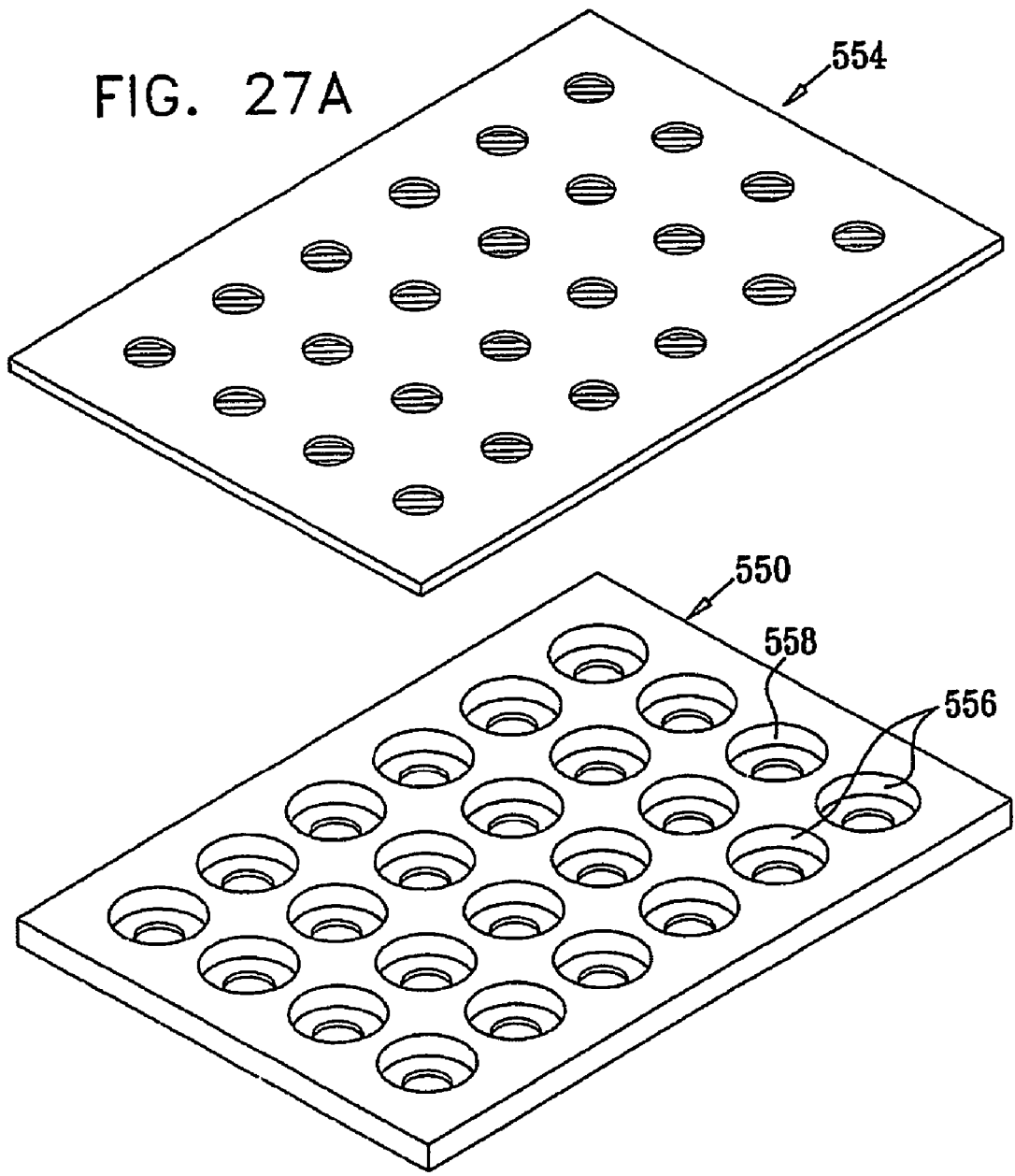

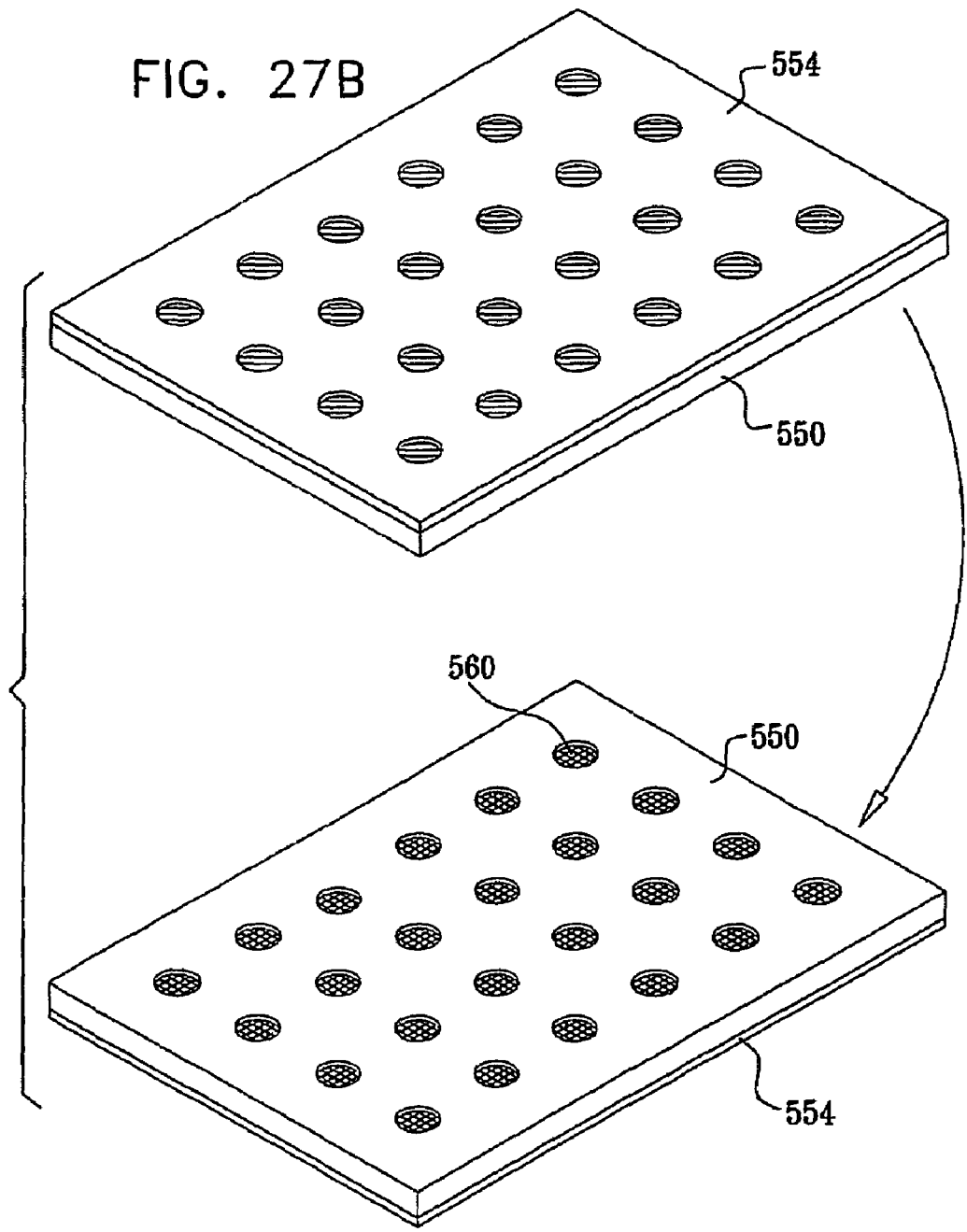

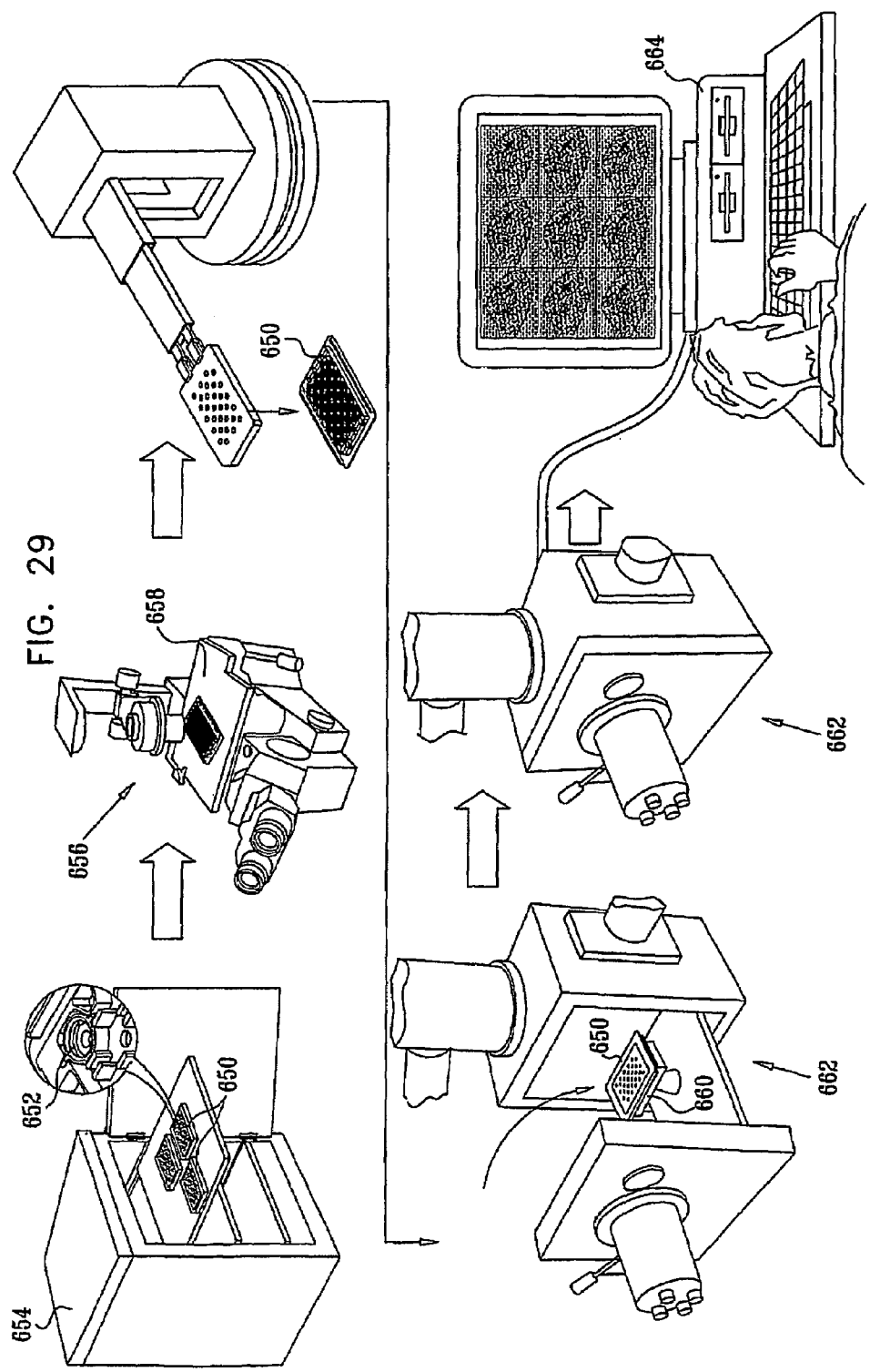

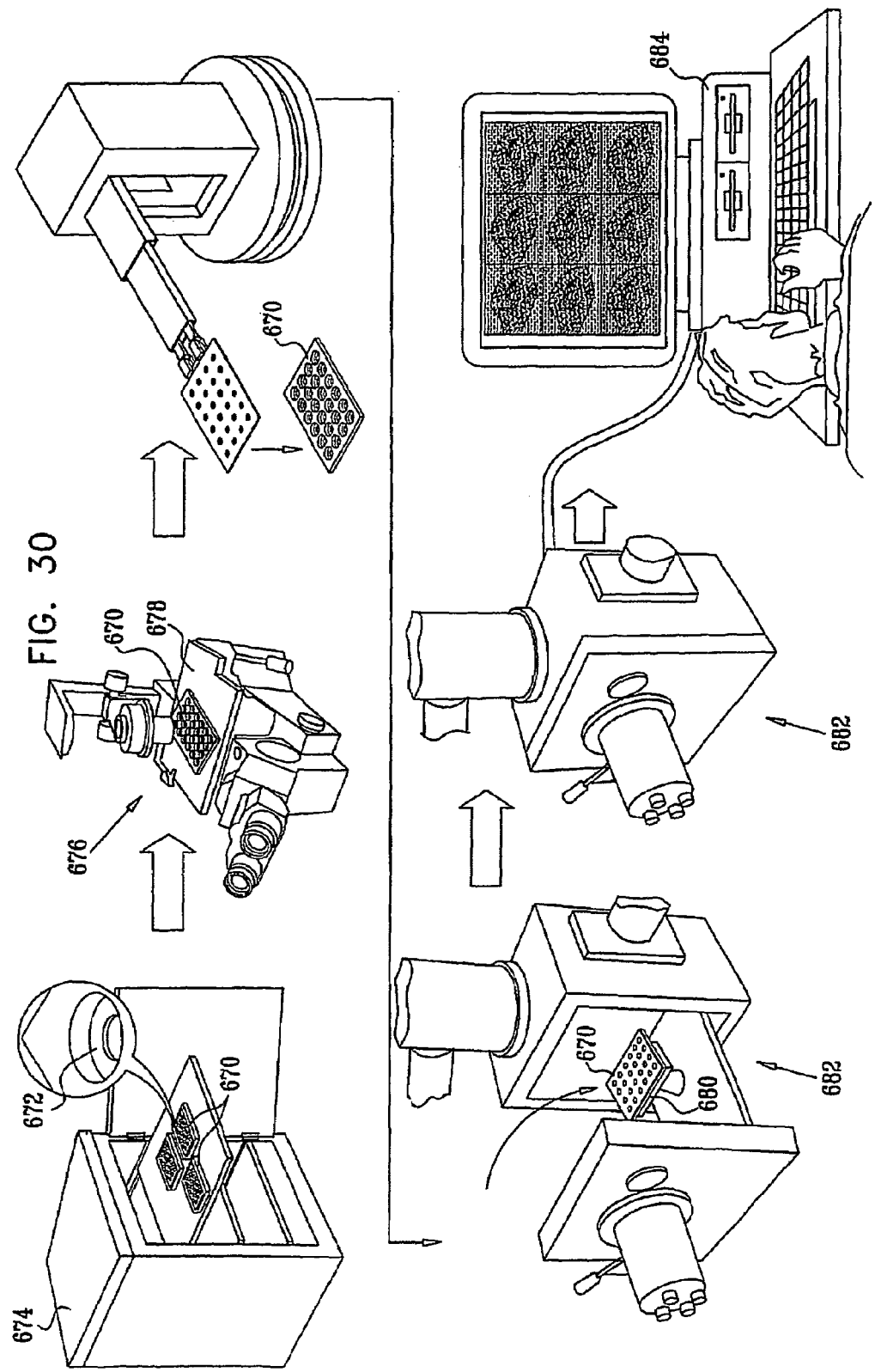

FIG. 31A
FIG. 31B
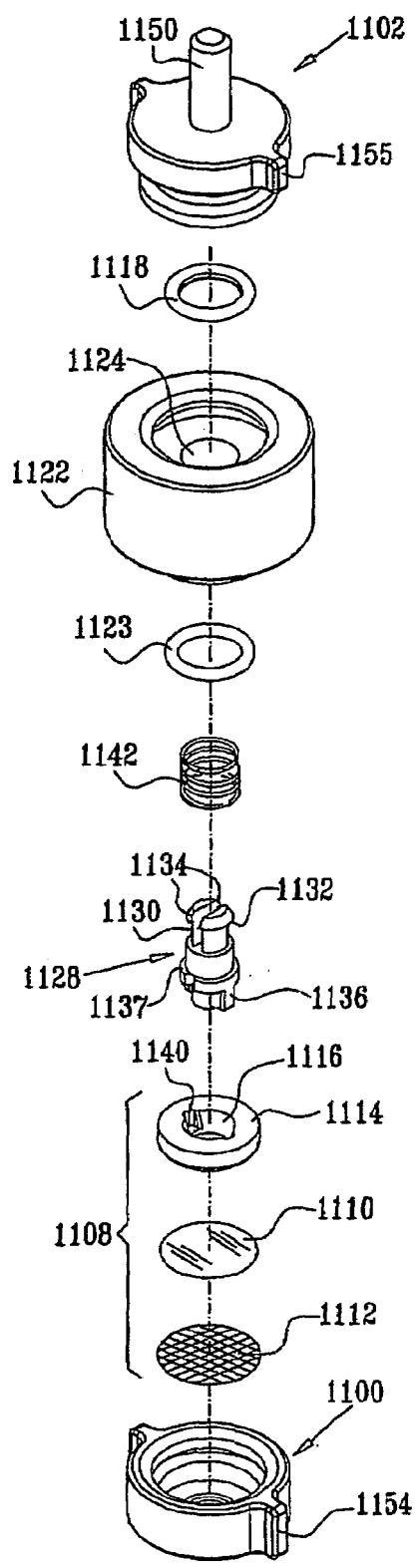
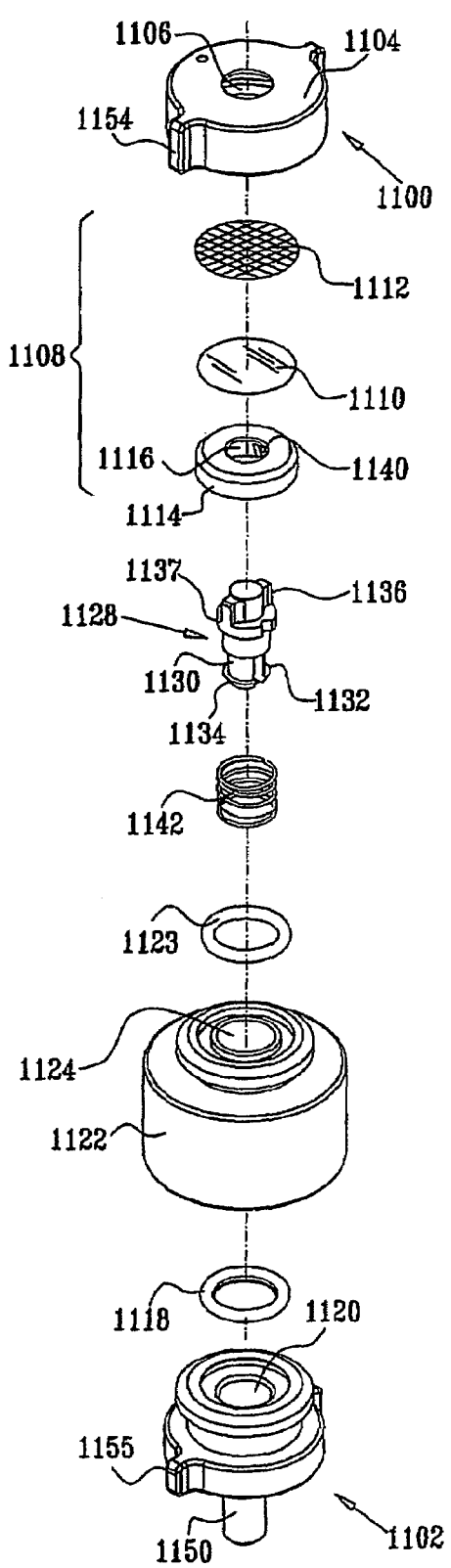

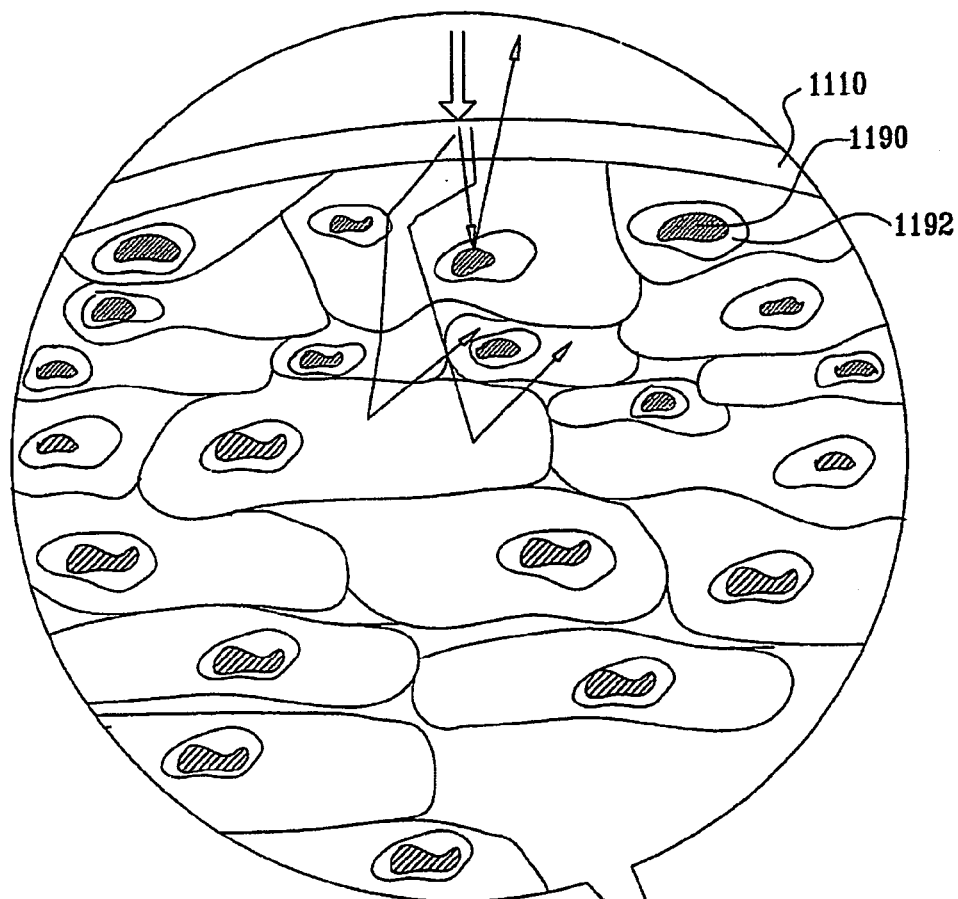
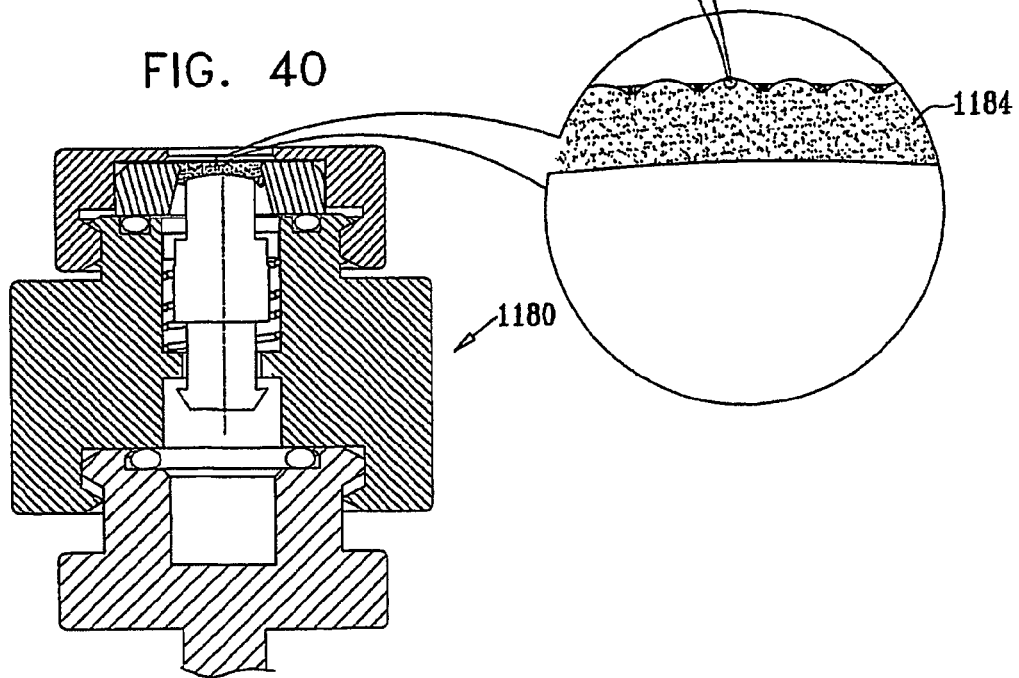
FIG. 40

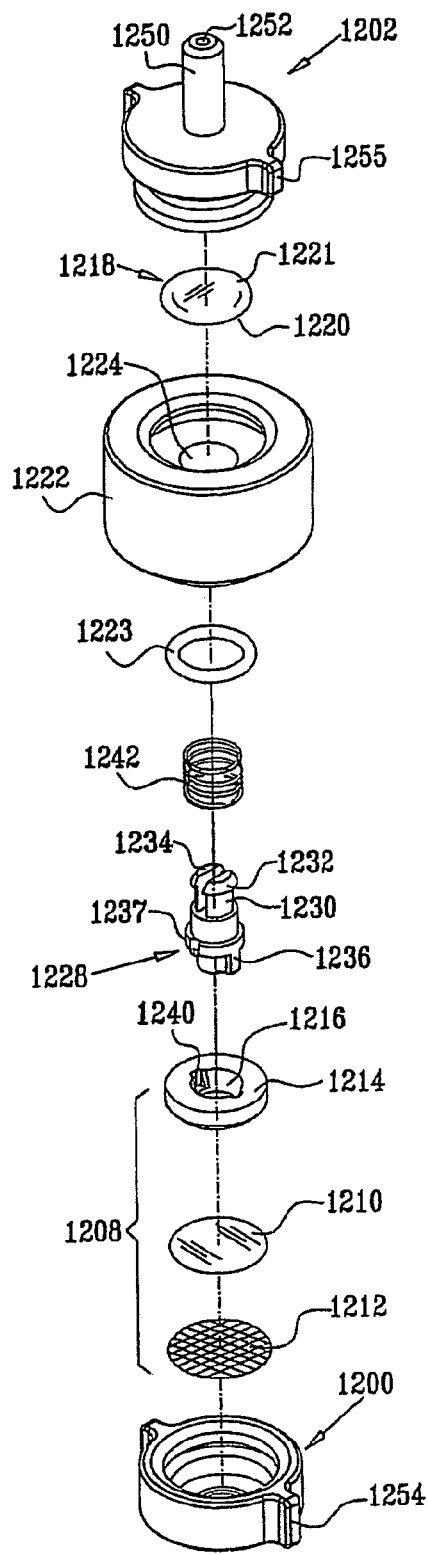
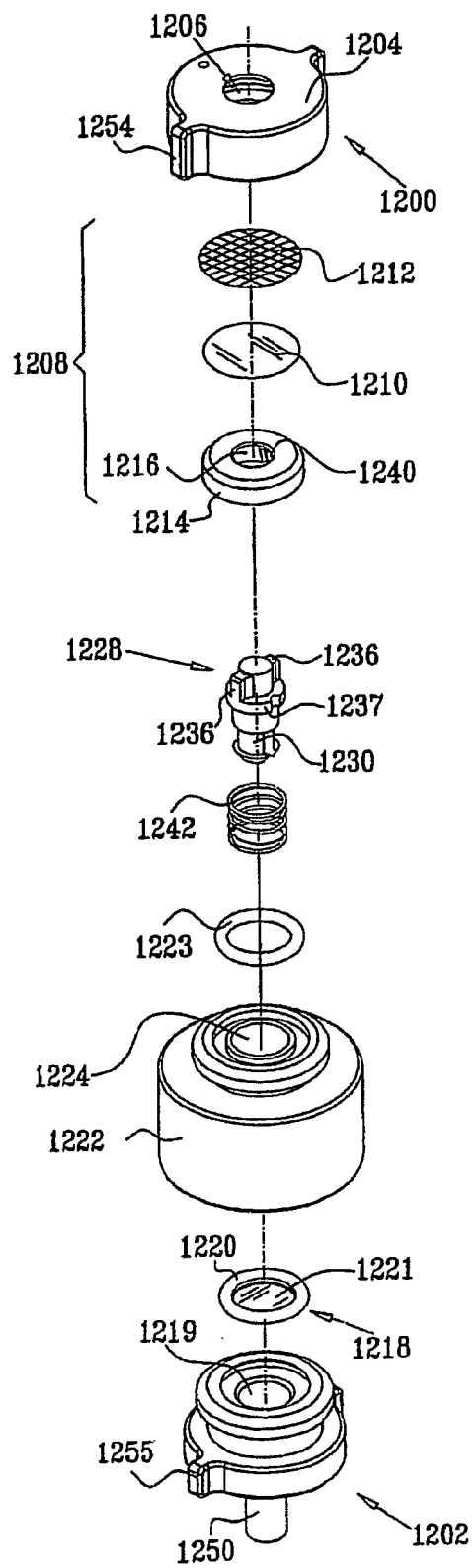
FIG. 41A
FIG. 41B

FIG. 45A
FIG. 45B
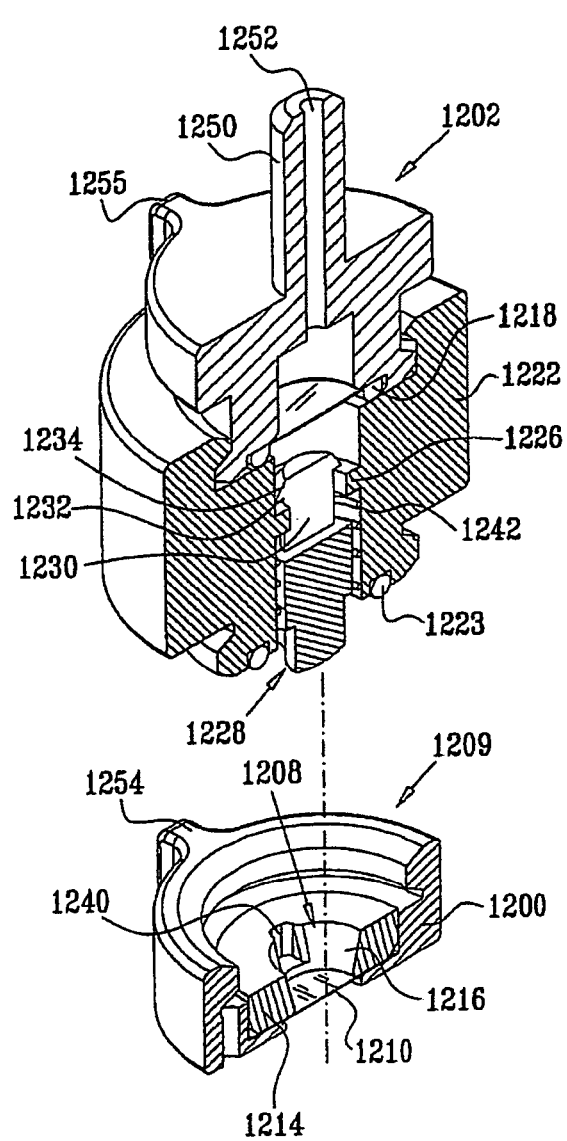
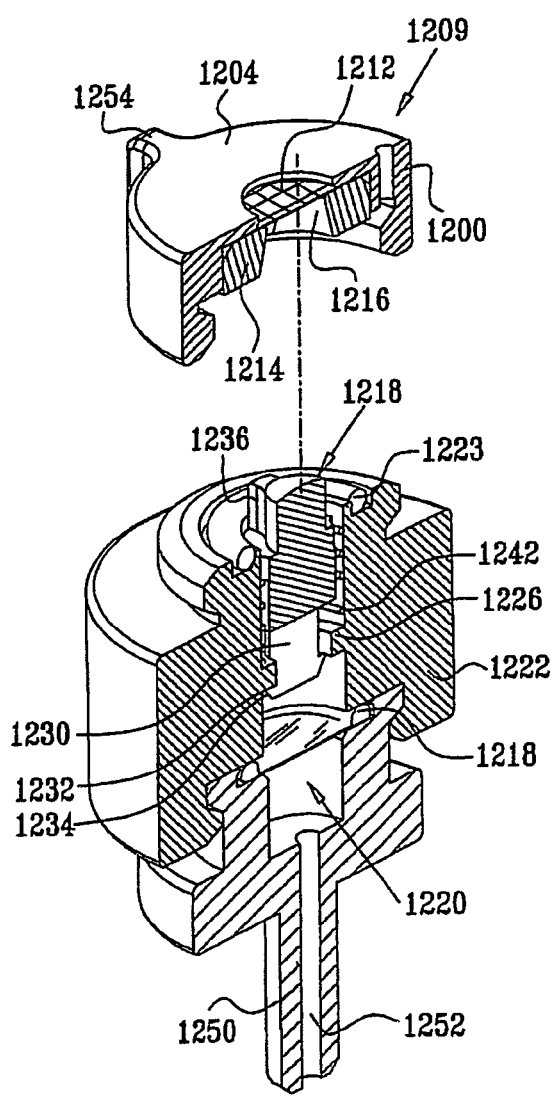

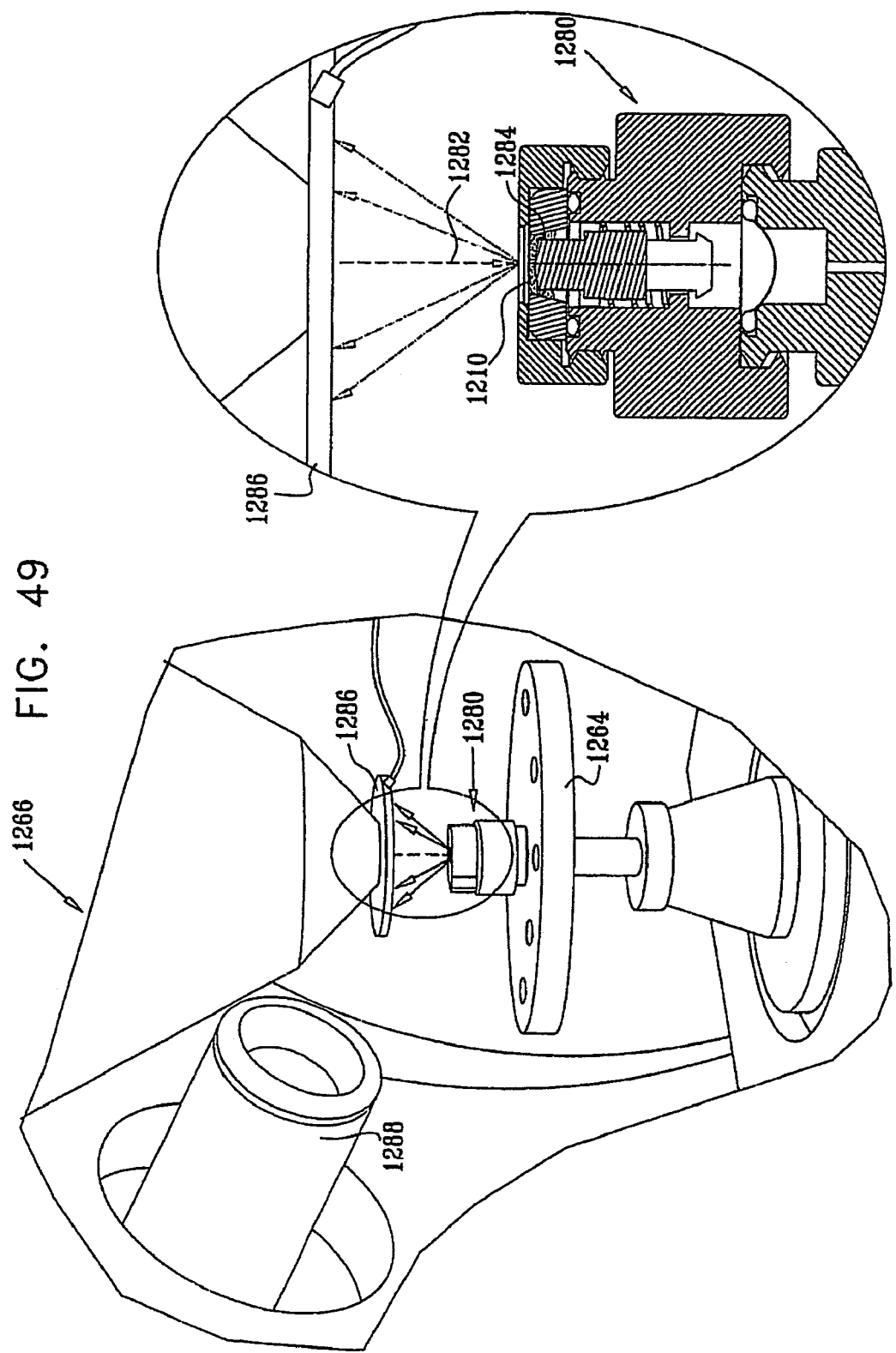

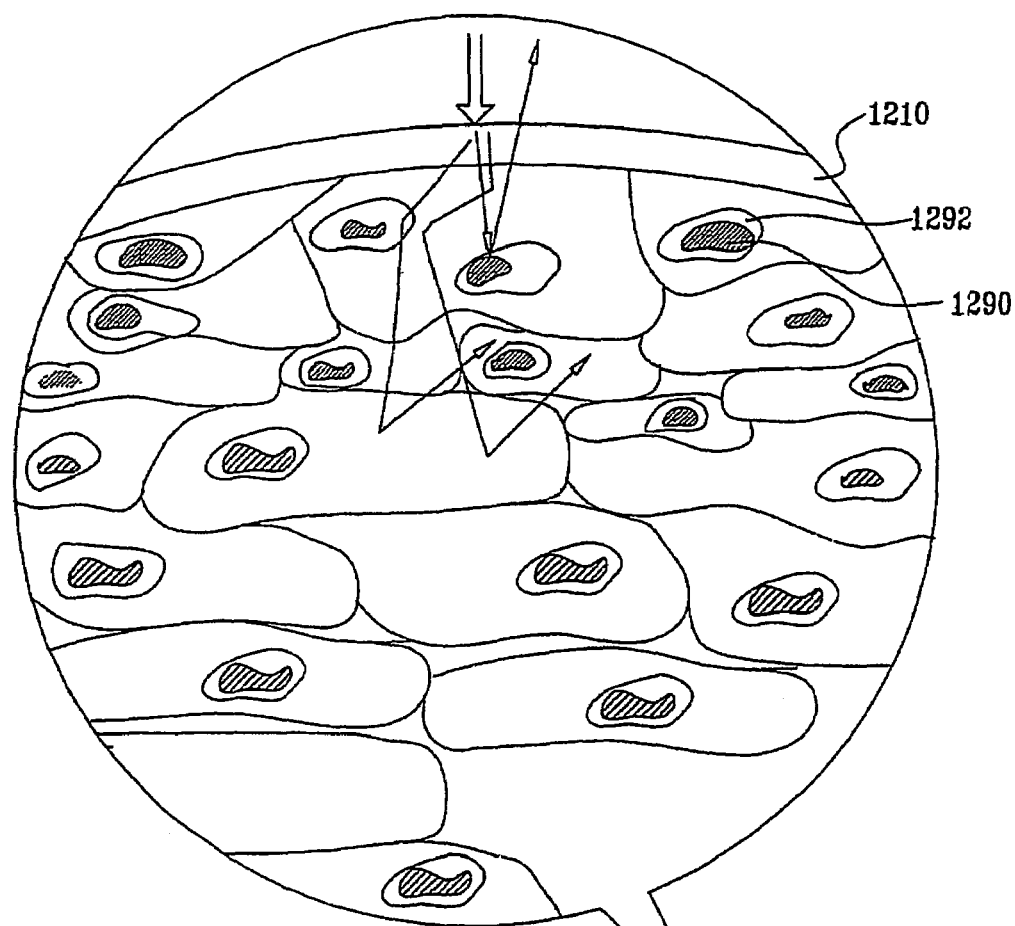
FIG. 50
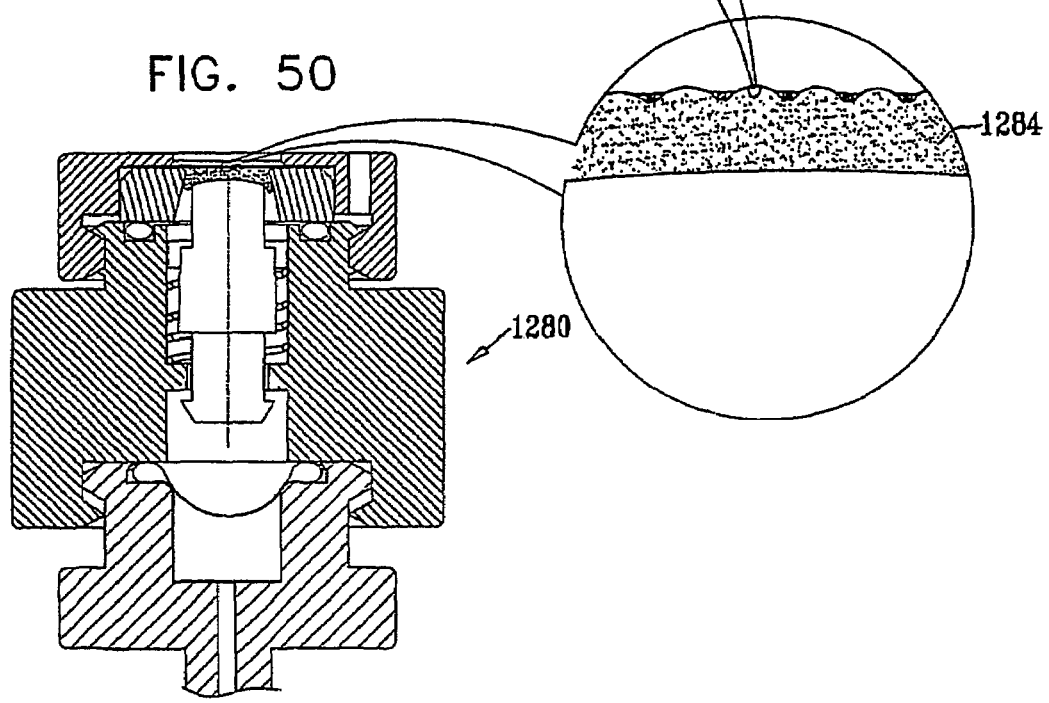

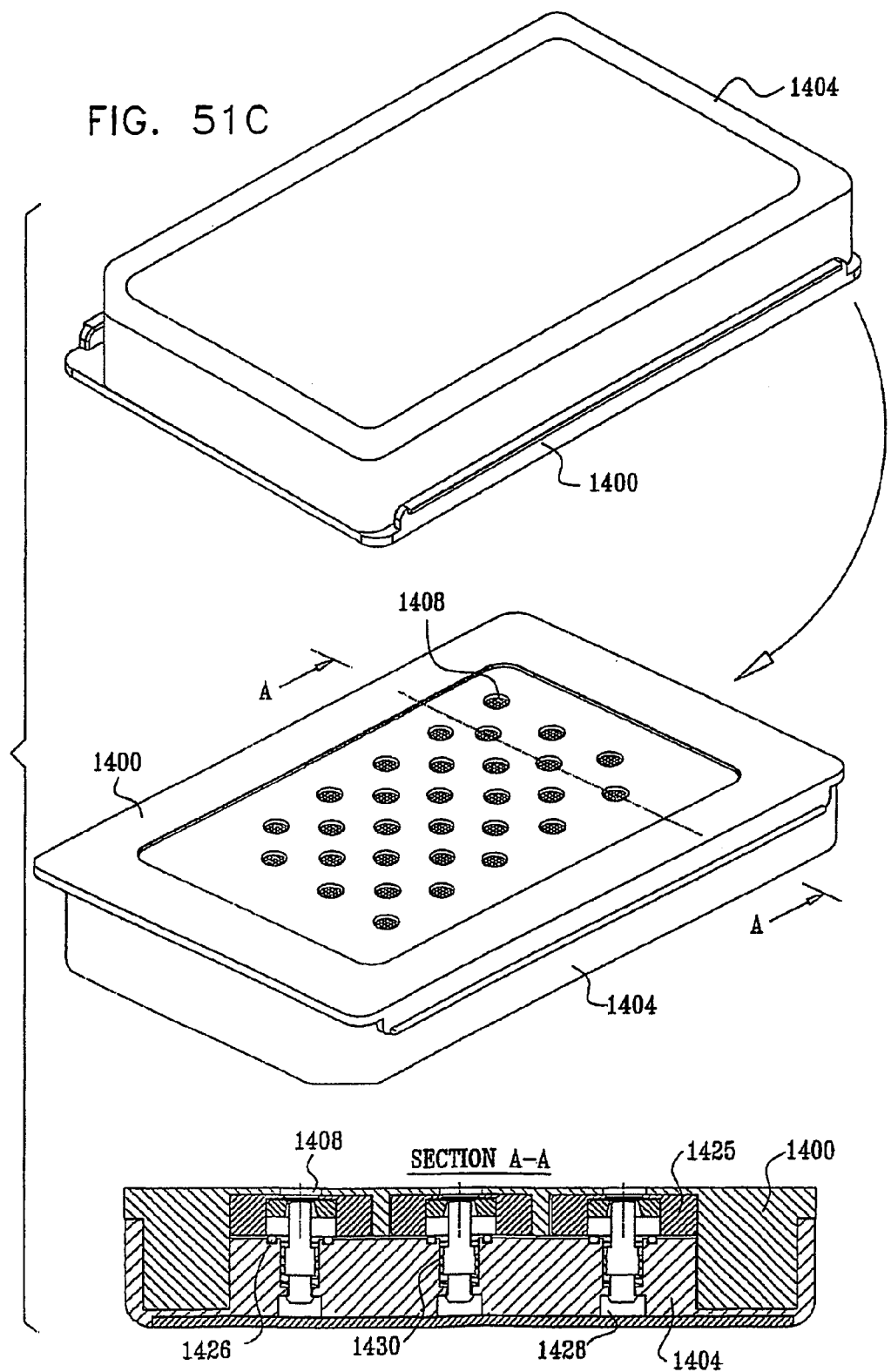

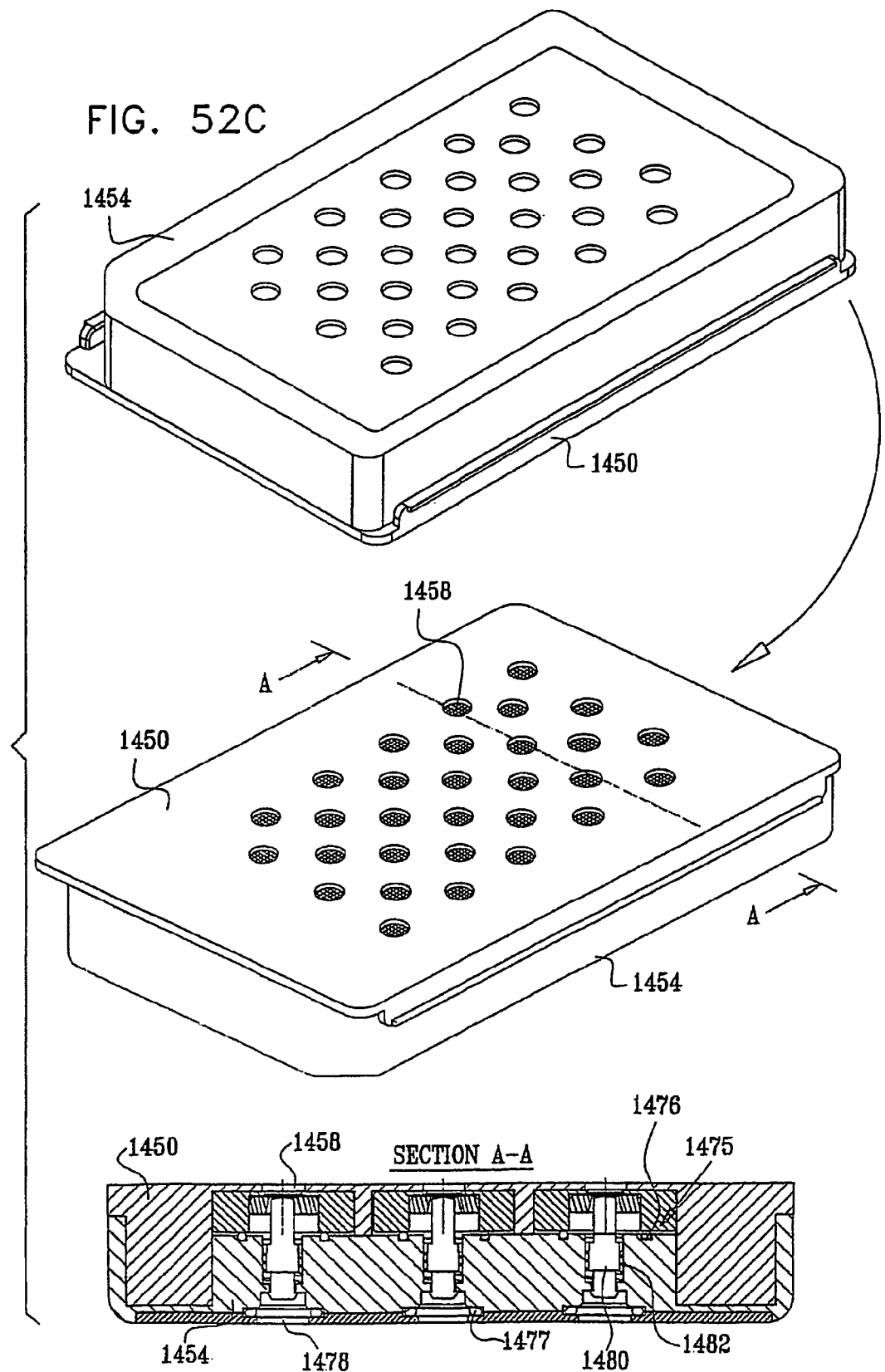

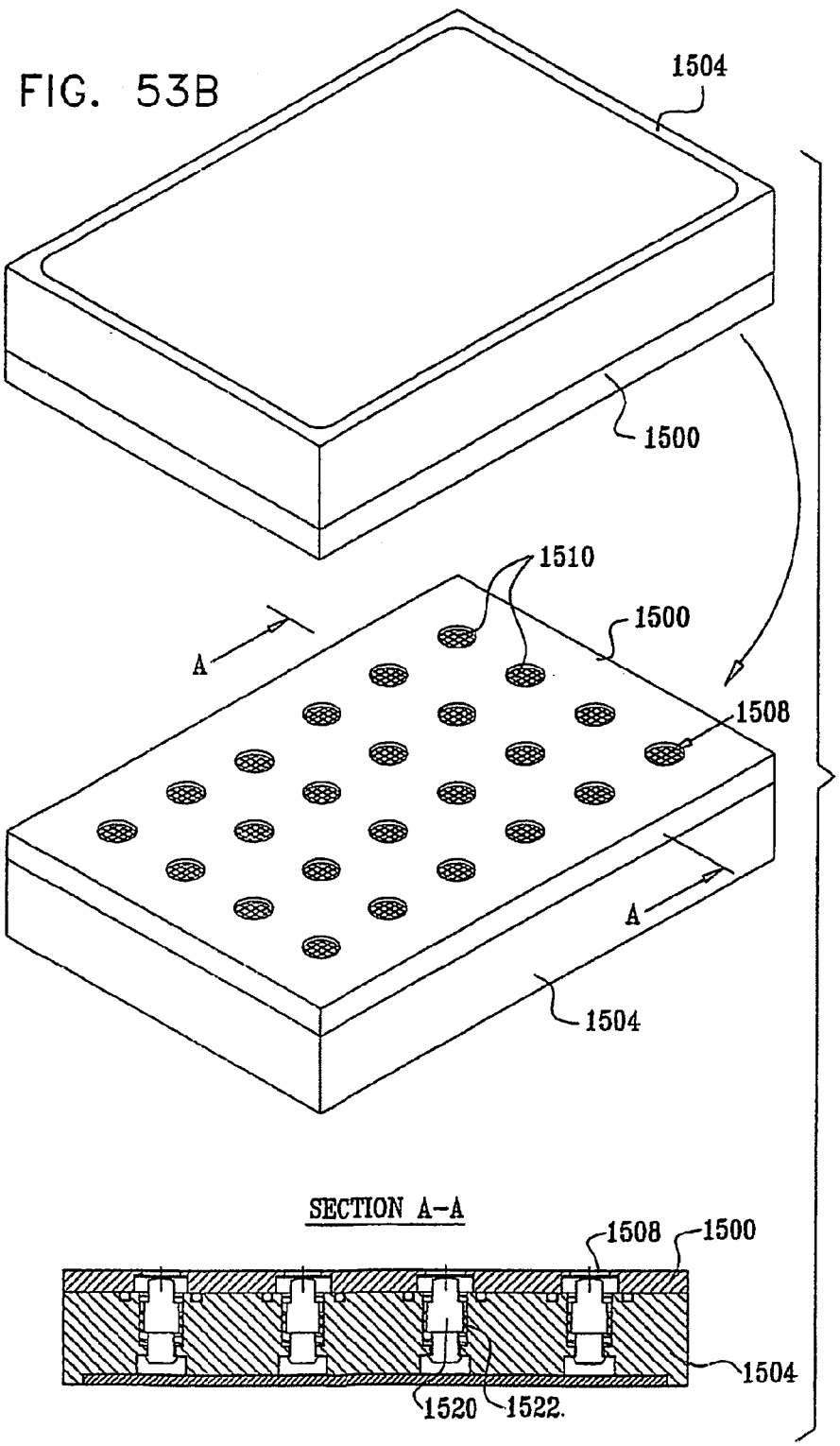

FIG. 54B
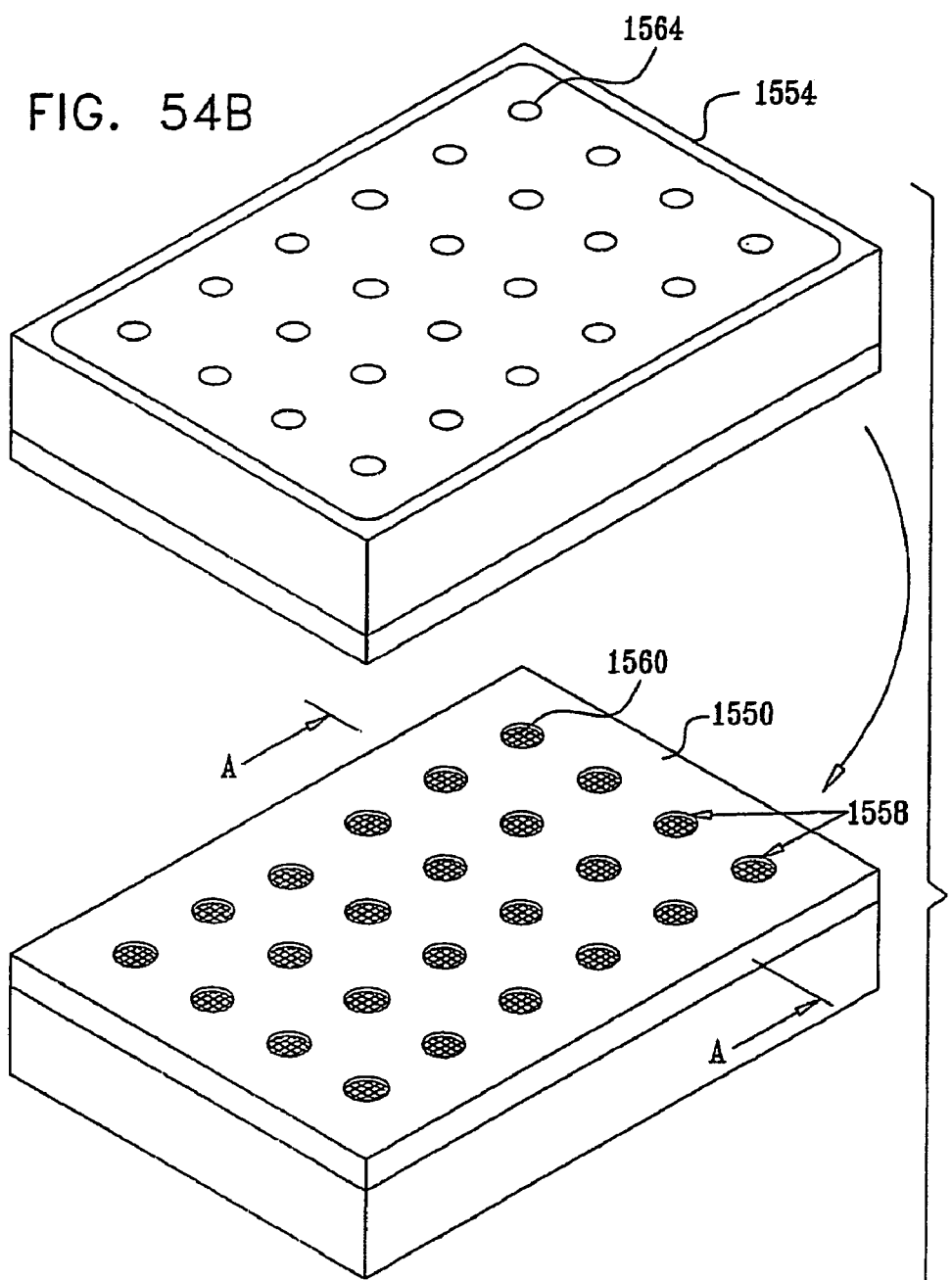
SECTION A-A
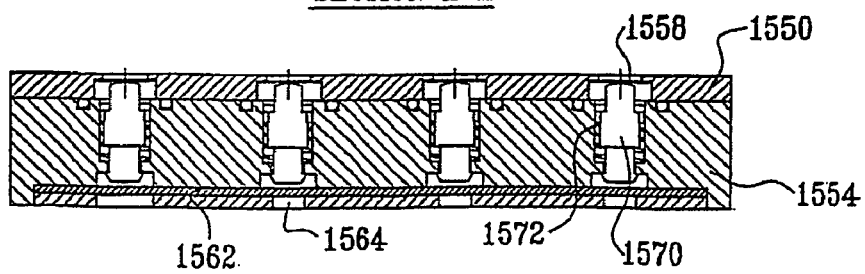

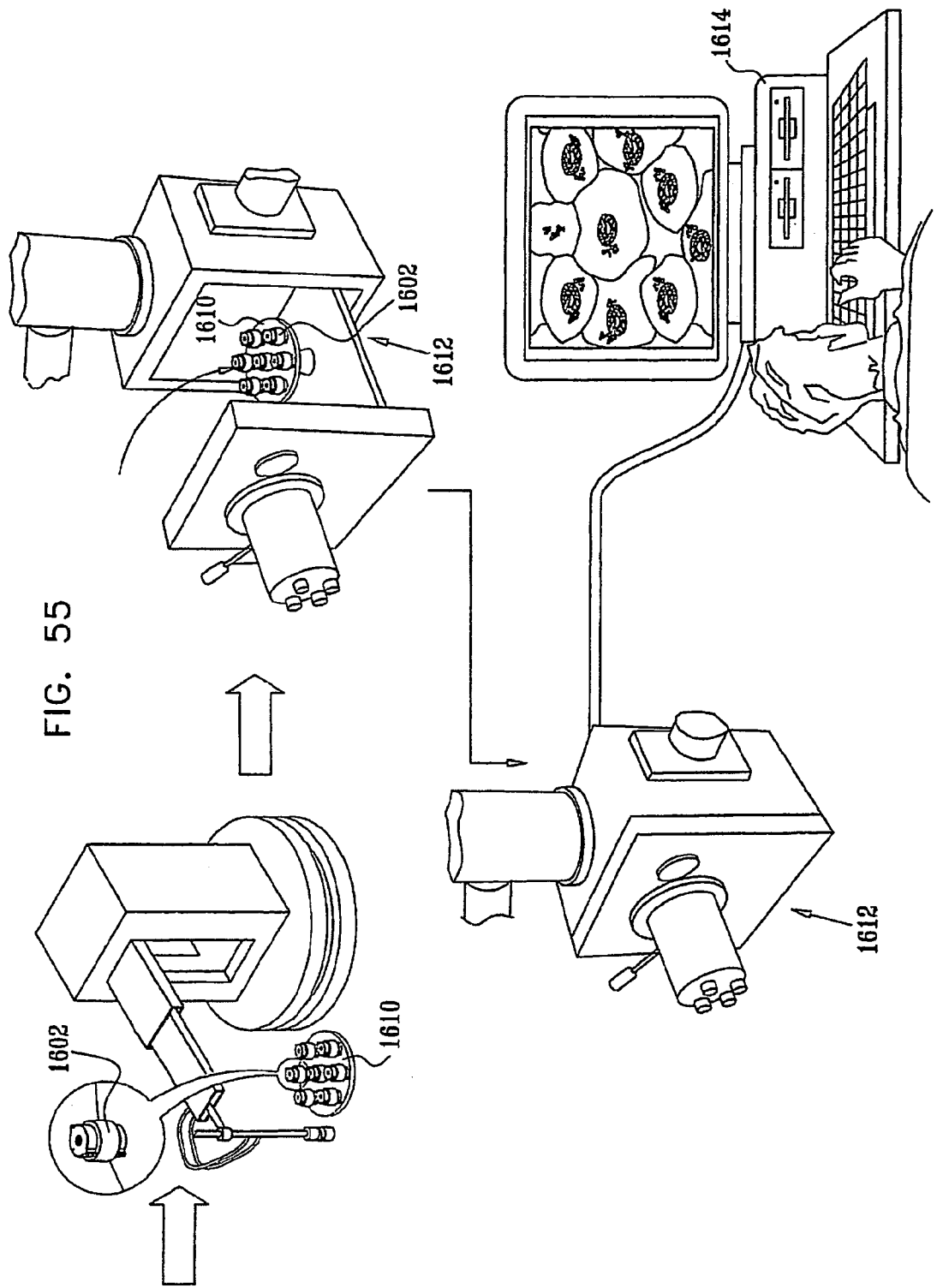

FIG. 58A
FIG. 58B
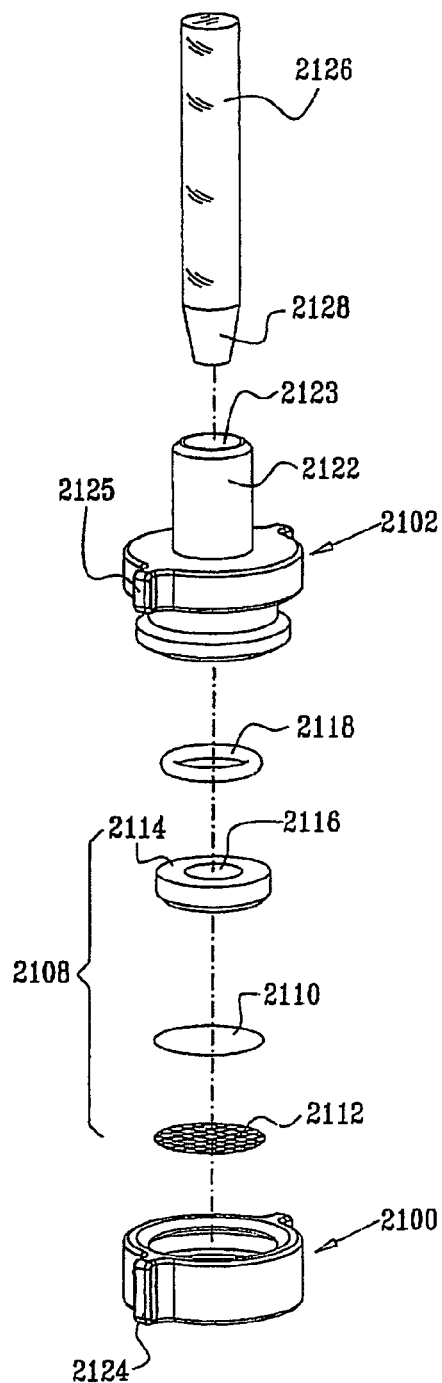
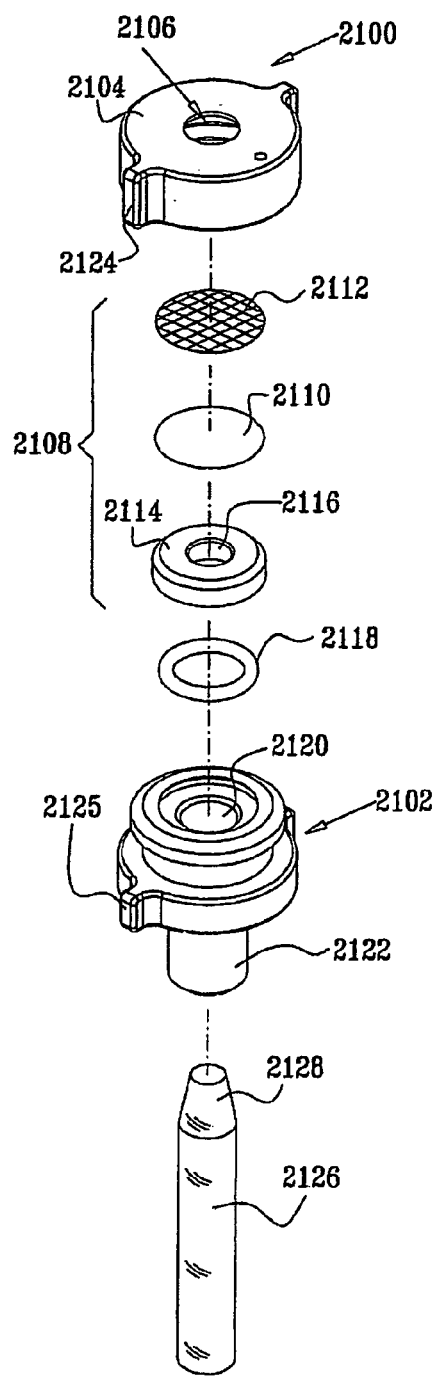

FIG. 60A
FIG. 60B
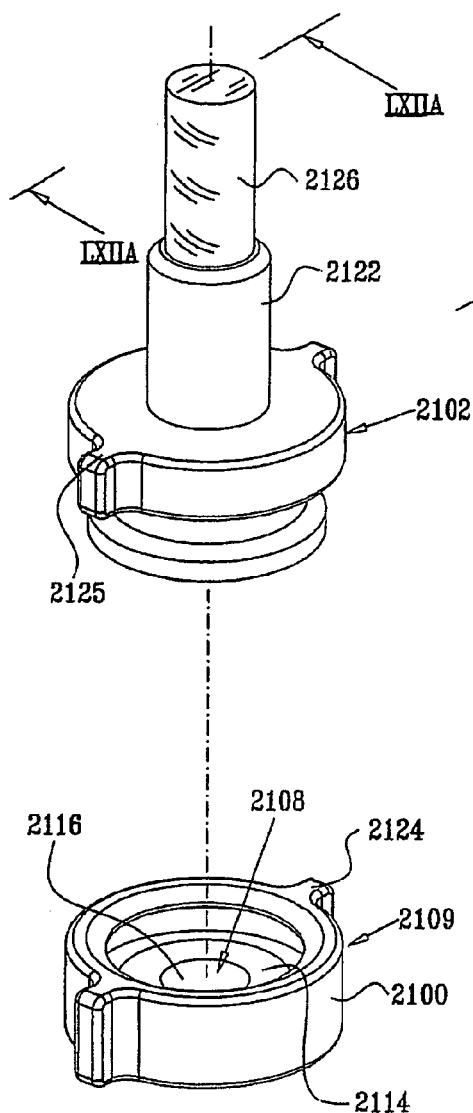
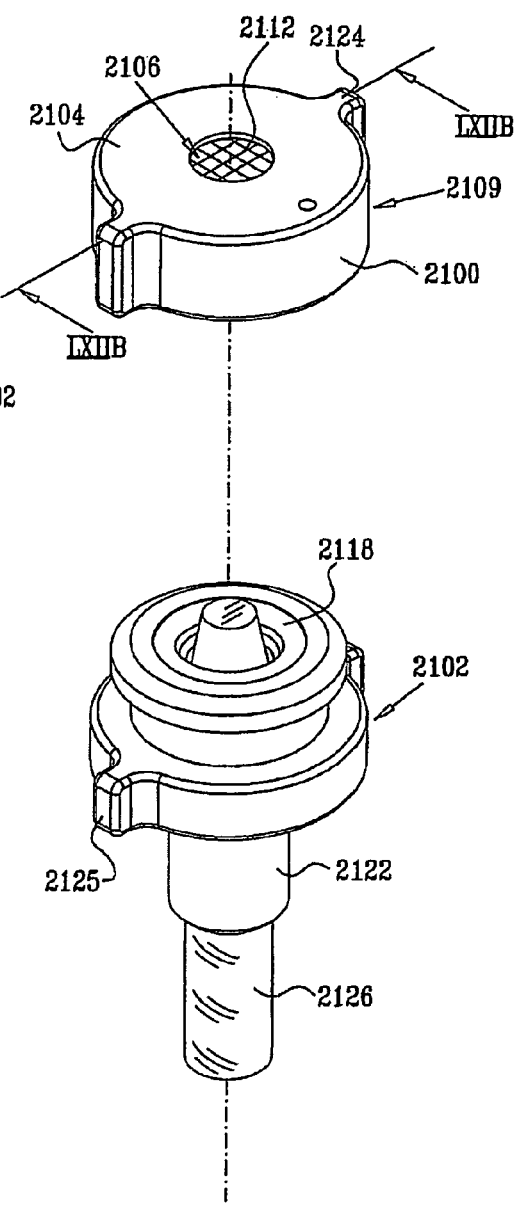

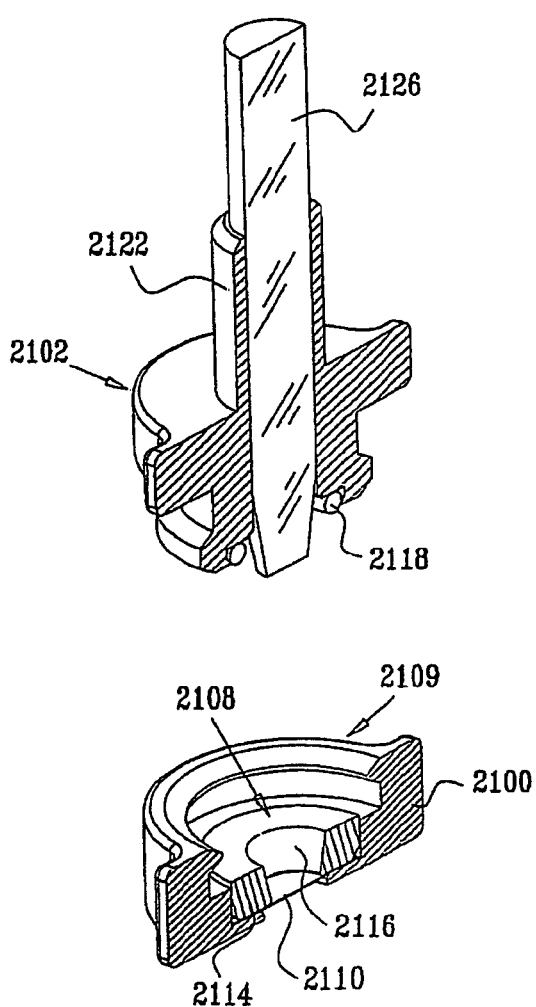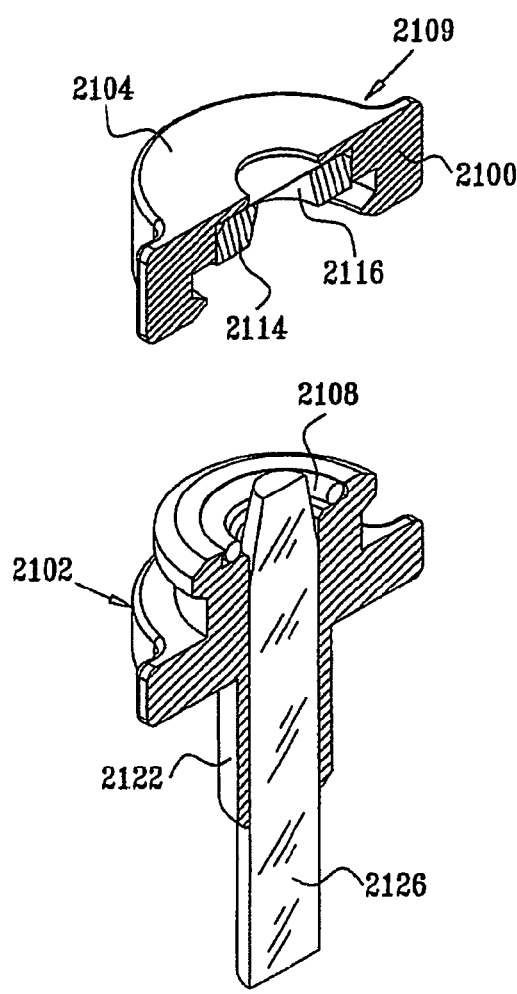
FIG. 62A
FIG. 62B

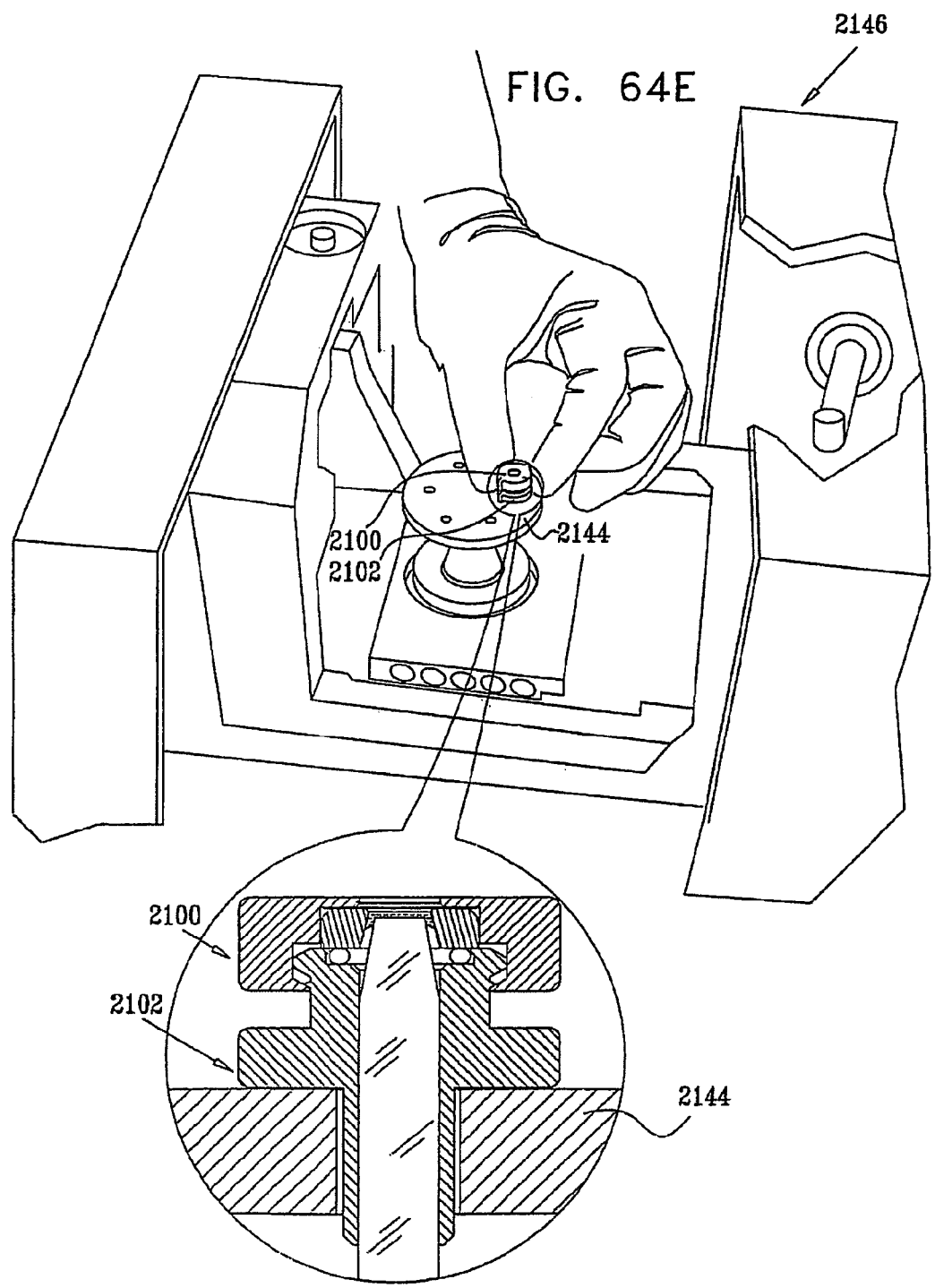

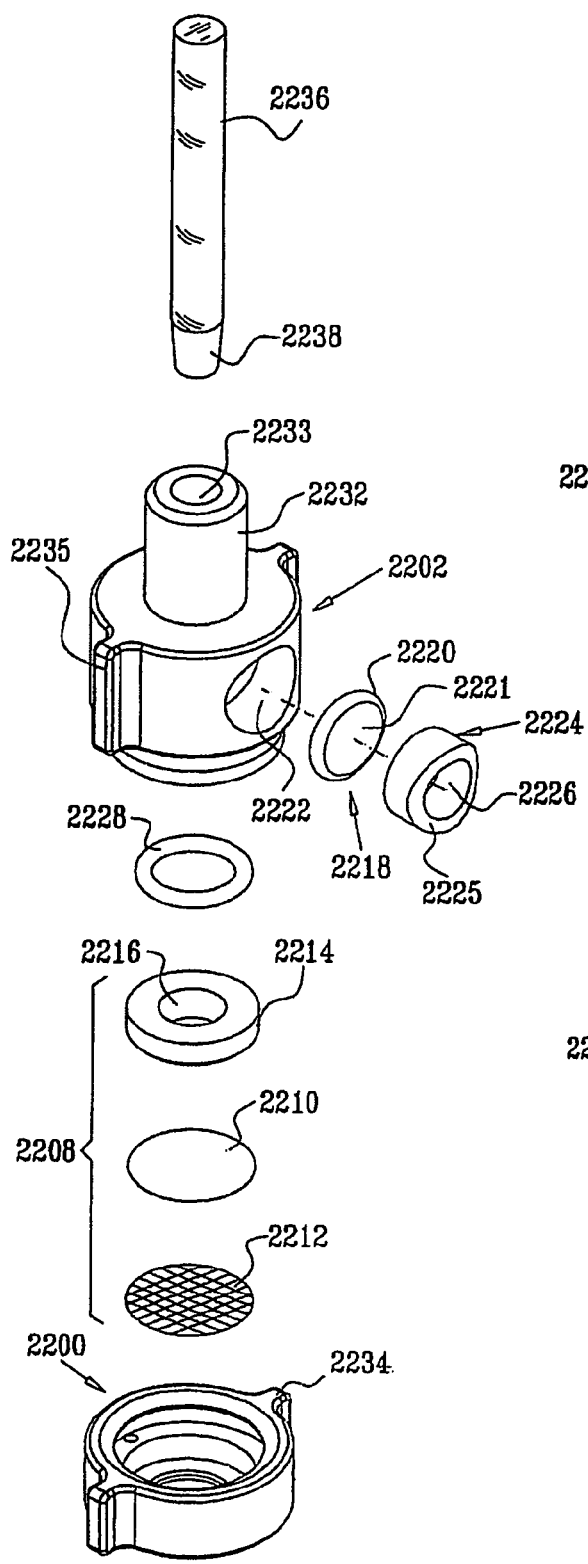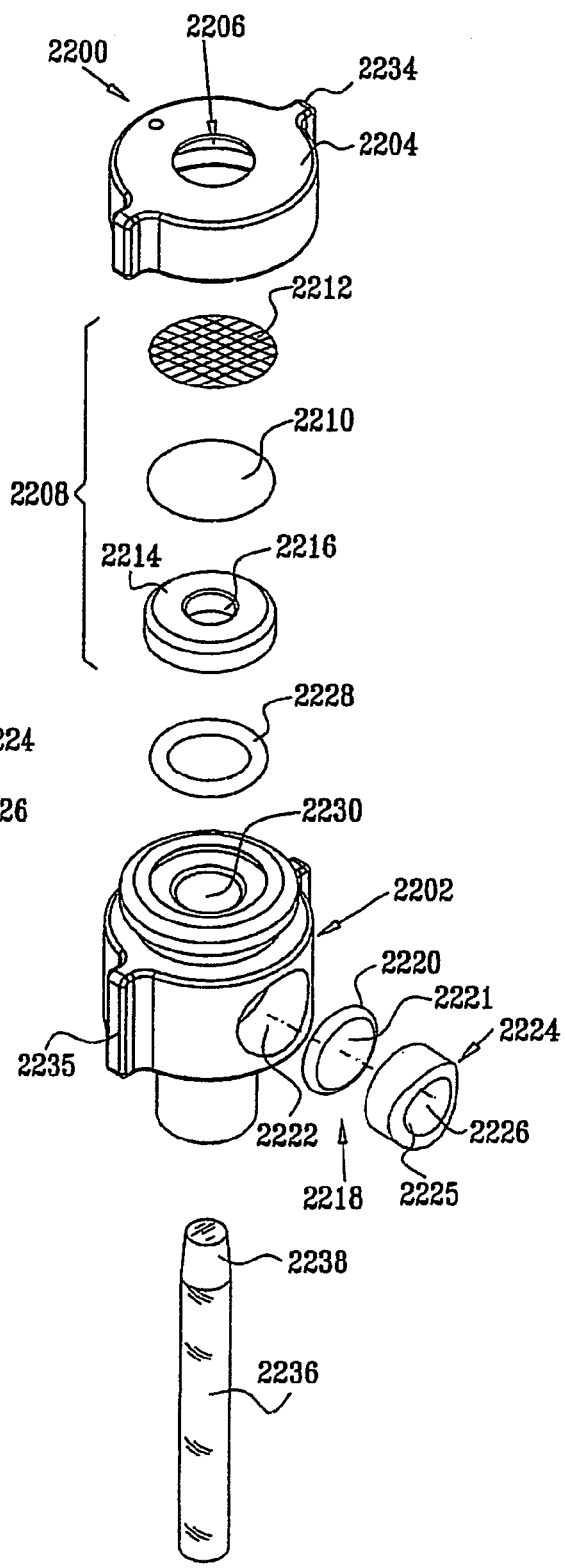

FIG. 70A
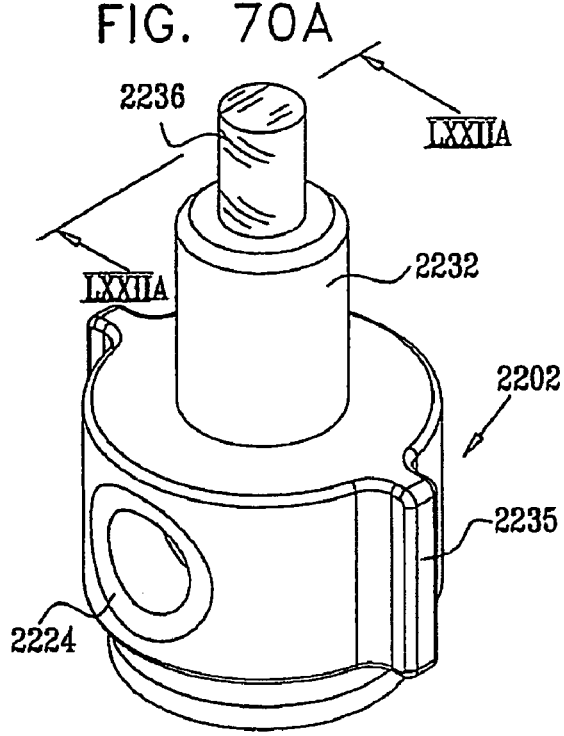
FIG. 70B
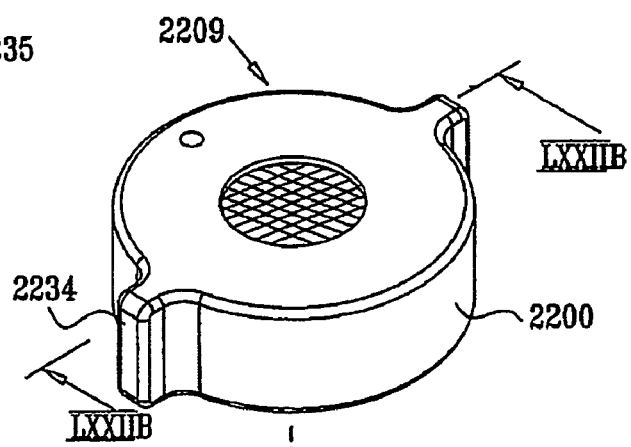
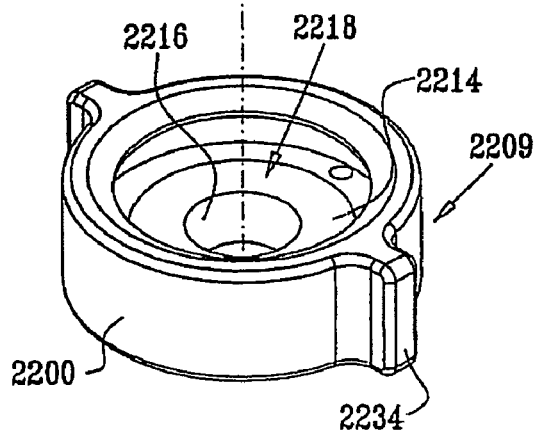
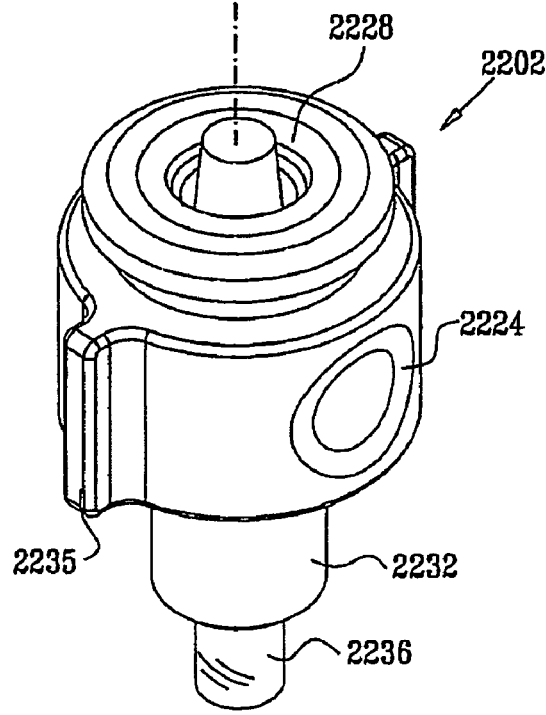

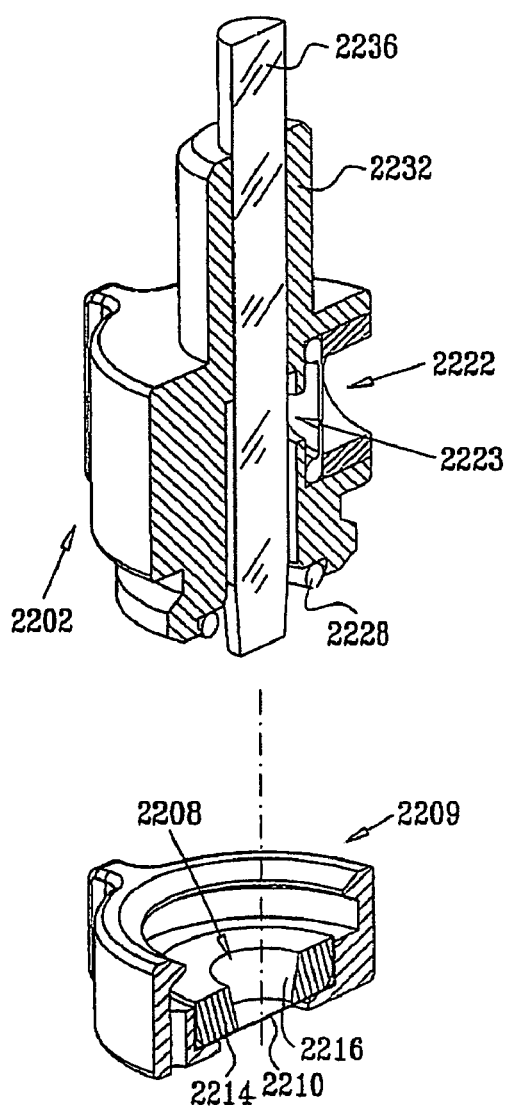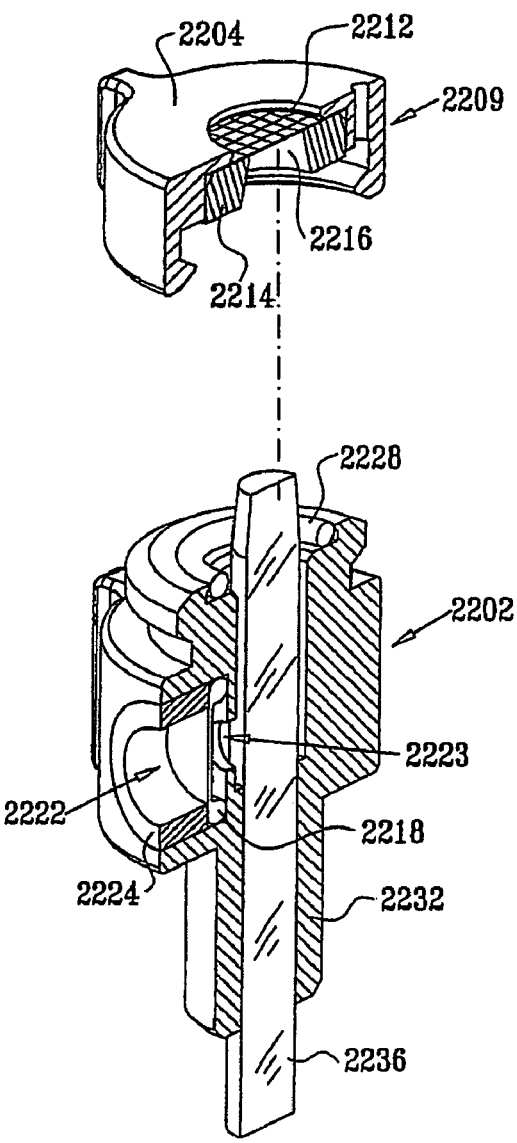

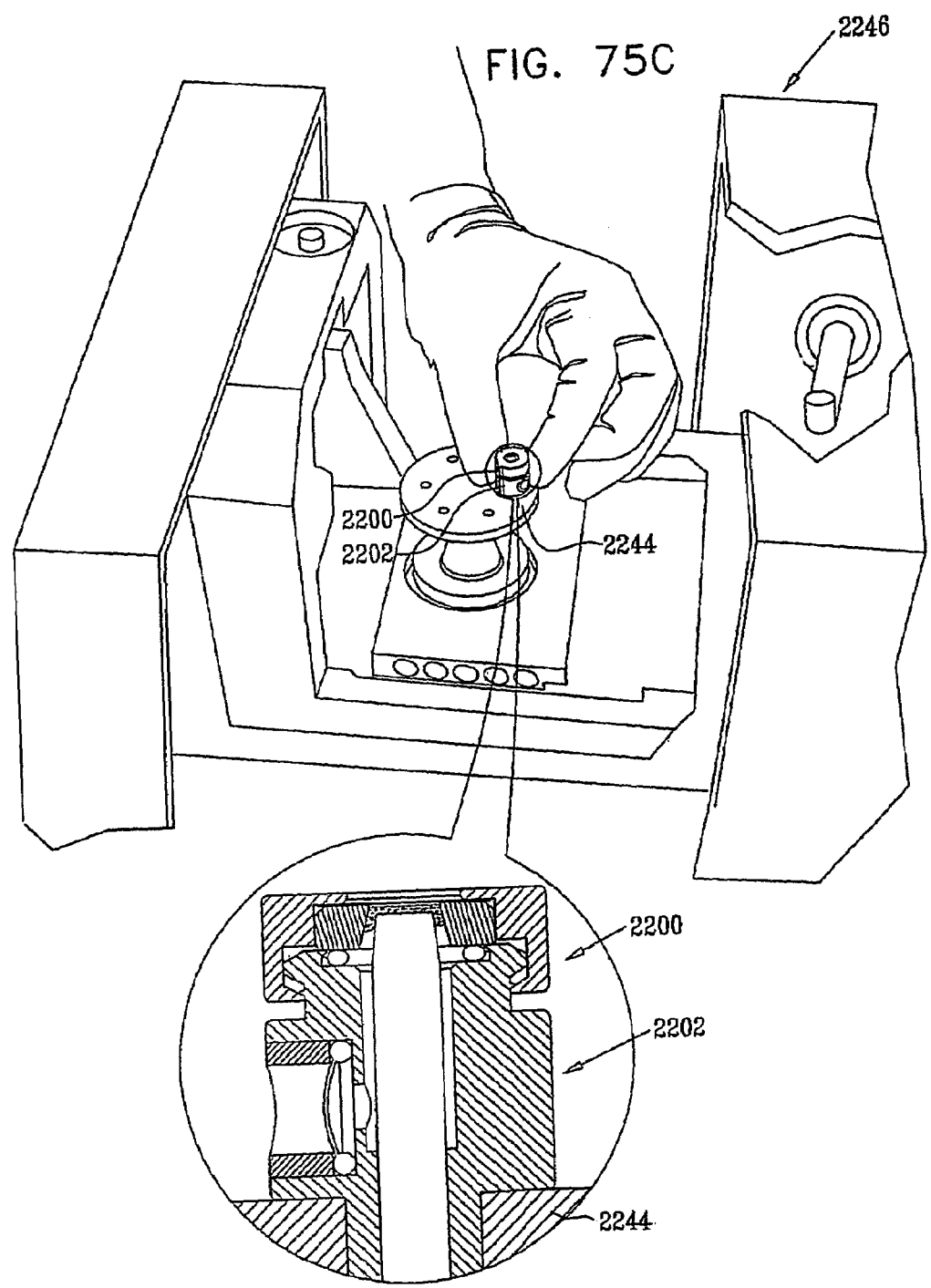

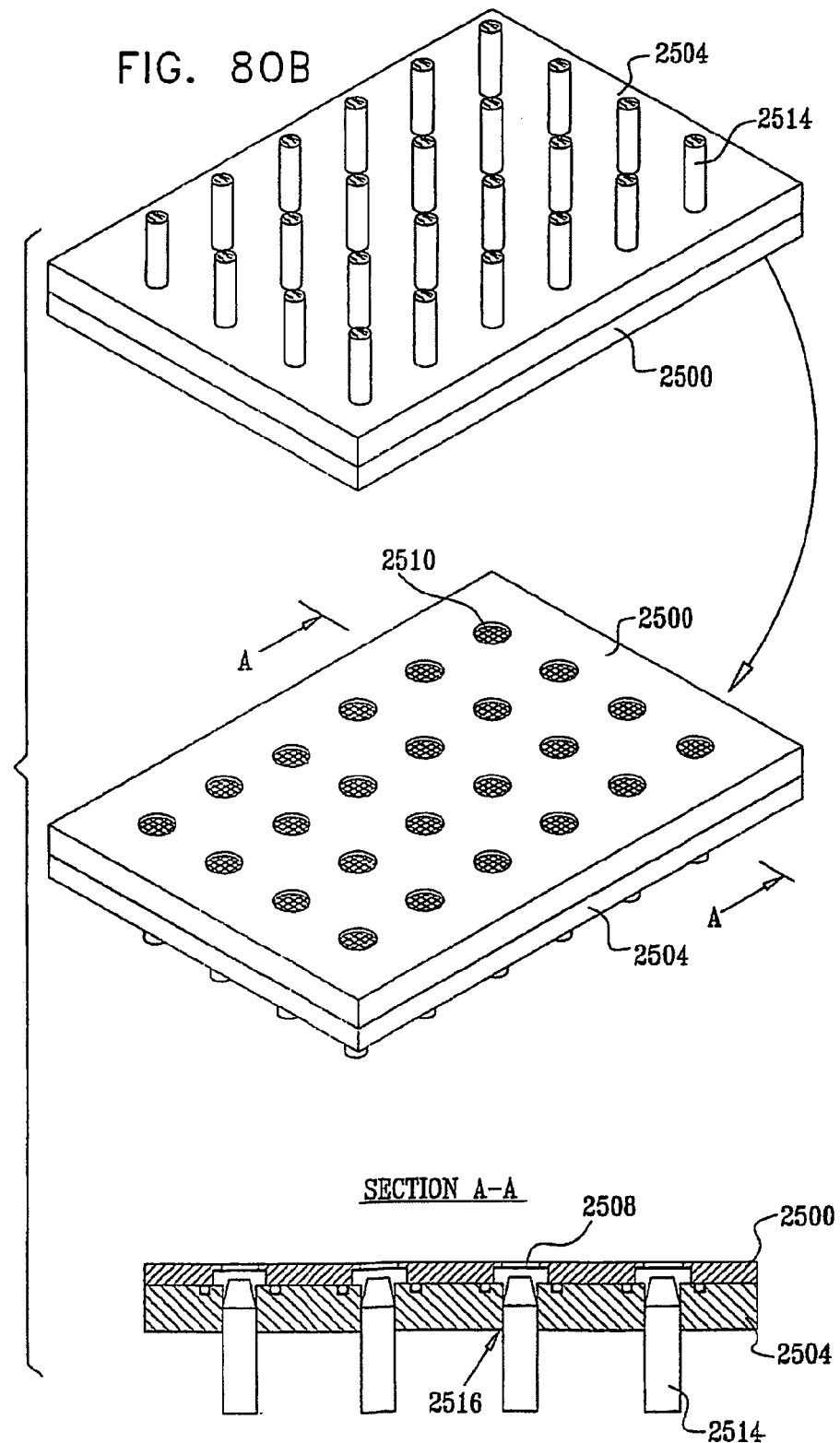

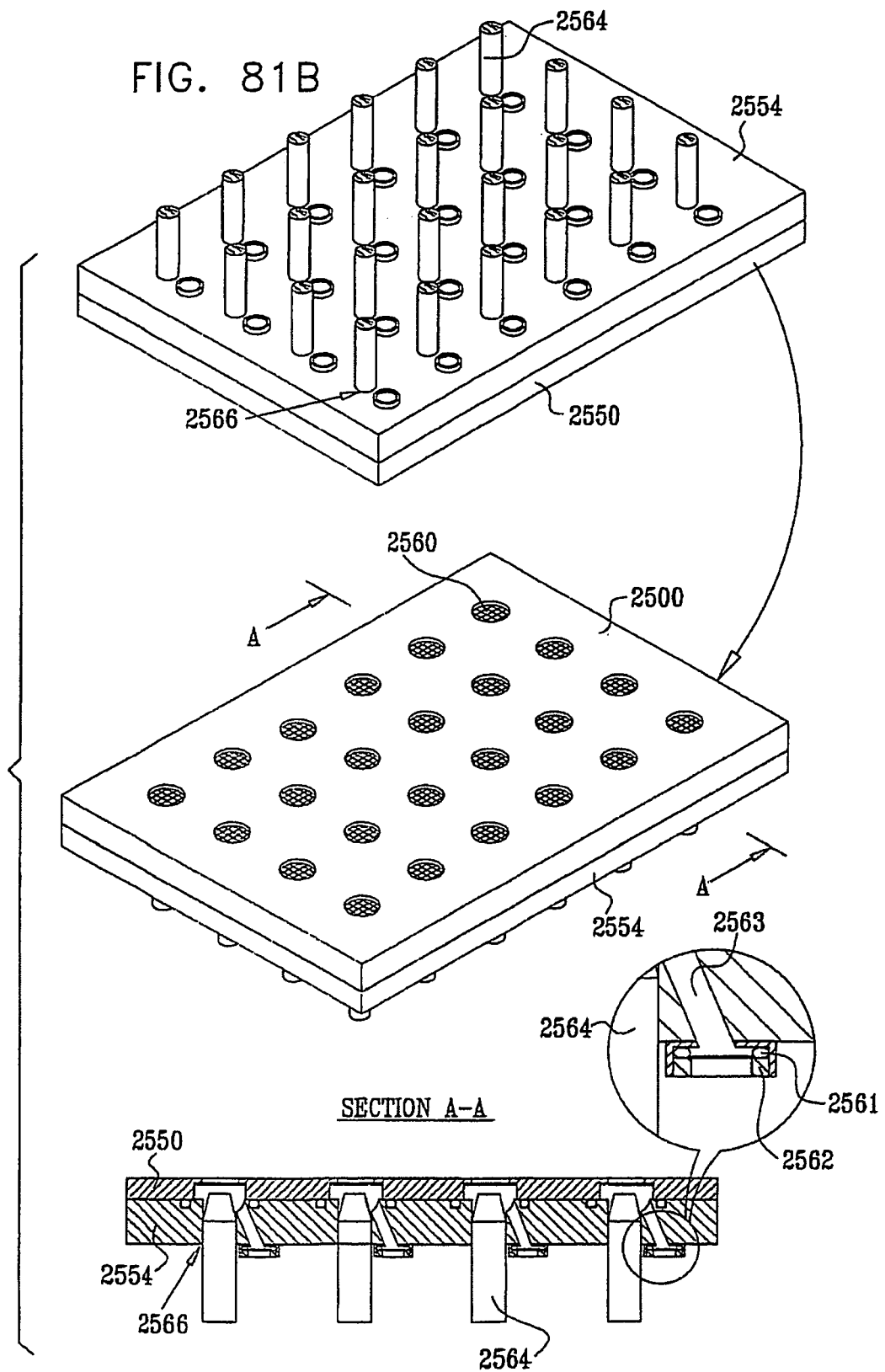

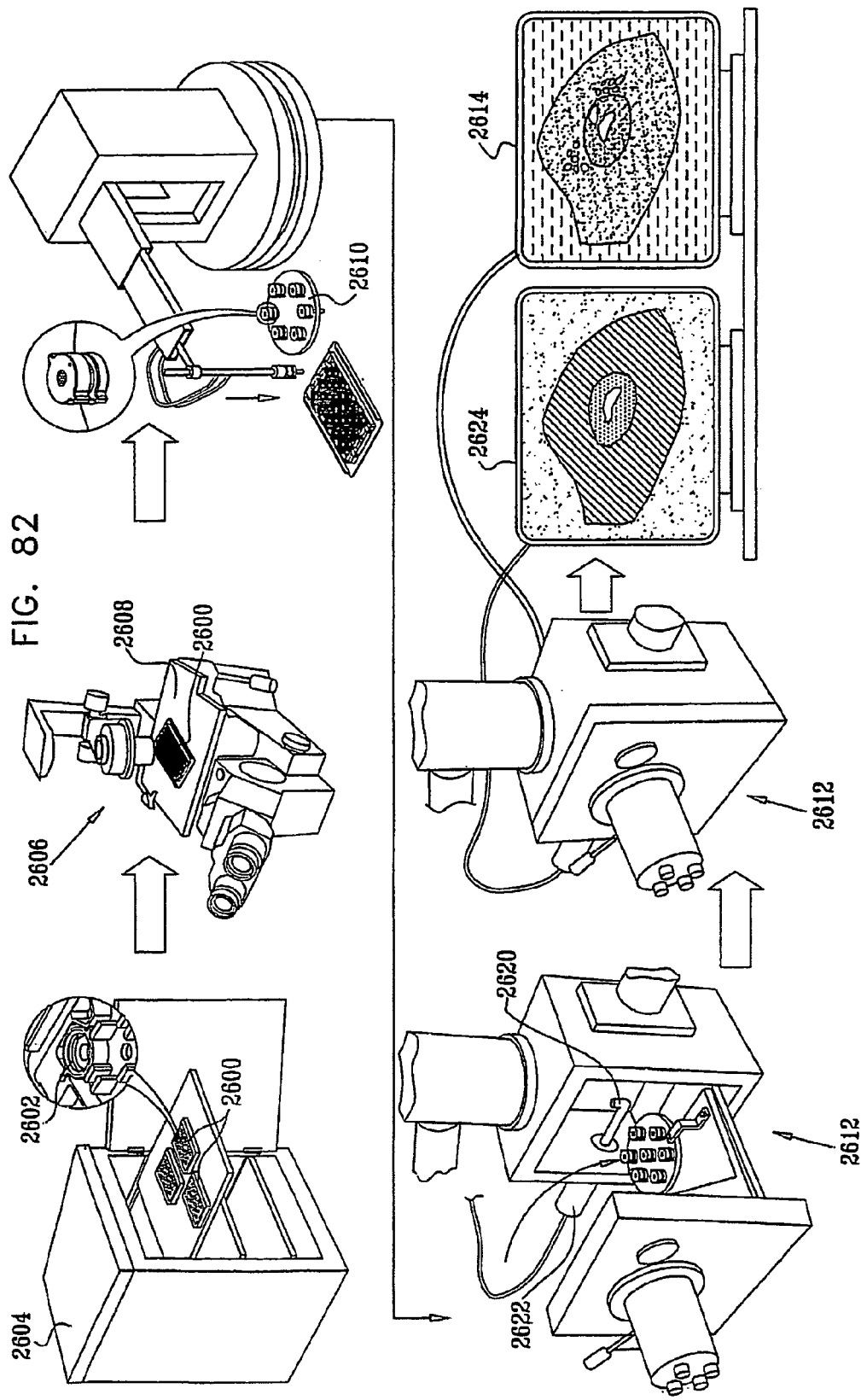

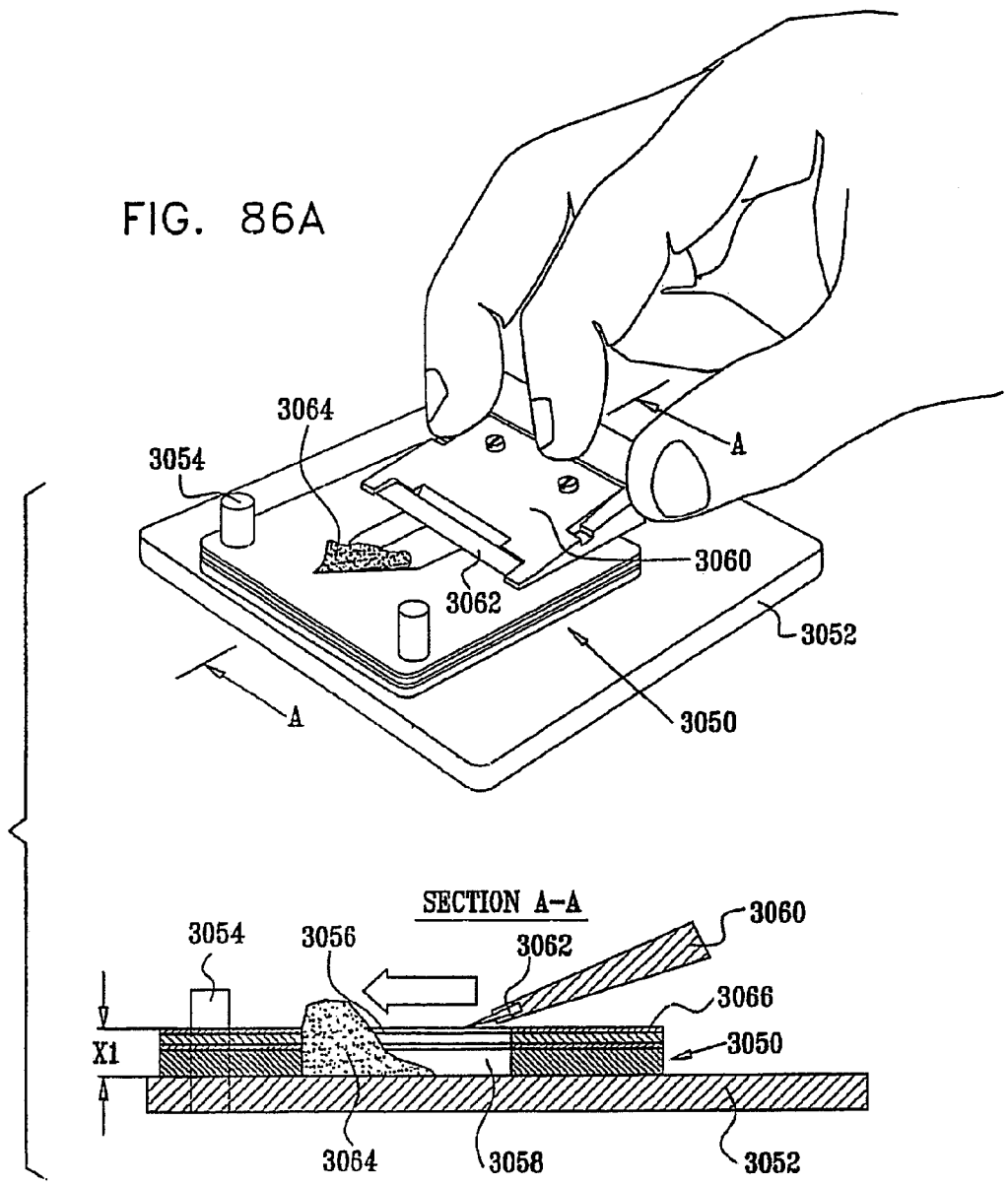

3280  3282

3286

3284

3290

3360

3370

3380

3390  3392

3394

3396  3398

3420

3438

3460

3462

Fig. 112A
Fig. 112B
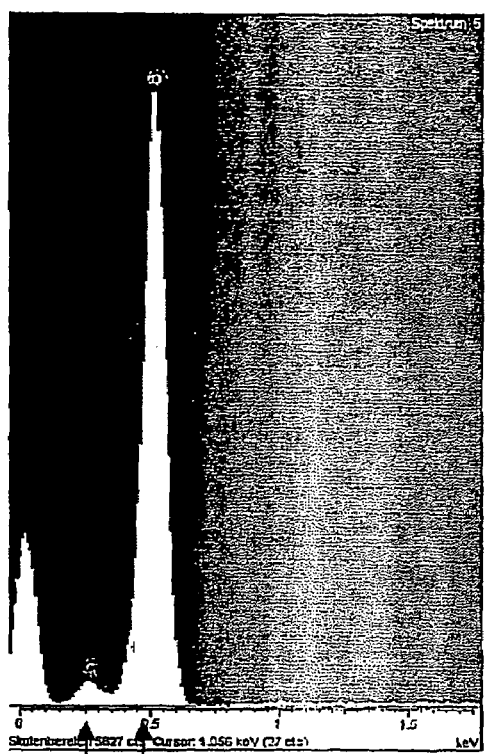
3472
3474
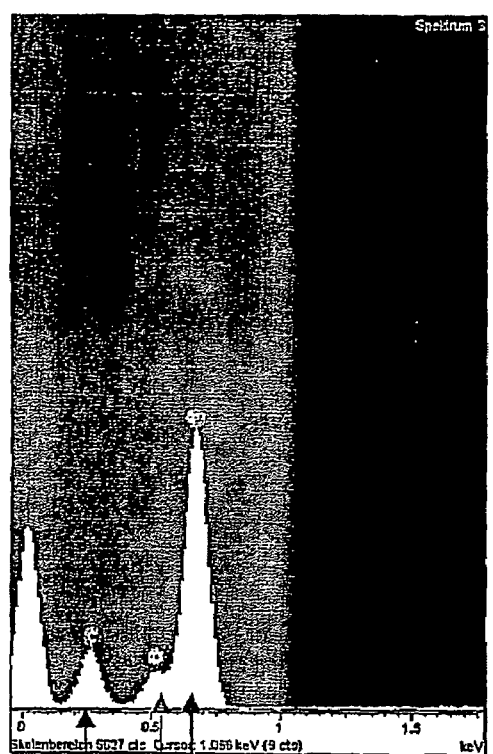
3476 | 3478
3477

Fig. 116
Place cells in specimen containers
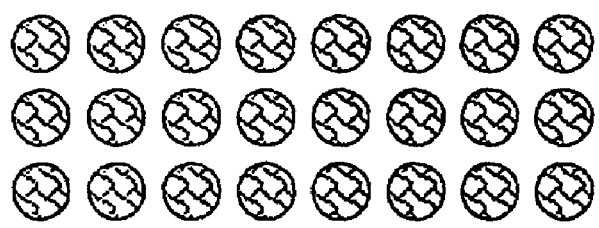
Apply treatments to cells in sample containers
Fix samples
Stain samples
Inspect samples in SEM
Analyze results of inspection

METHODS FOR SEM INSPECTION OF FLUID CONTAINING SAMPLES

CROSS-REFERENCE TO RELATED APPLICATIONS

This application is a National Phase Application of PCT International Application No. PCT/IL2003/000457, International Filing Date Jun. 1, 2003, claiming priority of Israel Patent Application Serial No., 150054, filed on Jun. 5, 2002, entitled "Device for Fluorescent Imaging of Biological Samples Using a Scanning Electron Microscope and Fluorescent or Scintillation Markers", Israel Patent Application Serial No., 150055, filed on Jun. 5, 2002, entitled "Automation Compatible Devices for Scanning Electron Microscopy Imaging of Samples in a Wet Environment", U.S. Provisional Patent Application Ser. No. 60/393,747 filed on Jul. 8, 2002 entitled "Quantitative Pattern Analysis of Molecules on Intact Cells Using Automated SEM", and U.S. Provisional Patent Application Ser. No. 60/448,808 filed on Feb. 20, 2003, entitled "A Specimen Enclosure for a Scanning Electron Microscope".

FIELD OF THE INVENTION

The present invention relates to SEM inspection of fluid containing samples generally and more particularly to methods of visualizing samples in a wet environment.

BACKGROUND OF THE INVENTION

The following documents are believed to represent the current state of the art, and the disclosures of each are incorporated by reference:
1. Tucker, J. A. (2000) The continuing value of electron microscopy in surgical pathology. *Ultrastructural Pathology* 24:383–9
2. Mathews, R. A. and Donald, A. M. (2002) Conditions for imaging emulsions in the environmental scanning electron microscope. *Scanning* 24:75–85.
3. Mittler, M. A., Walters, B. C. and Stopa, E. G. (1996) Observer reliability in histological grading of astrocytoma stereotactic biopsies. *J. Neurosurg* 85:1091–4.
4. Levit-Binnun, N., Lindner A. B., Zik O., Eshhar Z. and Moses, E. (2003) Quantitative detection of protein arrays. *Anal Chem.* 75:1436–41.
5. Becker, R. P. and Sogard, M. (1979) Visualization of subsurface structures in cells and tissues by backscattered electron imaging. *Scan. Electron. Microsc.* 1979 (II): 835–70.
6. Sedar, A. W., Silver, M. J. and Ingerman-Wolenski, C. M. (1983) Backscattered electron imaging to visualize arterial endothelial detachment in the scanning electron microscope. *Scan. Electron. Microsc.* 1983 (II): 969–74.
7. Burns, W. A., Zimmerman, H. J., Hammond, J., Howatson, A. Katz, A and White, J. (1975) The clinician's view of diagnostic electron microscopy. *Hum. Pathol.* 6:467–78.
8. Gyorkey, F., Min, K. W., Krisko, I. And Gyorkey, P. (1975) The usefulness of electron microscopy in the diagnosis of human tumors. *Hum. Pathol.* 6:421–41.
9. Hayat, M. A. (2000) Principles and Techniques of Electron Microscopy-Biological Applications (Fourth edition; Cambridge University Press)
10. Hermann, R., Walther, P. and Müller, M. (1996) Immunogold-labeling in SEM. *Histochem. Cell. Biol.* 106: 31–39.
11. Spargo, B. H. (1975) Practical use of electron microscopy for the diagnosis of glomerular disease. *Hum. Pathol.* 6:405–20.
12. Gu, X. and Herrera, G. A. (2002) The value of electron microscopy in the diagnosis of IgA nephropathy. *Ultrastruct Pathol.* 26:203–10
13. Fisher, C, Ramsay, A D, Griffiths, M and McDougall, J. (1985) An assessment of the value of electron microscopy in tumor diagnosis. *J. Clin Pathol.* 38:403–8
14. Brocker, W, Pfefferkorn G. (1975) Applications of the cathodoluminescence method in biology and medicine. *Scan. Electron. Microsc.* 1979;(II): 125–32
15. Carlen, B. and Englund, E. (2001) Diagnostic value of electron microscopy in a case of juvenile neuronal ceroid lipofuscinosis. *Ultrastruct. Pathol.* 25:285–8
16. Hollinshead M, Sanderson J. & Vaux D. J. (1997). Anti-biotin antibodies offer superior organelle-specific labeling of mitochondria over avidin or streptavidin. *J. Histochem. Cytochem.* 45:1053–7
17. Kristiansen, E. and Madsen, C. (1995) Induction of protein droplet (alpha-2 microglobulin) nephropathy in male rats after short-term dosage with 1,8-cineole and 1-limonene. *Toxicol. Letters* 80:147–52.
18. Goldstein, J. I., Newbury, D. E., Echlin, P., and Joy, D. (1992). Scanning Electron Microscopy and X-ray microanalysis: a text for biologists, matrials scientists, and geologists. Plenum Press, 1992.
19. Schlessinger, J. (2002) Ligand-induced, receptor-mediated dimerization and activation of EGF receptor. *Cell* 110:669–72.

U.S. patents documents:
U.S. Pat. Nos. 3,218,459; 3,378,684; 4,037,109; 4,071,766; 4,115,689; 4,448,311; 4,587,666; 4,596,928; 4,618,938; 4,705,949; 4,720,622; 4,720,633; 4,880,976; 4,929,041; 4,992,662; 5,103,102; 5,250,808; 5,323,441; 5,326,971; 5,362,964; 5,406,087; 5,412,211; 5,811,803; 5,898,261; 5,945,672; 6,025,592; 6,072,178; 6,114,695; 6,130,434; 6,365,898 and 6,452,177.

Published PCT application WO02/14830-PCT/IL01/00764.

Microscopic examination of biological cells and tissues is a central tool in clinical diagnosis as well as in diverse areas of research in the life sciences. Light microscopy (LM) is performed with thin (several micron) samples, which may include cells, acellular material, or thin layers or sections of tissue, which may be stained with contrast agents such as chemicals or antibodies. Transmission electron microscopy (TEM) usually requires specially prepared ultrathin sections (0.1 micron or less), and reveals a wealth of subcellular information. Each of the aforementioned techniques has limitations: the resolution of light microscopy is limited by diffraction to approximately 0.25 microns and the use of TEM is encumbered by extensive processing of the sample, which may alter its structure significantly. Preparation of samples for standard TEM also requires specific skills and takes at least a few days to achieve. The very thin slices present a very limited, and often arbitrary, portion of the sample, necessitating the imaging of multiple serial sections.

High resolution images can also be achieved by scanning election microscopy (SEM), in which a focused electron beam scans the sample sequentially, and ensuing signals are used to generate an image. Most often, secondary electrons are detected, yielding information on the surface topography of the sample. Detection of backscattered electrons yields information on material distribution of a region of the sample lying a short distance below the surface, typically up to a few microns. SEM is a reflective mode of imaging, in the sense that electrons do not need to traverse the sample to yield an image. Therefore, samples can be of any thickness, and do not need to be sectioned. However, samples must be placed in a vacuum environment to allow unimpeded motion of the scanning electron beam; therefore, the sample has to be extensively dehydrated and dried. Furthermore, when dried, biological and other organic samples become electrically insulating, leading to artifacts due to charging of the samples by the electron beam. Consequently, samples are usually coated with a conductive layer of carbon or metal.

One approach to observing biological or other wet samples without extensive drying has been the development of environmental SEM and similar techniques. These methods are based on differential pumping and multiple apertures, allowing a localized pressure close to the vapor pressure of water in the close vicinity of the sample, while maintaining a high vacuum through most of the path of the scanning electron beam. In these methods the sample is exposed to a partial vacuum, and maintenance of the hydrated state requires both a low temperature and complicated, manual maintenance of the right pressure. Indeed, the paucity of published reports of biological research using this technique attests to the difficulty in obtaining consistent results of a high standard High resolution imaging has wide-spread applications in biology, including imaging of cells, tissues, microbes, and viruses, as well as a cellular samples such as biological, environmental or industrial fluids, emulsions and suspensions.

A recent review discusses the use of electron microscopy in clinical diagnosis (Tucker J. A., 2000). It is found that in a small but significant proportion of cases (3–8%) proper diagnosis can only be made based on electron microscopy, this is particularly pronounced in oncology and in selected areas such as kidney diseases (Tucker 2000). These numbers are probably an underestimate, since the use of electron microscopy is not primarily limited by lack of utility, but by considerations of cost, the time needed to produce results, and the low throughput. Thus, there is a significant need for an imaging system for biological tissues and cells that achieves electron microscopic resolution with sample preparation procedures comparable with those of light microscopy.

SUMMARY OF THE INVENTION

Co-pending patent application PCT/IL01/01108, by one of the present inventors, entitled "device and method for the examination of samples in a non-vacuum environment using a scanning electron microscope", discloses a non-vacuum Scanning Electron Microscope (SEM) device that enables the imaging of wet samples in a wet environment, at near-atmospheric pressure and a wide range of temperatures. This obviates the need for extensive sample preparation procedures, thus combining some advantages of electron microscopy, such as high resolution and high contrast or spatial signal to noise ratio, with advantages of light microscopy, such as ease and speed of sample preparation. This is accomplished by the use of a sample container covered by a thin partition membrane that is permeable to electrons but is fluid impermeable and sufficiently strong to withstand the pressure difference between the interior of the container, which is typically one atmosphere, and the vacuum in the imaging region of an SEM. This type of membrane is referred to hereinbelow as a partition membrane or as an electron-permeable, fluid impermeable, membrane.

The aforementioned features of non-vacuum SEM are applied to the observation of fluid-containing samples, especially biological samples, in the following manner:

1. Separation of a sample from the vacuum allows direct visualization of wet samples. This immediately obviates the need for all dehydration procedures, including water replacement and critical-point drying. A wet state most closely resembles the native state of the sample, preserving features that are distorted or destroyed during dehydration. This advantage is particularly important in the observation of tissues, where the true architecture involves both cells and extracellular matrix. In addition, the presence of fluid in and around the sample allows efficient dissipation of electrical charge and of excess heat. This eliminates artifacts due to sample charging, as well as thermal damage.

2. Electron microscopy of biological tissues is most frequently done in two imaging modes. Transmission electron microscopy (TEM) utilizes electrons transmitted through the sample; the entire thickness of the sample contributes to the image. Transmission techniques impose a severe constraint on the thickness of the samples: typically, 50 nm, which can be increased to 3 µm in ultrahigh voltage microscopes. Scanning electron microscopy uses a reflective mode, most frequently detecting secondary electrons that image only the surface topography of the sample. The non-vacuum SEM technique uses backscattered electron detection in a scanning electron microscope. The electron beam penetrates into the sample, and the backscattered electrons reveal sample features beyond the sample surface to a depth of up to a few microns. Thus, although an electron scanning/reflecting mode of imaging is employed, the image is not limited to the surface, and internal structure of the sample is revealed. Furthermore, because detection is done in a reflective mode, any material lying beyond the interaction volume has no effect on imaging. Therefore, the samples can be of a thickness far exceeding the imaged region. Typically, a tissue fragment several millimeters thick can be viewed; only the material layer of a few micrometers or less that is closest to the surface contributes to the scanned image, without interference from the bulk of the sample. The thickness of the imaged region can be modulated by varying the acceleration voltage of the electron beam. Non-vacuum SEM thus yields "virtual sections" without the need for actual sectioning of the sample. This eliminates the need for embedding or freezing the sample, which is otherwise required to enable sectioning of the sample. Finally, the dependence of electron backscattering efficiency on the material composition of the sample (through the atomic number Z) creates contrast even in the absence of heavy metal staining that is characteristic of TEM imaging. Subcellular organelles can be distinguished based on differences in local concentrations of lipids, phosphates, and salts within biological samples; and a wide variety of stains and labels can be used to enhance contrast.

An additional capability of the non-vacuum SEM technology is concurrent detection of light emitted from the sample while scanning with the electron beam. The scanning electron beam excites molecules in the sample, which may then emit light at characteristic wavelengths (cathodoluminescence). The light intensity is then used to derive an image of the distribution of scintillating molecules, either endogenous to the biological sample or labels that can be introduced extraneously. This image is obtained simultaneously with the imaging by backscattered electrons (BSE), at a resolution limited by electron-matter interactions and not by light diffraction. Similarly, X-rays emitted from the scanned sample can be detected using conventional detectors and methods, yielding additional information on the material composition and distribution of the fully hydrated sample. Specifically, X-ray analysis can be used to localize and quantitate regions containing metals such as calcium, iron, sodium, potassium, copper or zinc, or other elements such as iodine, sulfur, or phosphor.

It is another objective of the present invention to provide means for automated electron microscopy of wet samples, and specifically of biological samples. Such automated microscopy has been widely applied in the semiconductor industry. The main barrier to the application of automated electron microscopy to wet samples is the need to employ sample preparation procedures such as drying, embedding, sectioning or coating, which are highly complex and not amenable to automation. The present invention provides means for direct imaging of wet samples in a scanning electron microscope, thus obviating the need for the aforementioned preparative procedures. The present invention thus provides means for automated electron microscopy of wet samples.

There is thus provided in accordance with a preferred embodiment of the present invention a method of visualizing a sample in a wet environment including introducing a sample into a specimen enclosure in a wet environment and scanning the sample in the specimen enclosure in a scanning electron microscope, thereby visualizing the sample.

There is also provided in accordance with another preferred embodiment of the present invention a method of visualization of a sample in a wet environment including introducing a sample into a specimen enclosure in a wet environment and scanning the sample in the specimen enclosure in a scanning electron microscope at multiple different electron energy levels.

There is further provided in accordance with yet another preferred embodiment of the present invention a method of visualizing at least one component in a multi-component sample in a wet environment including introducing a multi-component sample into a specimen enclosure in a wet environment and scanning the multi-component sample in the specimen enclosure in a scanning electron microscope, thereby visualizing at least one component of the multi-component sample.

There is even further provided in accordance with still another preferred embodiment of the present invention a method for visualization of a sample in a wet environment including obtaining a wet sample, scanning the wet sample in a scanning electron microscope at a resolution which is not limited by the diffraction limit of light and detecting light emitted from the wet sample.

In accordance with another preferred embodiment of the present invention the method also includes enhancing contrast between plural elements in the sample prior to scanning of the sample. Preferably, the enhancing includes specific labeling of at least some of the plural elements in the sample. Alternatively, the enhancing includes specific labeling of molecules in the sample. In accordance with another preferred embodiment the enhancing includes specific labeling of receptors in the sample. Alternatively, the enhancing includes specific labeling of organelles in the sample. Additionally, the enhancing includes specific labeling of binding sites in the sample. Preferably, the enhancing includes specific labeling of structural elements in the sample. Alternatively, the enhancing includes specific labeling of functional elements in the sample.

In accordance with yet another preferred embodiment of the present invention the scanning visualizes elements in the sample having contrast due to differences in atomic numbers of constituent atoms thereof.

In accordance with still another preferred embodiment of the present invention, the enhancing introduces differences in atomic numbers of constituent atoms of elements of the samples.

Preferably, the scanning visualizes lipid containing entities in the sample. Alternatively, the scanning visualizes nucleic acid containing entities in the sample. Additionally, the scanning visualizes protein containing entities in the sample. In accordance with another preferred embodiment of the present invention the scanning visualizes carbohydrate containing entities in the sample. Alternatively, the scanning visualizes metal containing entities in the sample. Additionally, the scanning visualizes iodine containing entities in the sample.

In accordance with another preferred embodiment of the present invention the sample is a biological sample. Additionally, the biological sample includes cells in a liquid. Preferably, the sample includes lipids within cells and the scanning visualizes the lipids.

In accordance with yet another preferred embodiment of the present invention the scanning visualizes cells in the sample. Alternatively, the scanning visualizes tissue in tissue slices. Preferably, the scanning visualizes tissue. In accordance with another preferred embodiment of the present invention the scanning visualizes cells in the sample which are adherent to an electron beam permeable membrane.

In accordance with another preferred embodiment of the present invention the specimen enclosure includes an electron beam permeable membrane and the method also includes growing cells on the electron beam permeable membrane prior to the scanning. Alternatively or additionally, the specimen enclosure includes an electron beam permeable membrane and the method also includes manipulating cells on the electron beam permeable membrane prior to the scanning. Additionally or alternatively, the scanning visualizes an outcome of introduction of an extrinsic molecule to the sample In accordance with another preferred embodiment of the present invention the method also includes detecting electromagnetic radiation emitted from the sample as a result of the scanning. Additionally, the method also includes analyzing the electromagnetic radiation. Preferably, the analyzing the electromagnetic radiation includes spectral analysis.

In accordance with another preferred embodiment of the present invention the method also includes detecting an electron beam backscattered from the sample as well as electromagnetic radiation emitted from the sample as a result of the scanning. Preferably, the electromagnetic radiation includes X-ray radiation. Alternatively or additionally, the electromagnetic radiation includes visible radiation. Additionally or alternatively, the electromagnetic radiation includes radiation having a wavelength within the range of 200–1000 nm. Alternatively or additionally, the electromagnetic radiation includes radiation providing information relating to molecular structure of the sample. Additionally or alternatively, the electromagnetic radiation includes radiation providing information relating to material distribution within the sample.

In accordance with another preferred embodiment of the present invention the scanning includes scanning the sample in the specimen enclosure in a scanning electron microscope at multiple different electron energy levels. Additionally, the method also includes reconstructing a three-dimensional image of the sample by using multiple visualizations of the sample at the multiple different electron energy levels.

In accordance with another preferred embodiment of the present invention the sample is a multi-component sample and the scanning includes scanning the multi-component sample in the specimen enclosure in a scanning electron microscope, thereby visual zing at least one component of the multi-component sample. Additionally or alternatively, the method also includes obtaining the sample to be inspected, the sample being in a wet environment.

There is still further provided in accordance with another preferred embodiment of the present invention a method for manufacture of a biocompatible implant including forming a biocompatible implant of a biocompatible material, inspecting at least a portion of the biocompatible implant in a scanning electron microscope in a wet environment, analyzing results of the inspecting and classifying the inspected biocompatible implant in accordance with results of the analyzing.

In accordance with another preferred embodiment of the present invention, the inspecting includes introducing a sample including at least the portion into a specimen enclosure in a wet environment and scanning the sample in the specimen enclosure in the scanning electron microscope, thereby visualizing the sample.

There is also provided in accordance with yet another preferred embodiment of the present invention a method for detection, identification or characterization of microbiological entities including obtaining a wet sample containing at least one microbiological entity, scanning the wet sample in a scanning electron microscope while in an environment characterized by a pressure exceeding the vapor pressure of water and analyzing results of the scanning.

Preferably, the scanning includes introducing the wet sample including the at least one microbiological entity into a specimen enclosure in a wet environment and scanning the wet sample in the specimen enclosure in the scanning electron microscope, thereby visualizing the wet sample.

In accordance with a preferred embodiment of the present invention the wet sample includes urine. Alternatively, the wet sample includes feces. Additionally, the wet sample includes blood. Additionally or alternatively, the wet sample includes sputum. In accordance with another preferred embodiment of the present invention, the wet sample includes lavage of the respiratory system. Additionally, the wet sample includes a tissue biopsy. Alternatively, the wet sample includes an environmental sample. Additionally or alternatively, the wet sample includes cerebro-spinal fluid. In accordance with yet another preferred embodiment of the present invention, the wet sample includes a soil sample. Alternatively, the wet sample includes food. Additionally, the wet sample includes industrial products. Alternatively or additionally, the wet sample includes a medical, industrial or household device.

In accordance with another preferred embodiment of the present invention the method also includes specific staining of the sample. Additionally, the method also includes treating the microbiological entity with chemicals. Alternatively or additionally, he method also includes applying radiation to the microbiological entity. Additionally or alternatively, the analyzing includes analyzing the morphology of the microbiological entity.

There is further provided in accordance with yet another preferred embodiment of the present invention a method for characterization of biofilms including obtaining a wet sample of a biofilm, scanning the wet sample of a biofilm in a scanning electron microscope and analyzing results of the scanning.

Preferably, the scanning includes introducing the wet sample including the biofilm into a specimen enclosure in a wet environment and scanning the wet sample in the specimen enclosure in the scanning electron microscope, thereby visualizing the wet sample.

There is even further provided in accordance with still another preferred embodiment of the present invention a method of visualizing a sample including obtaining a sample and scanning the sample in a wet environment in a scanning electron microscope while in an environment characterized by a pressure exceeding the vapor pressure of water, without an intermediate solidifying, coating or slicing step thereby visualizing the sample.

There is yet further provided in accordance with another preferred embodiment of the present invention a method of visualizing a sample including obtaining a sample and scanning the sample in a wet environment in a scanning electron microscope while in an environment characterized by a pressure exceeding the vapor pressure of water, without morphologically impacting preparation prior to scanning.

There is still further provided in accordance with yet another preferred embodiment of the present invention a method of visualizing a sample including obtaining a sample and scanning the sample in a wet environment in a scanning electron microscope while in an environment characterized by a pressure exceeding the vapor pressure of water, following at most fixing and staining before scanning.

There is also provided in accordance with still another preferred embodiment of the present invention a method of visualizing a sample including obtaining a sample and scanning the sample in a wet environment in a scanning electron microscope while in an environment characterized by a pressure exceeding the vapor pressure of water, following at most treatment with at least one aqueous solution prior to scanning.

There is further provided in accordance with yet another preferred embodiment of the present invention a method of visualizing a sample including obtaining a sample and scanning the sample in a wet environment in a scanning electron microscope while in an environment characterized by a pressure exceeding the vapor pressure of water, without having been treated with a non-aqueous solution prior to scanning.

There is even further provided in accordance with another preferred embodiment of the present invention a method of visualizing a sample including obtaining a sample of thickness exceeding 20 microns and scanning the sample in a scanning electron microscope while in an environment characterized by a pressure exceeding the vapor pressure of water.

There is also provided in accordance with yet another preferred embodiment of the present invention a method of inspecting adipose tissue including obtaining a sample of adipose tissue and scanning the sample of adipose tissue in a scanning electron microscope while in an environment characterized by a pressure exceeding the vapor pressure of water.

Preferably, the sample is not stained prior to the scanning.

There is further provided in accordance with still another preferred embodiment of the present invention a method of inspecting adipose tissue including obtaining a sample of adipose tissue and scanning the sample of adipose tissue in a scanning electron microscope without the sample having been stained prior to the scanning.

There is even further provided in accordance with another preferred embodiment of the present invention a method for visualization of a sample including scanning the sample in a scanning electron microscope while in an environment characterized by a pressure exceeding the vapor pressure of water, the scanning taking place over an area of the sample which exceeds 25 square millimeters without displacement of the sample relative to a stage of the scanning electron microscope.

There is also provided in accordance with yet another preferred embodiment of the present invention a method of inspecting an extracellular matrix including obtaining a sample of an extracellular matrix and scanning the sample of the extracellular matrix in a scanning electron microscope while in an environment characterized by a pressure exceeding the vapor pressure of water.

There is further provided in accordance with still another preferred embodiment of the present invention a method of inspecting epithelial tissue including obtaining a sample of epithelial tissue and scanning the sample of the epithelial tissue in a scanning electron microscope while in an environment characterized by a pressure exceeding the vapor pressure of water.

There is even further provided in accordance with another preferred embodiment of the present invention a method of inspecting kidney tissue including obtaining a sample of kidney tissue and scanning the sample of the kidney tissue in a scanning electron microscope while in an environment characterized by a pressure exceeding the vapor pressure of water.

There is also provided in accordance with yet another preferred embodiment of the present invention a method of inspecting a tissue biopsy including obtaining a sample of a tissue biopsy and scanning the sample of the tissue biopsy in a scanning electron microscope while in an environment characterized by a pressure exceeding the vapor pressure of water.

There is further provided in accordance with still another preferred embodiment of the present invention a method of inspecting biological material including immunolabeling biological material and scanning the immunolabeled biological material in a scanning electron microscope while in an environment characterized by a pressure exceeding the vapor pressure of water.

There is also provided in accordance with still another preferred embodiment of the present invention a method of inspecting tissue including immunolabeling tissue and scanning the immunolabeled tissue in a scanning electron microscope while in an environment characterized by a pressure exceeding the vapor pressure of water.

There is further provided in accordance with yet another preferred embodiment of the present invention a method of inspecting a sample including scanning the sample in a scanning electron microscope while in an environment characterized by a pressure exceeding the vapor pressure of water and inspecting the sample using light microscopy.

There is also provided in accordance with another preferred embodiment of the present invention a method of analyzing toxic effects of exposure to a chemical or combination of chemicals including subjecting an experimental animal to the exposure to the chemical or combination of chemicals, obtaining a sample from the experimental animal and scanning the sample from the experimental animal in a scanning electron microscope while in an environment characterized by a pressure exceeding the vapor pressure of water.

There is further provided in accordance with yet another preferred embodiment of the present invention a method of analyzing toxic effects following exposure to environmental conditions including identify at least one individual that was exposed to the environmental conditions, obtaining at least one sample from at least one of the at least one individual and scanning the at least one sample in a scanning electron microscope while in an environment characterized by a pressure exceeding the vapor pressure of water.

There is even further provided in accordance with still another preferred embodiment of the present invention a method of characterizing chemical entities including applying a chemical entity to cells in a SEM-compatible sample enclosure and scanning the cells in a scanning electron microscope while in an environment characterized by a pressure exceeding the vapor pressure of water.

Preferably, the method also includes analyzing changes in cell shape. Additionally or alternatively, the method also includes analyzing the cytoskeleton of the cells. Additionally, the method also includes analyzing the distribution of biomolecules in the cells.

In accordance with another preferred embodiment of the present invention the method also includes detecting x-rays from a region of the sample and analyzing the x-rays to detect the presence of at least one of iodine, metals and phosphorous in the sample. Preferably, the method also includes determining the concentration of the at least one of iodine, metals, and phosphorus.

In accordance with yet another preferred embodiment of the present invention the sample is impinged upon by electrons passing through an electron-permeable, fluid-impermeable membrane. Additionally, the method also includes urging the sample against the electron-permeable, fluid-impermeable membrane.

BRIEF DESCRIPTION OF THE DRAWINGS

The present invention will be understood and appreciated more fully from the following detailed description, taken in conjunction with the drawings in which:

FIGS. 1A & 1B are oppositely facing simplified exploded view pictorial illustrations of a disassembled SEM compatible sample container constructed and operative in accordance with a preferred embodiment of the present invention;

FIGS. 8A, 8B and 8C are simplified sectional illustrations of liquid containing samples, sealing and insertion into a SEM respectively using the SEM compatible sample container of FIGS. 1A–6C;

FIG. 9 is a simplified pictorial and sectional illustration of a SEM inspection of a sample using the SEM compatible sample container of FIGS. 1A–6C;

FIGS. 11A & 11B are oppositely facing simplified exploded view pictorial illustrations of a disassembled SEM compatible sample container constructed and operative in accordance with another preferred embodiment of the present invention;

FIGS. 16A, 16B & 16C are three sectional illustrations showing the operative orientation of the SEM compatible sample container of FIGS. 11A–15B at three stages of operation;

FIGS. 21A and 21B are simplified exploded view illustrations of a pre-microscopy multi-sample holder in use with SEM compatible sample containers of the type shown in FIGS. 1A–20;

FIGS. 24A, 24B and 24C are simplified illustrations of a microscopy multi-sample holder in use with a SEM compatible sample dish of the type shown in FIGS. 1A–10;

FIGS. 25A, 25B and 25C are simplified illustrations of a microscopy multi-sample holder in use with a SEM compatible sample dish of the type shown in FIGS. 11A–20;

FIGS. 27A and 27B are simplified illustrations of a microscopy multi-sample holder defining a plurality of SEM compatible sample containers in accordance with a preferred embodiment of the present invention;

FIG. 29 is a simplified illustration of a SEM based sample inspection system constructed and operative in accordance with another preferred embodiment of the present invention;

FIG. 30 is a simplified illustration of a SEM based sample inspection system constructed and operative in accordance with yet another preferred embodiment of the present invention;

FIGS. 31A & 31B are oppositely facing simplified exploded view pictorial illustrations of a disassembled SEM compatible sample container constructed and operative in accordance with another preferred embodiment of the present invention;

FIG. 40 is a greatly enlarged simplified schematic illustration of the SEM inspection of a sample in the context of FIG. 39;

FIGS. 41A & 41B are oppositely facing simplified exploded view pictorial illustrations of a disassembled SEM compatible sample container constructed and operative in accordance with another preferred embodiment of the present invention;

FIGS. 45A & 45B are oppositely facing simplified partially pictorial, partially sectional illustrations taken along lines XLVA—XLVA and XLVB—XLVB, respectively, in FIGS. 43A & 43B;

FIGS. 48A, 49B, 48C and 48D are simplified sectional illustrations showing the operative orientation of a SEM compatible sample container at various stages of operation and insertion into a SEM using the SEM compatible sample container constructed and operative in accordance with another preferred embodiment of the present invention;

FIG. 49 is a simplified pictorial and sectional illustration of a SEM inspection of a sample using the SEM compatible sample container of FIGS. 41A–46C;

FIG. 50 is a greatly enlarged simplified schematic illustration of the SEM inspection of a sample in the context of FIG. 49;

FIGS. 51A, 51B and 51C are simplified illustrations of a microscopy multi-sample holder in use with a SEM compatible sample dish of the type shown in FIGS. 31A–40;

FIGS. 52A, 52B and 52C are simplified illustrations of a microscopy multi-sample holder in use with a SEM compatible sample dish of the type shown in FIGS. 41A–50;

FIGS. 53A and 53B are simplified illustrations of a microscopy multi-sample holder defining a plurality of SEM compatible sample containers in accordance with a preferred embodiment of the present invention;

FIGS. 54A and 54B are simplified illustrations of a microscopy multi-sample holder defining a plurality of SEM compatible sample containers in accordance with a preferred embodiment of the present invention;

FIG. 55 is a simplified illustration of a SEM based sample inspection system constructed and operative in accordance with a preferred embodiment of the present invention;

FIGS. 58A & 58B are oppositely facing simplified exploded view pictorial illustrations of a disassembled SEM compatible sample container constructed and operative in accordance with yet another preferred embodiment of the present invention;

FIGS. 60A & 60B are oppositely facing simplified exploded view pictorial illustrations of the SEM compatible sample container of FIGS. 58A–59B in a partially assembled state;

FIGS. 62A & 62B are oppositely facing simplified partially pictorial, partially sectional illustrations taken along lines LXIIA—LXIIA and LXIIB—LXIIB, respectively, in FIGS. 60A & 60B;

FIGS. 64A, 64B, 64C, 64D and 64E are simplified sectional illustrations of cell growth, liquid removal, liquid addition, sealing and insertion into a SEM respectively using the SEM compatible sample container of FIGS. 58A–63C;

FIGS. 68A & 68B are oppositely facing simplified exploded view pictorial illustrations of a disassembled SEM compatible sample container constructed and operative in accordance with another preferred embodiment of the present invention;

FIGS. 70A & 70B are oppositely facing simplified exploded view pictorial illustrations of the SEM compatible sample container of FIGS. 68A–69B in a partially assembled state;

FIGS. 72A & 72B are oppositely facing simplified partially pictorial, partially sectional illustrations taken along lines LXXIIA—LXXIIA and LXXIIB—LXXIIB, respectively, in FIGS. 70A & 70B;

FIGS. 75A, 75B and 75C are simplified sectional illustrations of liquid containing samples, sealing and insertion into a SEM respectively using the SEM compatible sample container of FIGS. 68A–73C;

FIGS. 80A and 80B are simplified illustrations of a microscopy multi-sample holder defining a plurality of SEM compatible sample containers in accordance with a preferred embodiment of the present invention;

FIGS. 81A and 81B are simplified illustrations of a microscopy multi-sample holder defining a plurality of SEM compatible sample containers in accordance with a preferred embodiment of the present invention;

FIG. 82 is a simplified illustration of a SEM based sample inspection system constructed and operative in accordance with a preferred embodiment of the present invention;

FIGS. 86A and 86B are simplified partially pictorial and partially sectional illustration of a tissue sample slicing assembly constructed and operative in accordance with a preferred embodiment of the present invention;

FIGS. 112A and 112B are micrographs of SEM inspection of samples using X-ray detection in accordance with a preferred embodiment of the present invention;

FIG. 116 is a schematic depiction of a method for bioassaying pharmaceutical entities or suspected or known toxic entities, in accordance with still another preferred embodiment of the present invention.

DETAILED DESCRIPTION OF THE PRESENT INVENTION

Figure 2A:
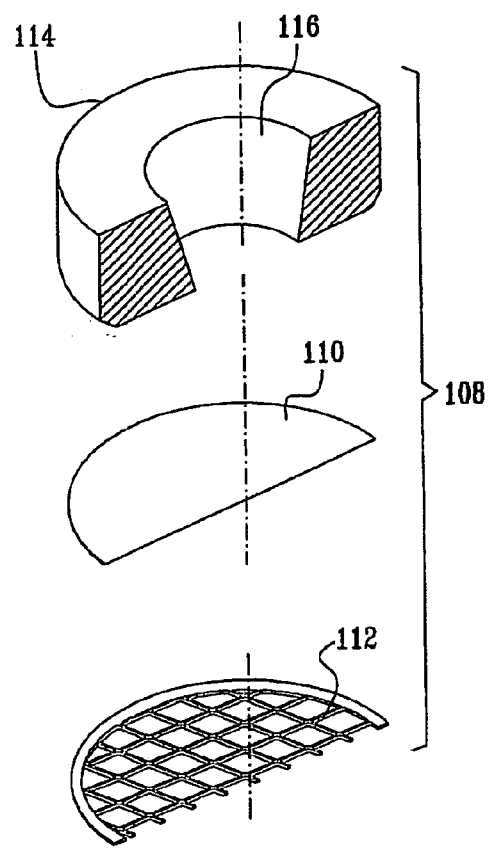
FIGS. 2A & 2B are oppositely facing simplified partially pictorial, partially sectional illustrations of a subassembly of the container of FIGS. 1A & 1B.

The present invention relates to methods for electron microscopic inspections of wet biological and environmental samples at a non-vacuum environment. More specifically, the patent application relates to methods for visualizing samples in a scanning electron microscope (SEM) without the need for dehydration procedures including water replacement and critical-point drying, which can destroy important structural detail and introduce artifacts in the sample to be observed. Absent the methods of the present invention, samples to be examined in an electron microscope must be held in a vacuum or a near vacuum to permit unimpeded access to the electron beam, which can only travel in a vacuum or near vacuum.

The methods of the present invention advantageously employ a novel SEM sample container, described hereinbelow, into which the sample to be scanned is placed. The sample's hydration and atmospheric pressure state is maintained therein, even after placement on the SEM stage when the SEM scanning chamber is evacuated.

Reference is now made to FIGS. 1A–5B, which are oppositely facing simplified exploded view pictorial illustrations of a disassembled scanning electron microscope (SEM) compatible sample container constructed and operative in accordance with a preferred embodiment of the present invention. As seen in FIGS. 1A & 1B, the SEM compatible sample container comprises first and second mutually threaded enclosure elements, respectively designated by reference numerals 100 and 102, arranged for enhanced ease and speed of closure. Enclosure elements 100 and 102 are preferably molded of plastic and coated with a conductive metal coating.

Figure 2B:
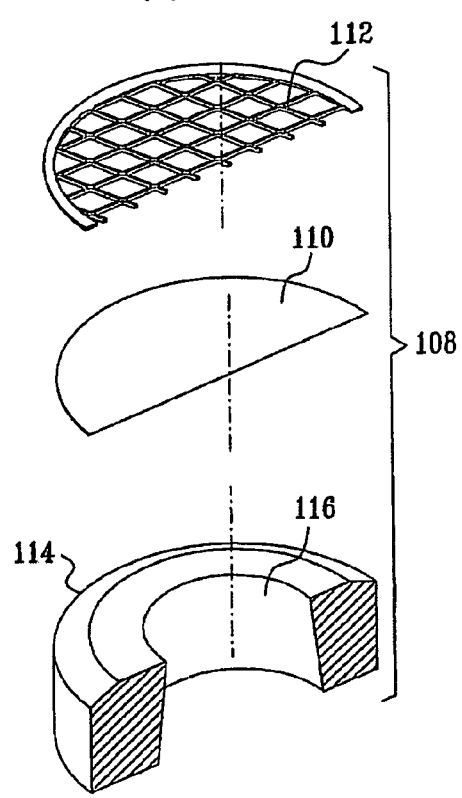
Figure 3A:
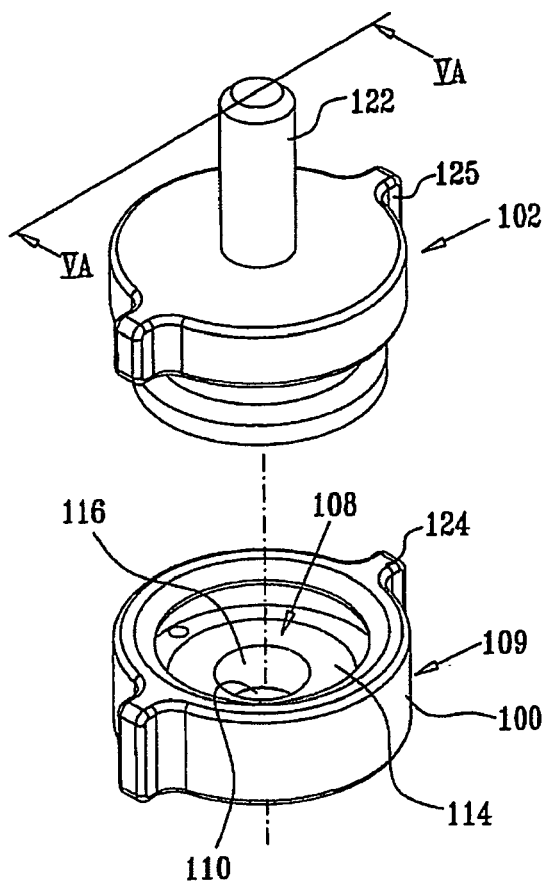
FIGS. 3A & 3B are oppositely facing simplified exploded view pictorial illustrations of the SEM compatible sample container of FIGS. 1A–2B in a partially assembled state.
Figure 3B:
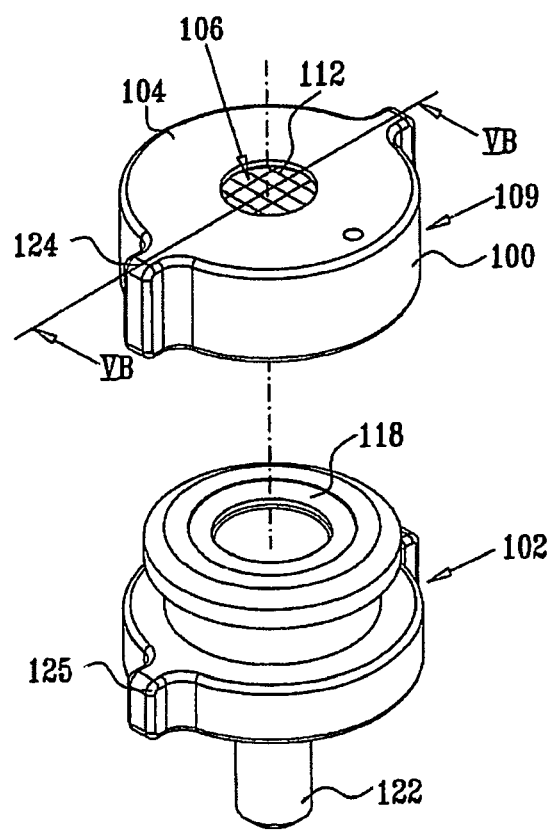

First enclosure element 100 preferably defines a liquid sample enclosure and has a base surface 104 having a generally central aperture 106. An electron beam permeable, fluid impermeable, membrane subassembly 108, shown in detail in FIGS. 2A and 2B, is seated inside enclosure element 100 against and over aperture 106, as shown in FIGS. 3A & 3B and 5A & 5B. A sample dish comprising subassembly 108 suitably positioned in enclosure element 100 is designated by reference numeral 109, as shown in FIGS. 3A–5B.

Turning additionally to FIGS. 2A and 2B, it is seen that an electron beam permeable, fluid impermeable, membrane 110, preferably a polyimide membrane, such as Catalog No. LWN00033, commercially available from Moxtek Inc. of Orem, Utah, U.S.A., is adhered, as by an adhesive, to a mechanically supporting grid 112. Grid 112, which is not shown to scale, is preferably Catalog No. BM 0090-01, commercially available from Buckbee-Mears of Cortland, N.Y., U.S.A., and the adhesive is preferably Catalog No. NOA61, commercially available from Norland Products Inc. of Cranbury, N.J., U.S.A. A liquid sample enclosure defining ring 114 is adhered to electron beam permeable, fluid impermeable, membrane 110, preferably by an adhesive, such as Catalog No. NOA61, commercially available from Norland Products Inc. of Cranbury, N.J., U.S.A. Ring 114 is preferably formed of PMMA (polymethyl methacrylate), such as Catalog No. 692106001000, commercially available from Irpen of Barcelona, Spain, and preferably defines a liquid sample enclosure with a volume of approximately 20 microliters and a height of approximately 2 mm. Preferably ring 114 is configured to define a liquid sample enclosure 116 having inclined walls.

Alternatively, membrane 110 may be formed from polyamide, polyamide-imide, polyethylene, polypyrrole, PARLODION, COLLODION, KAPTON, FORMVAR, VINYLEC, BUTVAR, PIOLOFORM, PARYLENE, silicon dioxide, silicon monoxide or carbon, or any combination thereof or any other suitable material.

An O-ring 118 is preferably disposed between ring 114 and an interior surface 120 of second enclosure element 102. O-ring 118 is operative, when enclosure elements 100 and 102 are in tight threaded engagement, to obviate the need for the threaded engagement of elements 100 and 102 to be a sealed engagement.

Second enclosure element 102 preferably is formed with a generally central stub 122, which is arranged to be seated in a suitable recess (not shown) in a specimen stage of a scanning electron microscope. It is a particular feature of the present invention that the container, shown in FIGS. 1A–10, is sized and operative with conventional stub recesses in conventional scanning electron microscopes and does not require any modification thereof whatsoever. It is appreciated that various configurations and sizes of stubs may be provided so as to fit various scanning electron microscopes.

Figure 4A:
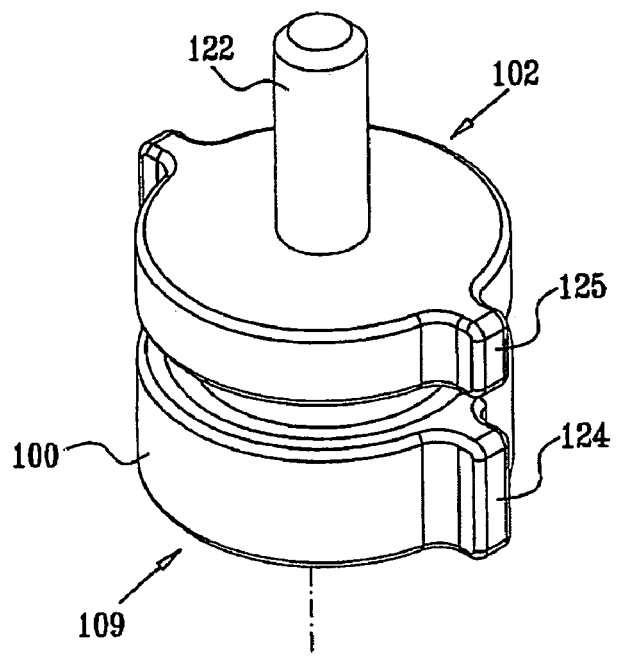
FIGS. 4A & 4B are oppositely facing simplified pictorial illustrations of the SEM compatible sample container of FIGS. 1A–3B in a fully assembled state.
Figure 4B:
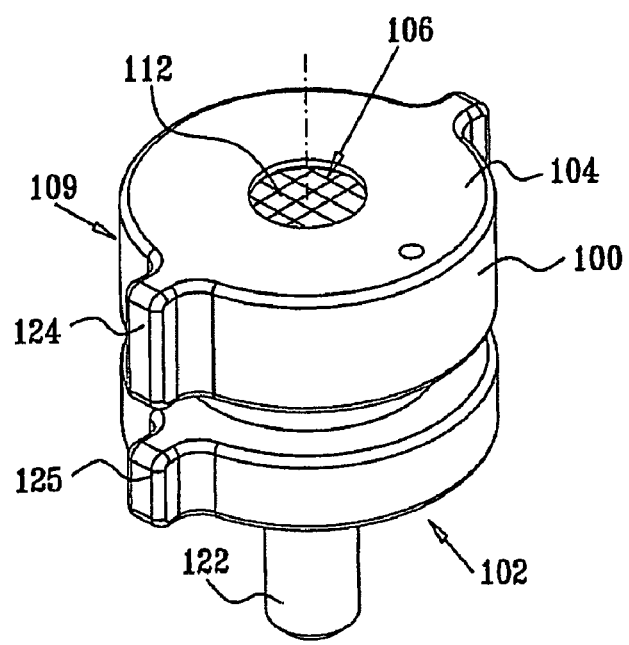
Figure 5A:
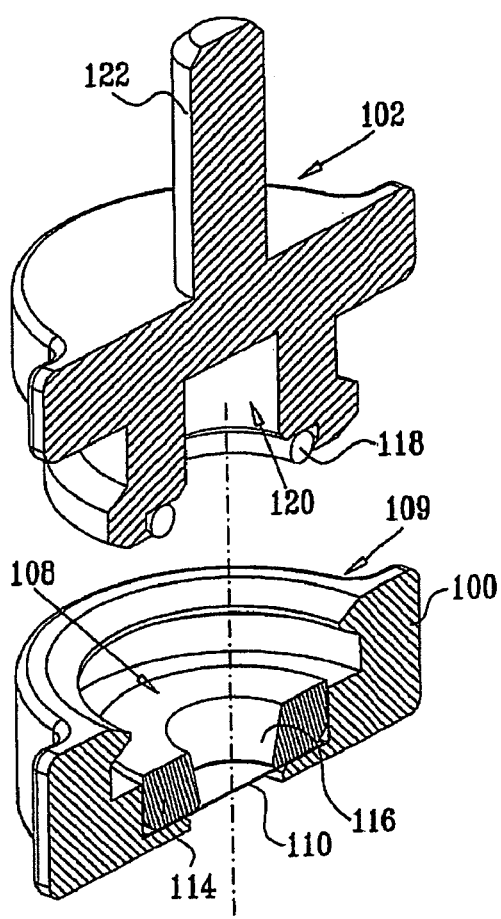
FIGS. 5A & 5B are oppositely facing simplified partially pictorial, partially sectional illustrations taken along lines VA—VA and VB—VB, respectively, in FIGS. 3A & 3B.
Figure 5B:
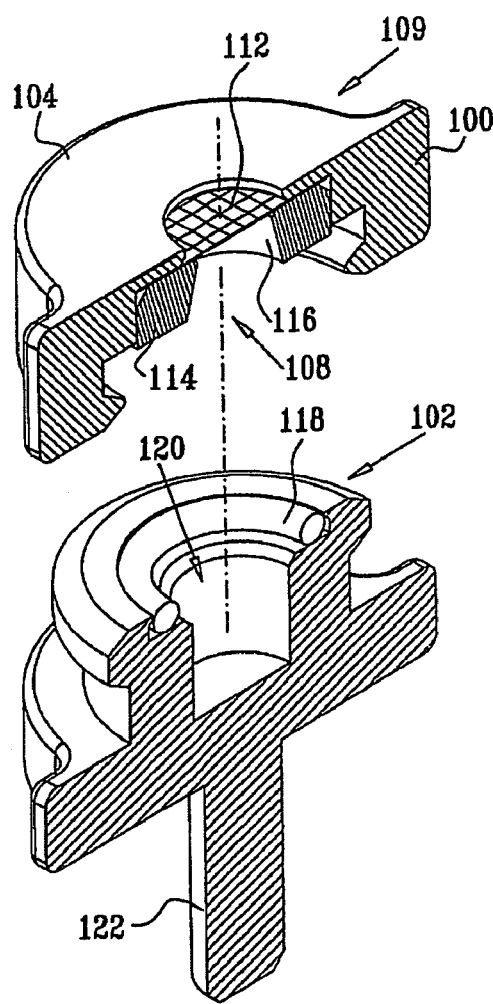

Enclosure elements 100 and 102 are preferably also provided with respective radially extending positioning and retaining protrusions 124 and 125, to enable the container to be readily seated in a suitable multi-container holder and also to assist users in threadably opening and closing the enclosure elements 100 and 102. Preferably, the mutual azimuthal positioning of the protrusions 124 and 125 on respective enclosure elements 100 and 102 is such that mutual azimuthal alignment therebetween indicates a desired degree of threaded closure therebetween, as shown in FIGS. 4A and 4B.

It is appreciated that in another embodiment of the present invention the sample dish may include enclosures 100 and 102.

Figure 6A:
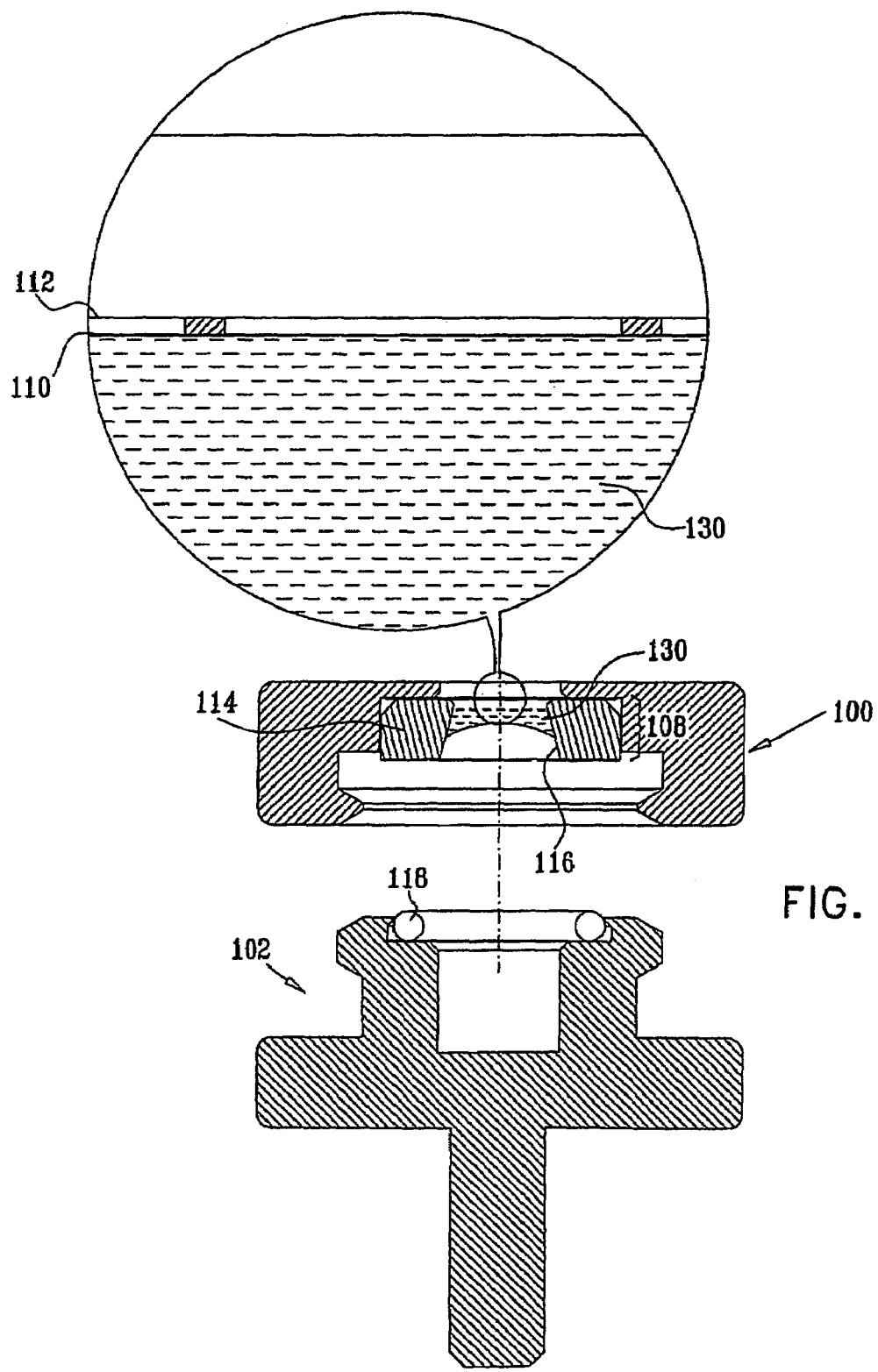
FIGS. 6A, 6B & 6C are three sectional illustrations showing the operative orientation of the SEM compatible sample container of FIGS. 1A–5B at three stages of operation.
Figure 6B:
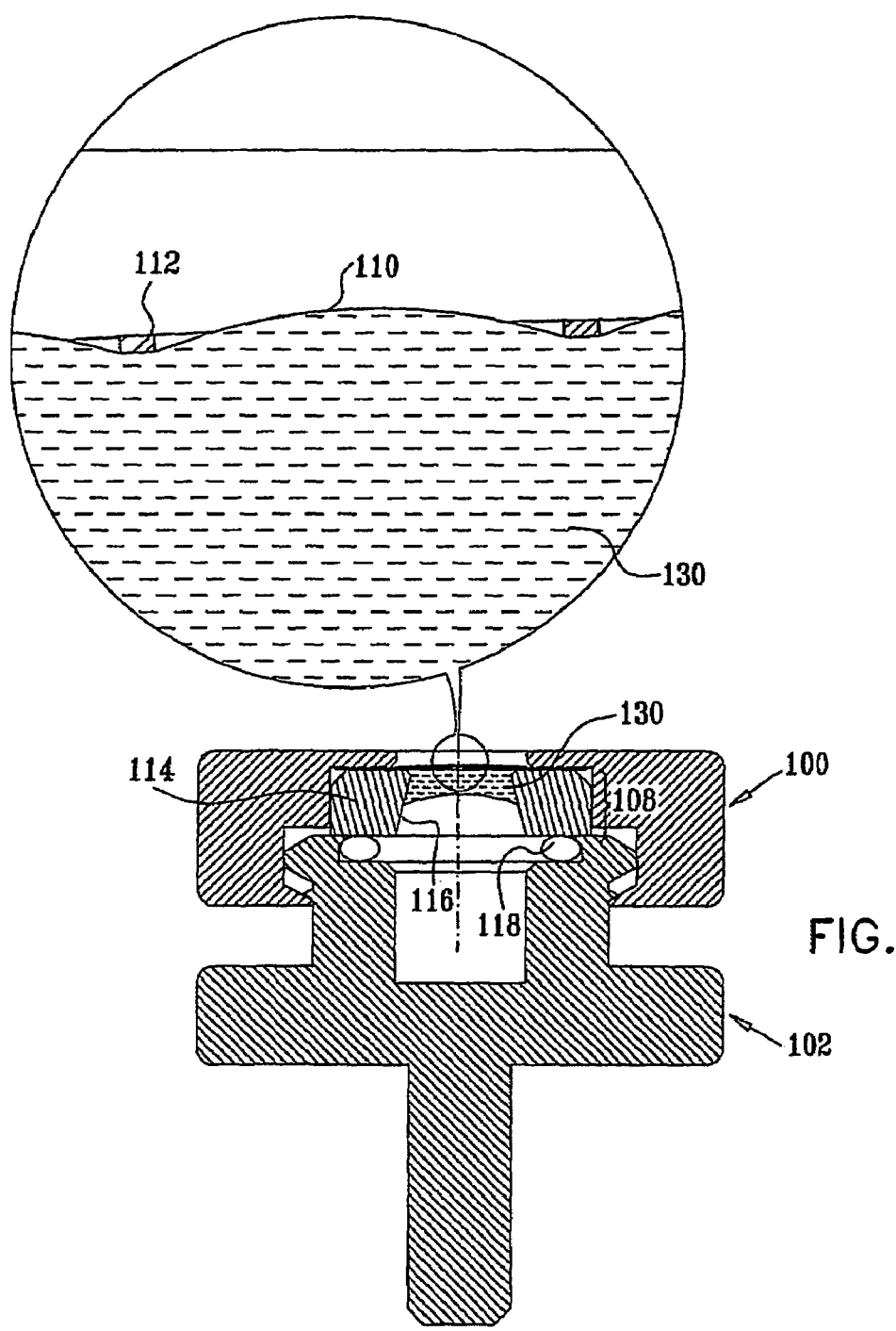
Figure 6C:
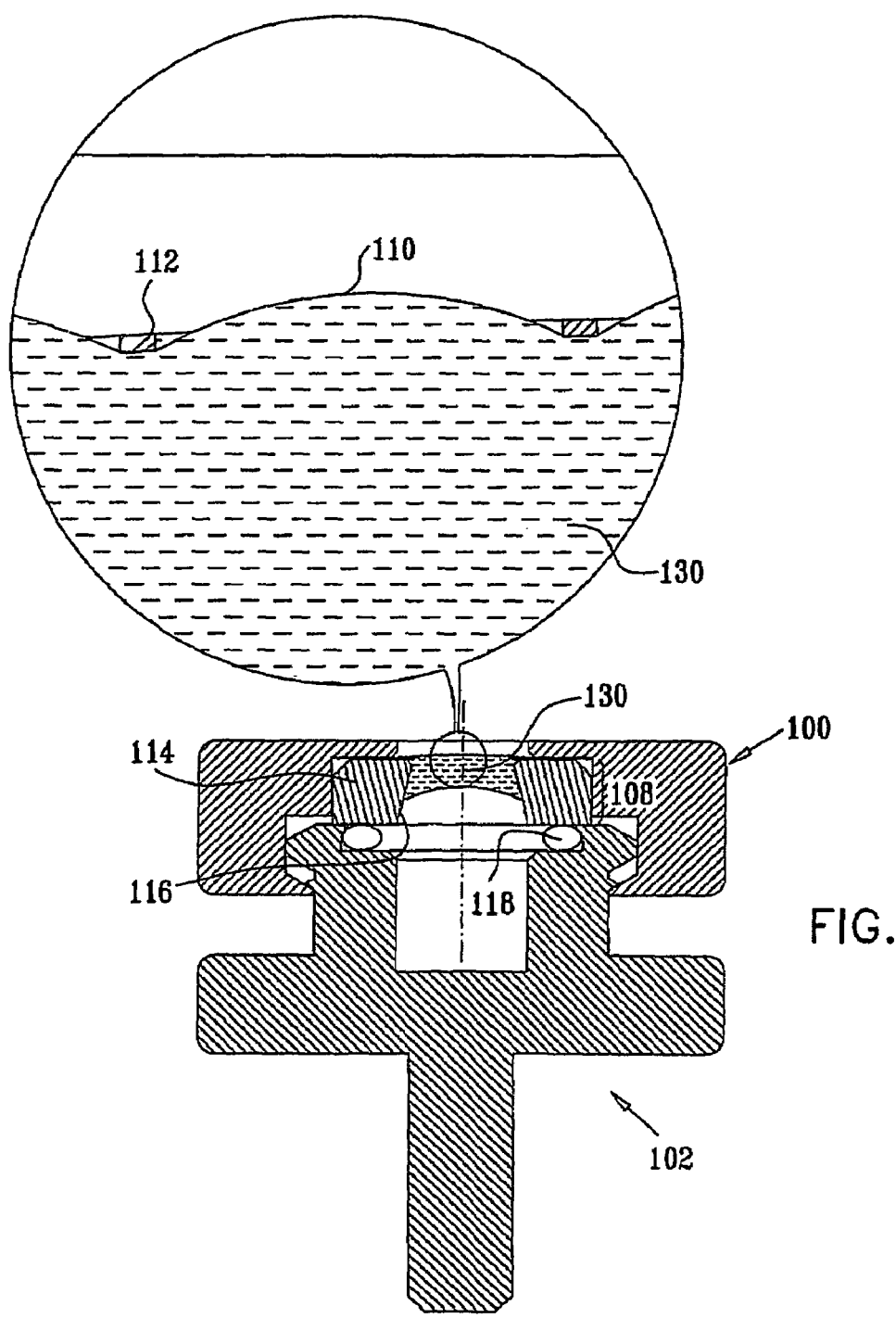

Reference is now made to FIGS. 6A, 6B & 6C, which are three sectional illustrations showing the operative orientation of the SEM compatible sample container of FIGS. 1A–5B at three stages of operation. FIG. 6A shows the container of FIGS. 1A–5B containing a liquid sample 130 and arranged in the orientation shown in FIG. 1B, prior to threaded closure of enclosure elements 100 and 102. It is noted that the liquid sample does not flow out of the liquid sample enclosure 116 due to surface tension. The electron beam permeable, fluid impermeable, membrane 110 is seen in FIG. 6A to be generally planar.

FIG. 6B shows the container of FIG. 6A immediately following full threaded engagement between enclosure elements 100 and 102, producing sealing of the liquid sample enclosure 116 from the ambient. It is seen that the electron beam permeable, fluid impermeable, membrane 110 and its supporting grid 112 bow outwardly due to pressure buildup in the liquid sample enclosure 116 as the result of sealing thereof in this manner.

FIG. 6C illustrates the container of FIG. 6B, when placed in an evacuated environment of a SEM, typically at a vacuum of $10^{-6}$–$10^6$ millibars. It is seen that in this environment, the electron beam permeable, fluid impermeable, membrane 110 and support grid 112 bow outwardly to a greater extent than in the ambient environment of FIG. 6B and further that the electron beam permeable, fluid impermeable, membrane 110 tends to be forced into and through the interstices of grid 112 to a greater extent than occurs in the ambient environment of FIG. 6B.

Figure 7A:
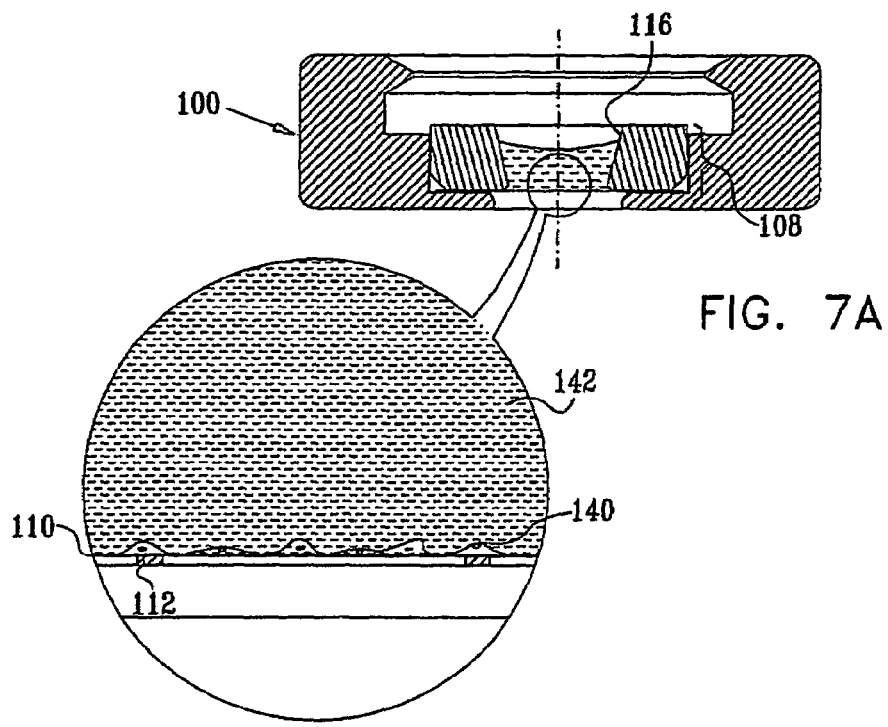
FIGS. 7A, 7B, 7C, 7D and 7E are simplified sectional illustrations of cell growth, liquid removal, liquid addition, sealing and insertion into a SEM respectively using the SEM compatible sample container of FIGS. 1A–6C.

Reference is now made to FIGS. 7A, 7B, 7C, 7D and 7E, which are simplified sectional illustrations of cell growth, liquid removal, liquid addition, sealing and insertion into a SEM respectively using the SEM compatible sample container of FIGS. 1A–6C. Turning to FIG. 7A, which illustrates a typical cell culture situation, it is seen that the enclosure element 100 having disposed therewithin subassembly 108 is in the orientation shown in FIG. 1A and cells 140 in a liquid medium 142 are located within liquid sample enclosure 116, the cells 140 lying against the electron beam permeable, fluid impermeable, membrane 110.

Figure 7B:
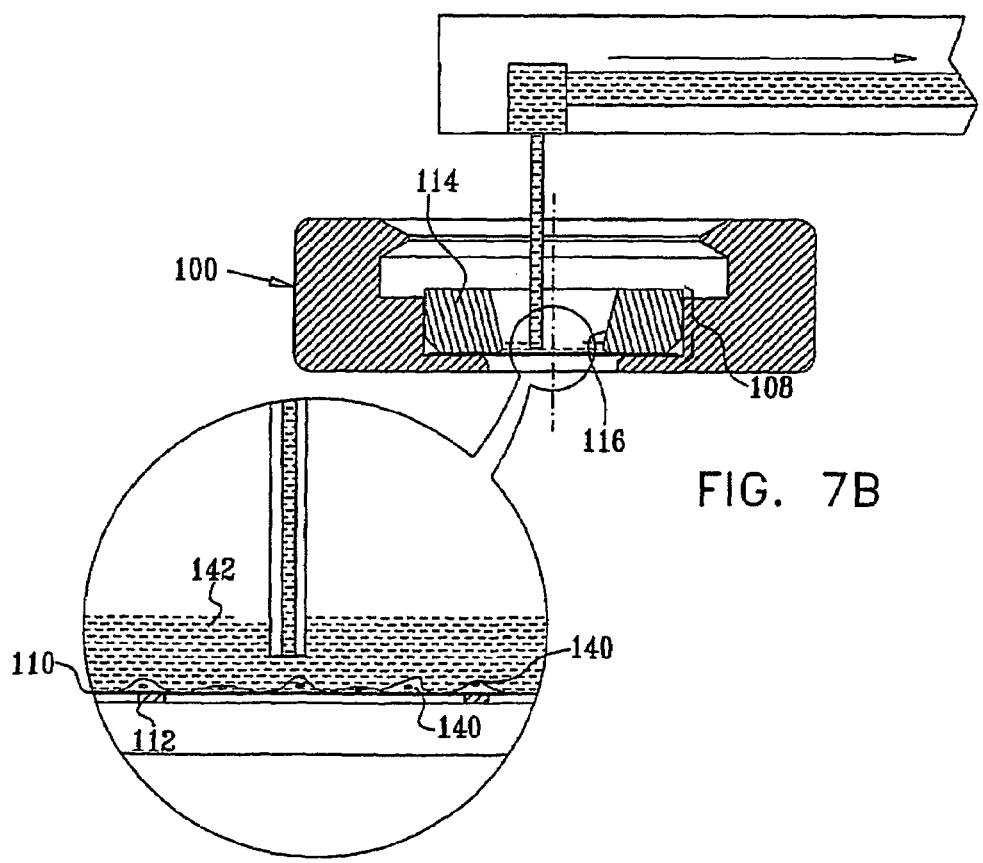
Figure 7C:
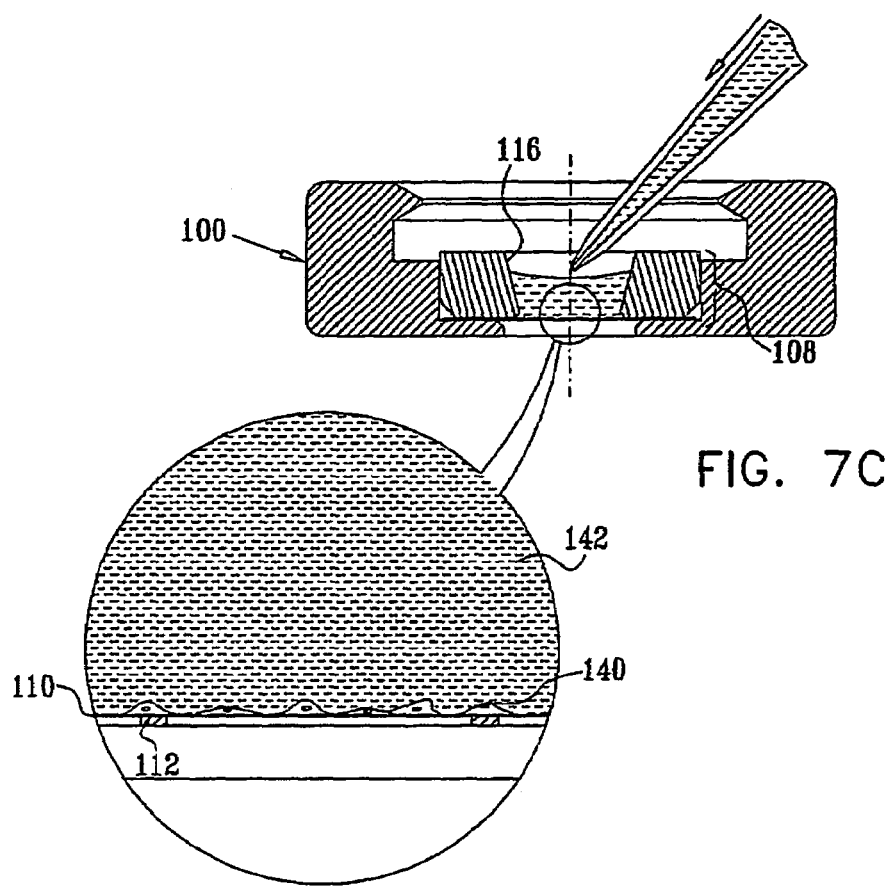

FIG. 7B shows removal of liquid from liquid sample enclosure 116, typically by aspiration, and FIG. 7C shows addition of liquid to liquid sample enclosure 116. It is appreciated that multiple occurrences of liquid removal and addition may take place with respect to a sample within liquid sample enclosure 116. Preferably, the apparatus employed for liquid removal and addition is designed or equipped such as to prevent inadvertent rupture of the electron beam permeable, fluid impermeable, membrane 110.

Figure 7D:
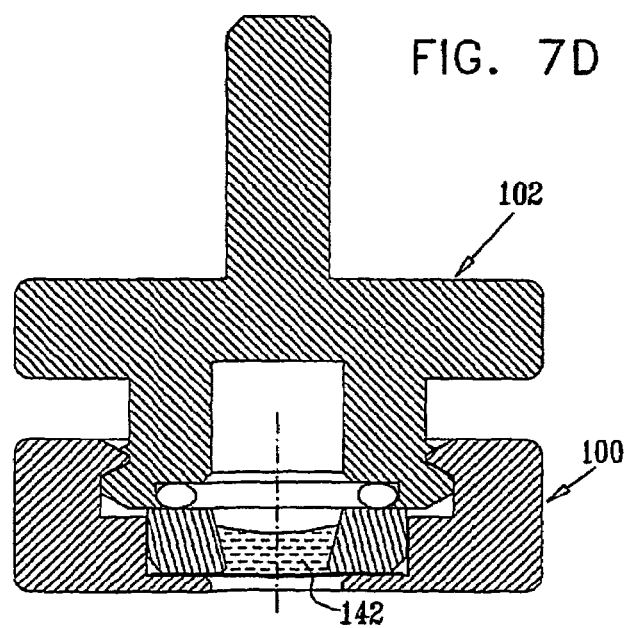
Figure 7E:
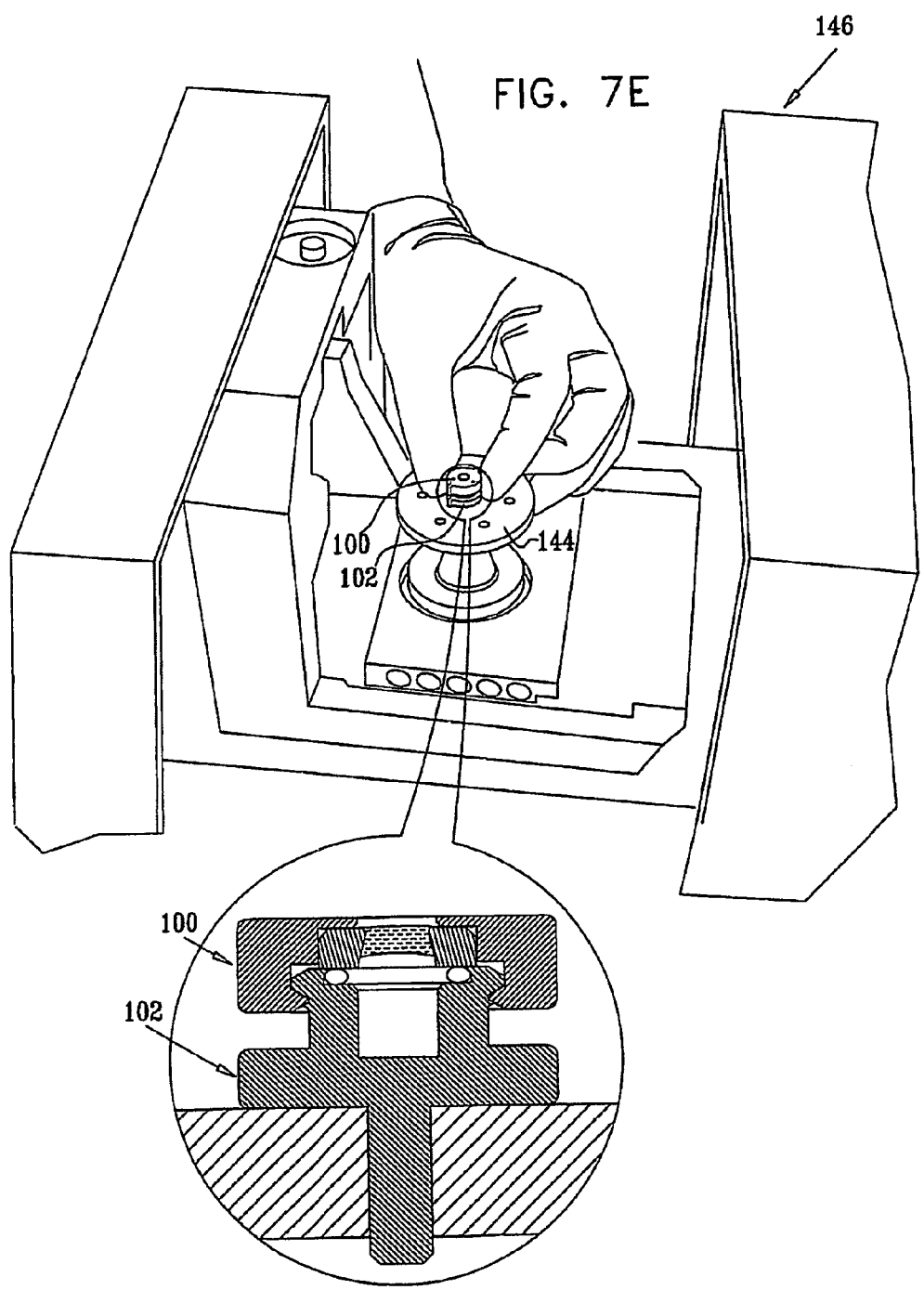

FIG. 7D illustrates closing of the container containing the cells 140, seen in FIG. 7C, in a liquid medium 142. FIG. 7E shows the closed container, in the orientation of FIG. 1B being inserted onto a stage 144 of a SEM 146. It is appreciated that there exist SEMs wherein the orientation of the container is opposite to that shown in FIG. 7E.

FIGS. 7A–7D exemplify a situation wherein at least a portion of a liquid containing sample remains in contact with the electron beam permeable, fluid impermeable, membrane 110 notwithstanding the addition or removal of liquid from liquid sample enclosure 116. This situation may include situations wherein part of the sample is adsorbed or otherwise adhered to the electron beam permeable, fluid impermeable, membrane 110. Examples of liquid containing samples may include cell cultures, blood, bacteria and acellular material.

Figure 8A:
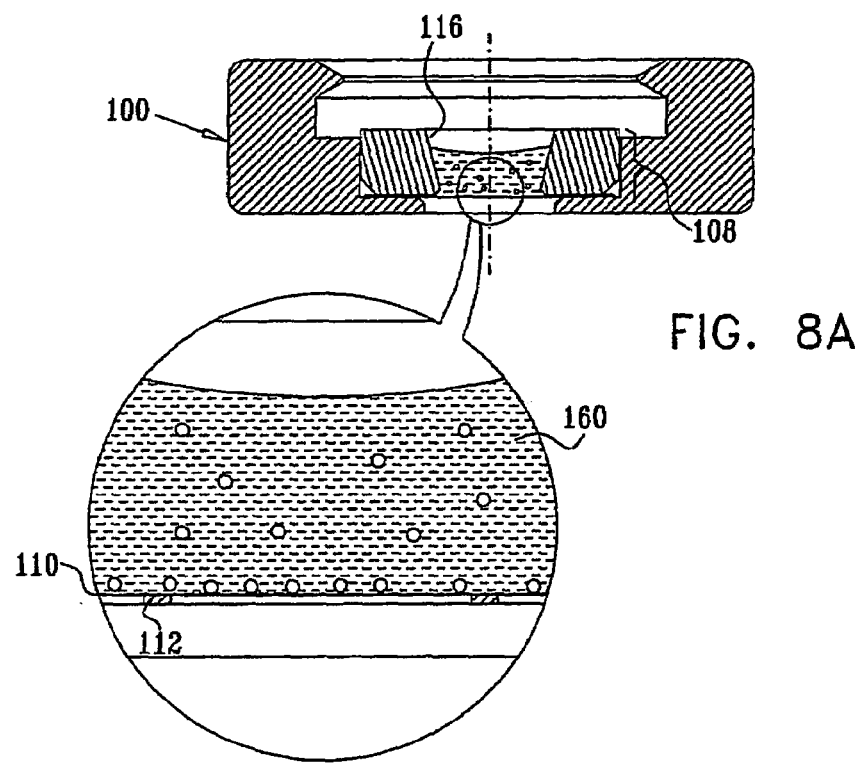
Figure 8B:
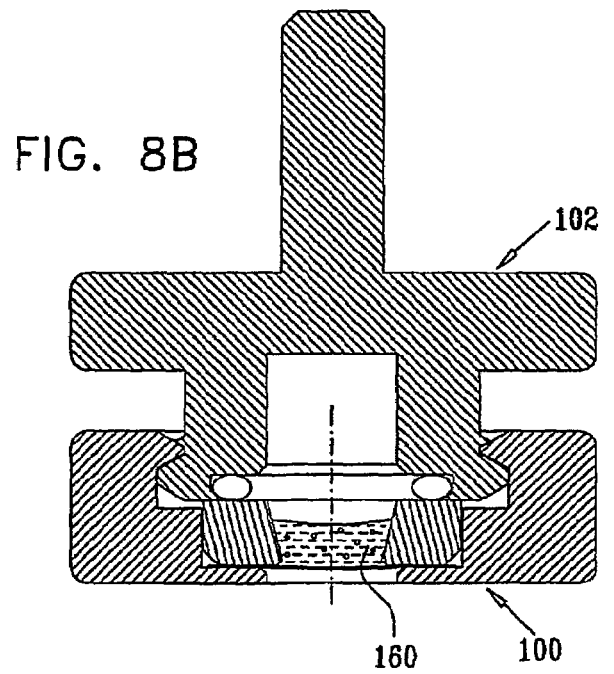

Reference is now made to FIGS. 8A, 8B and 8C which are simplified sectional illustrations of liquid containing samples in contact with the electron beam permeable, fluid impermeable, membrane 110, sealing and insertion into a SEM respectively using the SEM compatible sample container of FIGS. 1A–6C. FIGS. 8A–8C exemplify a situation wherein at least a portion of a liquid containing sample 160 is in contact with the electron beam permeable, fluid impermeable, membrane 110 but is not adhered thereto. Examples of liquid containing samples may include various emulsions and suspensions such as milk, cosmetic creams, paints, inks, and pharmaceuticals in liquid form. It is seen that the enclosure element 100 in FIGS. 8A–8B, having disposed therewithin subassembly 108, is in the orientation shown in FIG. 1A.

FIG. 8B illustrates closing of the container containing the sample 160. FIG. 8C shows the closed container, in the orientation of FIG. 1B, being inserted onto the stage 144 of the SEM 146. It is appreciated that there exist SEMs wherein the orientation of the container is opposite to that shown in FIG. 8C.

Reference is now made to FIG. 9, which is a simplified pictorial and sectional illustration of SEM inspection of a sample using the SEM compatible sample container of FIGS. 1A–6C. As seen in FIG. 9, the container, here designated by reference numeral 170, is shown positioned on stage 144 of a SEM 146 such that an electron beam 172, generated by the SEM, passes through electron beam permeable, fluid impermeable, membrane 110 and impinges on a liquid containing sample 174 within container 170. Backscattered electrons from sample 174 pass through electron beam permeable, fluid impermeable, membrane 110 and are detected by a detector 176, forming part of the SEM. One or more additional detectors, such as a secondary electron detector 178 may also be provided. An X-ray detector (not shown) may also be provided for detecting X-ray radiation emitted by the sample 174 due to electron beam excitation thereof.

Figure 10:
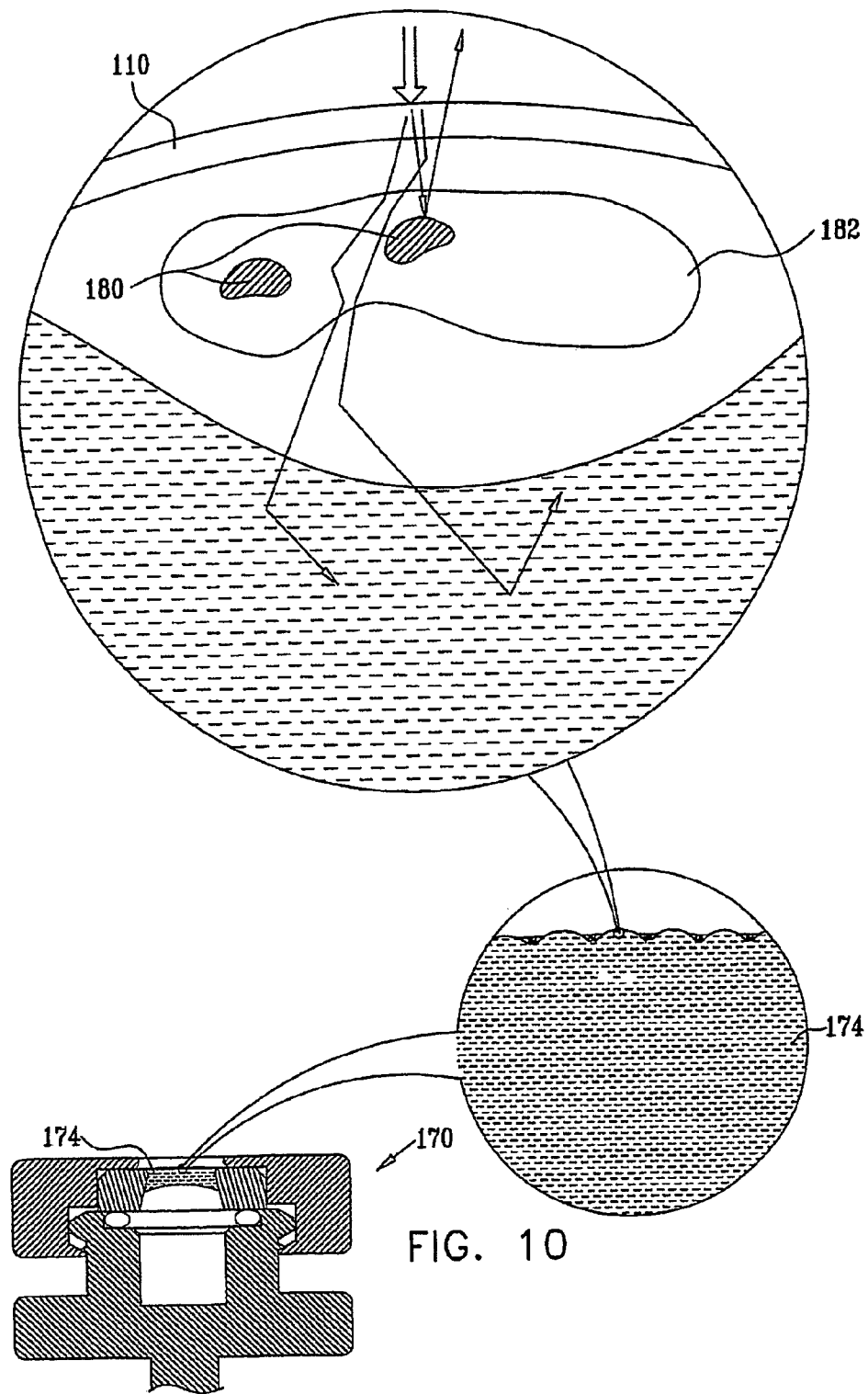
FIG. 10 is a greatly enlarged simplified schematic illustration of the SEM inspection of a sample in the context of FIG. 9.

Reference is now made additionally to FIG. 10, which schematically illustrates some details of the electron beam interaction with the sample 174 in container 170 in accordance with a preferred embodiment of the present invention. It is noted that the present invention enables high contrast imaging of features which are distinguished from each other by their average atomic number, as illustrated in FIG. 10. In FIG. 10 it is seen that nucleoli 180, having a relatively high average atomic number, backscatter electrons more than the surrounding nucleoplasm 182.

It is also noted that in accordance with a preferred embodiment of the present invention, imaging of the interior of the sample to a depth of up to approximately 2 microns is achievable for electrons having an energy level of less than 50 KeV, as seen in FIG. 10, wherein nucleoli 180 disposed below electron beam permeable, fluid impermeable, membrane 110 are imaged.

Reference is now made to FIGS. 11A–15B, which are oppositely facing simplified exploded view pictorial illustrations of a disassembled scanning electron microscope (SEM) compatible sample container constructed and operative in accordance with another preferred embodiment of the present invention. As seen in FIGS. 11A & 11B, the SEM compatible sample container comprises first and second mutually threaded enclosure elements, respectively designated by reference numerals 200 and 202, arranged for enhanced ease and speed of closure. Enclosure elements 200 and 202 are preferably molded of plastic and coated with a conductive metal coating.

Figure 12A:
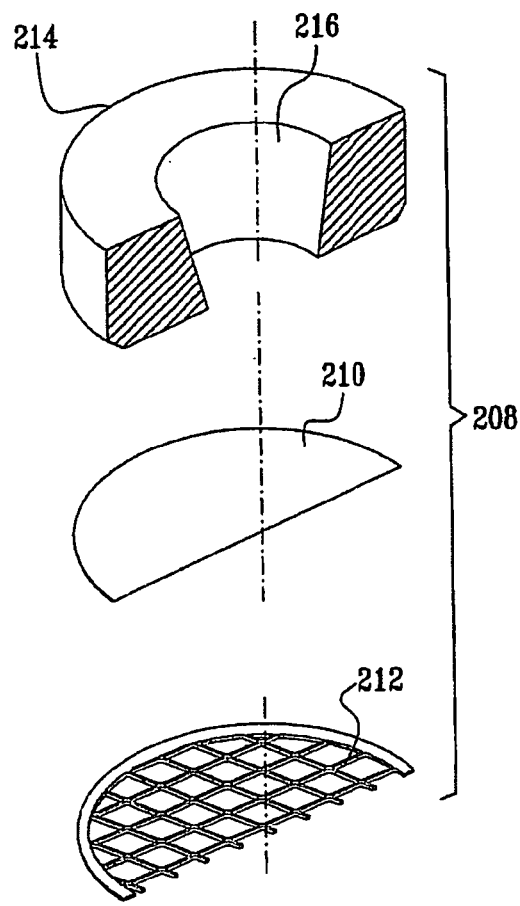
FIGS. 12A & 12B are oppositely facing simplified partially pictorial, partially sectional illustrations of a subassembly of the container of FIGS. 11A & 11B.
Figure 12B:
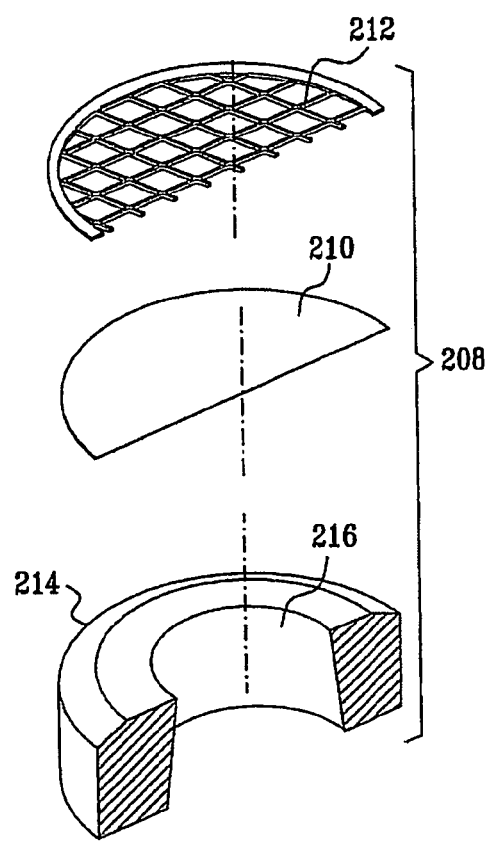
Figure 13A:
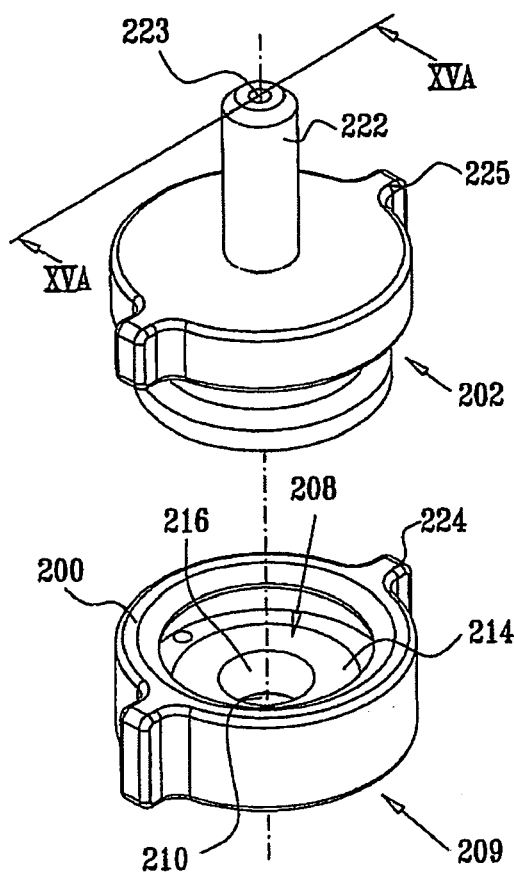
FIGS. 13A & 13B are oppositely facing simplified exploded view pictorial illustrations of the SEM compatible sample container of FIGS. 11A–12B in a partially assembled state.
Figure 13B:
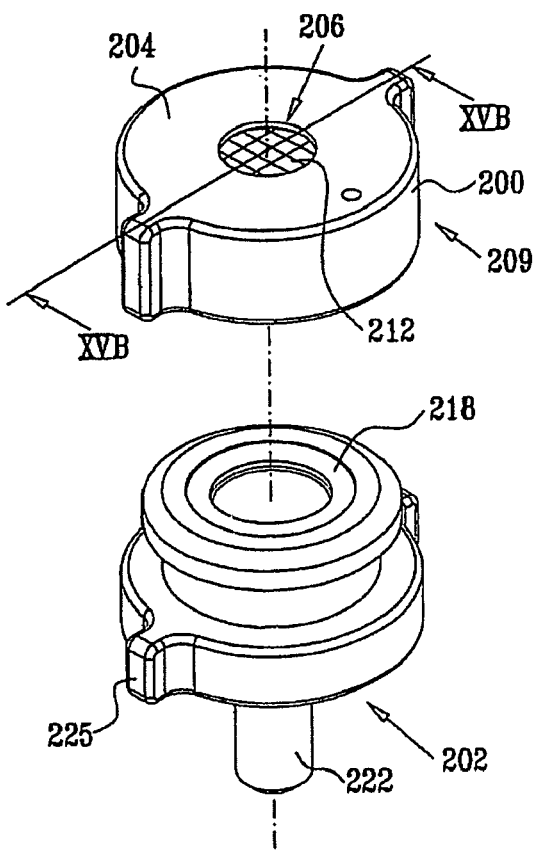

First enclosure element 200 preferably defines a liquid sample enclosure and has a base surface 204 having a generally central aperture 206. An electron beam permeable, fluid impermeable, membrane subassembly 208, shown in detail in FIGS. 12A and 12B, is seated inside enclosure element 200 against and over aperture 206, as shown in FIGS. 13A & 13B and 15A & 15B. A sample dish comprising subassembly 208 suitably positioned in enclosure element 200 is designated by reference numeral 209, as shown in FIGS. 13A–15B.

Turning additionally to FIGS. 12A and 12B, it is seen that an electron beam permeable, fluid impermeable, membrane 210, preferably a polyimide membrane, such as Catalog No. LWN00033, commercially available from Moxtek Inc. of Orem, Utah, U.S.A., is adhered, as by an adhesive, to a mechanically supporting grid 212. Grid 212, which is not shown to scale, is preferably Catalog No. BM 0090-01, commercially available from Buckbee-Mears of Cortland, N.Y., U.S.A., and the adhesive is preferably Catalog No. NOA61, commercially available from Norland Products Inc. of Cranbury, N.J., U.S.A. A liquid sample enclosure defining ring 214 is adhered to electron beam permeable, fluid impermeable, membrane 210, preferably by an adhesive, such as Catalog No NOA61, commercially available from Norland Products Inc. of Cranbury, N.J., U.S.A. Ring 214 is preferably formed of PMMA (polymethyl methacrylate), such as Catalog No. 692106001000, commercially available from Irpen of Barcelona, Spain, and preferably defines a liquid sample enclosure with a volume of approximately 20 microliters and a height of approximately 2 mm. Preferably ring 214 is configured to define a liquid sample enclosure 216 having inclined walls.

A diaphragm 218 is preferably disposed between ring 214 and an interior surface 219 of second enclosure element 202.

Diaphragm 218 is preferably integrally formed of an O-ring portion 220 to which is sealed an expandable sheet portion 221. The diaphragm 218 is preferably molded of silicon rubber having a Shore hardness of about 50 and the sheet portion 221 preferably has a thickness of 0.2–0.3 mm. Diaphragm 218 is operative, when enclosure elements 200 and 202 are in tight threaded engagement, to obviate the need for the threaded engagement of elements 200 and 202 to be a sealed engagement and to provide dynamic and static pressure relief.

Second enclosure element 202 preferably is formed with a generally central stub 222, having a throughgoing bore 223, which stub is arranged to be seated in a suitable recess (not shown) in a specimen stage of a scanning electron microscope. Bore 223 enables diaphragm 218 to provide pressure relief by defining a fluid communication channel between one side of the diaphragm 218 and the environment in which the (SEM) compatible sample container is located. It is a particular feature of the present invention that the container, shown in FIGS. 11A–20, is sized and operative with conventional stub recesses in conventional scanning electron microscopes and does not require any modification thereof whatsoever. It is appreciated that various configurations and sizes of stubs may be provided so as to fit various scanning electron microscopes.

Figure 14A:
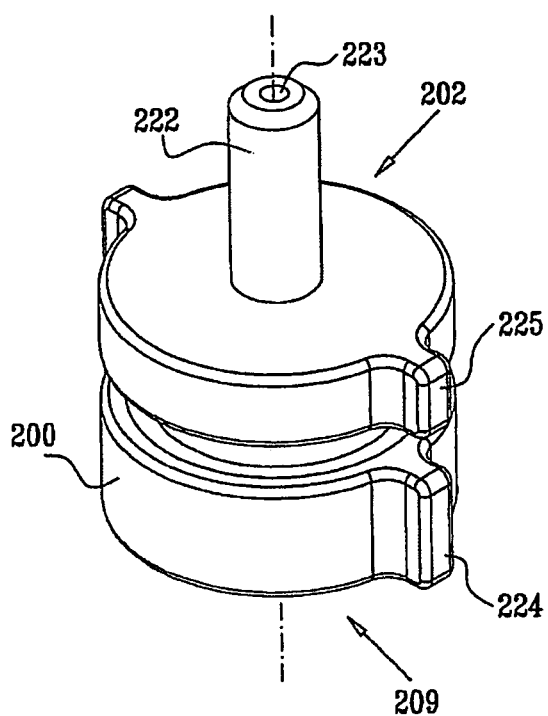
FIGS. 14A & 14B are oppositely facing simplified pictorial illustrations of the SEM compatible sample container of FIGS. 11A–13B in a fully assembled state.
Figure 14B:
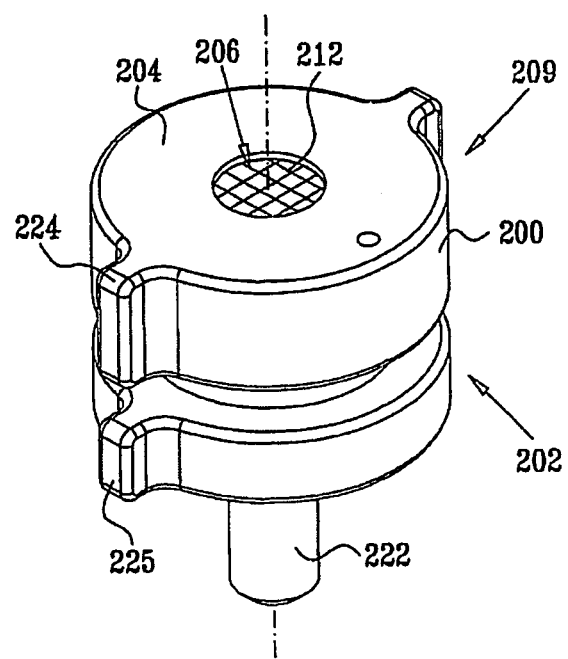
Figure 15A:
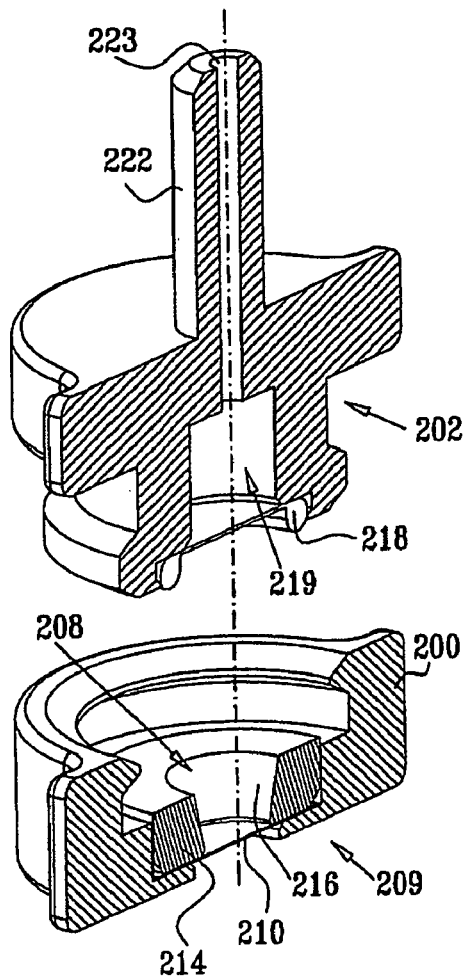
FIGS. 15A & 15B are oppositely facing simplified partially pictorial, partially sectional illustrations taken along lines XVA—XVA and XVB—XVB, respectively, in FIGS. 13A & 13B.
Figure 15B:
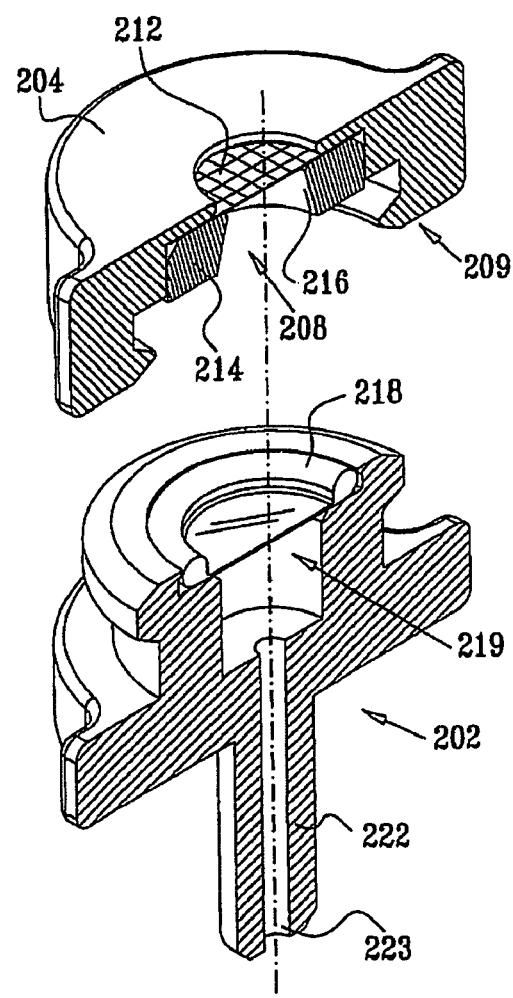

Enclosure elements 200 and 202 are preferably also provided with respective radially extending positioning and retaining protrusions 224 and 225, to enable the container to be readily seated in a suitable multi-container holder and also to assist users in threadably opening and closing the enclosure elements 200 and 202. Preferably, the mutual azimuthal positioning of the protrusions 224 and 225 on respective enclosure elements 200 and 202 is such that mutual azimuthal alignment therebetween indicates a desired degree of threaded closure therebetween, as shown in FIGS. 14A and 14B.

Figure 16A:
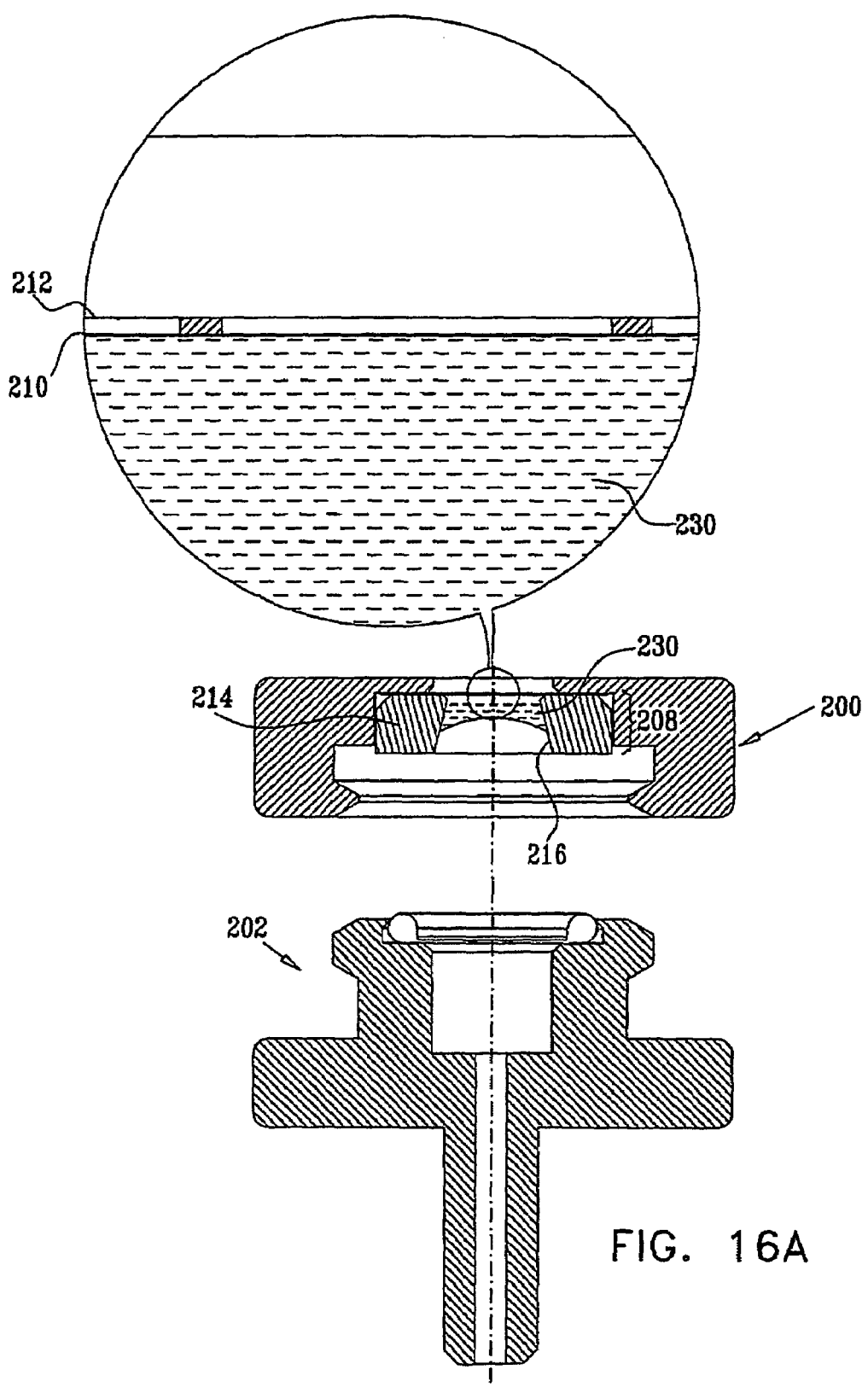
Figure 16C:
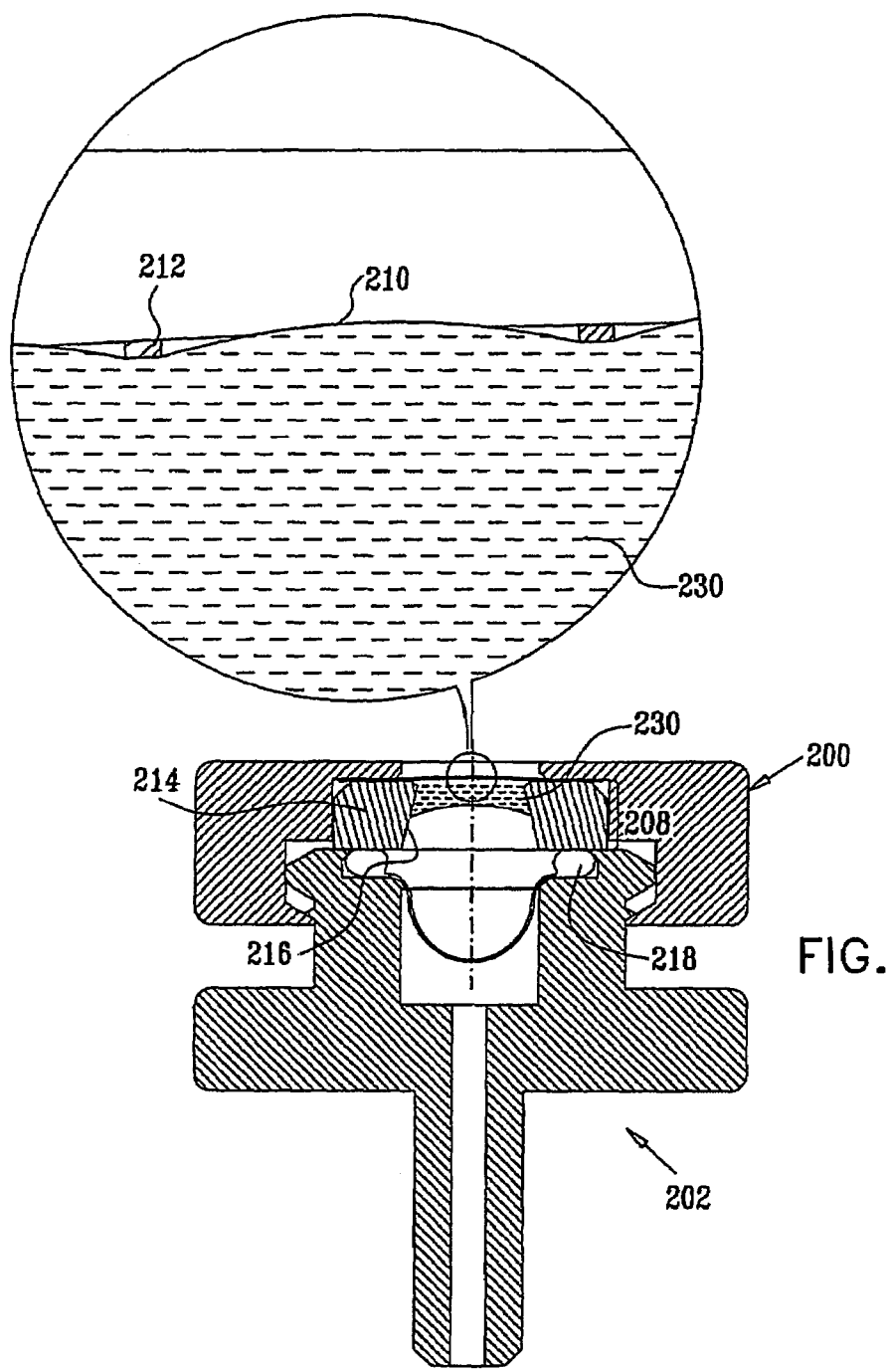

Reference is now made to FIGS. 16A, 16B & 16C, which are three sectional illustrations showing the operative orientation of the SEM compatible sample container of FIGS. 11A–15B at three stages of operation. FIG. 16A shows the container of FIGS. 11A–15B containing a liquid sample 230 and arranged in the orientation shown in FIG. 11B, prior to threaded closure of enclosure elements 200 and 202. It is noted that the liquid sample does not flow out of the liquid sample enclosure 216 due to surface tension. The electron beam permeable, fluid impermeable, membrane 210 is seen in FIG. 16A to be generally planar.

FIG. 16B shows the container of FIG. 16A immediately following full threaded engagement between enclosure elements 200 and 202, producing sealing of the liquid sample enclosure 216 from the ambient. It is seen that the diaphragm 218 bows outwardly due to pressure buildup in the liquid sample enclosure 216 as the result of sealing thereof in this manner. In this embodiment, electron beam permeable, fluid impermeable, membrane 210 and its supporting grid 212 also bow outwardly due to pressure buildup in the liquid sample enclosure 216 as the result of sealing thereof in this manner, however to a significantly lesser extent, due to the action of diaphragm 218. This can be seen by comparing FIG. 16B with FIG. 6B.

FIG. 16C illustrates the container of FIG. 16B, when placed in an evacuated environment of a SEM, typically at a vacuum of $10^{-2}$–$10^{-6}$ millibars. It is seen that in this environment, the diaphragm 218 bows outwardly to a greater extent than in the ambient environment of FIG. 16B and that electron beam permeable, fluid impermeable, membrane 210 and support grid 212 also bow outwardly to a greater extent than in the ambient environment of FIG. 16B, but to a significantly lesser extent than in the embodiment of FIG. 6C, due to the action of diaphragm 218. This can be seen by comparing FIG. 16C with FIG. 6C.

It is also noted that the electron beam permeable, fluid impermeable, membrane 210 tends to be forced into and through the interstices of grid 212 to a greater extent than occurs in the ambient environment of FIG. 16B but to a significantly lesser extent than in the embodiment of FIG. 6C, due to the action of diaphragm 218. This can also be seen by comparing FIG. 16C with FIG. 6C.

Figure 17A:
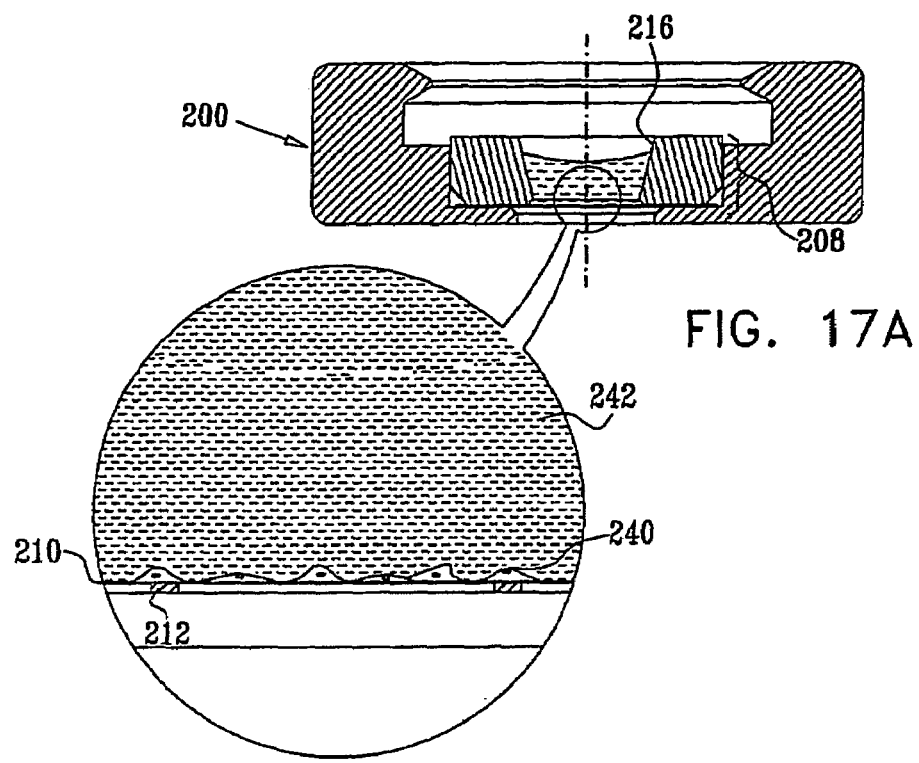
FIGS. 17A, 17B, 17C, 17D and 17E are simplified sectional illustrations of cell growth, liquid removal, liquid addition, sealing and insertion into a SEM respectively using the SEM compatible sample container of FIGS. 11A–16C.

Reference is now made to FIGS. 17A, 17B, 17C, 17D and 17E, which are simplified sectional illustrations of cell growth, liquid removal, liquid addition, sealing and insertion into a SEM respectively using the SEM compatible sample container of FIGS. 11A–16C. Turning to FIG. 17A, which is identical to FIG. 7A and illustrates a typical cell culture situation, it is seen that the enclosure element 200 having disposed therewithin subassembly 208 is in the orientation shown in FIG. 11A and cells 240 in a liquid medium 242 are located within liquid sample enclosure 216, the cells 240 lying against the electron beam permeable, fluid impermeable, membrane 210.

Figure 17B:
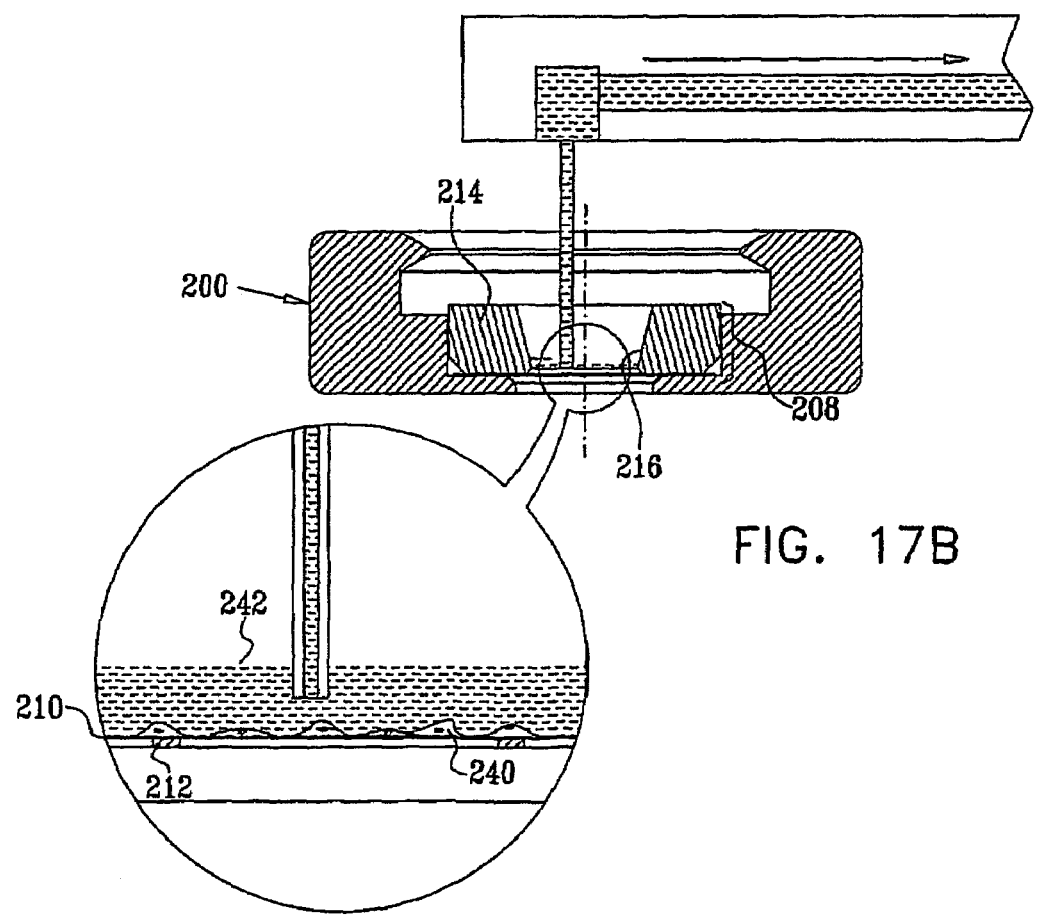
Figure 17C:
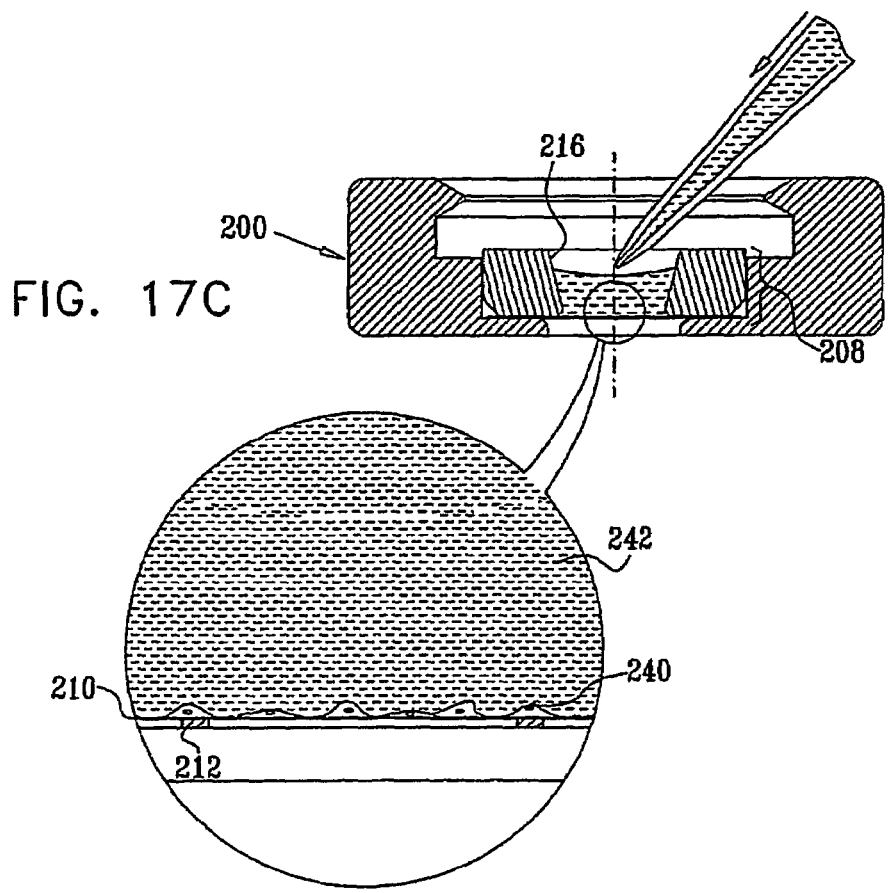

FIG. 17B, which is identical to FIG. 7B, shows removal of liquid from liquid sample enclosure 216, typically by aspiration, and FIG. 17C, which is identical to FIG. 7C, shows addition of liquid to liquid sample enclosure 216. It is appreciated that multiple occurrences of liquid removal and addition may take place with respect to a sample within liquid sample enclosure 216. Preferably, the apparatus employed for liquid removal and addition is designed or equipped such as to prevent inadvertent rupture of the electron beam permeable, fluid impermeable, membrane 210.

Figure 17D:
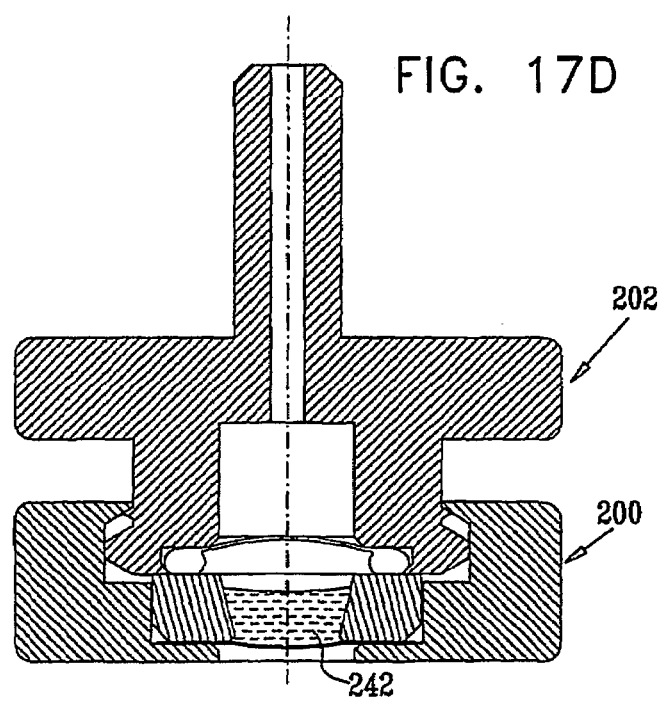
Figure 17E:
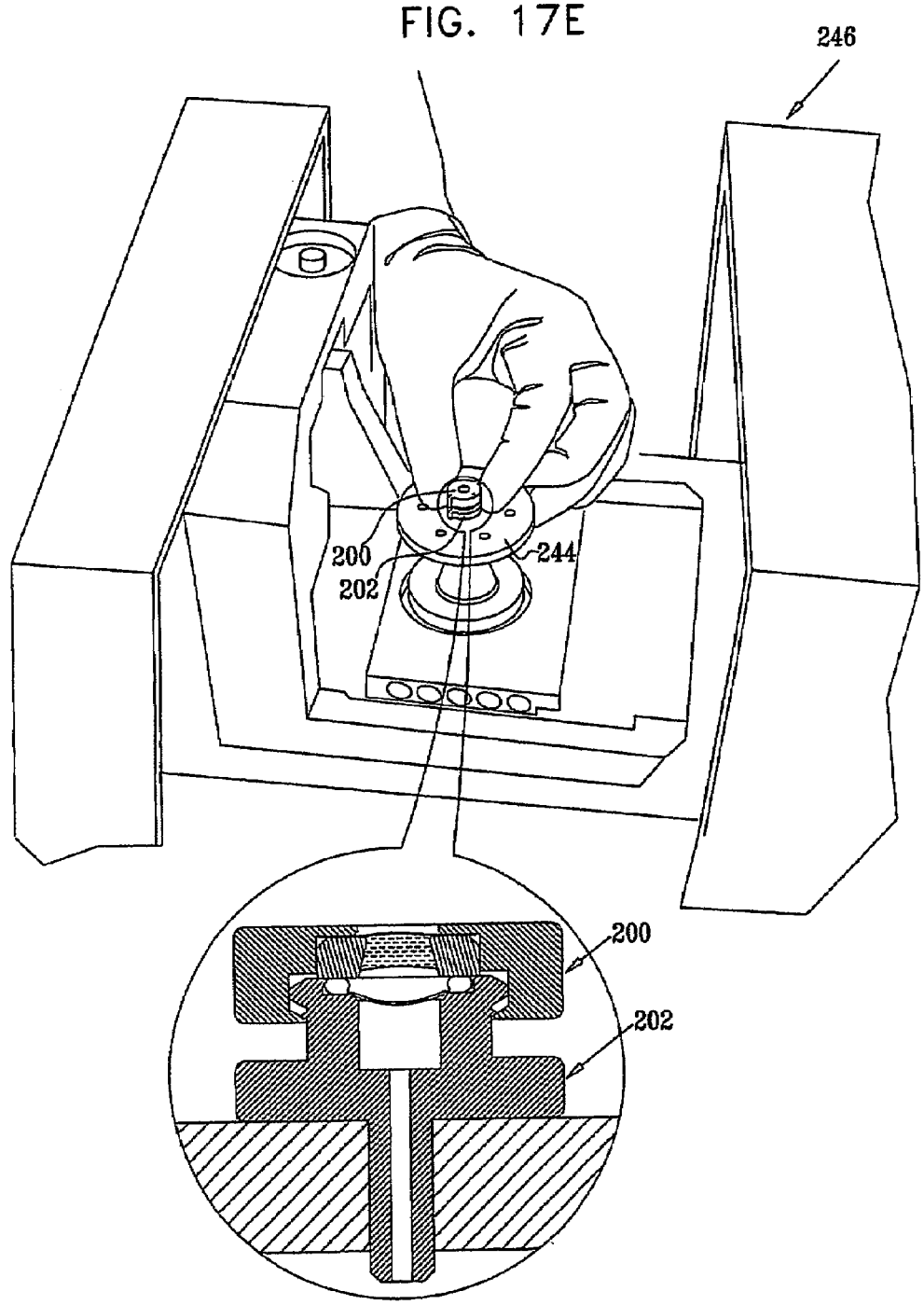

FIG. 17D illustrates closing of the container containing the cells 240, seen in FIG. 17C, in a liquid medium 242. FIG. 17 shows the closed container, in the orientation of FIG. 11B being inserted onto a stage 244 of a SEM 246. It is appreciated that there exist SEMs wherein the orientation of the container is opposite to that shown in FIG. 17E.

FIGS. 17A–17D exemplify a situation wherein at least a portion of a liquid containing sample remains in contact with the electron beam permeable, fluid impermeable, membrane 210 notwithstanding the addition or removal of liquid from liquid sample enclosure 216. This situation may include situations wherein part of the sample is adsorbed or otherwise adhered to the electron beam permeable, fluid impermeable, membrane 210. Examples of liquid containing samples may include cell cultures, blood, bacteria and acellular material.

Figure 18A:
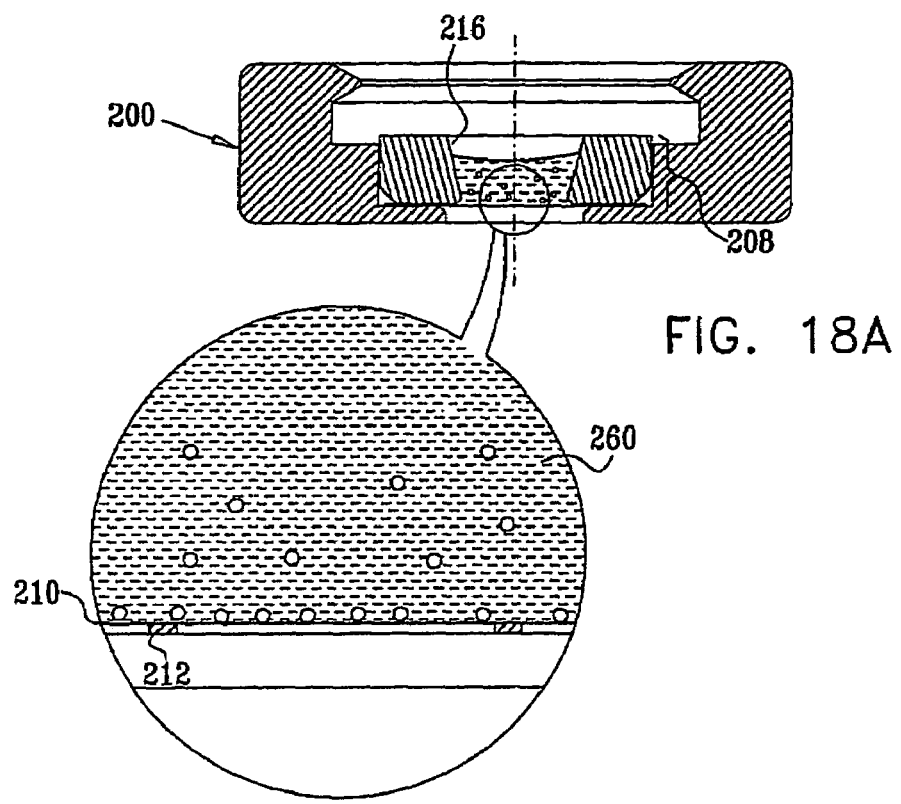
FIGS. 18A, 18B and 18C are simplified sectional illustrations of liquid containing samples, sealing and insertion into a SEM respectively using the SEM compatible sample container of FIGS. 11A–16C.
Figure 18B:
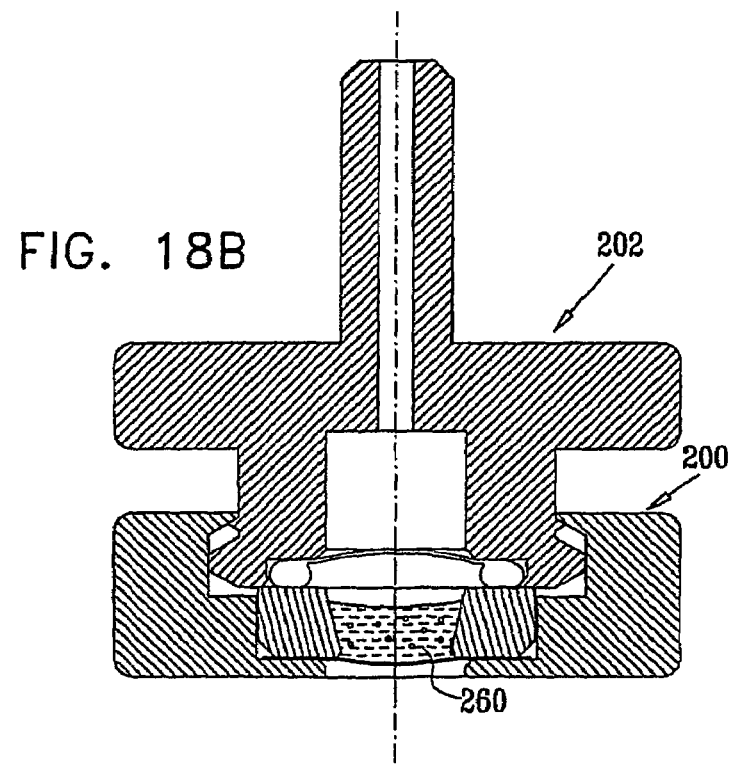
Figure 18C:
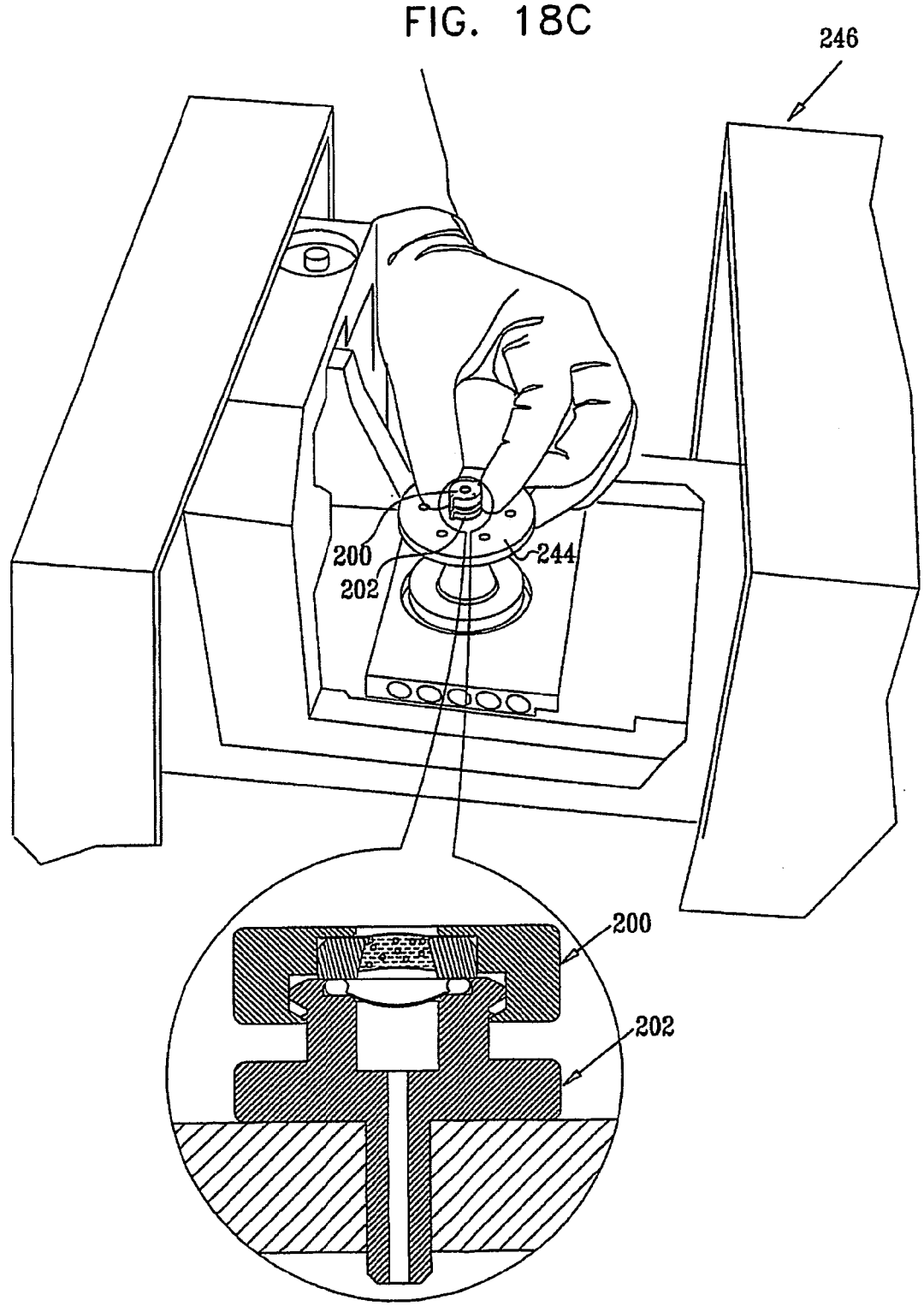

Reference is now made to FIGS. 18A, 18B and 18C which are simplified sectional illustrations of liquid containing samples in contact with the electron beam permeable, fluid impermeable, membrane 210, sealing and insertion into a SEM respectively using the SEM compatible sample container of FIGS. 11A–16C. FIGS. 18A–18C exemplify a situation wherein at least a portion of a liquid containing sample 260 is in contact with the electron beam permeable, fluid impermeable, membrane 210 but is not adhered thereto. Examples of liquid containing samples may include various emulsions and suspensions such as milk, cosmetic creams, paints, inks, and pharmaceuticals in liquid form. It is seen that the enclosure element 200, having disposed therewithin subassembly 208 in FIGS. 8A–8B, is in the orientation shown in FIG. 11A. FIG. 18A is identical to FIG. 8A.

FIG. 18B illustrates closing of the container containing the sample 260. FIG. 18C shows the closed container, in the orientation of FIG. 11B, being inserted onto the stage 244 of the SEM 246. It is appreciated that there exist SEMs wherein the orientation of the container is opposite to that shown in FIG. 18C.

Figure 19:
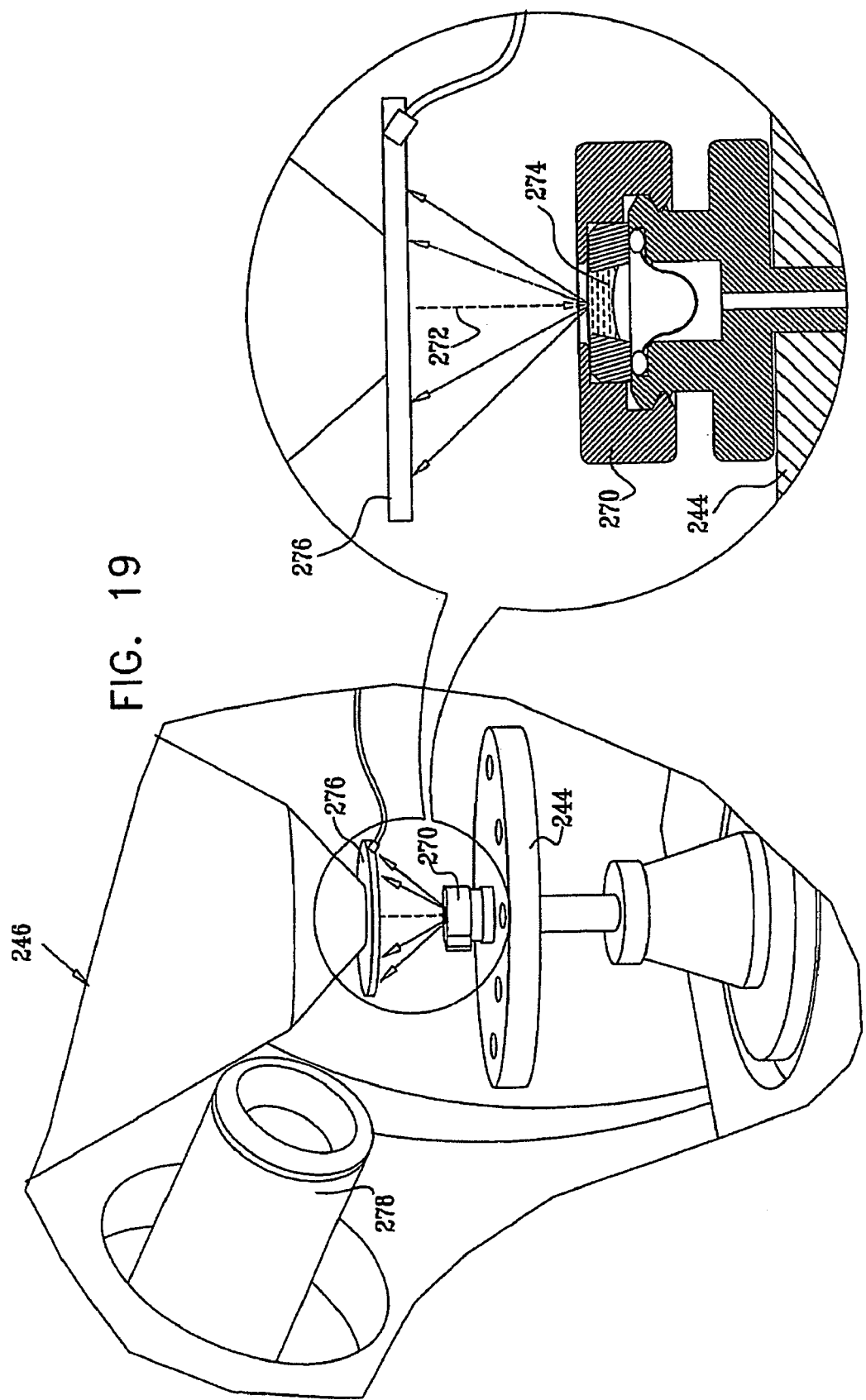
FIG. 19 is a simplified pictorial and sectional illustration of a SEM inspection of a sample using the SEM compatible sample container of FIGS. 11A–16C.

Reference is now made to FIG. 19, which is a simplified pictorial and sectional illustration of SEM inspection of a sample using the SEM compatible sample container of FIGS. 11A–16C. As seen in FIG. 19, the container, here designated by reference numeral 270, is shown positioned on stage 244 of a SEM 246 such that an electron beam 272, generated by the SEM, passes through electron beam permeable, fluid impermeable, membrane 210 and impinges on a liquid containing sample 274 within container 270. Backscattered electrons from sample 274 pass through electron beam permeable, fluid impermeable, membrane 210 and are detected by a detector 276, forming part of the SEM. One or more additional detectors, such as a secondary electron detector 278 may also be provided. An X-ray detector (not shown) may also be provided for detecting X-ray radiation emitted by the sample 274 due to electron beam excitation thereof.

Figure 20:
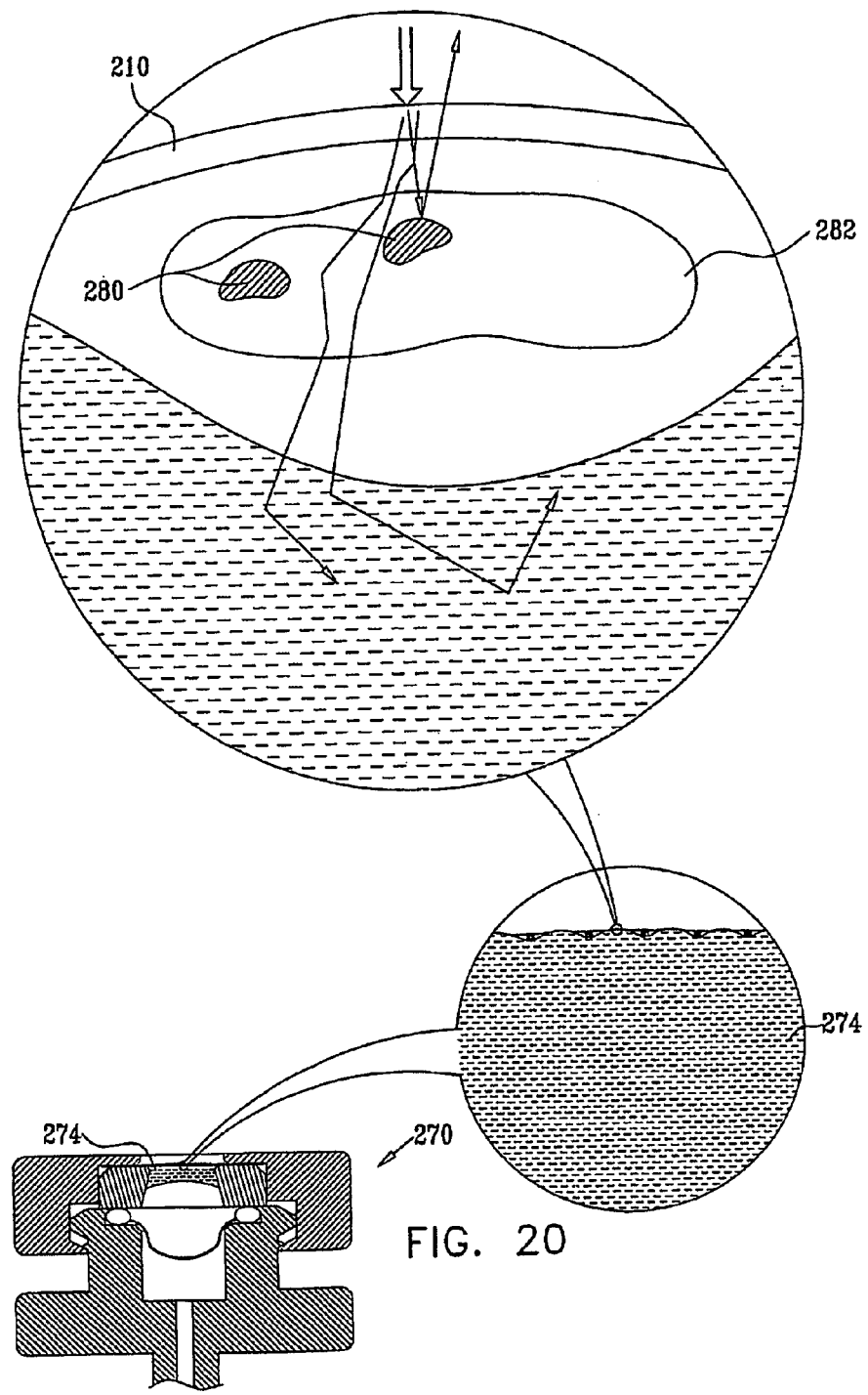
FIG. 20 is a greatly enlarged simplified schematic illustration of the SEM inspection of a sample in the context of FIG. 19.

Reference is now made additionally to FIG. 20, which schematically illustrates some details of the electron beam interaction with the sample 274 in container 270 in accordance with a preferred embodiment of the present invention. It is noted that the present invention enables high contrast imaging of features which are distinguished from each other by their average atomic number, as illustrated in FIG. 20. In FIG. 20 it is seen that nucleoli 280 having a relatively high average atomic number, backscatter electrons more than the surrounding nucleoplasm 282.

It is also noted that in accordance with a preferred embodiment of the present invention, imaging of the interior of the sample to a depth of up to approximately 2 microns is achievable for electrons having an energy level of less than 50 KeV, as seen in FIG. 20, wherein nucleoli 280 disposed below electron beam permeable, fluid impermeable, membrane 210 are imaged.

Figure 21B:
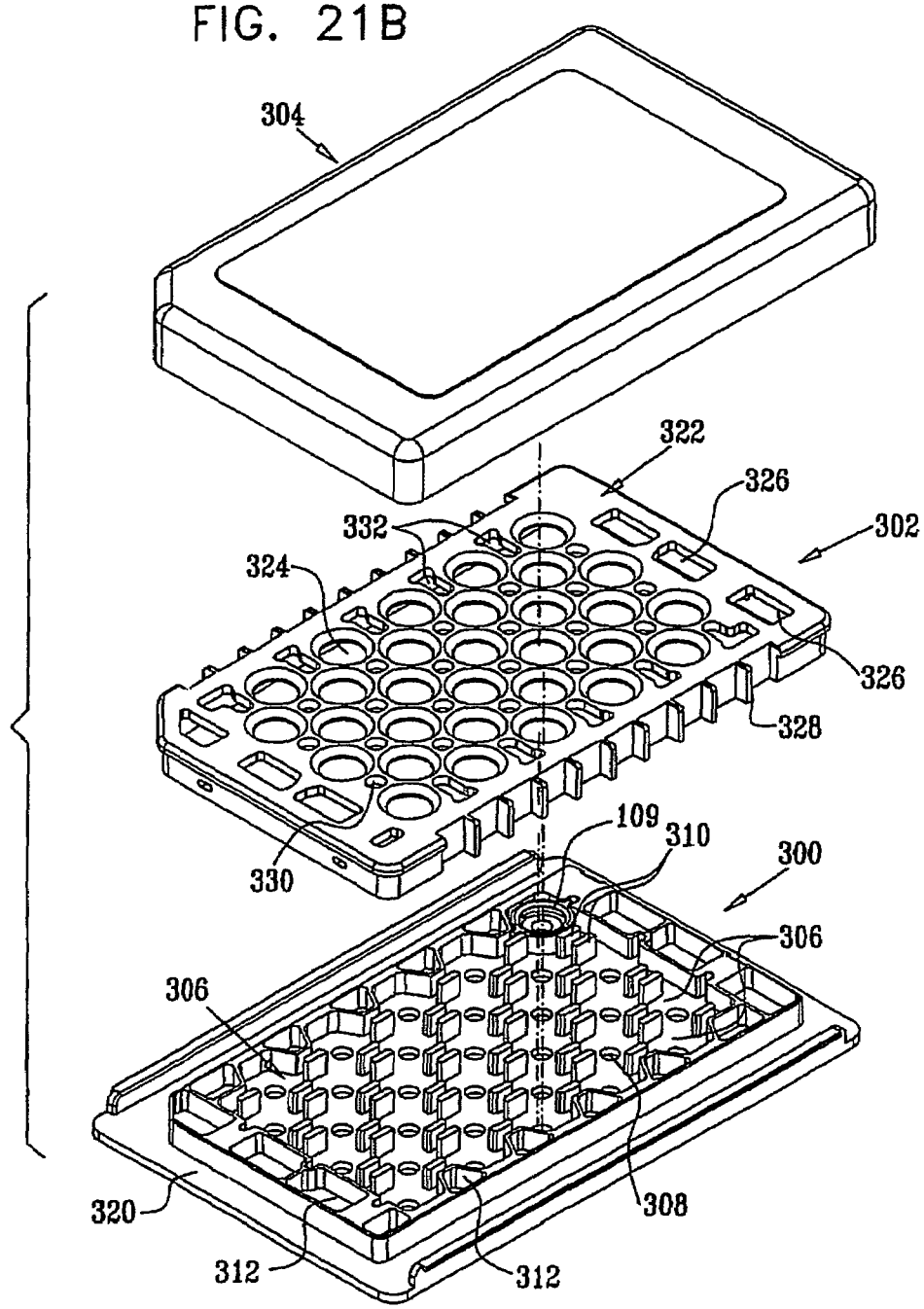
Figure 22A:
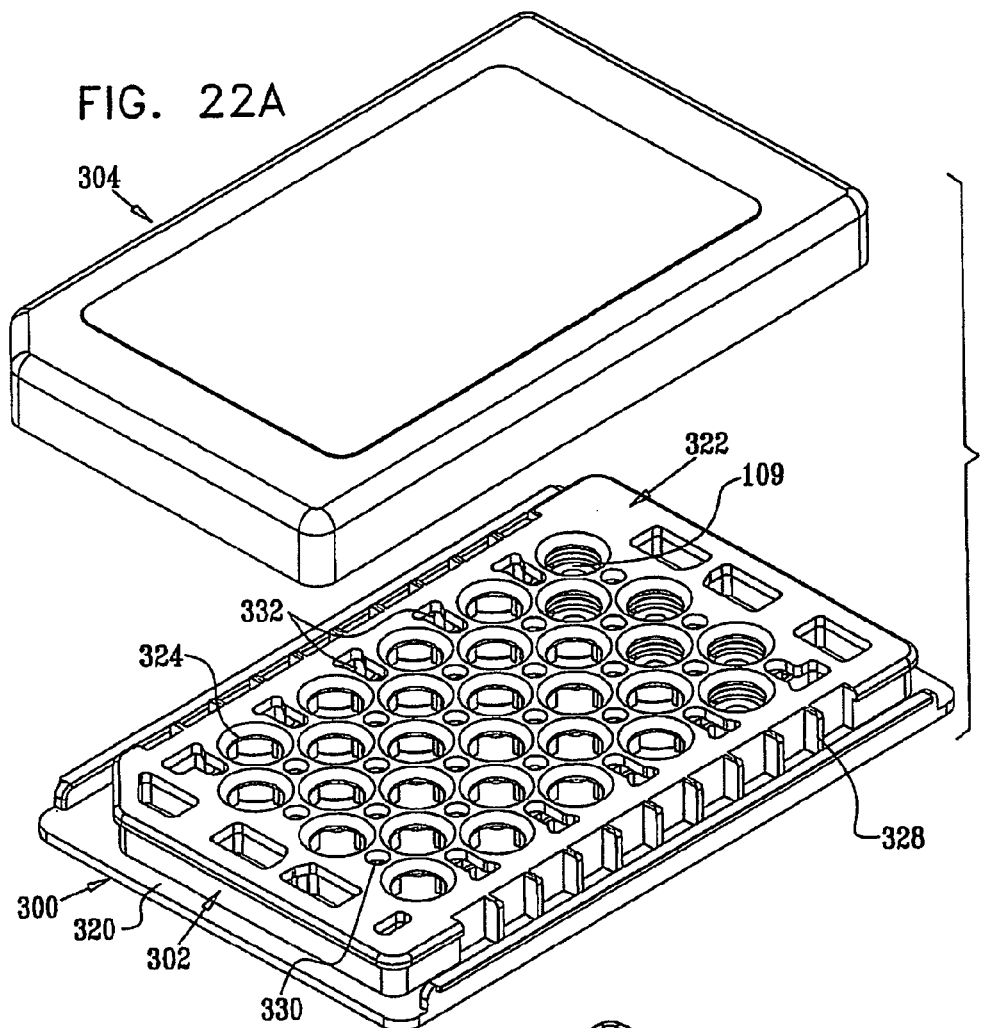
FIGS. 22A and 22B are simplified illustrations of the pre-microscopy multi-sample holder of FIGS. 21A & 21B respectively uncovered and covered in an assembled state.
Figure 22B:
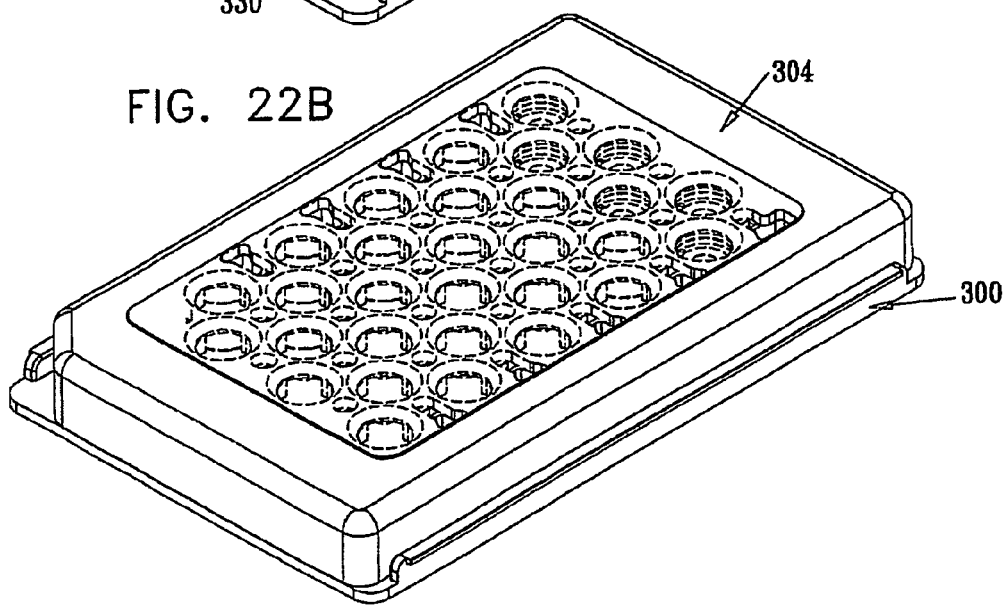

Reference is now made to FIGS. 21A and 21B, which are simplified exploded view illustrations of a pre-microscopy multi-sample holder in use with SEM compatible sample containers of the type shown in FIGS. 1A–20 and to FIGS. 22A and 22B which are simplified illustrations of the pre-microscopy multi-sample holder of FIGS. 21A & 21B respectively uncovered and covered in an assembled state.

As seen in FIGS. 21A and 21B, the pre-microscopy multi-sample holder preferably comprises a base 300, a top element 302 and a cover 304, Cover 304 is preferably provided to maintain sterility within the interior of the pre-microscopy multi-sample holder.

The base 300 is preferably injection molded of a plastic material and defines an array of container support locations 306. Each container support location 306 is preferably defined by a recess 308 having a light transparent bottom wall through which light microscopy may take place. Adjacent to each recess 308 there is preferably formed a pair of mutually aligned pairs of upstanding mutually spaced protrusions 310 arranged to receive protrusions, designated by reference numeral 124 in FIGS. 1A–4B, on enclosure elements, designated by reference numeral 100 in FIGS. 1A–8C, thereby fixing the azimuthal alignment thereof.

Base 300 preferably also defines a plurality of liquid reservoirs 312 which are adapted to hold liquid used to maintain a desired level of humidity in the interior of the pre-microscopy multi-sample holder. Base 300 is preferably formed with a floor 320. Top element 302 is arranged for removable snap-fit engagement with base 300 so as to retain sample dishes, designated by reference numeral 109 in FIGS. 3A–5B, in a desired array on base 300. Top element 302 is formed with a planar surface 322 having an array of apertures 324 which are arranged to overlie the sample dishes 109 when seated at container support locations 306. The size of apertures 324 is preferably selected to be less than the size of the enclosure elements 100, so as to prevent the sample dishes 109 from passing therethrough. Planar surface 322 preferably also includes apertures 326 communicating with liquid reservoirs 312.

Top element 302 also provides positioning guides 328 and dummy apertures 330 for use by a suction device in conjunction therewith, as described hereinbelow with reference to FIGS. 23A and 23B. Combination dummy apertures 332 are also provided. Only part of each aperture 332 covers a liquid reservoir 312, while the reminder of each aperture 332 serves as a dummy aperture for a suction device.

Cover 304 is provided to maintain sterility of the interior of the pre-microscopy multi-sample holder. Cover 304 is preferably transparent to light, as illustrated in FIG. 22B. The pre-microscopy multi-sample holder of FIGS. 21A–22B is preferably dimensioned so as to be compatible with conventional cell biology equipment, such as light microscopes, centrifuges and automated positioning devices, Preferred dimensions are 85 nm×127 mm.

Figure 23A:
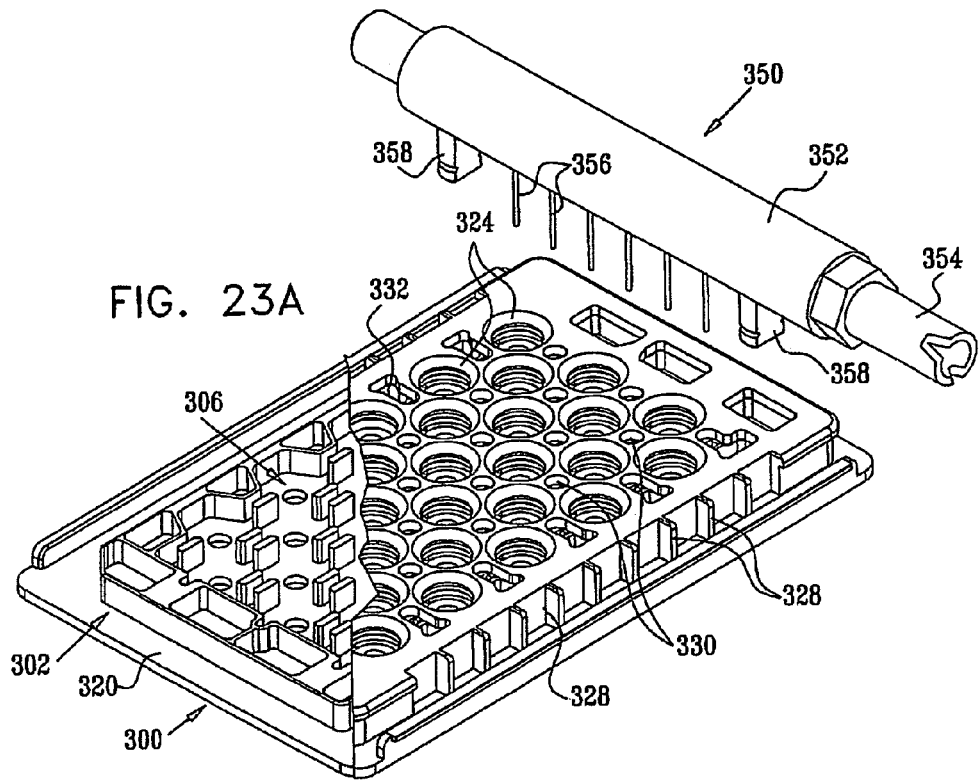
FIGS. 23A, 23B and 23C are simplified illustrations of the pre-microscopy multi-sample holder of FIGS. 21A–22B respectively associated with a suction device and pipettes.
Figure 23B:
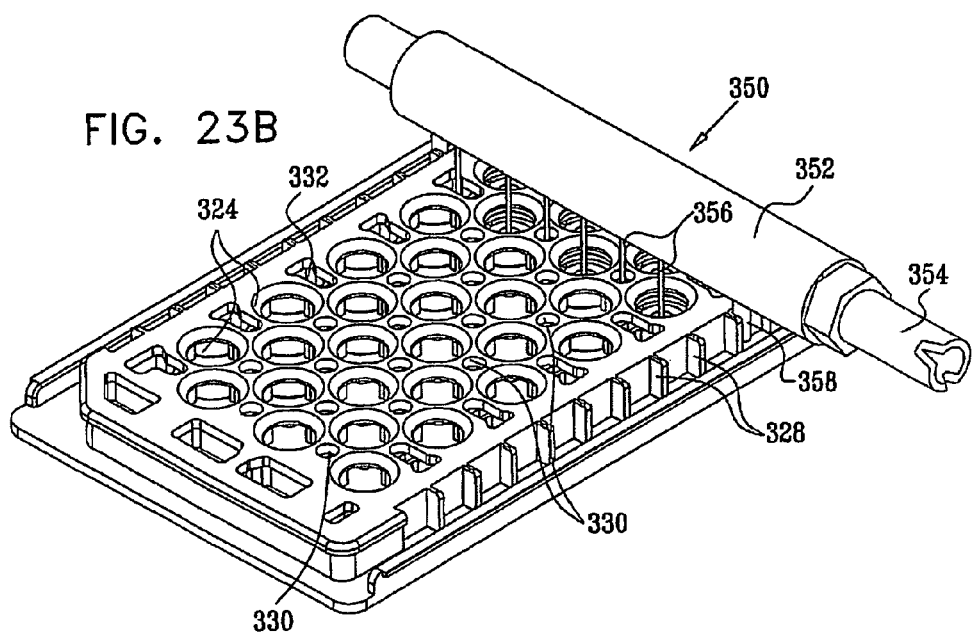
Figure 23C:
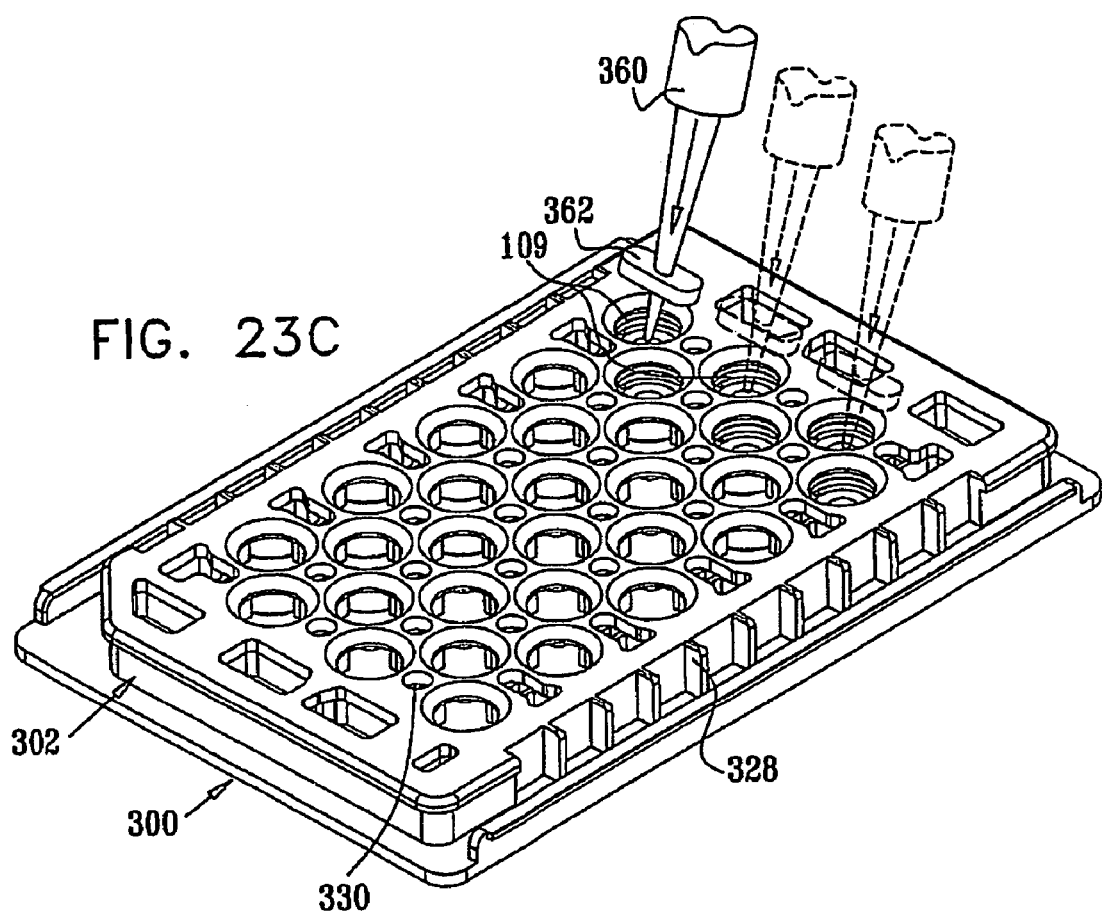

Reference is now made to FIGS. 23A, 23B and 23C, which are simplified illustrations of the pre-microscopy multi-sample holder of FIGS. 21A–22B respectively associated with a suction device and pipettes. Turning to FIG. 23A, it is seen that the suction device, here designated by reference numeral 350, comprises a manifold 352 coupled via a conduit 354 to a source of suction. The manifold 352 preferably communicates with a linear array of uniformly spaced needles 356. A pair of spacers 358 is attached to the manifold 352 or is integrally formed therewith. Spacers 358 are arranged in line with the linear array of needles 356. These spacers 358 preferably engage floor 320 of base 300 at intermediate adjacent positioning guides 328 on opposite sides of the top element 302. The spacers 358 ensure that the needles 356 do not engage electron beam permeable, fluid impermeable, membrane, designated by reference numeral 110 in FIGS. 1A–10.

As seen in FIG. 23A, the container support locations 306 are arranged in staggered rows on the pre-microscopy multi-sample holder. Thus, as seen in FIG. 23B, in every row, three of the needles 356 engage apertures 324, two of the needles 356 engage dummy apertures 330 and one of the needles 356 engages the part of an aperture 332 which serves as a dummy aperture.

FIG. 23C illustrates addition of liquid to individual sample dishes 109 by means of conventional pipettes 360. Collar elements 362 may be provided for use in association with pipettes 360 to prevent inadvertent engagement of the pipettes with electron beam permeable, fluid impermeable, membrane, designated by reference numeral 110 in FIGS. 1A–10.

Figure 24A:
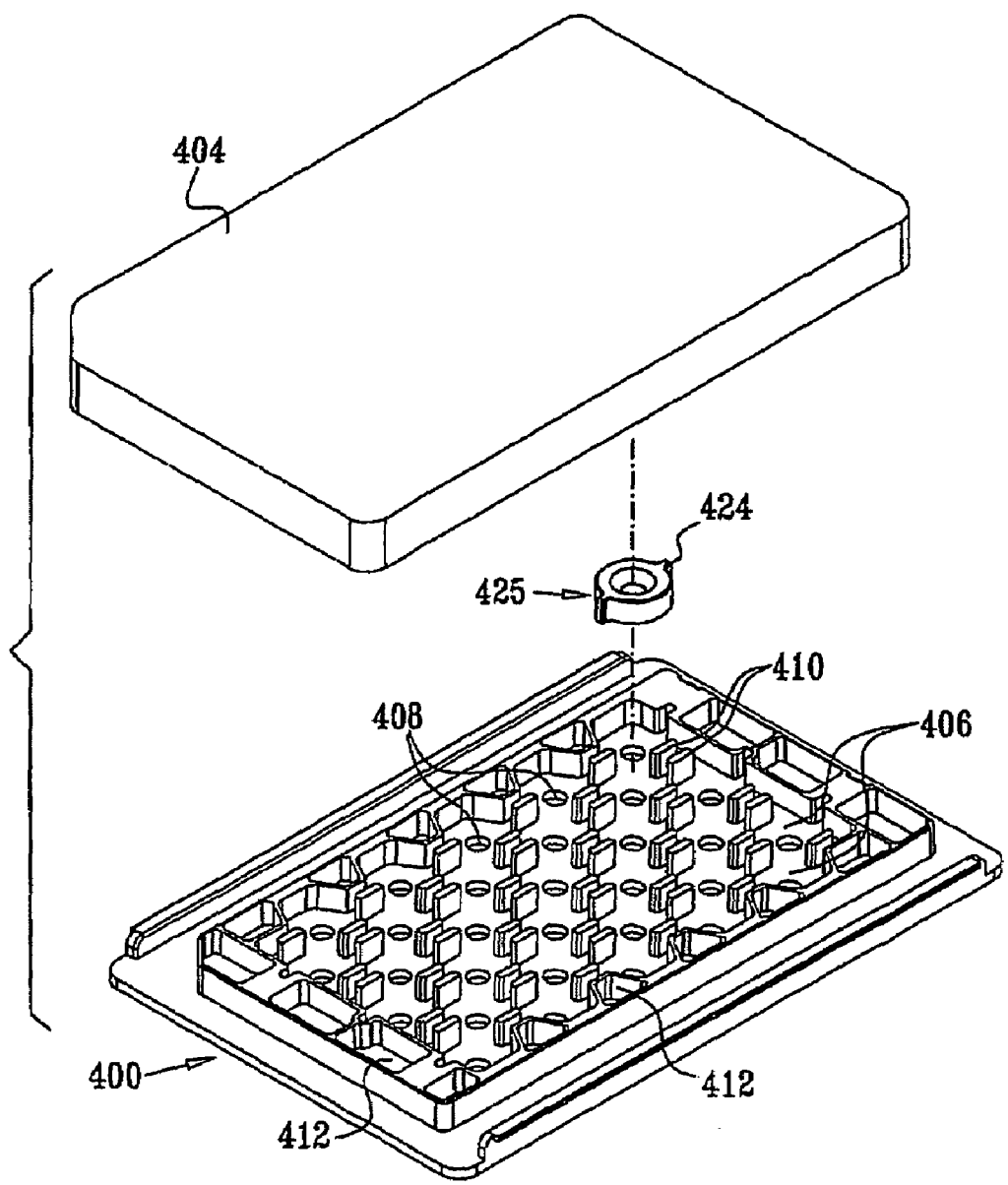
Figure 24B:
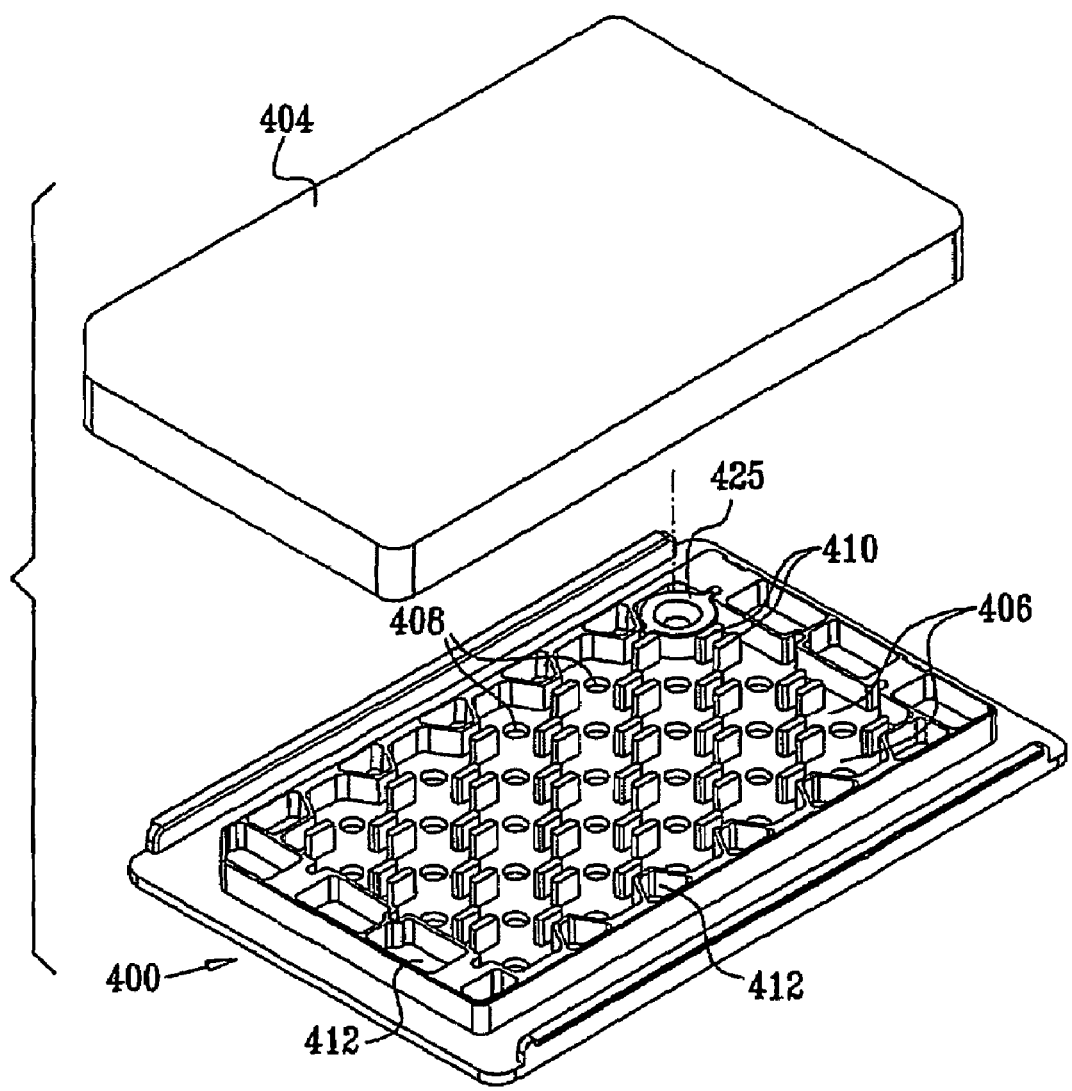

Reference is now made to FIGS. 24A, 24B and 24C, which are simplified illustrations of a microscopy multi-sample holder in use with a SEM compatible sample dish of the type shown in FIGS. 1A–10. As seen in FIG. 24A, the microscopy multi-sample holder preferably comprises a base 400 and a sealing cover 404. The base 400 is preferably injection molded of a plastic material and defines an array of dish support locations 406. Each dish support location 406 is preferably defined by an aperture 408 through which SEM microscopy may take place. Adjacent to each aperture 408 there is preferably formed a pair of mutually aligned pairs of upstanding mutually spaced protrusions 410 arranged to receive protrusions 424 on sample dishes 425. Sample dishes 425 may be generally identical to sample dishes 109, shown in FIGS. 3A–5B, but do not require any threading or other attachment mechanism.

Base 400 may define a plurality of liquid reservoirs 412 which are adapted to hold liquid used to maintain a desired level of humidity in the interior of the microscopy multi-sample holder.

Sealing cover 404 is arranged for individual sealing engagement with each of sample dishes 425. Preferably sealing cover 404 is provided on the underside thereof with an array of O-rings 426, shown in FIG. 24C, sealed thereto and arranged so as to sealingly engage a top rim surface of each of sample dishes 425, when the sealing cover 404 is in place, preferably in removable snap-fit engagement with base 400.

FIG. 24B shows the apparatus of FIG. 24A with one sample dish 425 positioned at a dish support location 406 in base 400. FIG. 24C shows sealing cover 404 in snap fit engagement with base 400, thereby providing individual sealing of each of sample dishes 425 by means of O-ring 426 and a portion of sealing cover 404 circumscribed thereby.

Figure 25A:
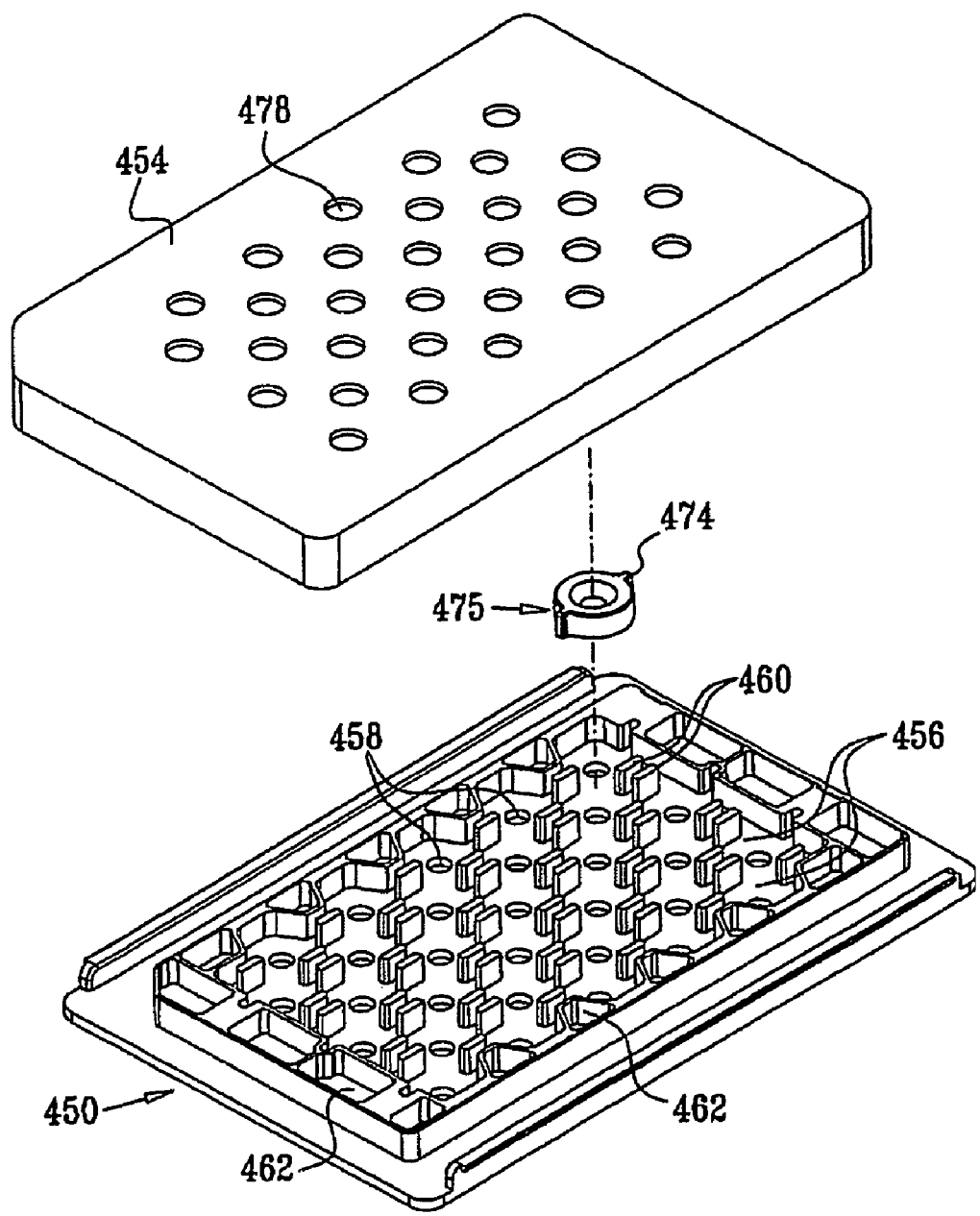
Figure 25B:
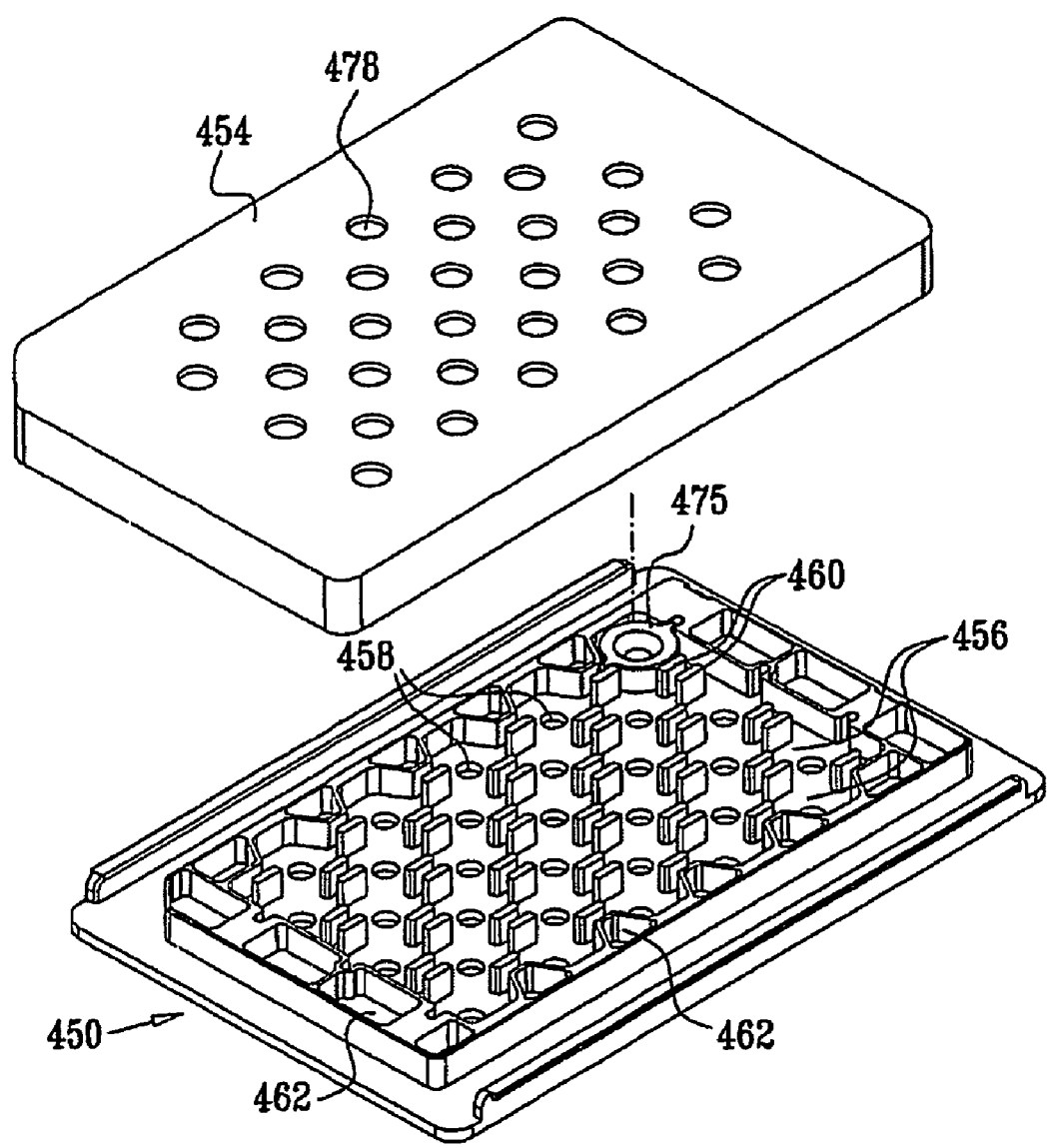

Reference is now made to FIGS. 25A, 25B and 25C, which are simplified illustrations of a microscopy multi-sample holder in use with a SEM compatible sample dish of the type shown in FIGS. 11A–20. As seen in FIG. 25A, the microscopy multi-sample holder preferably comprises a base 450 and a sealing cover 454. The base 450 is preferably injection molded of a plastic material and defines an array of dish support locations 456. Each dish support location 456 is preferably defined by an aperture 458 through which SEM microscopy may take place. Adjacent to each aperture 458 there is preferably formed a pair of mutually aligned pairs of upstanding mutually spaced protrusions 460 arranged to receive protrusions 474 on sample dishes 475. Sample dishes 475 may be generally identical to sample dishes 209, shown in FIGS. 13A–15B, but do not require any threading or other attachment mechanism.

Base 450 may define a plurality of liquid reservoirs 462 which are adapted to hold liquid used to maintain a desired level of humidity in the interior of the microscopy multi-sample holder.

Sealing cover 454 is arranged for individual sealing engagement of each of sample dishes 475 with a diaphragm 476, shown in FIG. 25C, which is sealingly mounted over an aperture 478 formed in sealing cover 454. Preferably an array of diaphragms 476, which may be identical to diaphragms 218 described hereinabove with reference to FIGS. 11A–20, is provided on the underside of sealing cover 454. The individual diaphragms 476 are arranged so as to sealingly engage a top rim surface of each of sample dishes 475, when the sealing cover 454 is in place, preferably in removable snap-fit engagement with base 450.

FIG. 25B shows the apparatus of FIG. 25A with one sample dish 475 positioned at a dish support location 456 in base 450. FIG. 25C shows sealing cover 454 in snap fit engagement-with base 450, thereby providing individual sealing of each of sample dishes 475 by means of diaphragm 476.

Figure 26A:
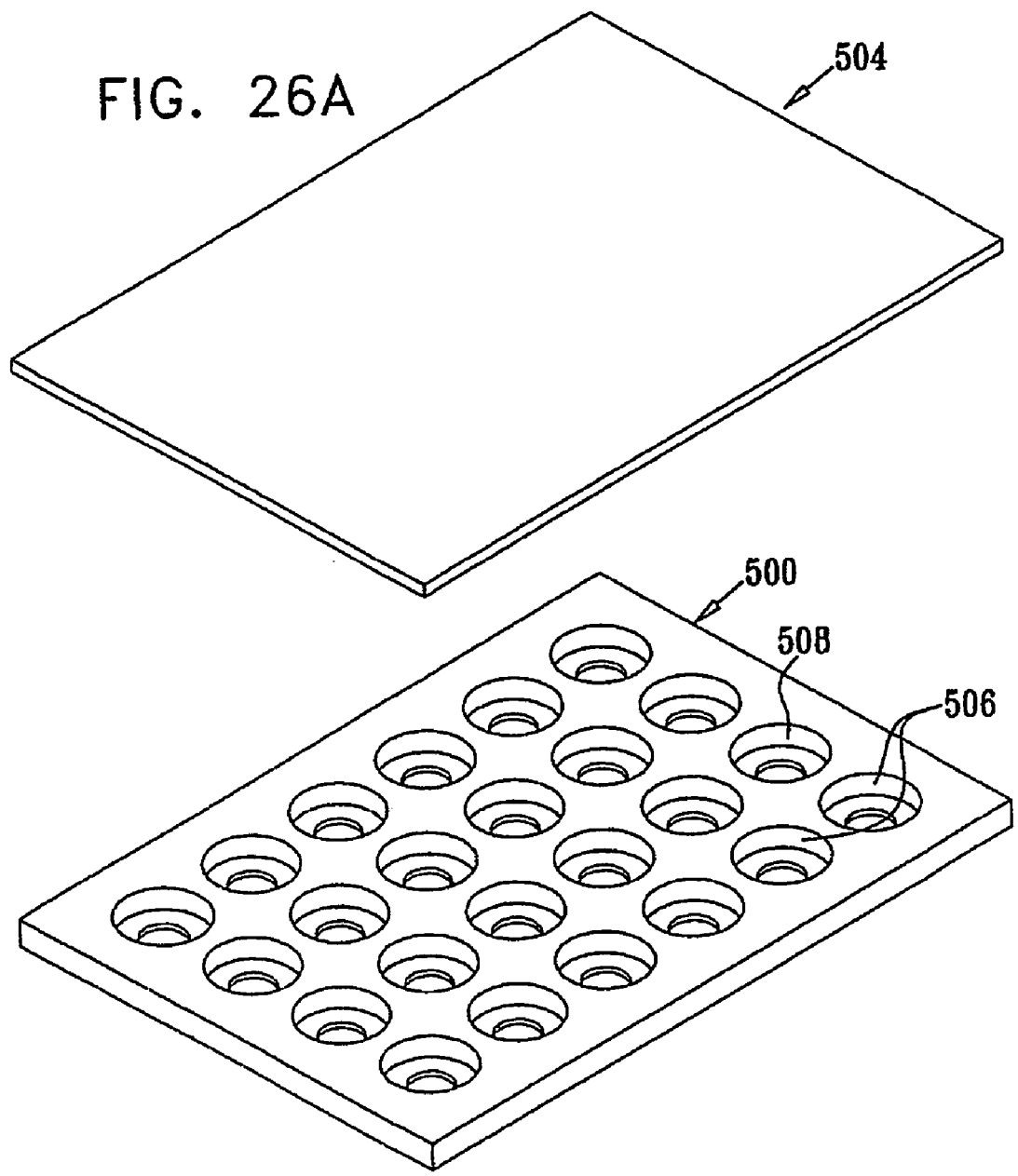
FIGS. 26A and 26B are simplified illustrations of a microscopy multi-sample holder defining a plurality of SEM compatible sample containers in accordance with a preferred embodiment of the present invention.
Figure 26B:
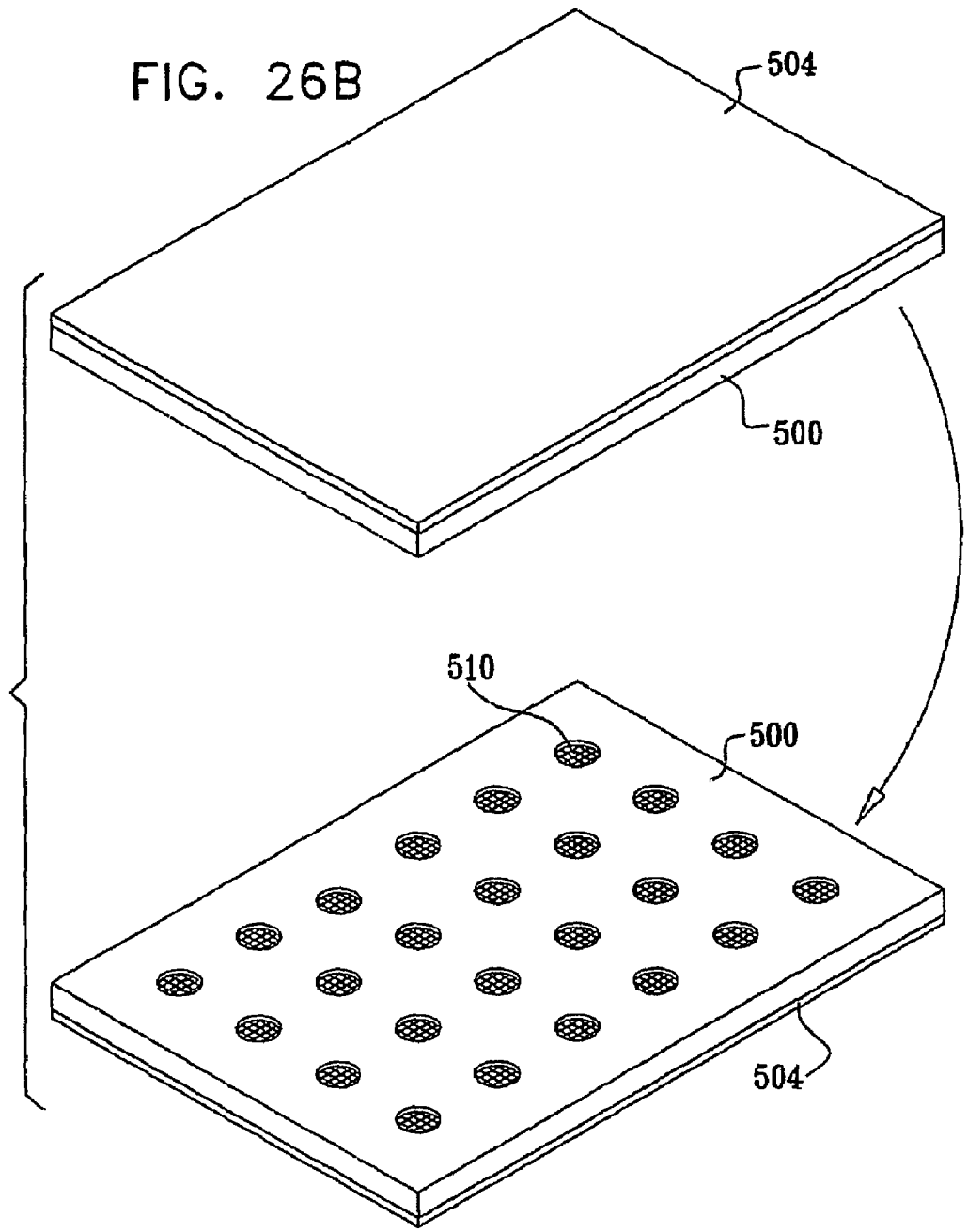

Reference is now made to FIGS. 26A and 26B, which are simplified illustrations of a microscopy multi-sample holder defining a plurality of SEM compatible sample containers in accordance with a preferred embodiment of the present invention. As seen in FIG. 26A, the microscopy multi-sample holder preferably comprises a base 500 and a sealing cover 504. The base 500 is preferably injection molded of a plastic material and defines an array of sample containers 506. Each sample container 506 preferably includes an aperture 508 through which SEM microscopy may take place. An electron beam permeable, fluid impermeable, membrane 510, shown in FIG. 26B, is sealed over each aperture 508. Membrane 510 is preferably identical to membrane 110 described hereinabove with reference to FIGS. 1A–10. Sealing cover 504 preferably is arranged for individual sealing engagement with each of sample containers 506.

FIG. 26B shows the apparatus of FIG. 26A in sealed engagement, thereby providing individual sealing of each of sample containers 506.

Reference is now made to FIGS. 27A and 27B, which are simplified illustrations of a microscopy multi-sample holder defining a plurality of SEM compatible sample containers in accordance with a preferred embodiment of the present invention As seen in FIG. 27A, the microscopy multi-sample holder preferably comprises a base 550 and a sealing cover 554. The base 550 is preferably injection molded of a plastic material and defines an array of sample containers 556. Each sample container 556 preferably includes an aperture 558 through which SEM microscopy may take place. An electron beam permeable, fluid impermeable, membrane 560, shown in FIG. 27B, is sealed over each aperture 558. Membrane 560 is preferably identical to membrane 210 described hereinabove with reference to FIGS. 11A–20. Sealing cover 554, preferably a diaphragm formed of resilient sheet material such as silicon rubber of 0.2–0.3 mm in thickness and having a Shore hardness of about 50, is arranged for individual sealing engagement with each of sample containers 556.

FIG. 27B shows the apparatus of FIG. 27A in sealed engagement, thereby providing individual sealing of each of sample containers 556.

Figure 28:
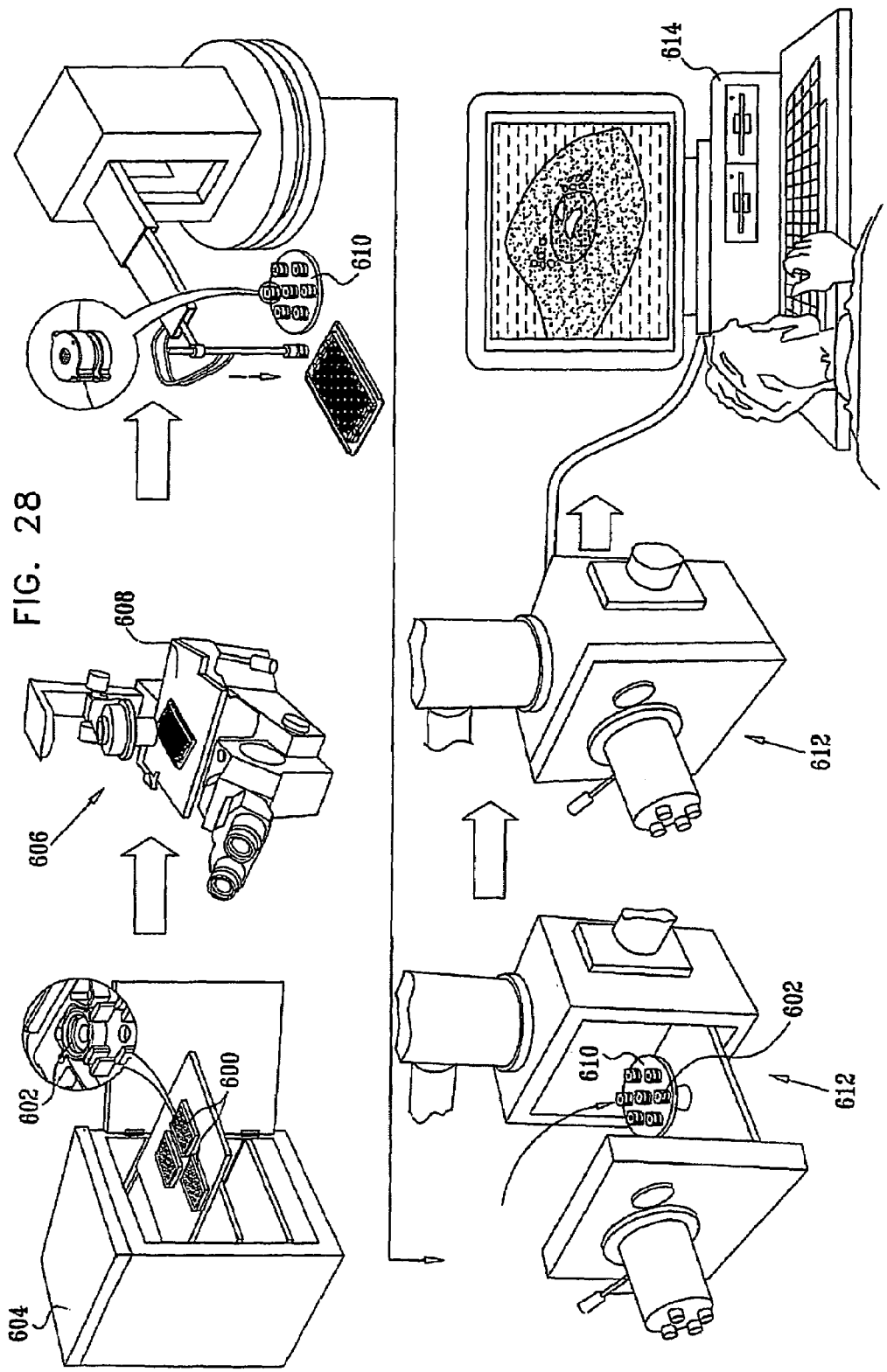
FIG. 28 is a simplified illustration of a SEM based sample inspection system constructed and operative in accordance with a preferred embodiment of the present invention.

Reference is now made to FIG. 28, which is a simplified illustration of a SEM based sample inspection system constructed and operative in accordance with a preferred embodiment of the present invention. As seen in FIG. 28, a plurality of pre-microscopy multi-sample holders 600, each containing a multiplicity of SEM compatible sample containers 602 of the type shown in FIGS. 1A–20, is shown in an incubator 604. Preferably, light microscopy inspection of the samples in containers 602 is carried out while the containers 602 are mounted in holder 600, as indicated at reference numeral 606, in order to identify samples of interest. Preferably an inverted light microscope 608 is employed for this purpose.

Preferably automated positioning systems, such as robotic arms, as shown, are used for conveying the pre-microscopy multi-sample holders 600 and the containers 602 throughout the system, it being appreciated that manual intervention may be employed at one or more stages as appropriate.

Thereafter, individual containers 602 are removed from holders 600 and placed on a removable electron microscope specimen stage 610, which is subsequently introduced into a scanning electron microscope 612. The resulting image may be inspected visually by an operator and/or analyzed by conventional image analysis functionality, typically embodied in a computer 614.

Reference is now made to FIG. 29, which is a simplified illustration of a SEM based sample inspection system constructed and operative in accordance with another preferred embodiment of the present invention. As seen in FIG. 29, a plurality of microscopy multi-sample holders 650, each containing a multiplicity of SEM compatible sample dishes 652 of either of the types shown in FIGS. 24A–25C, is shown in an incubator 654. Preferably, light microscopy inspection of the samples in sample dishes 652 is carried out while the sample dishes are mounted in holder 650, as indicated at reference numeral 656, in order to identify samples of interest. Preferably an inverted light microscope 658 is employed for this purpose.

Preferably automated positioning systems, such as robotic arms, as shown, are used for conveying the microscopy multi-sample holders 650 containing sample dishes 652 throughout the system, it being appreciated-that manual intervention may be employed at one or more stages as appropriate.

Thereafter, holders 650 are placed on an electron microscope specimen stage 660, which is subsequently introduced into a scanning electron microscope 662. The resulting images may be inspected visually by an operator and/or analyzed by conventional image analysis functionality, typically embodied in a computer 664.

Reference is now made to FIG. 30, which is a simplified illustration of a SEM based sample inspection system constructed and operative in accordance with yet another preferred embodiment of the present invention. As seen in FIG. 30, a plurality of microscopy multi-sample holders 670, each defining a multiplicity of SEM compatible sample containers 672, as shown in any of FIGS. 26A–27B, is seen in an incubator 674. Preferably, light microscopy inspection of the samples in sample containers 672 is carried out holder-wise, as indicated at reference numeral 676, preferably in order to identify samples of interest. Preferably an inverted light microscope 678 is employed for this purpose.

Preferably automated positioning systems, such as robotic arms, as shown, are used for conveying the microscopy multi-sample holders 670 throughout the system, it being appreciated that manual intervention may be employed at one or more stages as appropriate.

Thereafter, holders 670 are placed on an electron microscope specimen stage 680, which is subsequently introduced into a scanning electron microscope 682. The resulting images may be inspected visually by an operator and/or analyzed by conventional image analysis functionality, typically embodied in a computer 684.

Reference is now made to FIGS. 31A–35B, which are oppositely facing simplified exploded view pictorial illustrations of a disassembled scanning electron microscope (SEM) compatible sample container constructed and operative in accordance with another preferred embodiment of the present invention. As seen in FIGS. 31A & 31B, the SEM compatible sample container comprises first and second threaded enclosure elements, respectively designated by reference numerals 1100 and 1102, arranged for enhanced ease and speed of closure. Enclosure elements 1100 and 1102 are preferably molded of plastic and coated with a conductive metal coating.

Figure 32A:
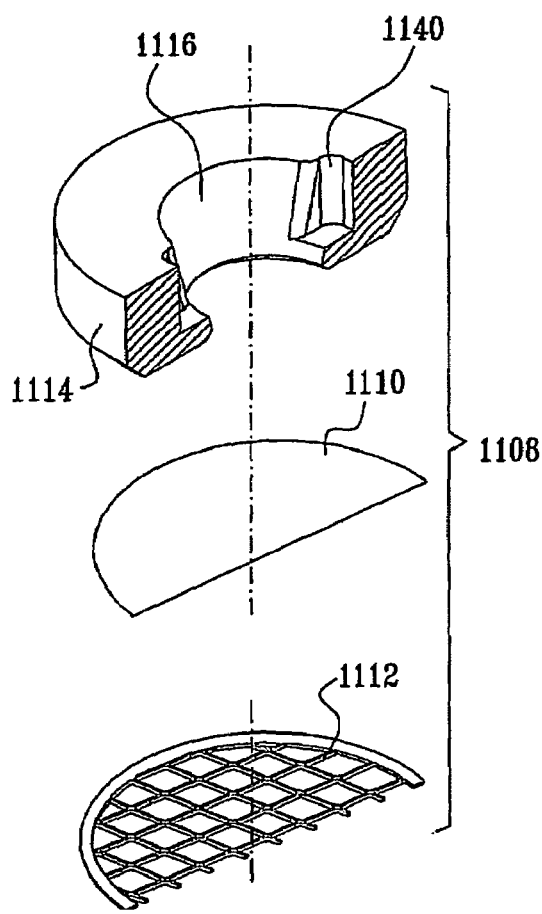
FIGS. 32A & 32B are oppositely facing simplified partially pictorial, partially sectional illustrations of a subassembly of the container of FIGS. 31A & 31B.
Figure 32B:
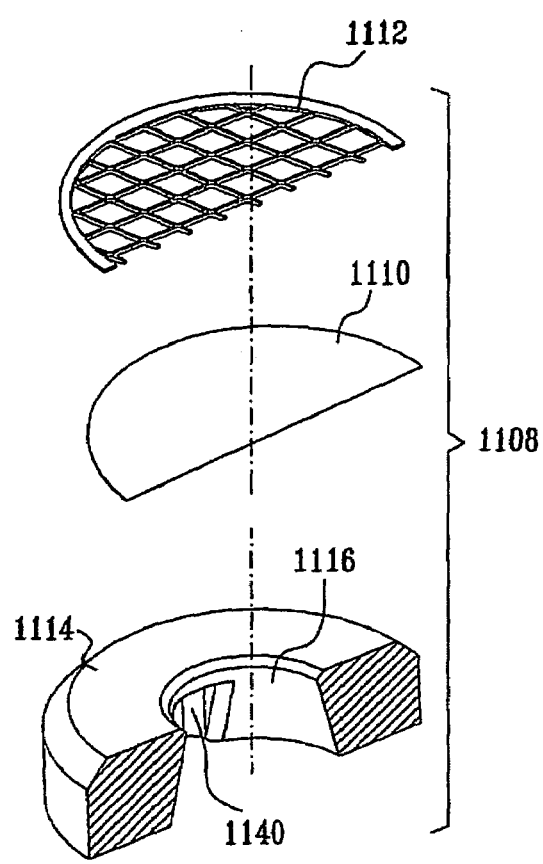
Figure 33A:
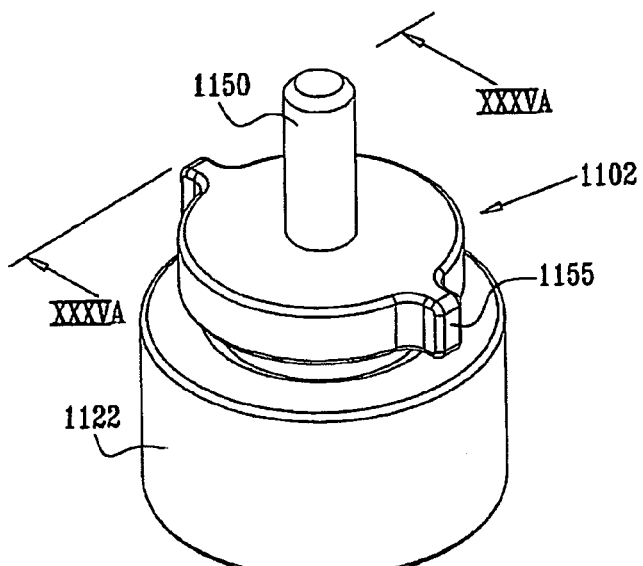
FIGS. 33A & 33B are oppositely facing simplified exploded view pictorial illustrations of the SEM compatible sample container of FIGS. 31A–32B in a partially assembled state.
Figure 33B:
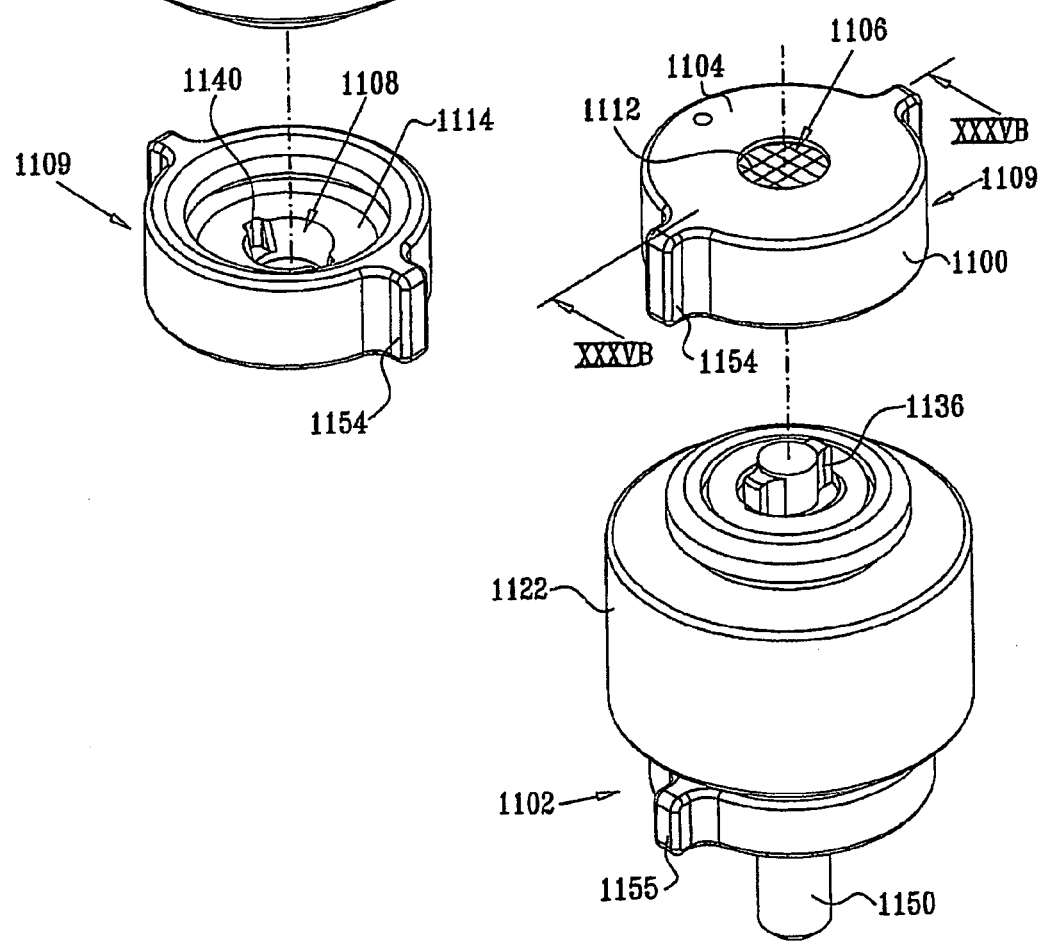

First enclosure element 1100 preferably defines a sample enclosure and has a base surface 1104 having a generally central aperture 1106. An electron beam permeable, fluid impermeable, membrane subassembly 1108, shown in detail in FIGS. 32A and 32B, is seated inside enclosure element 1100 against and over aperture 1106, as shown in FIGS. 33A & 33B and 35A & 35B. A sample dish comprising subassembly 1108 suitably positioned in enclosure element 1100 is designated by reference numeral 1109, as shown in FIGS. 33A–35B.

Turning additionally to FIGS. 32A and 32B, it is seen that an electron beam permeable, fluid impermeable, membrane 1110, preferably a polyimide membrane, such as Catalog No. LWN00033, commercially available from Moxtek Inc. of Orem, Utah, U.S.A., is adhered, as by an adhesive, to a mechanically supporting grid 1112. Grid 1112, which is not shown to scale, is preferably Catalog No. BM 0090-01, commercially available from Buckbee-Mears of Cortland, N.Y., U.S.A., and the adhesive is preferably Catalog No. NOA61, commercially available from Norland Products Inc. of Cranbury, N.J., U.S.A. A sample enclosure defining ring 1114 is adhered to electron beam permeable, fluid impermeable, membrane 1110, preferably by an adhesive, such as Catalog No. NOA61, commercially available from Norland Products Inc. of Cranbury, N.J., U.S.A. Ring 1114 is preferably formed of PMMA (polymethyl methacrylate), such as Catalog No. 692106001000, commercially available from Irpen of Barcelona, Spain, and preferably defines a sample enclosure with a volume of approximately 20 microliters and a height of approximately 2 mm. Preferably ring 1114 is configured to define a sample enclosure 1116 having inclined walls.

A first O-ring 1118 is preferably disposed between an interior surface 1120 of second enclosure element 1102 and a connecting element 1122. Connecting element 1122 is preferably molded of plastic and coated with a conductive metal coating. A second O-ring 1123 is preferably disposed between connecting element 1122 and ring 1114 of subassembly 1108. O-rings 1118 and 1123 are operative, when enclosure elements 1100 and 1102 and connecting element 1122 are in tight threaded engagement, to obviate the need for the threaded engagement of elements 1100 and 1102 and connecting element 1122 to be a sealed engagement.

Connecting element 1122 preferably has a recess 1124. Connecting element 1122 is also formed with a protrusion 1126, seen in FIGS. 35A & 35B, protruding into recess 1124.

Figure 35A:
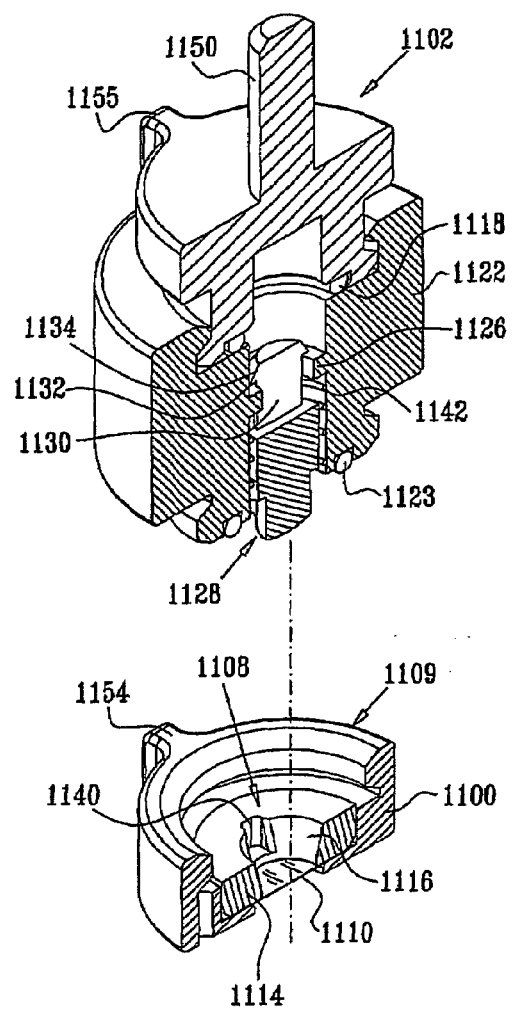
FIGS. 35A & 35B are oppositely facing simplified partially pictorial, partially sectional illustrations taken along lines XXXVA—XXXVA and XXXVB—XXXVB, respectively, in FIGS. 33A & 33B.
Figure 35B:
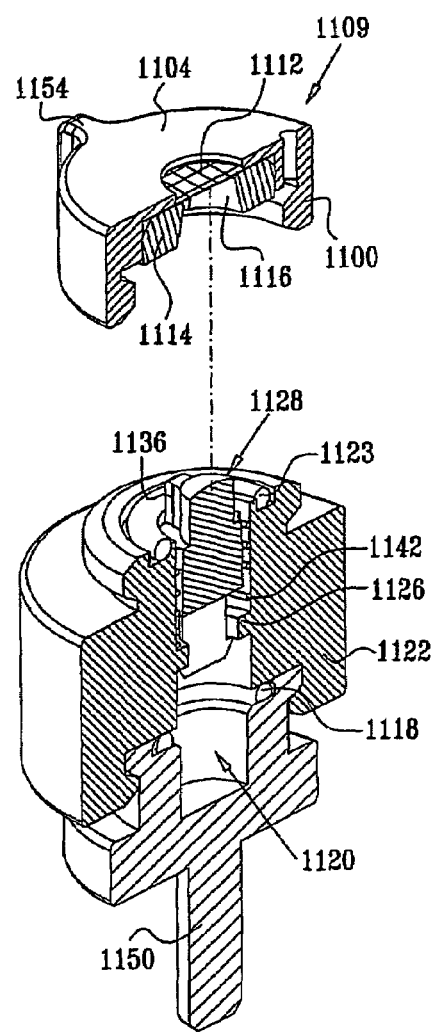

A positioner 1128 is preferably comprised of two upright flexible projections 1130, each with a ridge 1132 formed on an end 1134 of the projections 1130. Positioner 1128 is preferably molded of plastic. Projections 1130 press against each other when inserted into recess 1124 of connecting element 1122 and then snap back to an upright position once ridges 1132 are seated on the protrusion 1126 of connecting element 1122, as shown in FIGS. 35A & 35B.

Positioner 1128 is preferably also provided with respective radially extending positioning and retaining protrusions 1136 extending from a rim 1137. Positioning and retaining protrusions 1136 are seated in apertures 1140 formed in the inclined walls of sample enclosure 1116 of ring 1114 to prevent rotation of positioner 1128.

A coil spring 1142 is disposed on positioner 1128 between rim 1137 and ridges 1132 of projections 1130. Spring 1142 is preferably formed of hardened stainless steel.

The positioner 1128 and spring 1142 are operative to move a non-liquid sample up and against electron beam permeable, fluid impermeable, membrane 1110 when enclosure elements 1100 and 1102 and connecting element 1122 are in tight threaded engagement.

Second enclosure element 1102 is preferably formed with a generally central stub 1150, which is arranged to be seated in a suitable recess (not shown) in a specimen stage of a scanning electron microscope. It is a particular feature of the present invention that the container, shown in FIGS. 31A–40, is sized and operative with conventional stub recesses in conventional scanning electron microscopes and does not require any modification thereof whatsoever. It is appreciated that various configurations and sizes of stubs may be provided so as to fit various scanning election microscopes.

Figure 34A:
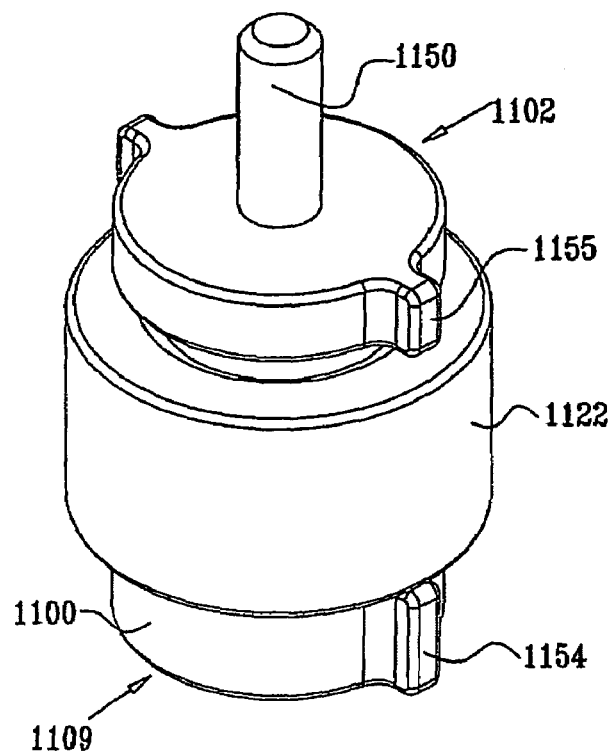
FIGS. 34A & 34B are oppositely facing simplified pictorial illustrations of the SEM compatible sample container of FIGS. 31A–33B in a fully assembled state.
Figure 34B:
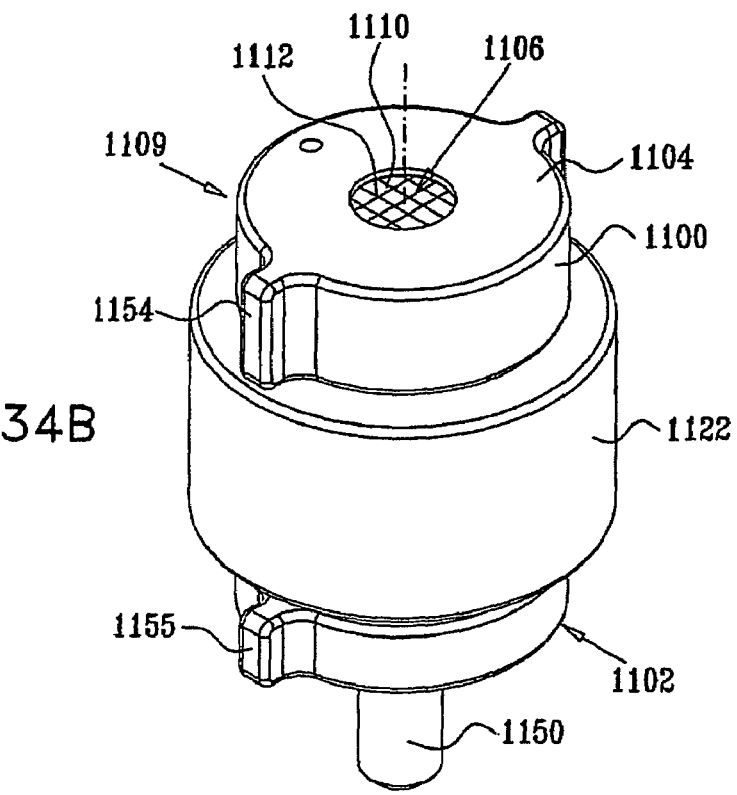

Enclosure elements 1100 and 1102 are preferably also provided with respective radially extending positioning and retaining protrusions 1154 and 1155, to enable the container to be readily seated in a suitable multi-container holder and also to assist users in threadably opening and closing the enclosure elements 1100 and 1102. Preferably, the mutual azimuthal positioning of the protrusions 1154 and 1155 on respective enclosure elements 1100 and 1102 is such that mutual azimuthal alignment therebetween indicates a desired degree of threaded closure therebetween, as shown in FIGS. 34A and 34B.

Figure 36A:
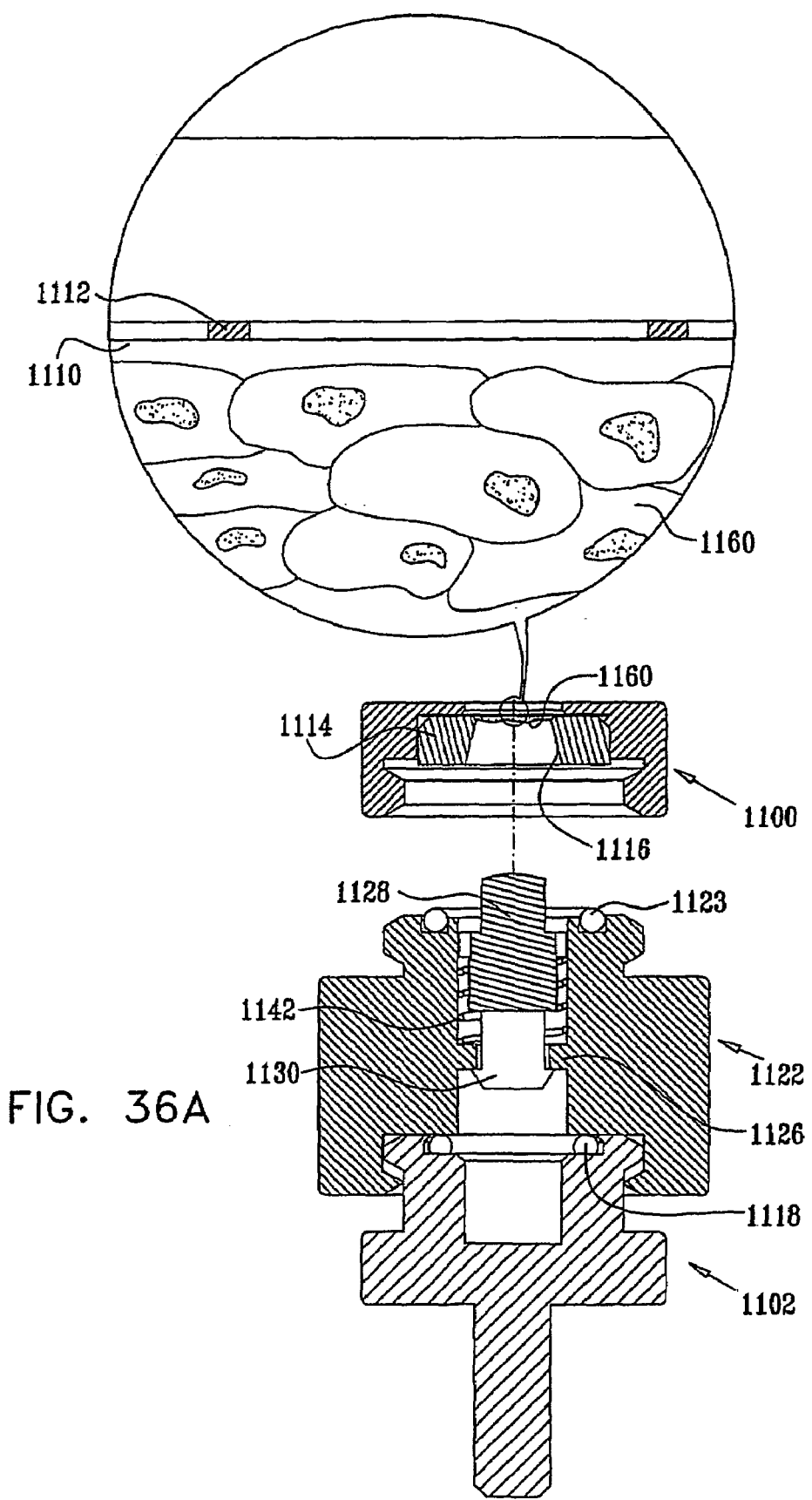
FIGS. 36A, 36B & 36C are three sectional illustrations showing the operative orientation of the SEM compatible sample container of FIGS. 31A–35B at three stages of operation.
Figure 36B:
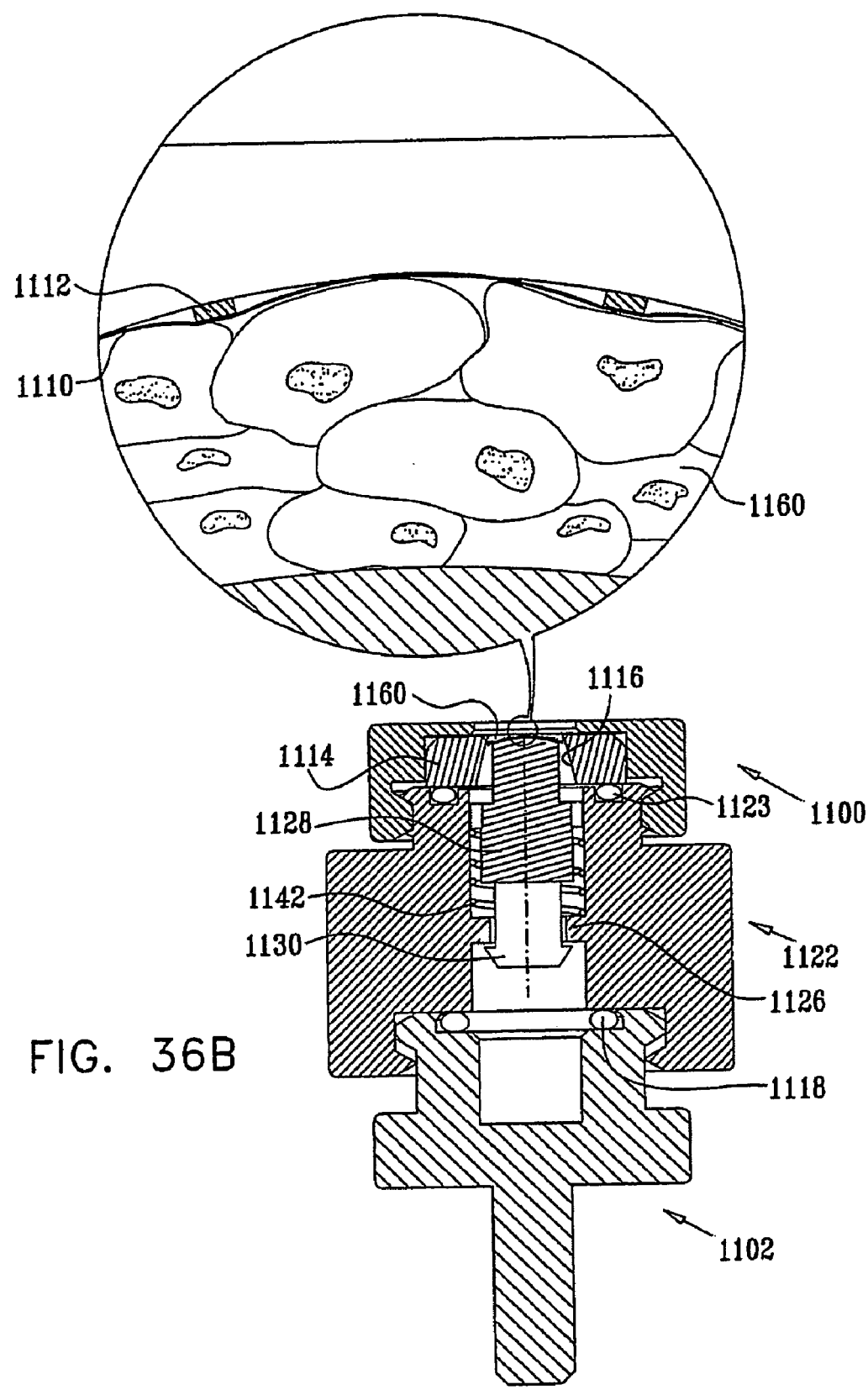
Figure 36C:
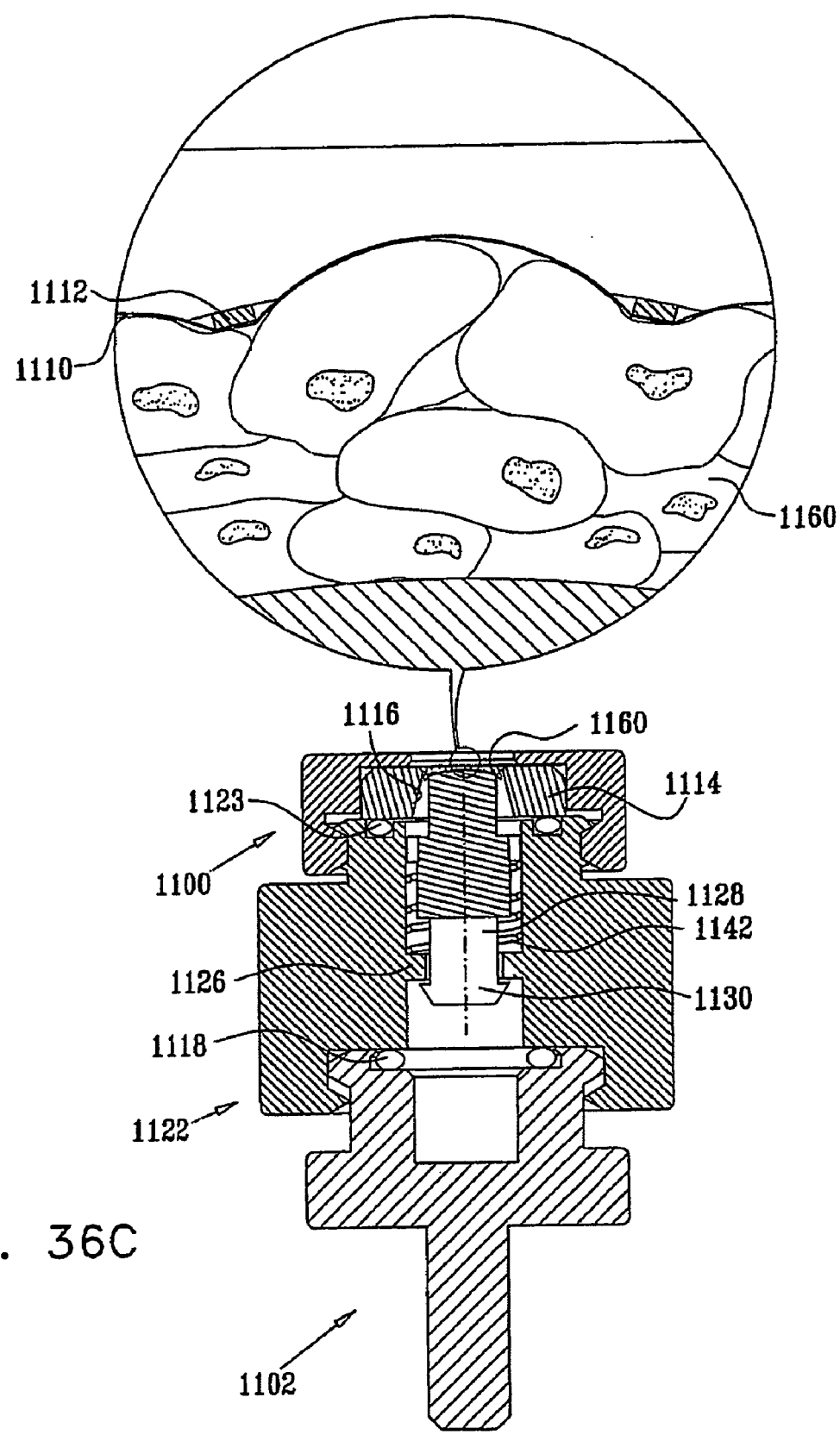

Reference is now made to FIGS. 36A, 36B & 36C, which are three sectional illustrations showing the operative orientation of the SEM compatible sample container of FIGS. 31A–35B at three stages of operation. FIG. 36A shows the container of FIGS. 31A–35B containing a tissue sample 1160 and arranged in the orientation shown in FIG. 31B, prior to threaded closure of enclosure elements 1100 and 1102 and connecting element 1122. The electron beam permeable, fluid impermeable, membrane 1110 is seen in FIG. 36A to be generally planar.

FIG. 36B shows the container of FIG. 36A immediately following full threaded engagement between enclosure elements 1100 and 1102 and connecting element 1122 producing sealing of the tissue sample enclosure 1116 from the ambient. It is noted that the tissue sample 1160 is in close contact with the electron beam permeable, fluid impermeable, membrane 1110 due to the force exerted by the positioner 1128. It is seen that the electron beam permeable, fluid impermeable, membrane 1110 and its supporting grid 1112 bow outwardly due to pressure buildup in the tissue sample enclosure 1116 as the result of sealing thereof in this manner.

FIG. 36C illustrates the container of FIG. 36B, when placed in an evacuated environment of a SEM, typically at a vacuum of $10^{-2}$–$10^{-6}$ millibars. It is seen that in this environment, the electron beam permeable, fluid impermeable, membrane 1110 and support grid 1112 bow outwardly to a greater extent than in the ambient environment of FIG. 36B and further that the electron beam permeable, fluid impermeable, membrane 1110 tends to be forced into and through the interstices of grid 1112 to a greater extent than occurs in the ambient environment of FIG. 36B.

Figure 37:
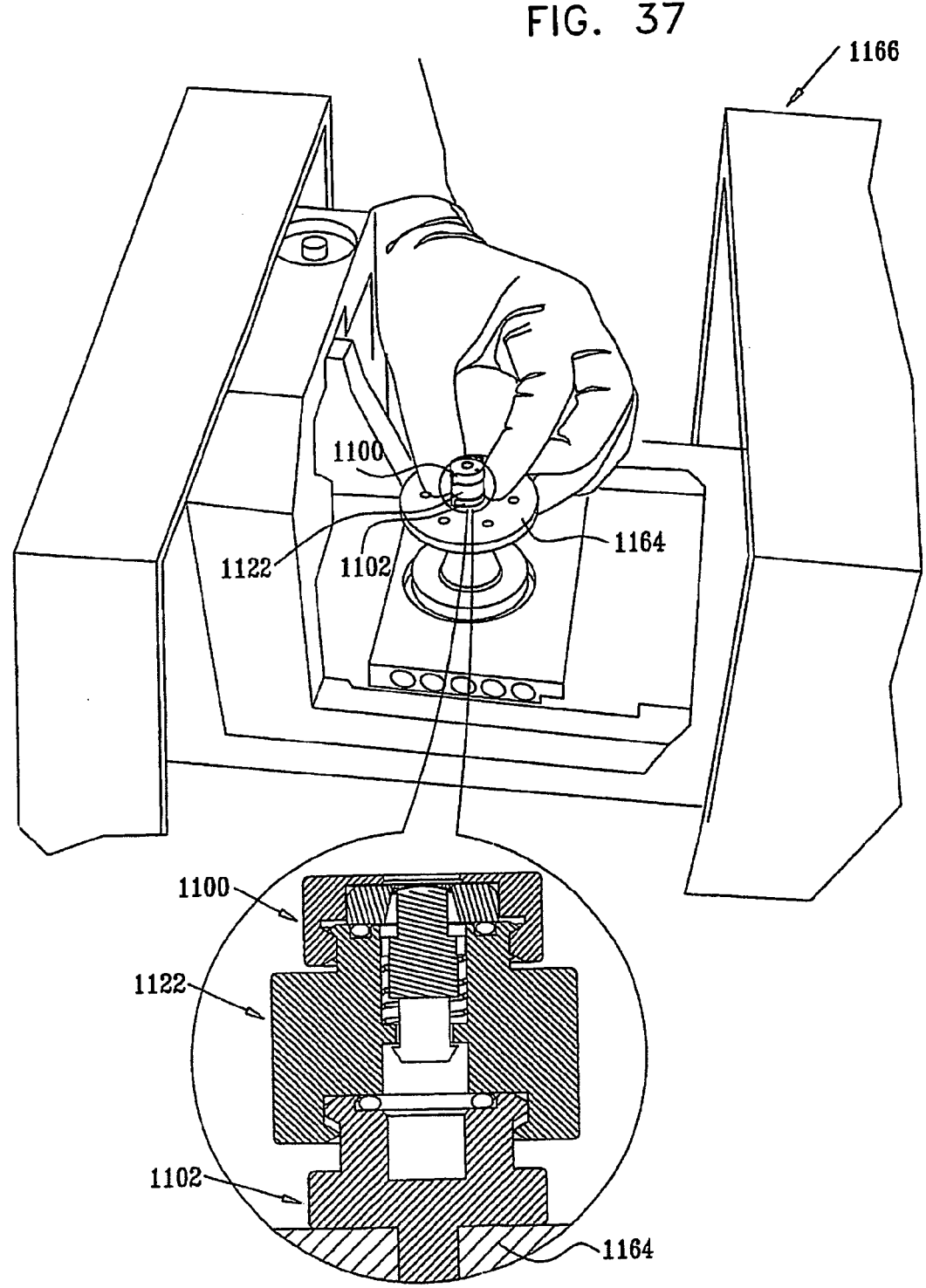
FIG. 37 is a simplified sectional and pictorial illustration of tissue containing samples and insertion into a SEM using the SEM compatible sample container of FIGS. 31A–36C.

Reference is now made to FIG. 37, which is a simplified sectional and pictorial illustration of the tissue containing sample and insertion into a SEM using the SEM compatible sample container of FIGS. 31A–36C.

FIG. 37 shows the closed container, in the orientation of FIG. 31B, being inserted onto a stage 1164 of a SEM 1166. It is appreciated that there exist SEMs wherein the orientation of the container is opposite to that shown in FIG. 37.

Figure 38A:
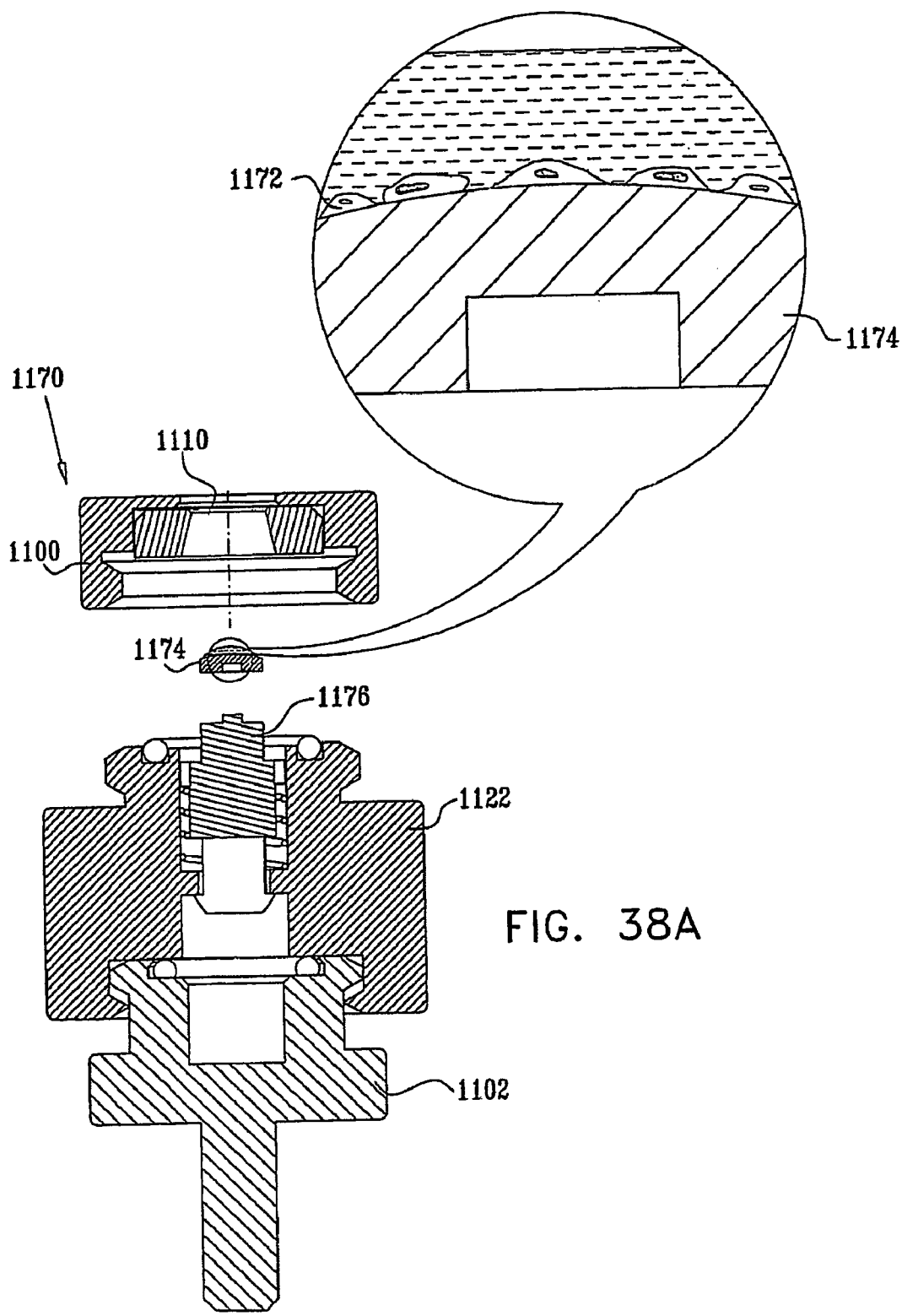
FIGS. 38A, 38B, 38C and 38D are simplified sectional illustrations showing the operative orientation of a SEM compatible sample container at various stages of operation and insertion into a SEM using the SEM compatible sample container constructed and operative in accordance with another preferred embodiment of the present invention.

Reference is now made to FIGS. 38A, 38B, 38C and 38D, which are four sectional illustrations showing the operative orientation of a variation of the SEM compatible sample container of FIGS. 31A–35B at four stages of operation. FIG. 38A shows a container 1170, identical to the container of FIGS. 31A–35B other than as specified hereinbelow, containing a sample including cells 1172 grown on a cell growth platform 1174 and arranged in the orientation shown in FIG. 31B, prior to threaded closure of enclosure elements 1100 and 1102 and connecting element 1122. The electron beam permeable, fluid impermeable, membrane 1110 is seen in FIG. 38A to be generally planar. Cell growth platform 1174 is removably mounted onto a suitably configured positioner 1176, which corresponds to positioner 1128 in the embodiment of FIGS. 31A–37. Typically, the cells are grown onto cell growth platform 1174 while platform 1174 is not mounted onto positioner 1176. The mounting of platform 1174 onto positioner 1176 typically occurs just before SEM inspection takes place.

Figure 38B:
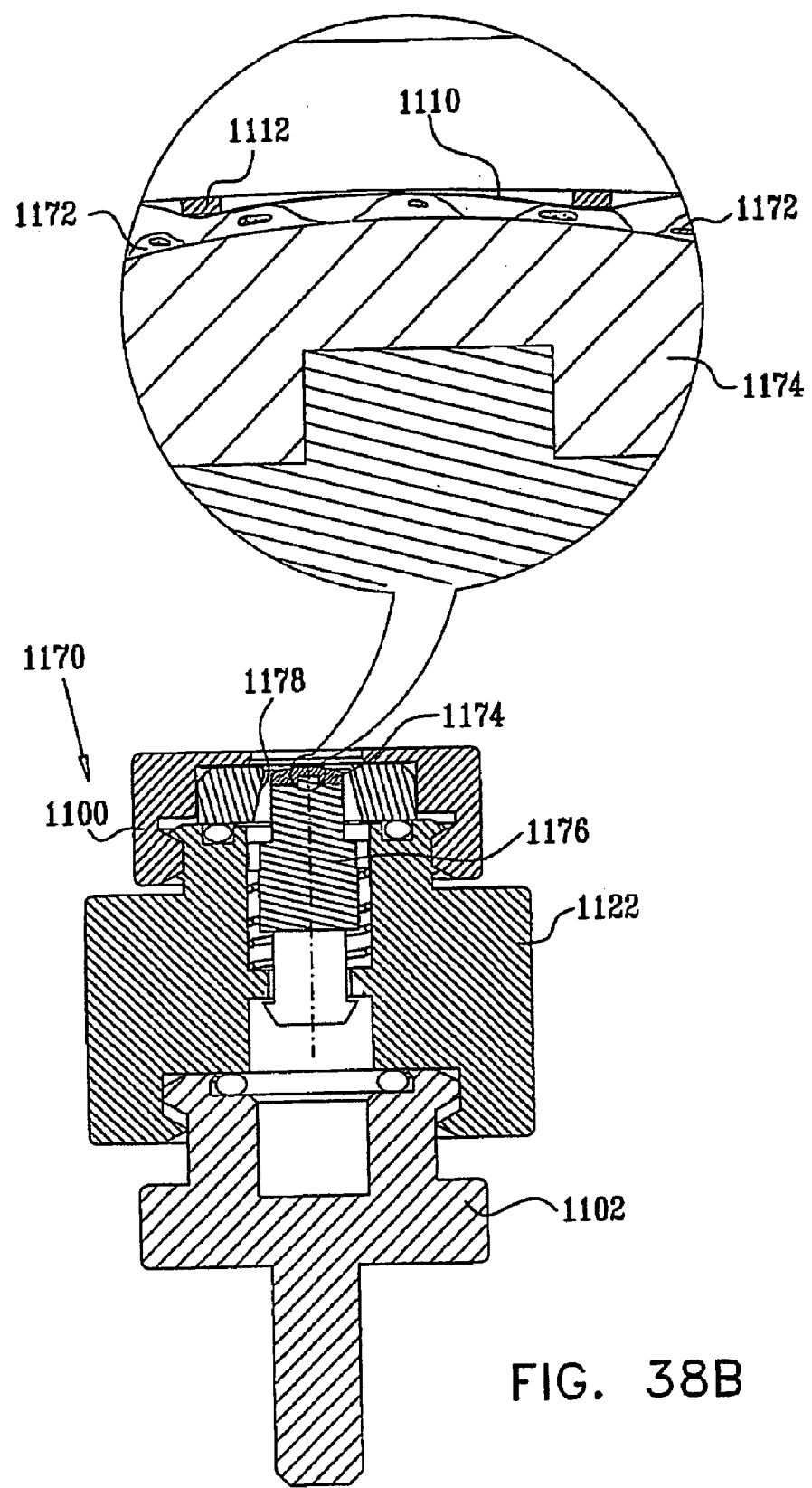

FIG. 38B shows the container of FIG. 38A immediately following full threaded engagement between enclosure elements 1100 and 1102 and connecting element 1122 producing sealing of a cell sample enclosure, here designated by reference numeral 1178, from the ambient. It is noted that the sample containing cells 1172 is in close contact with the electron beam permeable, fluid impermeable, membrane 1110 due to the force exerted by the positioner 1176. It is seen that the electron beam permeable, fluid impermeable, membrane 1110 and its supporting grid 1112 bow outwardly due to pressure buildup in the cell sample enclosure 1178 as the result of sealing thereof in this manner.

Figure 38C:
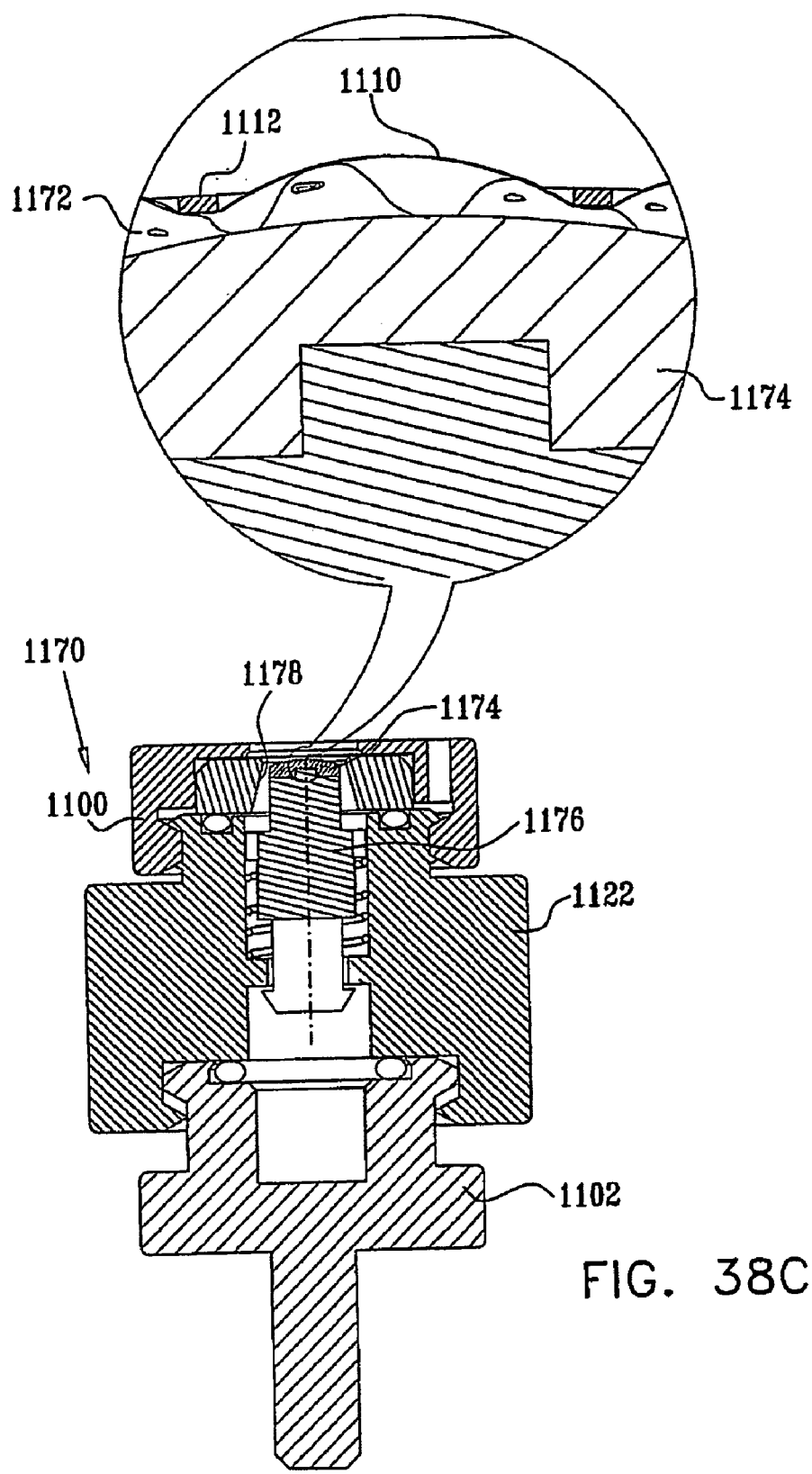

FIG. 38C illustrates the container of FIG. 38B, when placed in an evacuated environment of a SEM, typically at a vacuum of $10^{-2}$–$10^{-6}$ millibars. It is seen that in this environment, the electron beam permeable, fluid impermeable, membrane 1110 and support grid 1112 bow outwardly to a greater extent than in the ambient environment of FIG. 38B and further that the electron beam permeable, fluid impermeable, membrane 1110 tends to be forced into and through the interstices of grid 1112 to a greater extent than occurs in the ambient environment of FIG. 38B.

Figure 38D:
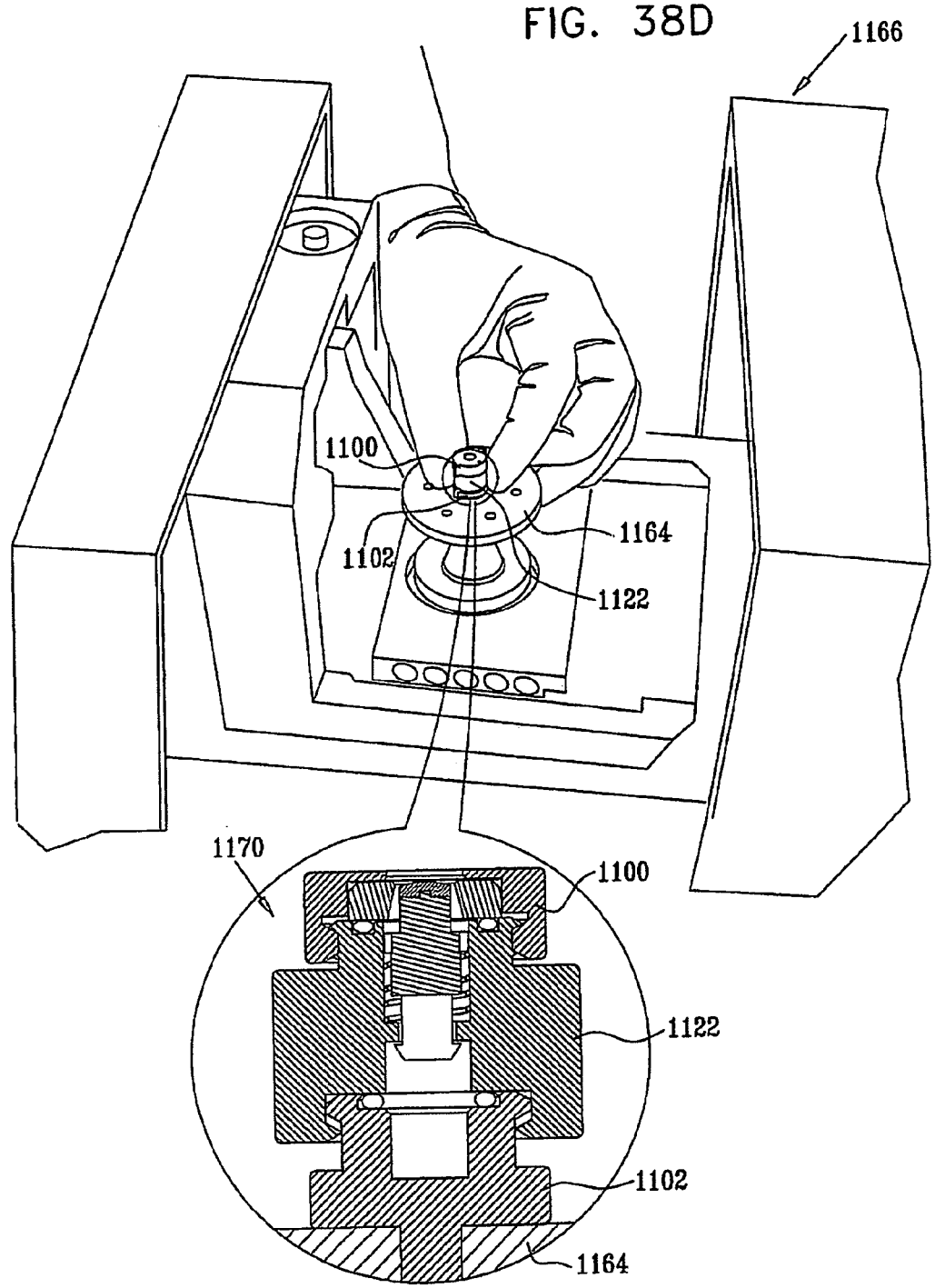

FIG. 38D shows the closed container 1170, in the orientation of FIG. 31B, being inserted onto stage 1164 of SEM 1166. It is appreciated that there exist SEMs wherein the orientation of the container is opposite to that shown in FIG. 38D.

Figure 39:
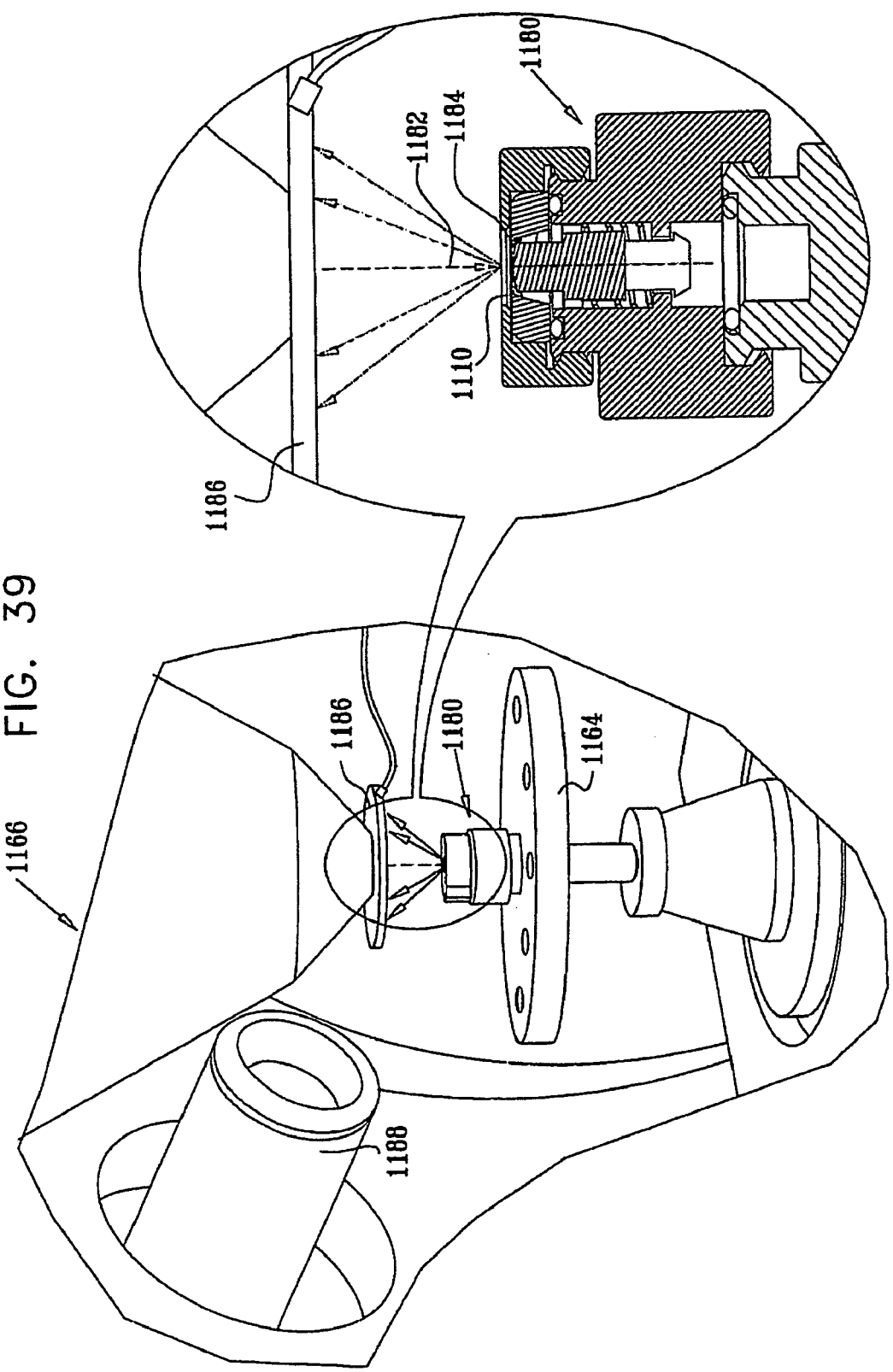
FIG. 39 is a simplified pictorial and sectional illustration of a SEM inspection of a sample using the SEM compatible sample container of FIGS. 31A–37.

Reference is now made to FIG. 39, which is a simplified pictorial and sectional illustration of SEM inspection of a sample using the SEM compatible sample container of FIGS. 31A–37. As seen in FIG. 39, the container, here designated by reference numeral 1180, is shown positioned on stage 1164 of SEM 1166 such that an electron beam 1182, generated by the SEM, passes through electron beam permeable, fluid impermeable, membrane 1110 and impinges on a tissue containing sample 1184 within container 1180. Backscattered electrons from sample 1184 pass through electron beam permeable, fluid impermeable, membrane 1110 and are detected by a detector 1186, forming part of the SEM. One or more additional detectors, such as a secondary electron detector 1188, may also be provided. An X-ray detector (not shown) may also be provided for detecting X-ray radiation emitted by the sample 1184 due to electron beam excitation thereof.

Reference is now made additionally to FIG. 40, which schematically illustrates some details of the electron beam interaction with the sample 1184 in container 1180 in accordance with a preferred embodiment of the present invention. It is noted that the present invention enables high contrast imaging of features which are distinguished from each other by their average atomic number, as illustrated in FIG. 40. In FIG. 40 it is seen that nucleoli 1190, having a relatively high average atomic number, backscatter electrons more than the surrounding nucleoplasm 1192.

It is also noted that in accordance with a preferred embodiment of the present invention, imaging of the interior of the sample to a depth of up to approximately 2 microns is achievable for electrons having an energy level of less than 50 KeV, as seen in FIG. 40, wherein nucleoli 1190 disposed below electron beam permeable, fluid impermeable, membrane 1110 are imaged.

Reference is now made to FIGS. 41A–45B, which are oppositely facing simplified exploded view pictorial illustrations of a disassembled scanning electron microscope (SEM) compatible sample container constructed and operative in accordance with another preferred embodiment of the present invention. As seen in FIGS. 41A & 41B, the SEM compatible sample container comprises first and second threaded enclosure elements, respectively designated by reference numerals 1200 and 1202, arranged for enhanced ease and speed of closure. Enclosure elements 1200 and 1202 are preferably molded of plastic and coated with a conductive metal coating.

Figure 42A:
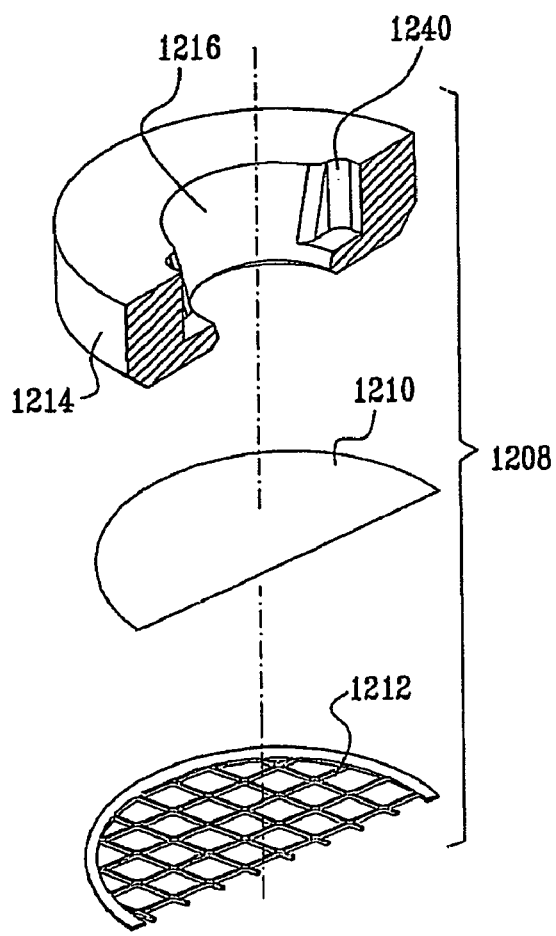
FIGS. 42A & 42B are oppositely facing simplified partially pictorial, partially sectional illustrations of a subassembly of the container of FIGS. 41A & 41B.
Figure 42B:
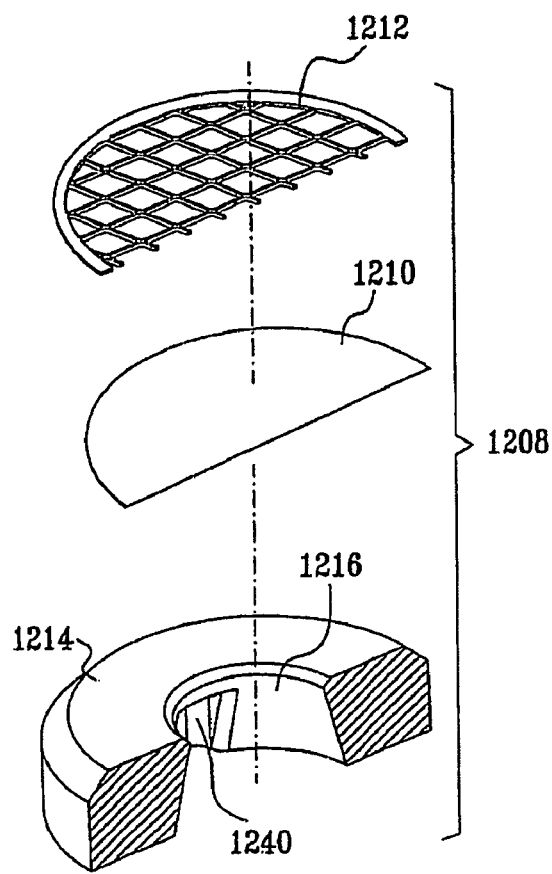
Figure 43A:
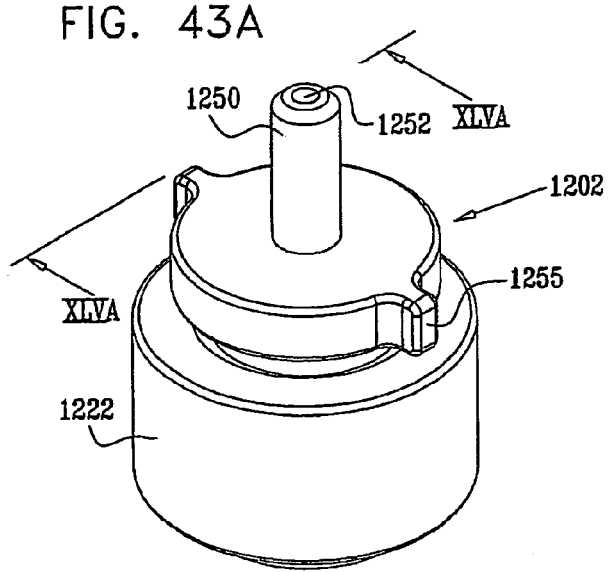
FIGS. 43A & 43B are oppositely facing simplified exploded view pictorial illustrations of the SEM compatible sample container of FIGS. 41A–42B in a partially assembled state.
Figure 43B:
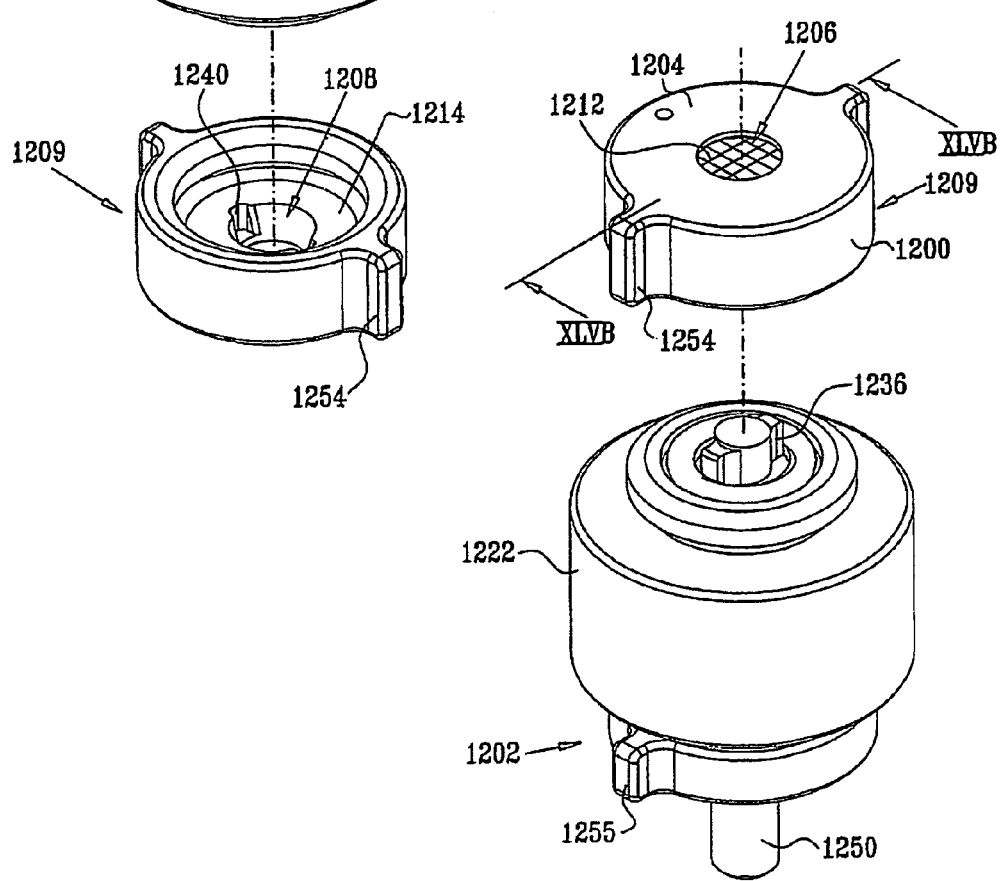

First enclosure element 1200 preferably defines a sample enclosure and has a base surface 1204 having a generally central aperture 1206. An electron beam permeable, fluid impermeable, membrane subassembly 1208, shown in detail in FIGS. 42A and 42B, is seated inside enclosure element 1200 against and over aperture 1206, as shown in FIGS. 43A & 43B and 45A & 45B. A sample dish comprising subassembly 1208 suitably positioned in enclosure element 1200 is designated by reference numeral 1209, as shown in FIGS. 43A–45B.

Turning additionally to FIGS. 42A and 42B, it is seen that an electron beam permeable, fluid impermeable, membrane 1210, preferably a polyimide membrane, such as Catalog No. LWN00033, commercially available from Moxtek Inc. of Orem, Utah, U.S.A., is adhered, as by an adhesive, to a mechanically supporting grid 1212. Grid 1212, which is not shown to scale, is preferably Catalog No. BM 0090-01, commercially available from Buckbee-Mears of Cortland, N.Y., U.S.A., and the adhesive is preferably Catalog No. NOA61, commercially available from Norland Products Inc. of Cranbury, N.J., U.S.A. A sample enclosure defining ring 1214 is adhered to electron beam permeable, fluid impermeable, membrane 1210, preferably by an adhesive, such as Catalog No. NOA61, commercially available from Norland Products Inc. of Cranbury, N.J., U.S.A. Ring 1214 is preferably formed of PMMA (polymethyl methacrylate), such as Catalog No. 692106001000, commercially available from Irpen of Barcelona, Spain, and preferably defines a sample enclosure with a volume of approximately 20 microliters and a height of approximately 2 mm. Preferably ring 1214 is configured to define a sample enclosure 1216 having inclined walls.

A diaphragm 1218 is preferably integrally formed of an O-ring portion 1220 to which is sealed an expandable sheet portion 1221. The diaphragm 1218 is preferably disposed between an interior surface 1219 of second enclosure element 1202 and a connecting element 1222. Connecting element 1222 is preferably molded of plastic and coated with a conductive metal coating. The diaphragm 1218 is preferably molded of silicon rubber having a Shore hardness of about 50 and the sheet portion 1221 preferably has a thickness of 0.2–0.3 mm.

An O-ring 1223 is preferably disposed between connecting element 1222 and ring 1214 of subassembly 1208. Diaphragm 1218 and O-ring 1223 are operative, when enclosure elements 1200 and 1202 and connecting element 1222 are in tight threaded engagement, to obviate the need for the threaded engagement of elements 1200 and 1202 and connecting element 1222 to be a sealed engagement and to provide dynamic and static pressure relief.

Connecting element 1222 preferably has a central recess 1224. Connecting element 1222 is also formed with a protrusion 1226, seen in FIGS. 45A & 45B, protruding into recess 1224.

A positioner 1228 is preferably comprised of two upright flexible projections 1230, each with a ridge 1232 formed on an end 1234 of the projections 1230. Positioner 1128 is preferably molded of plastic. Projections 1230 press against each other when inserted into recess 1224 of connecting element 1222 and then snap back to an upright position once ridges 1232 are seated on the protrusion 1226 of connecting element 1222, as shown in FIGS. 45A & 45B.

Positioner 1228 is preferably also provided with respective radially extending positioning and retaining protrusions 1236 extending from a rim 1237. Positioning and retaining protrusions 1236 are seated in apertures 1240 formed in inclined walls of sample enclosure 1216 of ring 1214 to prevent rotation of positioner 1228.

A coil spring 1242 is disposed on positioner 1228 between rim 1237 and ridges 1232 of projections 1230. Spring 1242 is preferably formed of hardened stainless steel.

The positioner 1228 and spring 1242 are operative to move a non-liquid sample up and against electron beam permeable, fluid impermeable, membrane 1210 when enclosure elements 1200 and 1202 and connecting element 1222 are in tight threaded engagement.

Second enclosure element 1202 is preferably formed with a generally central stub 1250, having a throughgoing bore 1252, which stub is arranged to be seated in a suitable recess (not shown) in a specimen stage of a scanning electron microscope. Bore 1252 enables diaphragm 1218 to provide pressure relief by defining a fluid communication channel between one side of the diaphragm 1218 and the environment in which the (SEM) compatible sample container is located. It is a particular feature of the present invention that the container, shown in FIGS. 41A–50, is sized and operative with conventional stub recesses in conventional scanning electron microscopes and does not require any modification thereof whatsoever. It is appreciated that various configurations and sizes of stubs may be provided so as to fit various scanning electron microscopes.

Figure 44A:
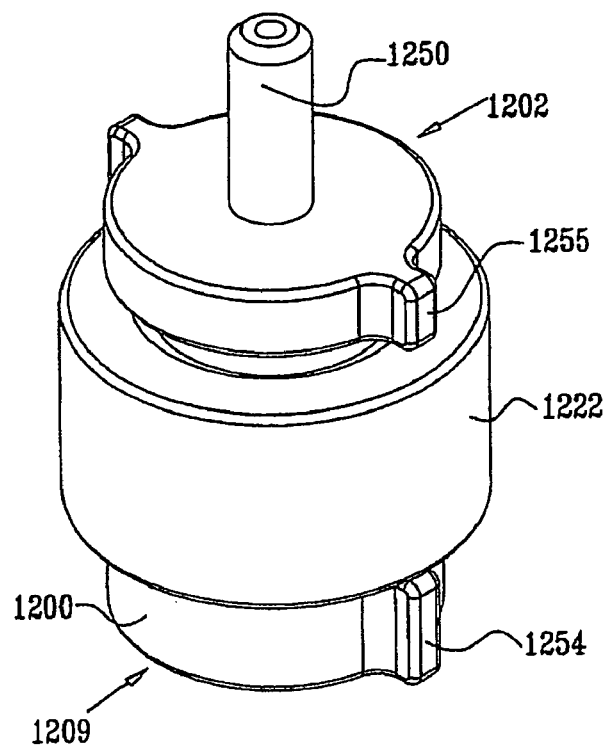
FIGS. 44A & 44B are oppositely facing simplified pictorial illustrations of the SEM compatible sample container of FIGS. 41A–43B in a fully assembled state.
Figure 44B:
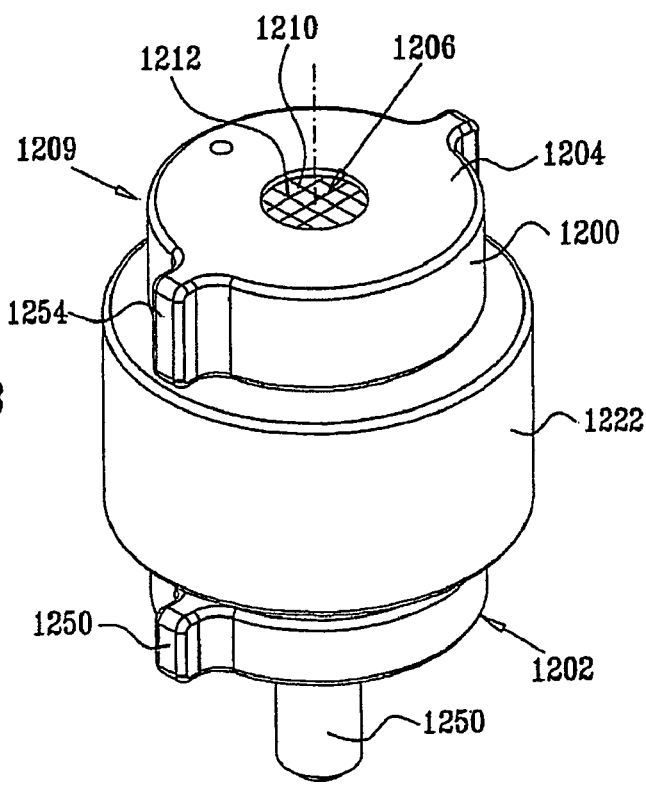

Enclosure elements 1200 and 1202 are preferably also provided with respective radially extending positioning and retaining protrusions 1254 and 1255, to enable the container to be readily seated in a suitable multi-container holder and also to assist users in threadably opening and closing the enclosure elements 1200 and 1202. Preferably, the mutual azimuthal positioning of the protrusions 1254 and 1255 on respective enclosure elements 1200 and 1202 is such that mutual azimuthal alignment therebetween indicates a desired degree of threaded closure therebetween, as shown in FIGS. 44A and 44B.

Figure 46A:
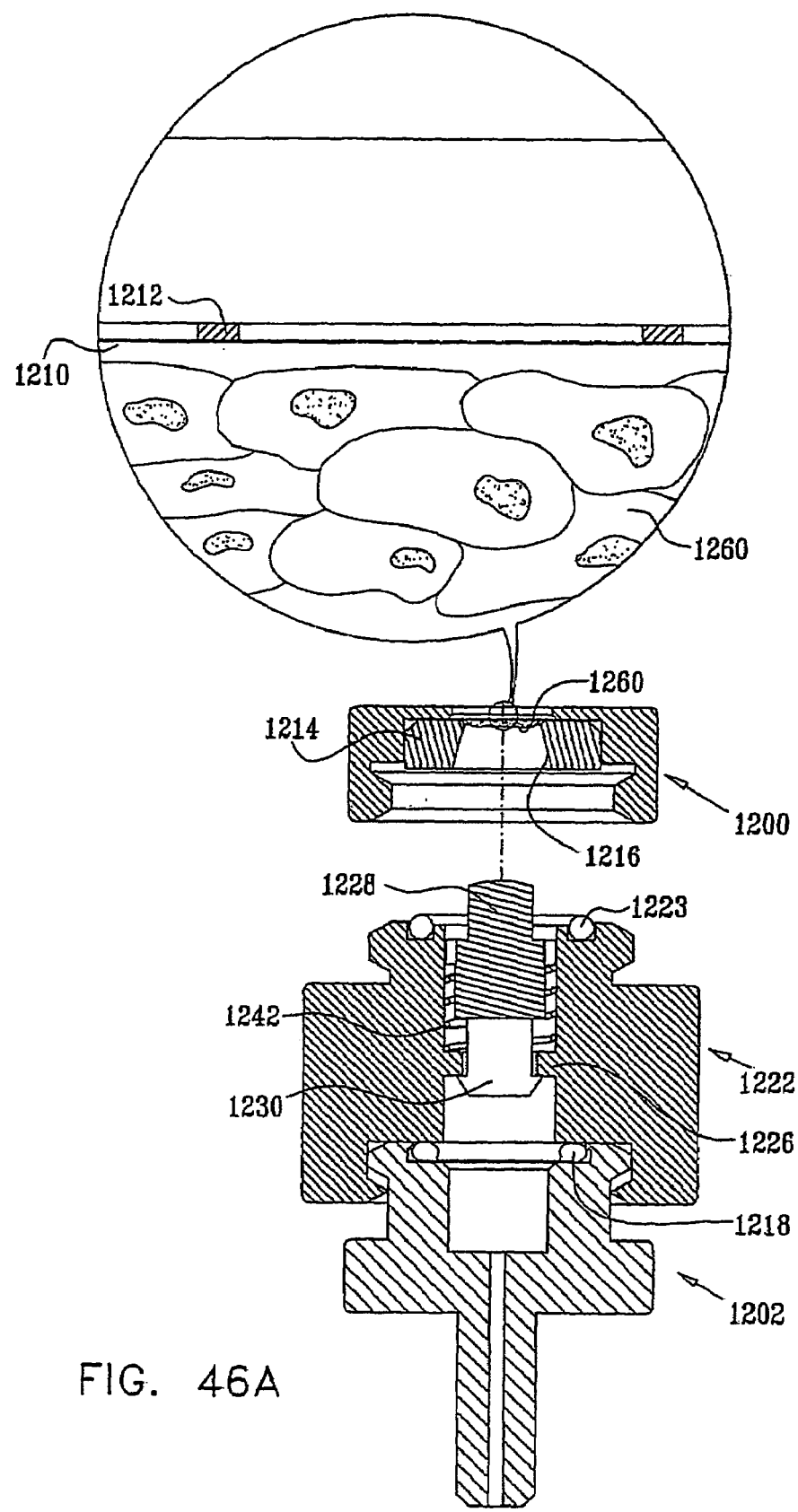
FIGS. 46A, 46B & 46C are three sectional illustrations showing the operative orientation of the SEM compatible sample container of FIGS. 41A–45B at three stages of operation.
Figure 46B:
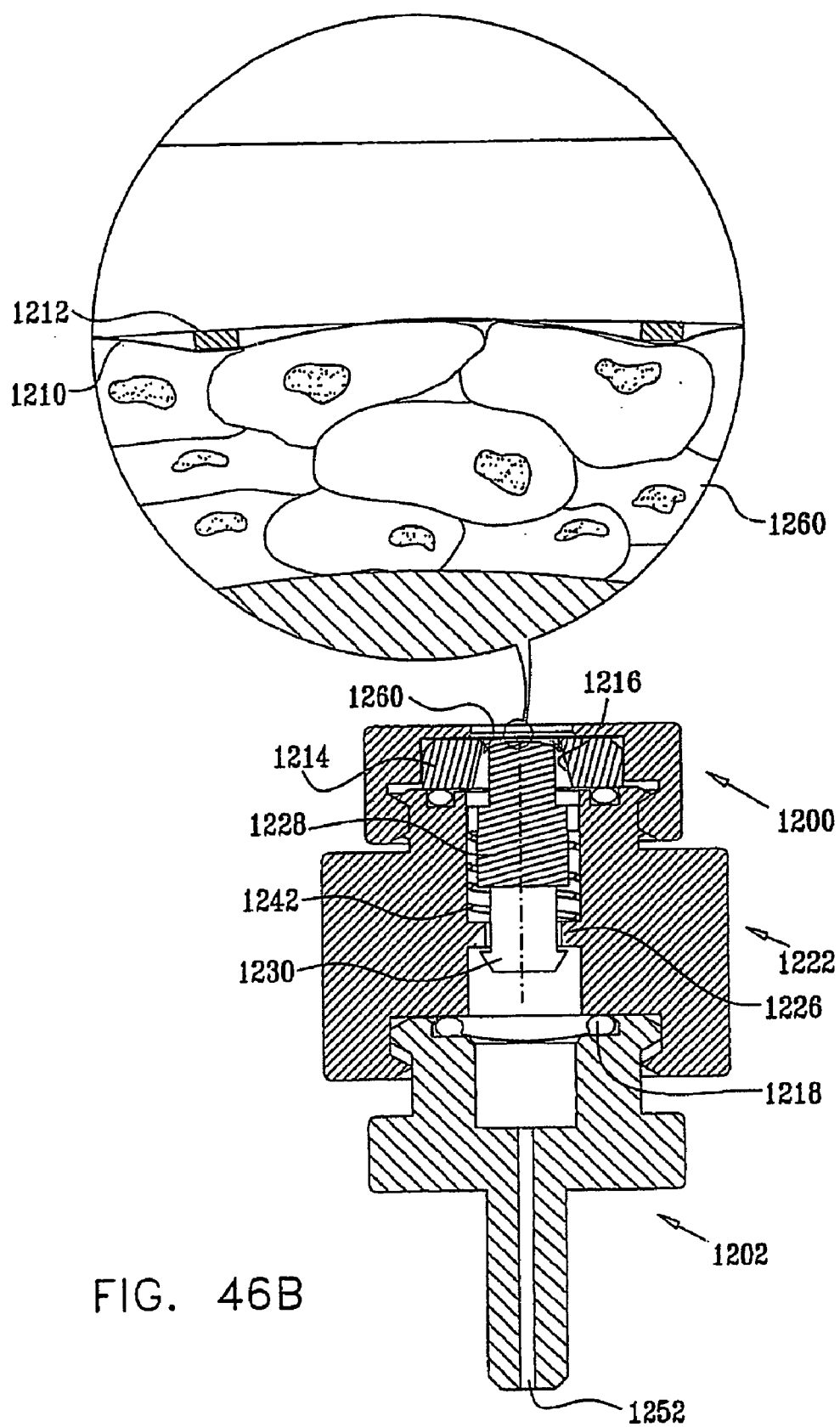
Figure 46C:
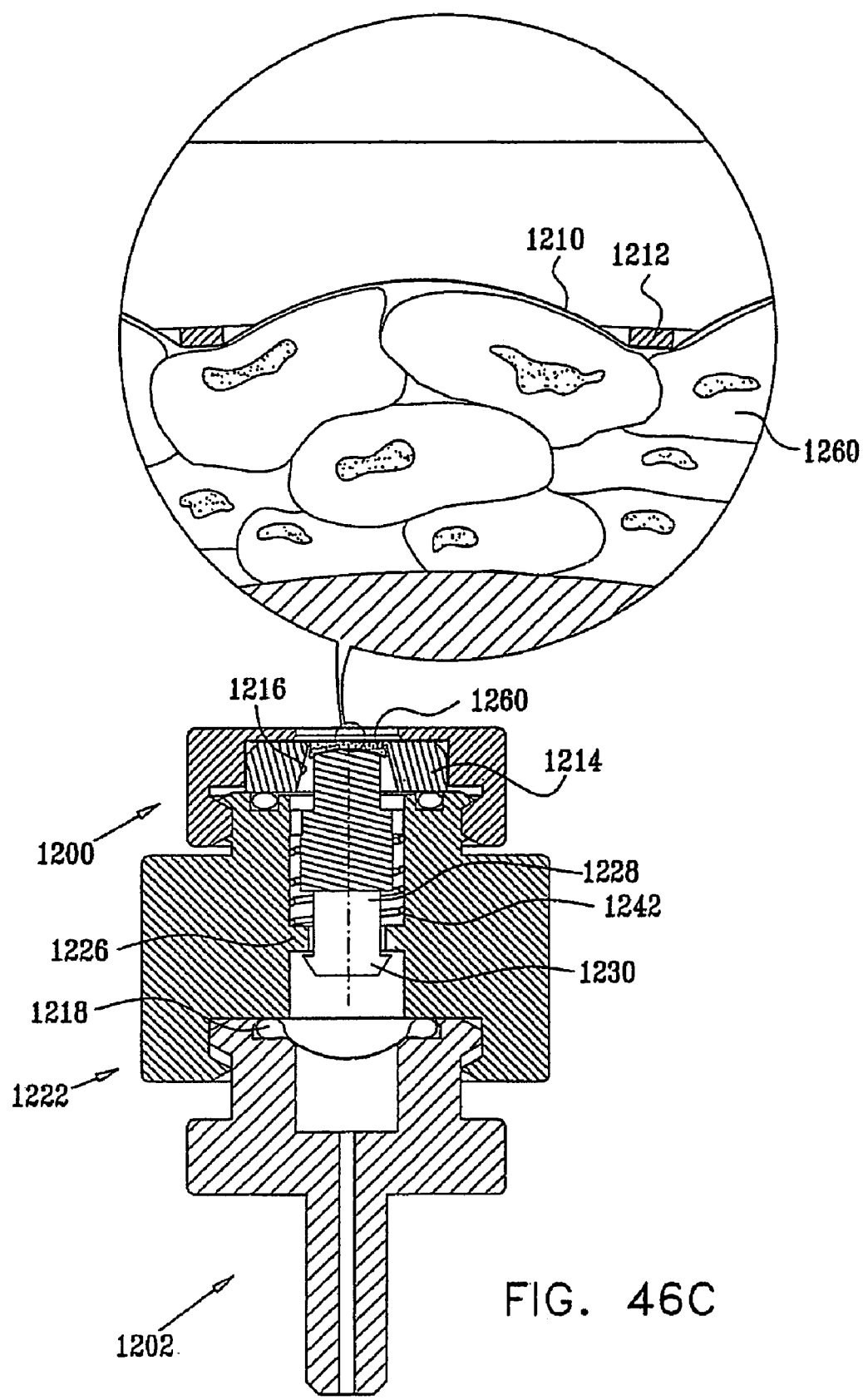

Reference is now made to FIGS. 46A, 46B & 46C, which are three sectional illustrations showing the operative orientation of the SEM compatible sample container of FIGS. 41A–45B at three stages of operation. FIG. 46A shows the container of FIGS. 41A–45B containing a tissue sample 1260 and arranged in the orientation shown in FIG. 41B, prior to threaded closure of enclosure elements 1200 and 1202 and connecting element 1222. The electron beam permeable, fluid impermeable, membrane 1210 is seen in FIG. 46A to be generally planar.

FIG. 46B shows the container of FIG. 46A immediately following full threaded engagement between enclosure elements 1200 and 1202 and connecting, element 1222, producing sealing of the tissue sample enclosure 1216 from the ambient It is noted that the tissue sample 1260 is in close contact with the electron beam permeable, fluid impermeable, membrane 1210 due to the force exerted by the positioner 1228. It is seen that the diaphragm 1218 bows outwardly due to pressure buildup in the tissue sample enclosure 1216 as the result of sealing thereof in this manner. In this embodiment, electron beam permeable, fluid impermeable, membrane 1210 and its supporting grid 1212 also bow outwardly due to pressure buildup in the tissue sample enclosure 1216 as the result of sealing thereof in this manner, however to a significantly lesser extent, due to the action of diaphragm 1218. This can be seen by comparing FIG. 46B with FIG. 36B.

FIG. 46C illustrates the container of FIG. 46B, when placed in an evacuated environment of a SEM, typically at a vacuum of $10^{-2}$–$10^{-6}$ millibars. It is seen that in this environment, the diaphragm 1218 bows outwardly to a greater extent than in the ambient environment of FIG. 46B and that electron beam permeable, fluid impermeable, membrane 1210 and support grid 1212 also bow outwardly to a greater extent than in the ambient environment of FIG. 46B, but to a significantly lesser extent than in the embodiment of FIG. 36C, due to the action of diaphragm 1218. This can be seen by comparing FIG. 46C with FIG. 36C.

It is also noted that the electron beam permeable, fluid impermeable, membrane 1210 tends to be forced into and through the interstices of grid 1212 to a greater extent than occurs in the ambient environment of FIG. 46B but to a significantly lesser extent than in the embodiment of FIG. 36C, due to the action of diaphragm 1218. This can also be seen by comparing FIG. 46C with FIG. 36C.

Figure 47:
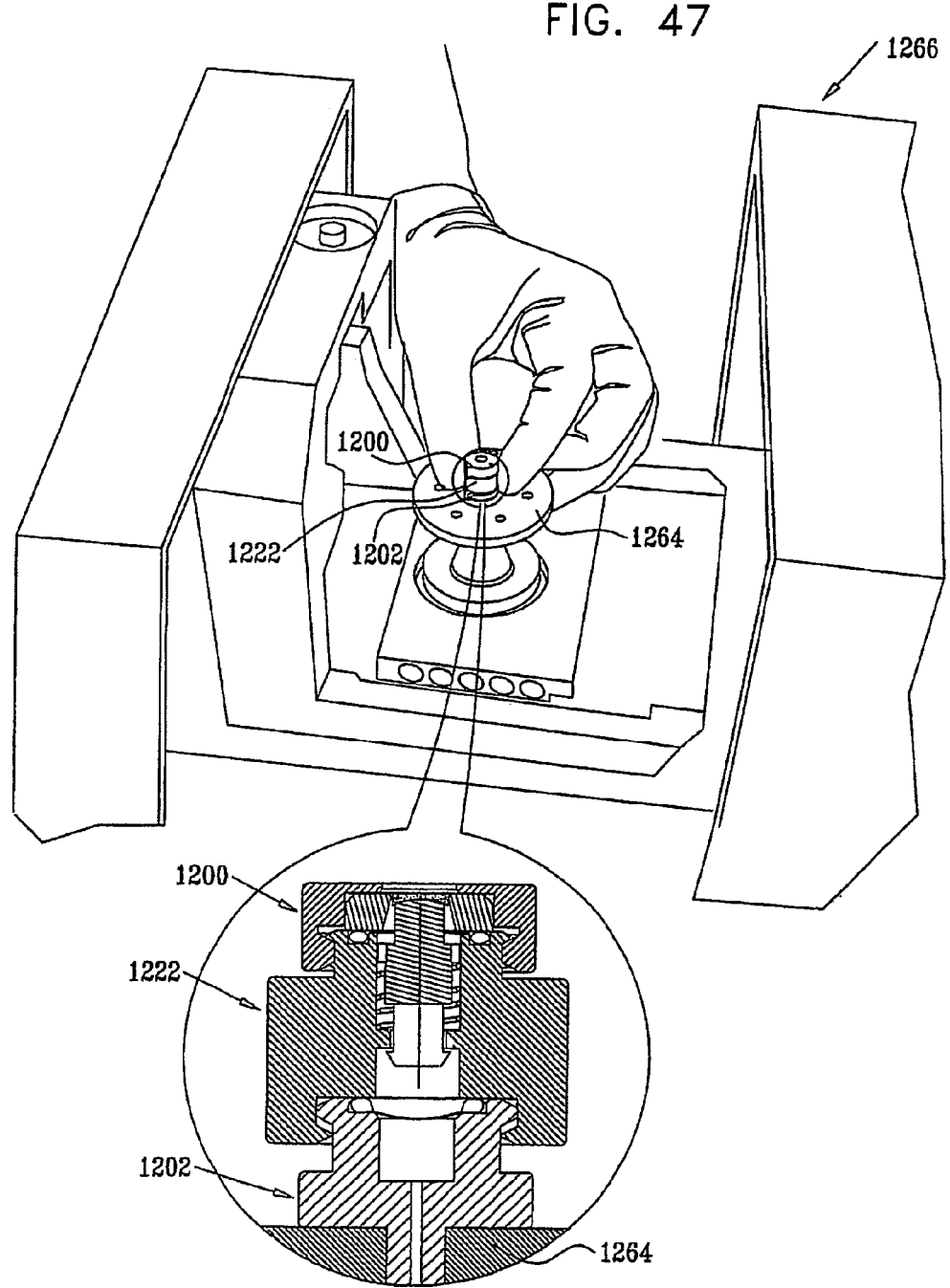
FIG. 47 is a simplified sectional and pictorial illustrations of tissue containing samples and insertion into a SEM using the SEM compatible sample container of FIGS. 41A–46C.

Reference is now made to FIG. 47, which is a simplified sectional and pictorial illustration of tissue containing samples and insertion into a SEM using the SEM compatible sample container of FIGS. 41A–46C.

FIG. 47 shows the closed container, in the orientation of FIG. 41B, being inserted onto a stage 1264 of a SEM 1266. It is appreciated that there exist SEMs wherein the orientation of the container is opposite to that shown in FIG. 47.

Figure 48A:
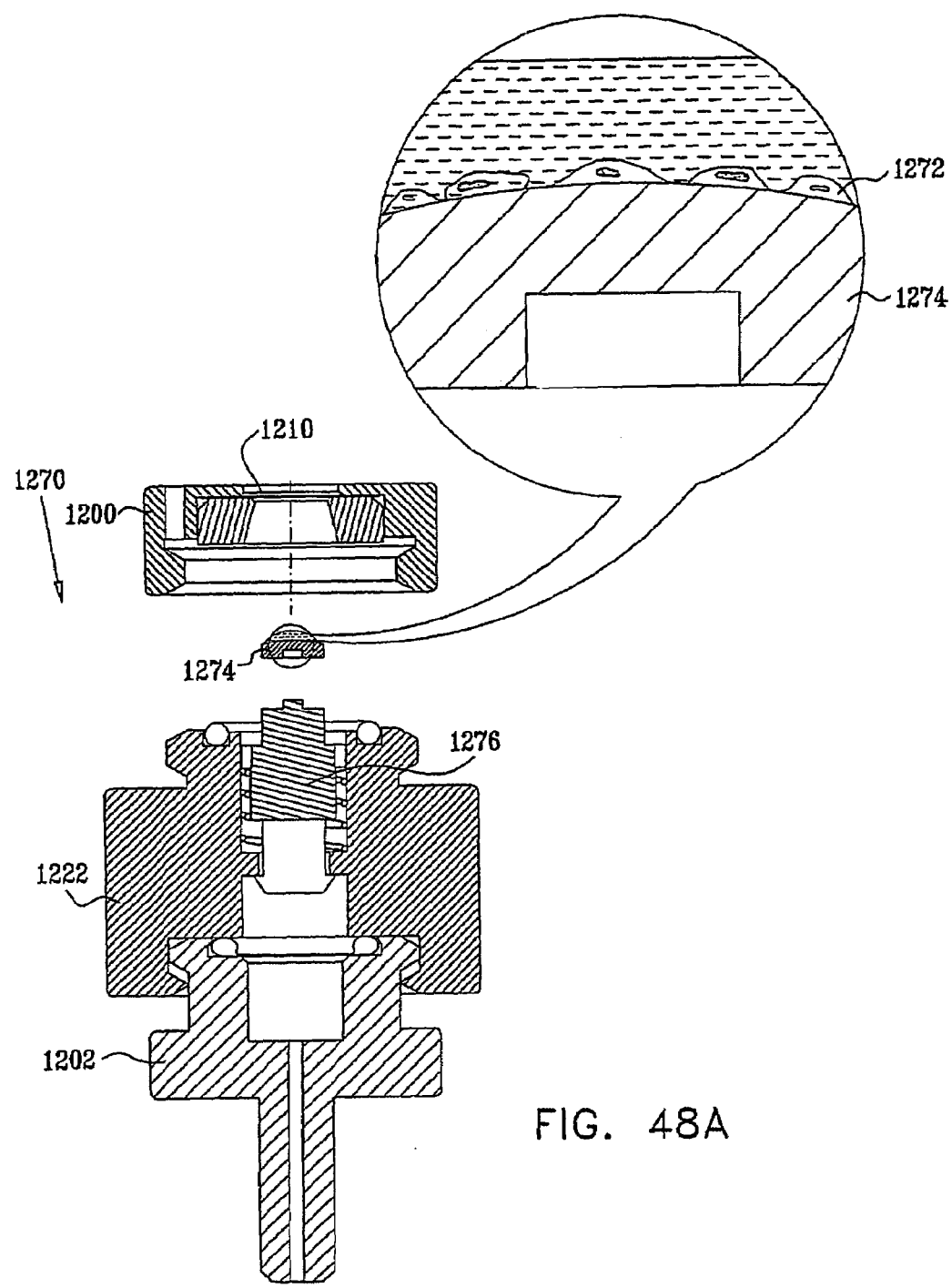

Reference is now made to FIGS. 48A, 48B, 48C and 48D, which are four sectional illustrations showing the operative orientation of a variation of the SEM compatible sample container of FIGS. 41A–45B at four stages of operation. FIG. 48A shows a container 1270, identical to the container of FIGS. 41A–45B other than as specified hereinbelow, containing a sample including cells 1272 grown on a cell growth platform 1274 and arranged in the orientation shown in FIG. 41B, prior to threaded closure of enclosure elements 1200 and 1202 and connecting element 1222. The electron beam permeable, fluid impermeable, membrane 1210 is seen in FIG. 48A to be generally planar. Cell growth platform 1274 is removably mounted onto a suitably configured positioner 1276, which corresponds to positioner 1228 in the embodiment of FIGS. 41A–47. Typically, the cells are grown onto cell growth platform 1274 while platform 1274 is not mounted onto positioner 1276. The mounting of platform 1274 onto positioner 1276 typically occurs just before SEM inspection takes place.

Figure 48B:
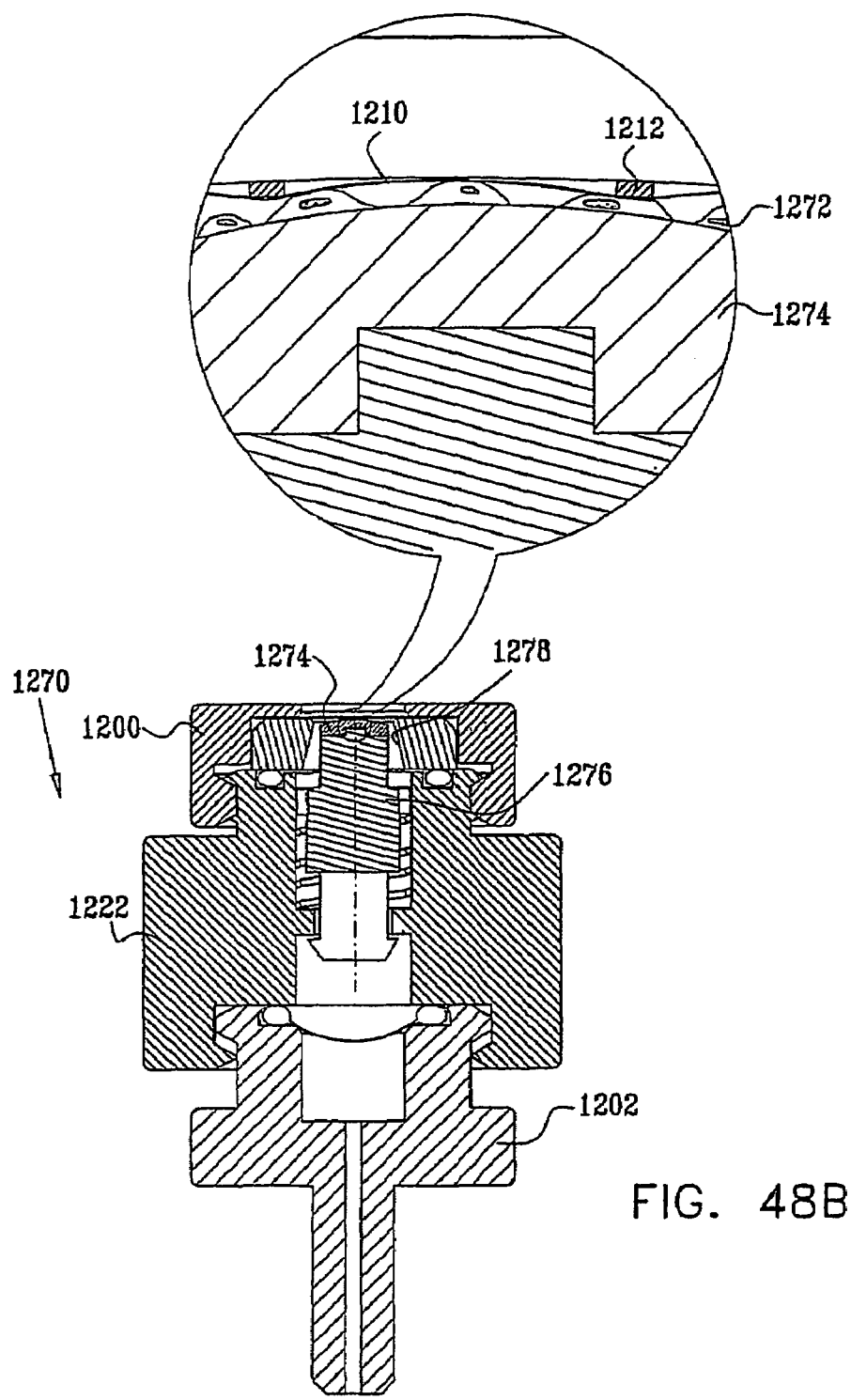

FIG. 48B shows the container of FIG. 48A immediately following full threaded engagement between enclosure elements 1200 and 1202 and connecting element 1222 producing sealing of the cell sample enclosure, here designated by reference numeral 1278, from the ambient It is noted that the sample containing cells 1272 is in close contact with the electron beam permeable, fluid impermeable, membrane 1210 due to the force exerted by the positioner 1276. It is seen that the electron beam permeable, fluid impermeable, membrane 1210 and its supporting grid 1212 bow outwardly due to pressure buildup in the cell sample enclosure 1278 as the result of sealing thereof in this manner, however to a significantly lesser extent than in the embodiment of FIG. 38B, due to the action of diaphragm 1218. This can be seen by comparing FIG. 48B with FIG. 38B.

Figure 48C:
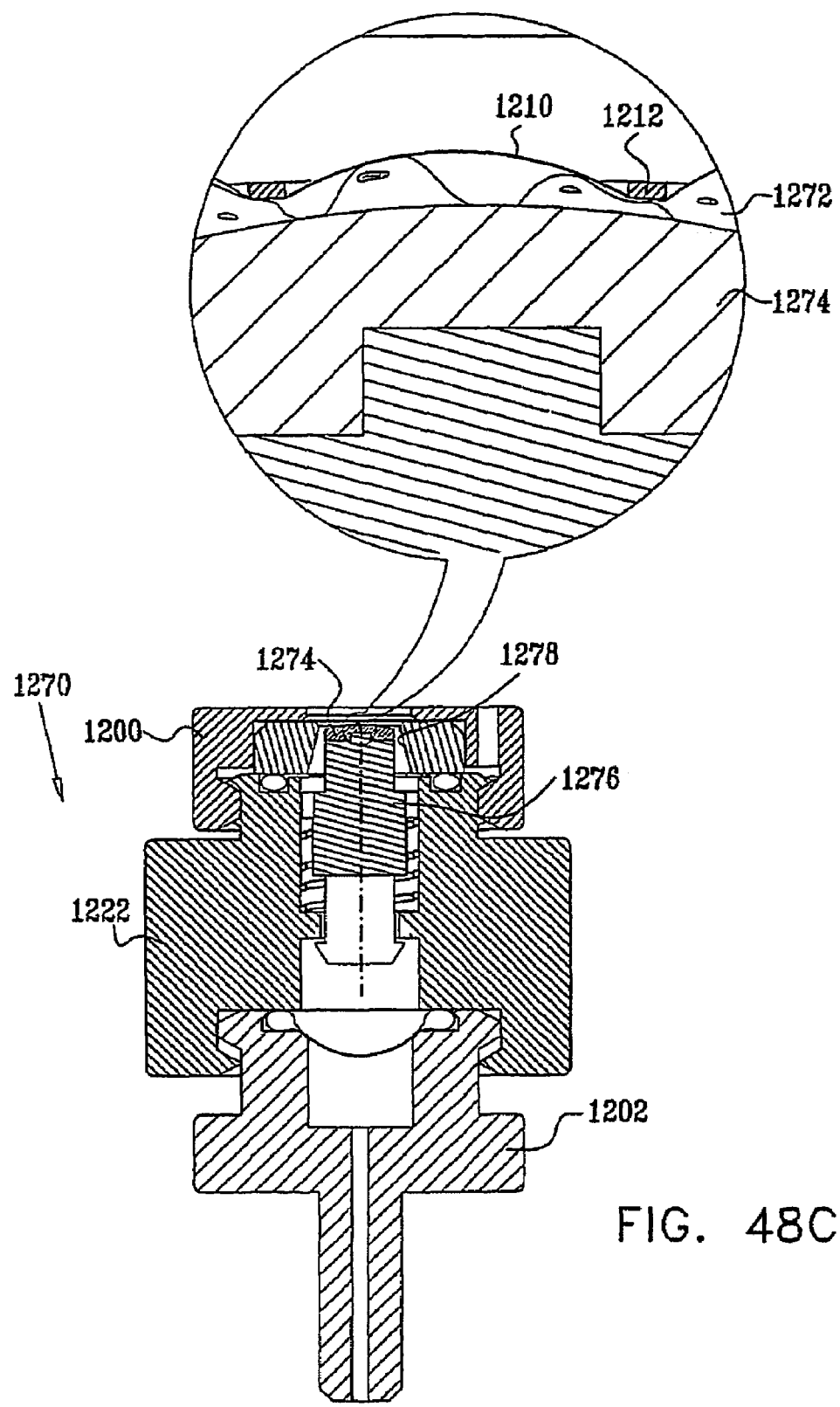

FIG. 48C illustrates the container of FIG. 48B, when placed in an evacuated environment of a SEM, typically at a vacuum of $10^{-2}$–$10^{-6}$ millibars. It is seen that in this environment, the electron beam permeable, fluid impermeable, membrane 1210 and support grid 1212 bow outwardly to a greater extent than in the ambient environment of FIG. 48B and further that the electron beam permeable, fluid impermeable, membrane 1210 tends to be forced into and through the interstices of grid 1212 to a greater extent than occurs in the ambient environment of FIG. 48B, but to a significantly lesser extent than in the embodiment of FIG. 38C, due to the action of diaphragm 1218. This can be seen by comparing FIG. 48C with FIG. 38C.

Figure 48D:
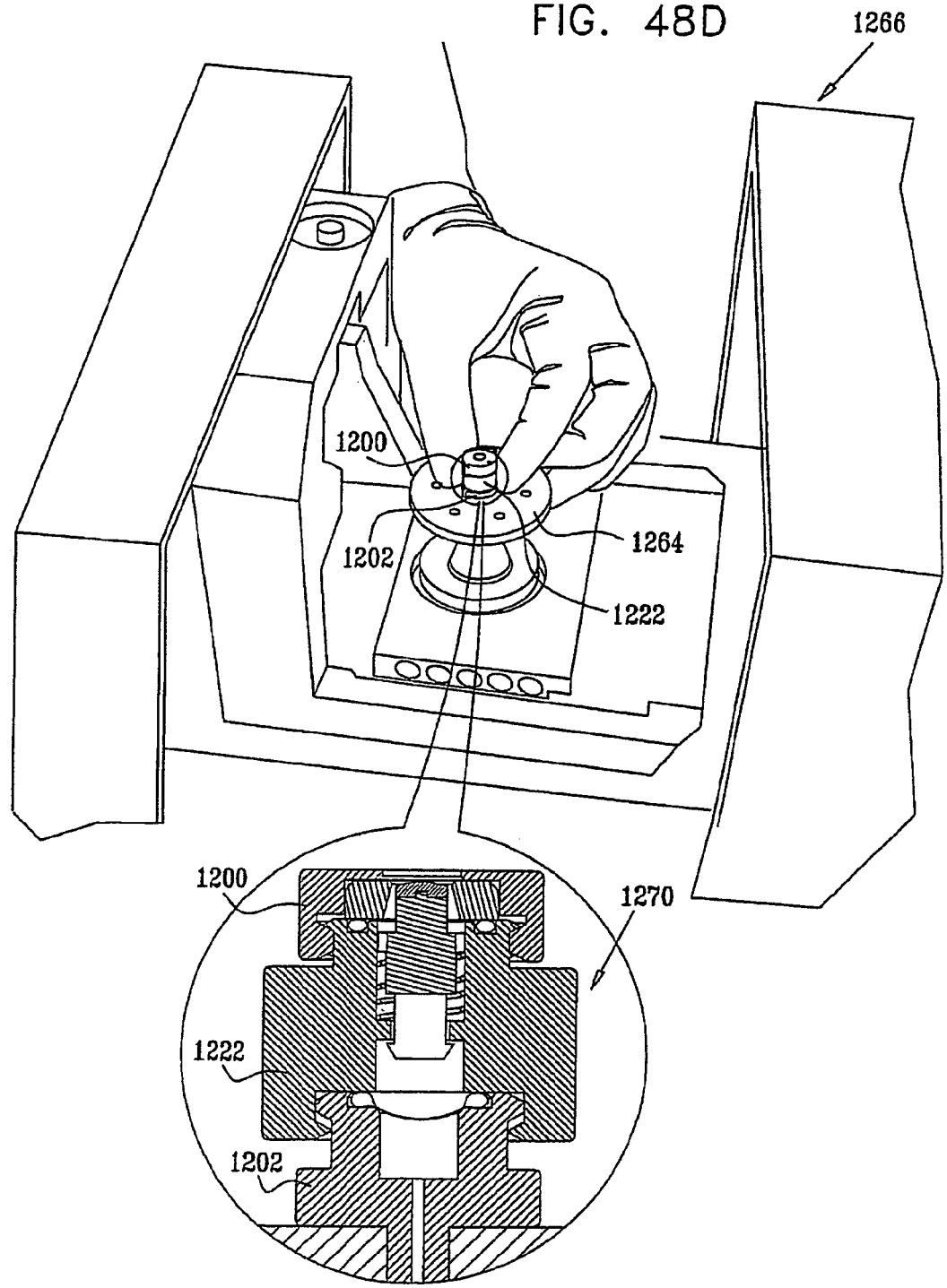

FIG. 48D shows the closed container 1270, in the orientation of FIG. 41B, being inserted onto stage 1264 of SEM 1266. It is appreciated that there exist SEMs wherein the orientation of the container is opposite to that shown in FIG. 48D.

Reference is now made to FIG. 49, which is a simplified pictorial and sectional illustration of SEM inspection of a sample using the SEM compatible sample container of FIGS. 41A–47. As seen in FIG. 49, the container, here designated by reference numeral 1280, is shown positioned on stage 1264 of SEM 1266 such that an electron beam 1282, generated by the SEM, passes through electron beam permeable, fluid impermeable, membrane 1210 and impinges on a tissue containing sample 1284 within container 1280. Backscattered electrons from sample 1284 pass through electron beam permeable, fluid impermeable, membrane 1210 and are detected by a detector 1286, forming part of the SEM. One or more additional detectors, such as a secondary electron detector 1288, may also be provided. An X-ray detector (not shown) may also be provided for detecting X-ray radiation emitted by the sample 1284 due to electron beam excitation thereof.

Reference is now made additionally to FIG. 50, which schematically illustrates some details of the electron beam interaction with the sample 1284 in container 1280 in accordance with a preferred embodiment of the present invention It is noted that the present invention enables high contrast imaging of features which are distinguished from each other by their average atomic number, as illustrated in FIG. 50. In FIG. 50 it is seen that nucleoli 1290, having a relatively high average atomic number, backscatter electrons more than the surrounding nucleoplasm 1292.

It is also noted that in accordance with a preferred embodiment of the present invention, imaging of the interior of the sample to a depth of up to approximately 2 microns is achievable for electrons having an energy level of less than 50 KeV, as seen in FIG. 50, wherein nucleoli 1290 disposed below electron beam permeable, fluid impermeable, membrane 1210 are imaged.

Figure 51A:
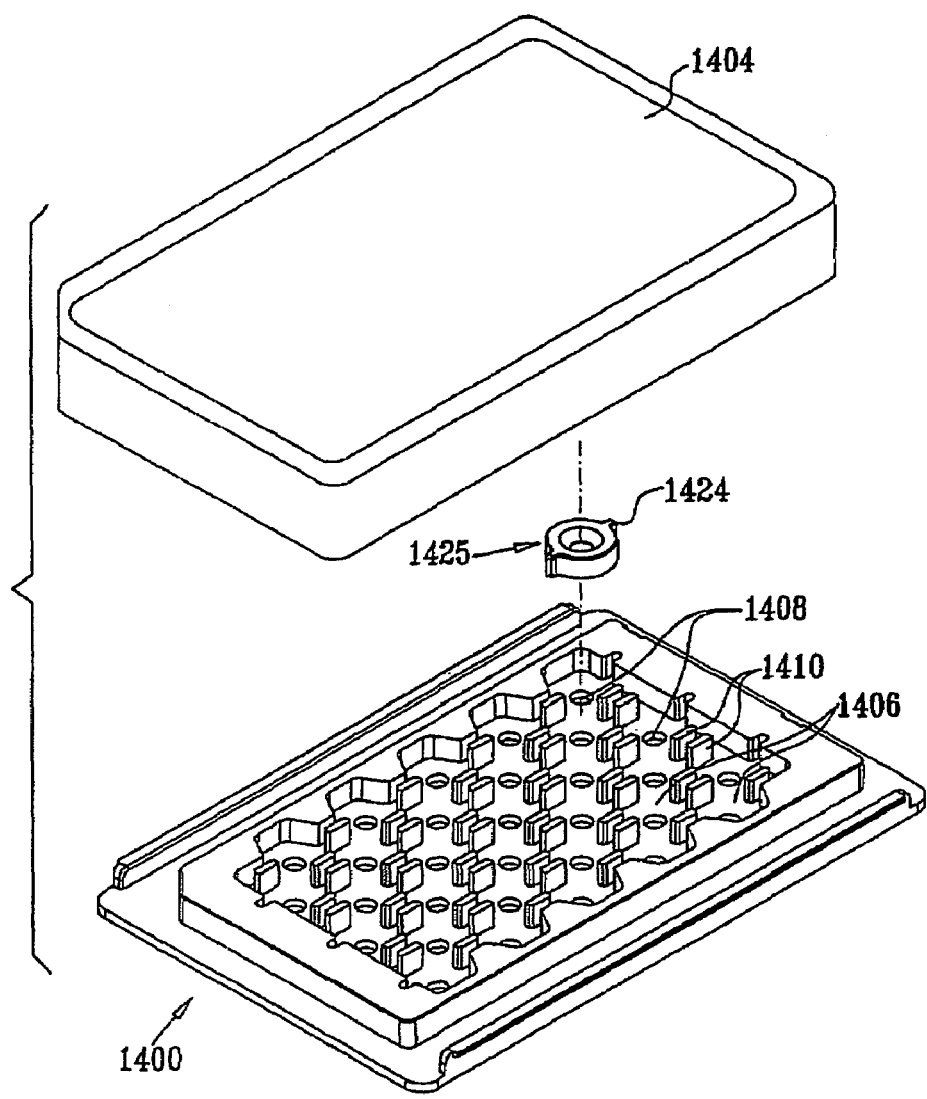
Figure 51B:
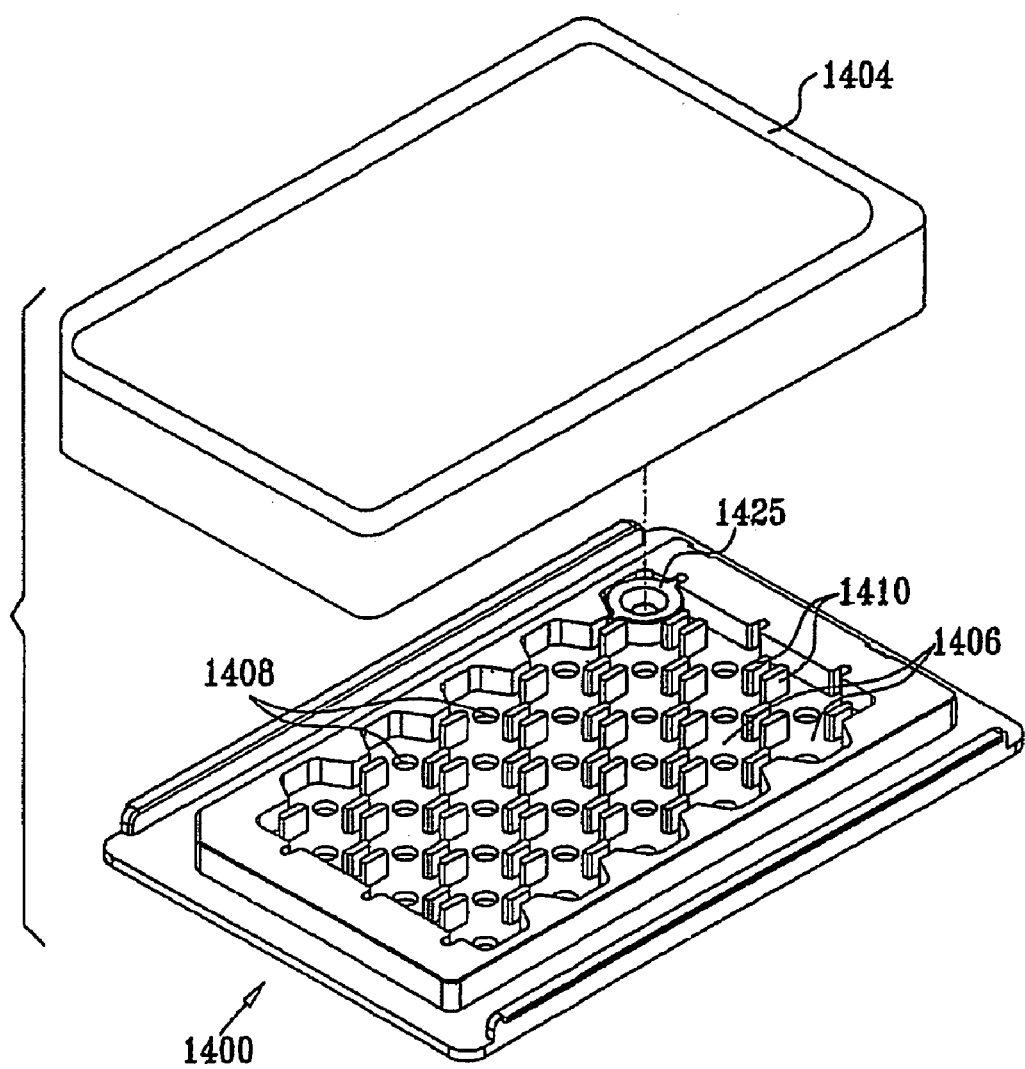

Reference is now made to FIGS. 51A, 51B and 51C, which are simplified illustrations of a microscopy multi-sample holder in use with a SEM compatible sample dish of the type shown in FIGS. 31A–40. As seen in FIG. 51A, the microscopy multi-sample holder preferably comprises a base 1400 and a sealing cover 1404. The base 1400 is preferably injection molded of a plastic material and defines an array of dish support locations 1406. Each dish support location 1406 is preferably defined by an aperture 1408 through which SEM microscopy may take place. Adjacent to each aperture 1408 there is preferably formed a pair of mutually aligned pairs of upstanding mutually spaced protrusions 1410 arranged to receive protrusions 1424 on sample dishes 1425. Sample dishes 1425 may be generally identical to sample dishes 1109, shown in FIGS. 33A–35B, but do not require any threading or other attachment mechanism.

Sealing cover 1404 is preferably arranged for individual sealing engagement with each of sample dishes 1425. Preferably sealing cover 1404 is provided on the underside thereof with an array of O-rings 1426, shown in FIG. 51C, sealed thereto and arranged so as to sealingly engage a top rim surface of each of sample dishes 1425, when the sealing cover 1404 is in place, preferably in removable snap-fit engagement with base 1400.

Preferably, sealing cover 1404 is provided on the underside thereof with an array of positioners 1428, shown in FIG. 51C, and arranged so as to move non-liquid samples up and against electron beam permeable, fluid impermeable, membrane 1110 (shown in FIGS. 31A–40) seated in sample dish 1425. Individual positioners 1428 are suspended within coils 1430, as shown in FIG. 51C.

FIG. 51B shows the apparatus of FIG. 51A with one sample dish 1425 positioned at a dish support location 1406 in base 1400. FIG. 51C shows sealing cover 1404 in snap fit engagement with base 1400, thereby providing individual sealing of each of sample dishes 1425 by means of O-ring 1426 and a portion of sealing cover 1404 circumscribed thereby.

Figure 52A:
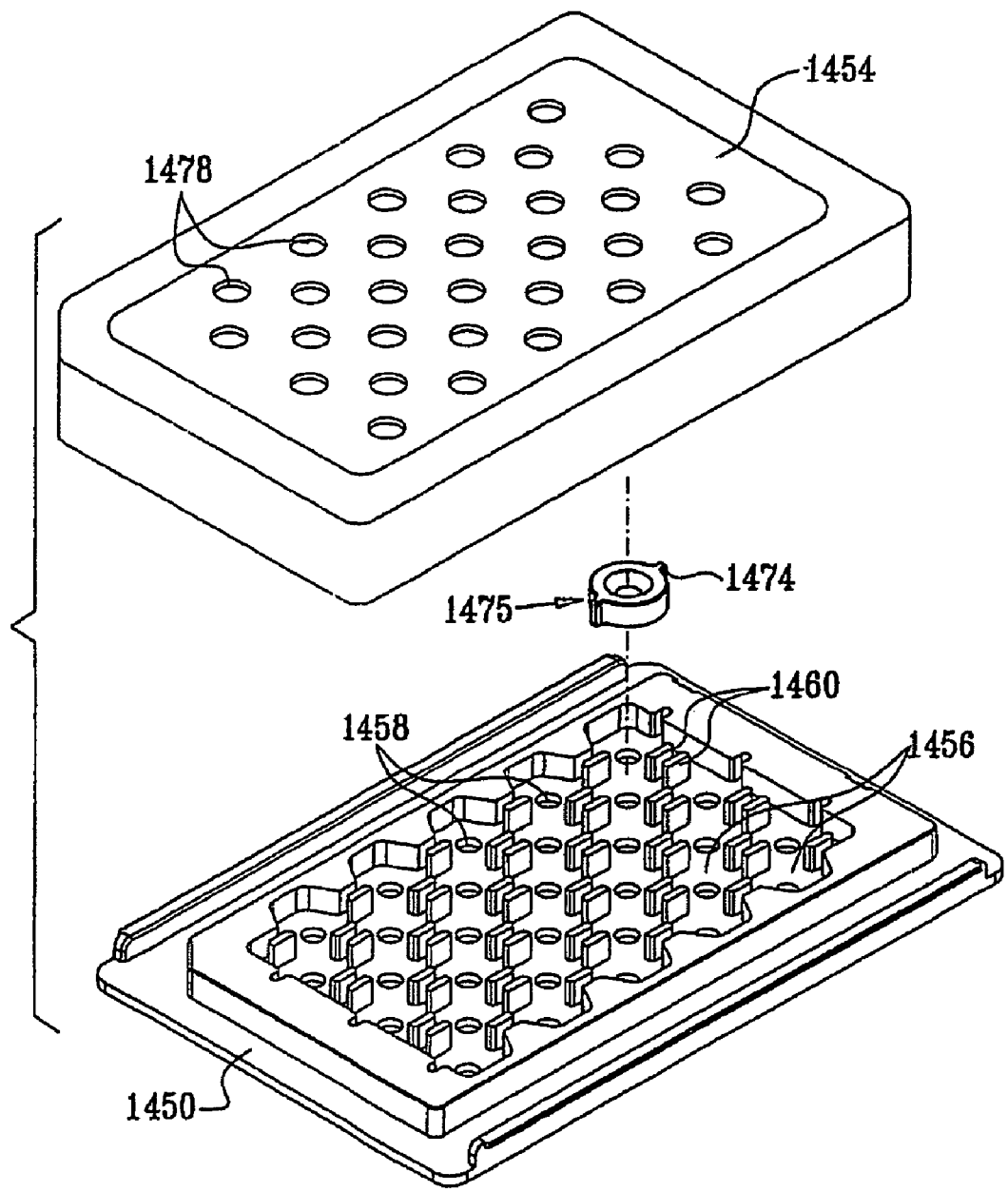
Figure 52B:
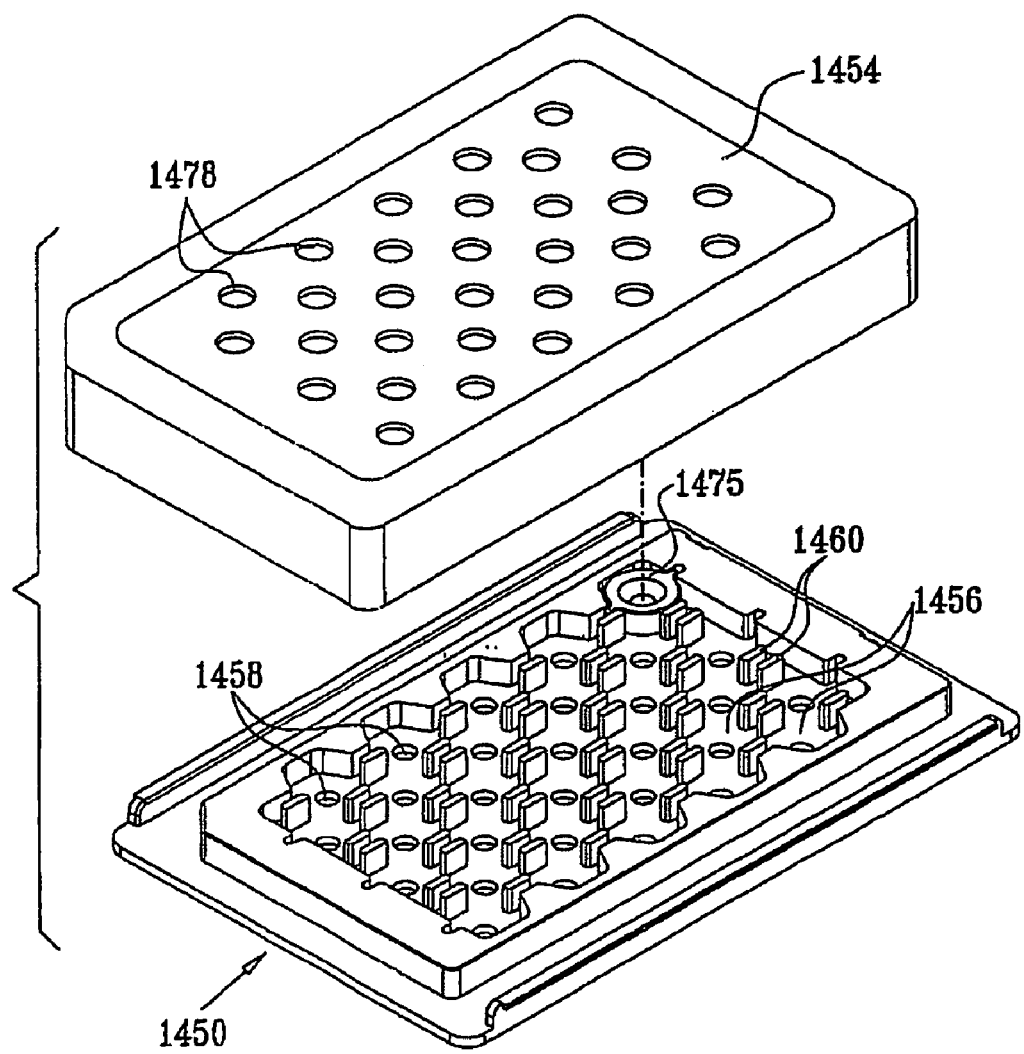

Reference is now made to FIGS. 52A, 52B and 52C, which are simplified illustrations of a microscopy multi-sample holder in use with a SEM compatible sample dish of the type shown in FIGS. 41A–50. As seen in FIG. 52A, the microscopy multi-sample holder preferably comprises a base 1450 and a sealing cover 1454. The base 1450 is preferably injection molded of a plastic material and defines an array of dish support locations 1456. Each dish support location 1456 is preferably defined by an aperture 1458 through which SEM microscopy may take place. Adjacent to each aperture 1458 there is preferably formed a pair of mutually aligned pairs of upstanding mutually spaced protrusions 1460 arranged to receive protrusions 1474 on sample dishes 1475. Sample dishes 1475 may be generally identical to sample dishes 1209, shown in FIGS. 43A–45B, but do not require any threading or other attachment mechanism.

Preferably sealing cover 1454 is provided on the underside thereof with an array of O-rings 1476, shown in FIG. 52C, sealed thereto and arranged so as to sealingly engage a top rim surface of each of sample dishes 1475, when the sealing cover 1454 is in place, preferably in removable snap-fit engagement with base 1450.

Sealing cover 1454 is arranged for individual sealing engagement of each of sample dishes 1475 with a diaphragm 1477, shown in FIG. 52C, which is sealingly mounted over an aperture 1478 formed in sealing cover 1454. Preferably an array of diaphragms 1477, which may be identical to diaphragms 1218 described hereinabove with reference to FIGS. 41A–50, is provided on the underside of sealing cover 1454. The individual diaphragms 1477 are arranged so as to sealingly engage a top rim surface of each of sample dishes 1475, when the sealing cover 1454 is in place, preferably in removable snap-fit engagement with base 1450.

Preferably, sealing cover 1454 is provided with an array of positioners 1480. Individual positioners 1480 are suspended within coils 1482, as shown in FIG. 51C, so as to move non-liquid samples up and against electron beam permeable, fluid impermeable, membrane 1210 (shown in FIGS. 41A–50) seated in sample dish 1475.

FIG. 52B shows the apparatus of FIG. 52A with one sample dish 1475 positioned at a dish support location 1456 in base 1450. FIG. 52C shows sealing cover 1454 in snap fit engagement with base 1450, thereby providing individual sealing of each of sample dishes 1475 by means of diaphragm 1476.

Figure 53A:
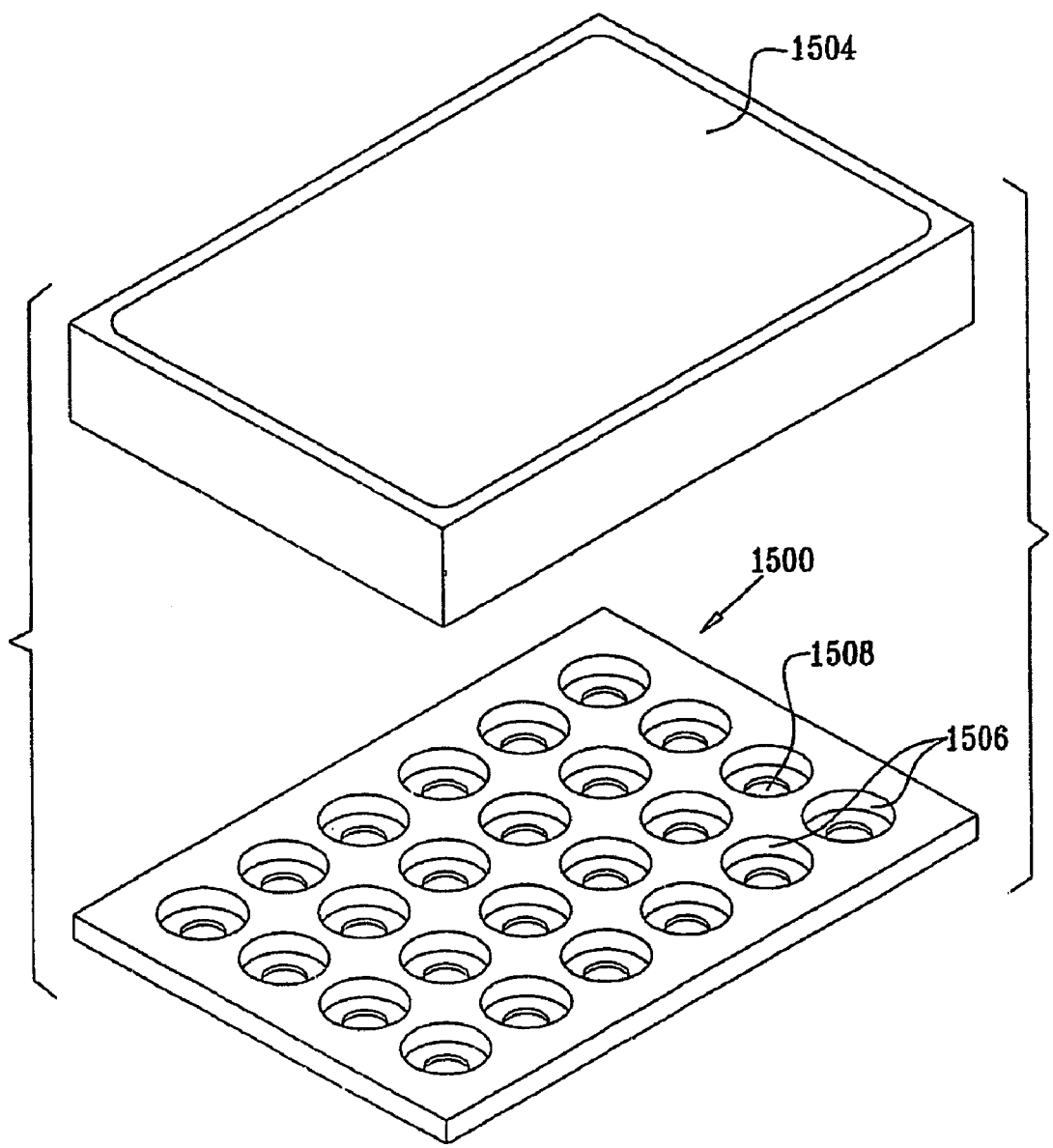

Reference is now made to FIGS. 53A and 53B, which are simplified illustrations of a microscopy multi-sample holder defining a plurality of SEM compatible sample containers in accordance with a preferred embodiment of the present invention. As seen in FIG. 53A, the microscopy multi-sample holder preferably comprises a base 1500 and a sealing cover 1504. The base 1500 is preferably injection molded of a plastic material and defines an array of sample containers 1506. Each sample container 1506 preferably includes an aperture 1508 through which SEM microscopy may take place. An electron beam permeable, fluid impermeable, membrane 1510, shown in FIG. 53B, is sealed over each aperture 1508. Membrane 1510 is preferably identical to membrane 1110 described hereinabove with reference to FIGS. 31A–40. Sealing cover 1504 preferably is arranged for individual sealing engagement with each of sample containers 1506.

Preferably, sealing cover 1504 is provided with an array of positioners 1520, shown in FIG. 53B. Individual positioners 1520 are suspended within coils 1522, as shown in FIG. 53B, so as to move non-liquid samples up and against electron beam permeable, fluid impermeable, membrane 1510.

FIG. 53B shows the apparatus of FIG. 53A in sealed engagement, thereby providing individual sealing of each of sample containers 1506.

Figure 54A:
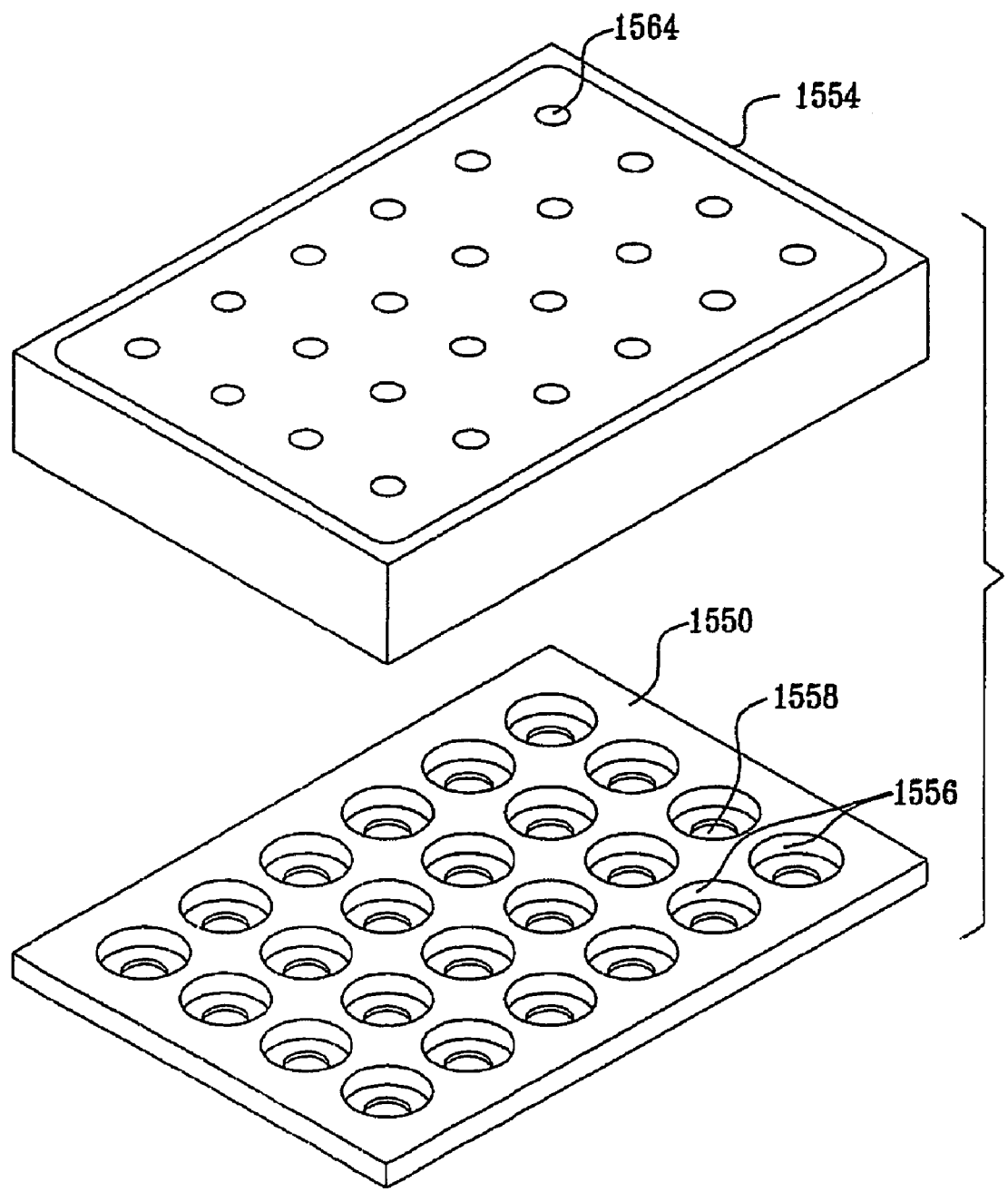

Reference is now made to FIGS. 54A and 54B, which are simplified illustrations of a microscopy multi-sample holder defining a plurality of SEM compatible sample containers in accordance with a preferred embodiment of the present invention. As seen in FIG. 54A, the microscopy multi-sample holder preferably comprises a base 1550 and a sealing cover 1554. The base 1550 is preferably injection molded of a plastic material and defines an array of sample containers 1556. Each sample container 1556 preferably includes an aperture 1558 through which SEM microscopy may take place.

An electron beam permeable, fluid impermeable, membrane 1560, shown in FIG. 54B, is sealed over each aperture 1558. Membrane 1560 is preferably identical to membrane 1210 described hereinabove with reference to FIGS. 41A–50. Sealing cover 1554 preferably comprises a diaphragm 1562 formed of resilient sheet material such as silicon rubber of 0.2–0.3 mm in thickness and having a Shore hardness of about 50. Diaphragm 1562 is sealingly mounted over apertures 1564 formed in sealing cover 1554 and is arranged for individual sealing engagement with each of sample containers 1556.

Preferably, sealing cover 1554 is provided with an array of positioners 1570, shown in FIG. 54B. Individual positioners 1570 are suspended within coils 1572, as shown in FIG. 54B, so as to move non-liquid samples up and against electron beam permeable, fluid impermeable, membrane 1560.

FIG. 54B shows the apparatus of FIG. 54A in sealed engagement, thereby providing individual sealing of each of sample containers 1556.

Reference is now made to FIG. 55, which is a simplified illustration of a SEM based sample inspection system constructed and operative in accordance with a preferred embodiment of the present invention. As seen in FIG. 55, preferably, automated positioning systems, such as robotic arms, as shown, are used for conveying a multiplicity of SEM compatible sample containers 1602 throughout the system, it being appreciated that manual intervention may be employed at one or more stages as appropriate.

Thereafter, individual containers 1602 are placed on a removable electron microscope specimen stage 1610, which is subsequently introduced into a scanning electron microscope 1612. The resulting image may be inspected visually by an operator and/or analyzed by conventional image analysis functionality, typically embodied in a computer 1614.

Figure 56:
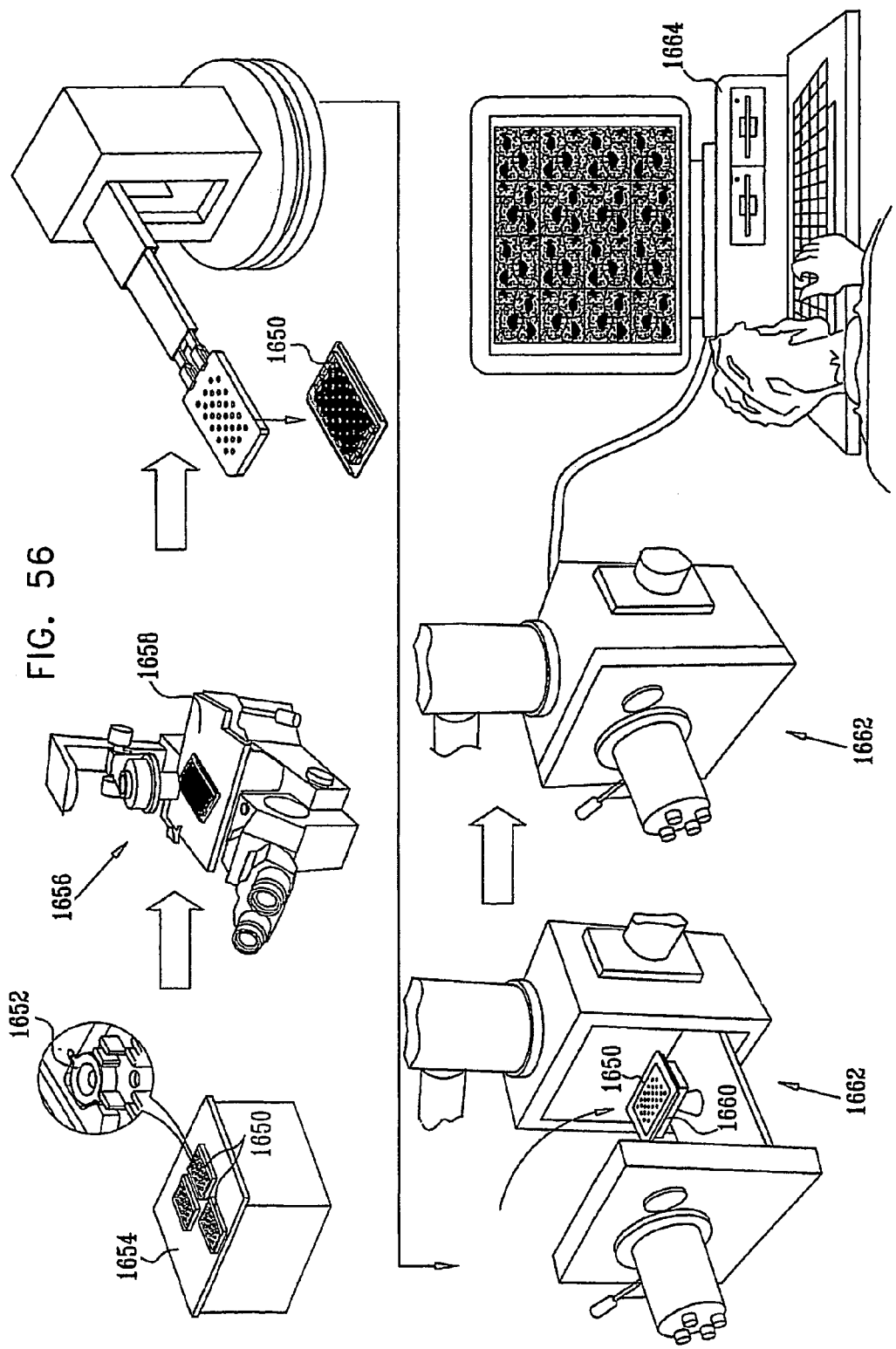
FIG. 56 is a simplified illustration of a SEM based sample inspection system constructed and operative in accordance with another preferred embodiment of the present invention.

Reference is now made to FIG. 56, which is a simplified illustration of a SEM based sample inspection system constructed and operative in accordance with another preferred embodiment of the present invention. As seen in FIG. 56, a plurality of microscopy multi-sample holders 1650, each containing a multiplicity of SEM compatible sample dishes 1652 of either of the types shown in FIGS. 51A–52C, is shown on a table 1654. Preferably, light microscopy inspection of the samples in sample dishes 1652 is carried out while the sample dishes are mounted in holder 1650, as indicated at reference numeral 1656, in order to identify samples of interest. Preferably a dissection microscope 1658 is employed for this purpose.

Preferably automated positioning systems, such as robotic arms, as shown, are used for conveying the microscopy multi-sample holders 1650 containing sample dishes 1652 throughout the system, it being appreciated that manual intervention may be employed at one or more stages as appropriate.

Thereafter, holders 1650 are placed on an electron microscope specimen stage 1660, which is subsequently introduced into a scanning electron microscope 1662. The resulting images may be inspected visually by an operator and/or analyzed by conventional image analysis functionality, typically embodied in a computer 1664.

Figure 57:
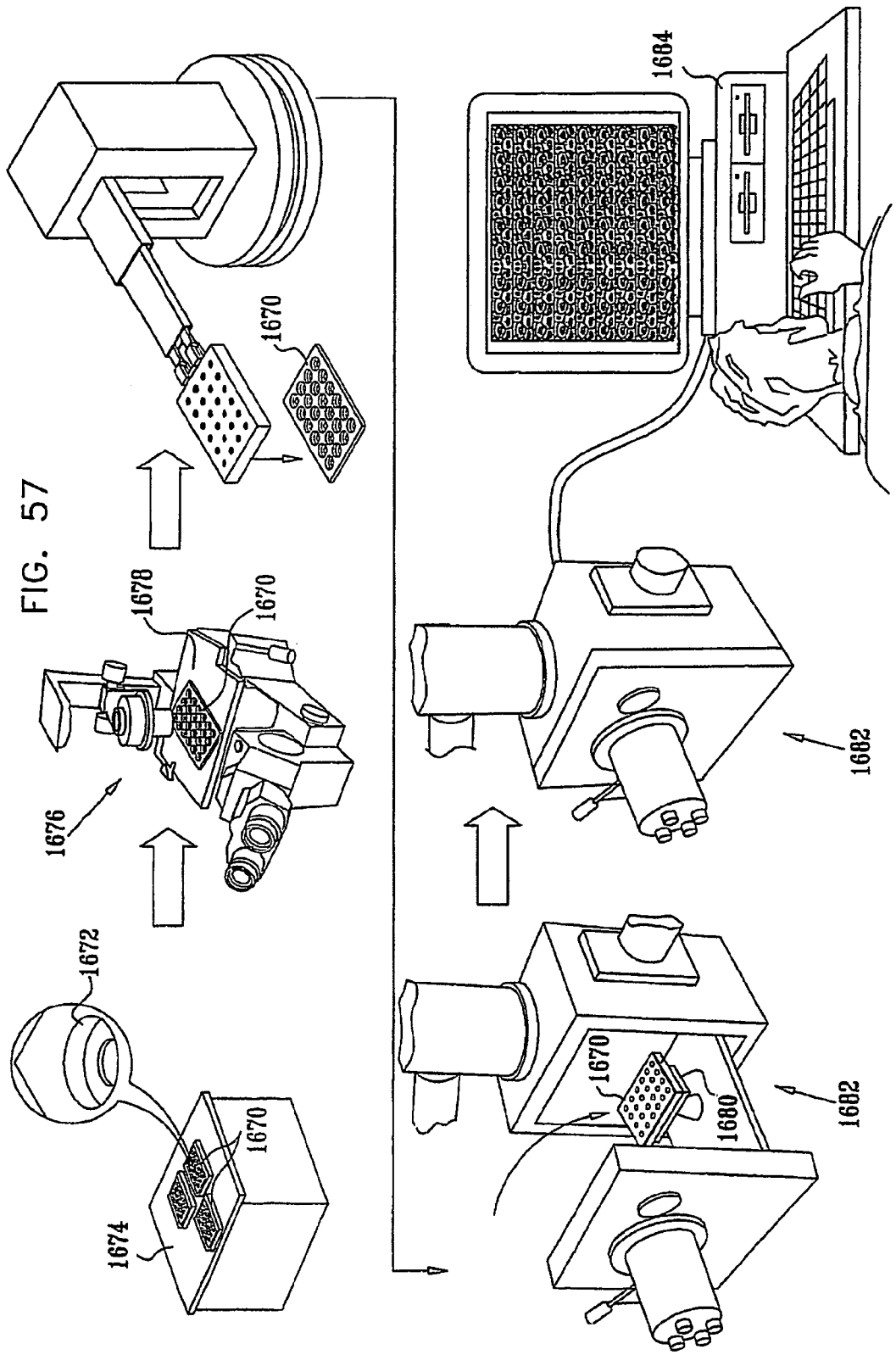
FIG. 57 is a simplified illustration of a SEM based sample inspection system constructed and operative in accordance with yet another preferred embodiment of the present invention.

Reference is now made to FIG. 57, which is a simplified illustration of a SEM based sample inspection system constructed and operative in accordance with yet S another preferred embodiment of the present invention. As seen in FIG. 57, a plurality of microscopy multi-sample holders 1670, each defining a multiplicity of SEM compatible sample containers 1672, as shown in any of FIGS. 53A–54B, are seen on a table 1674. Preferably, light microscopy inspection of the samples in sample containers 1672 is carried out holder-wise, as indicated at reference numeral 1676, in order to identify samples of interest. Preferably a dissection microscope 1678 is employed for this purpose.

Preferably automated positioning systems, such as robotic arms, as shown, are used for conveying the microscopy multi-sample holders 1670 throughout the system, it being appreciated that manual intervention may be employed at one or more stages as appropriate.

Thereafter, holders 1670 are placed on an electron microscope specimen stage 1680, which is subsequently introduced into a scanning electron microscope 1682. The resulting images may be inspected visually by an operator and/or analyzed by conventional image analysis functionality, typically embodied in a computer 1684.

Reference is now made to FIGS. 58A–62B, which are oppositely facing simplified exploded view pictorial illustrations of a disassembled scanning electron microscope (SEM) compatible sample container constructed and operative in accordance with yet another preferred embodiment of the present invention. As seen in FIGS. 58A & 58B, the SEM compatible sample container comprises first and second mutually threaded enclosure elements, respectively designated by reference numerals 2100 and 2102, arranged for enhanced ease and speed of closure. Enclosure elements 2100 and 2102 are preferably molded of plastic and coated with a conductive metal coating.

Figure 59A:
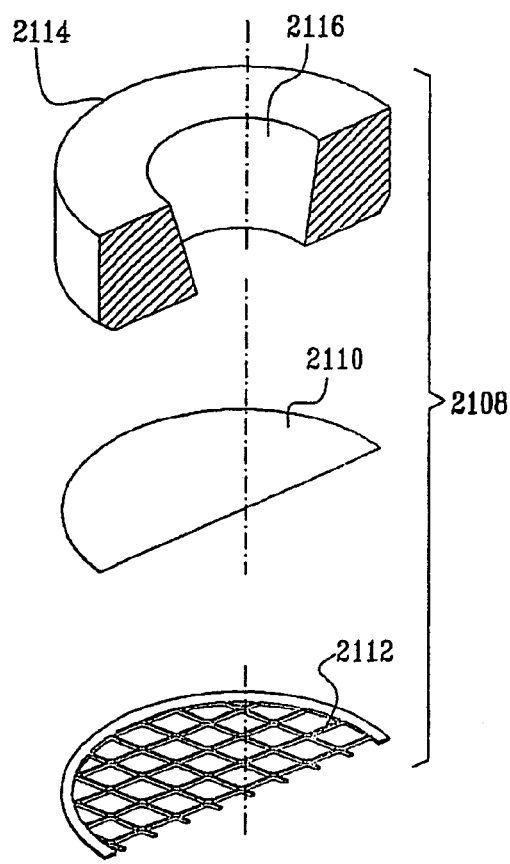
FIGS. 59A & 59B are oppositely facing simplified partially pictorial, partially sectional illustrations of a subassembly of the container of FIGS. 58A & 58B.
Figure 59B:
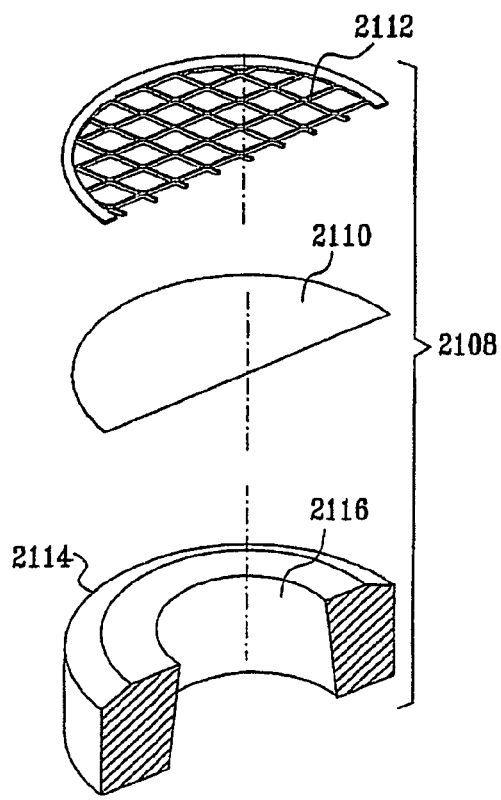

First enclosure element 2100 preferably defines a liquid sample enclosure and has a base surface 2104 having a generally central aperture 2106. An electron beam permeable, fluid impermeable, membrane subassembly 2108, shown in detail in FIGS. 59A and 59B, is seated inside enclosure element 2100 against and over aperture 2106, as shown in FIGS. 60A & 60B and 62A & 62B. A sample dish comprising subassembly 2108 suitably positioned in enclosure element 2100 is designated by reference numeral 2109, as shown in FIGS. 60A–62B.

Turning additionally to FIGS. 59A and 59B, it is seen that an electron beam permeable, fluid impermeable, membrane 2110, preferably a polyimide membrane, such as Catalog No. LWN00033, commercially available from Moxtek Inc. of Orem, Utah, U.S.A., is adhered, as by an adhesive, to a mechanically supporting grid 2112. Grid 2112, which is not shown to scale, is preferably Catalog No. BM 0090-01, commercially available from Buckbee-Mears of Cortland, N.Y., U.S.A., and the adhesive is preferably Catalog No. NOA61, commercially available from Norland Products Inc. of Cranbury, N.J., U.S.A. A liquid sample enclosure defining ring 2114 is adhered to electron beam permeable, fluid impermeable, membrane 2110, preferably by an adhesive, such as Catalog No. NOA61, commercially available from Norland Products Inc. of Cranbury, N.J., U.S.A. Ring 2114 is preferably formed of PMMA (polymethyl methacrylate), such as Catalog No. 692106001000, commercially available from Irpen of Barcelona, Spain, and preferably defines a liquid sample enclosure with a volume of approximately 20 microliters and a height of approximately 2 mm. Preferably ring 2114 is configured to define a liquid sample enclosure 2116 having inclined walls.

An O-ring 2118 is preferably disposed between ring 2114 and an interior surface 2120 of second enclosure element 2102. O-ring 2118 is operative, when enclosure elements 2100 and 2102 are in tight threaded engagement, to obviate the need for the threaded engagement of elements 2100 and 2102 to be a sealed engagement.

Second enclosure element 2102 preferably is formed with a generally central stub 2122, having a throughgoing bore 2123, which stub is arranged to be seated in a suitable recess (not shown) in a specimen stage of a scanning electron microscope.

Figure 61A:
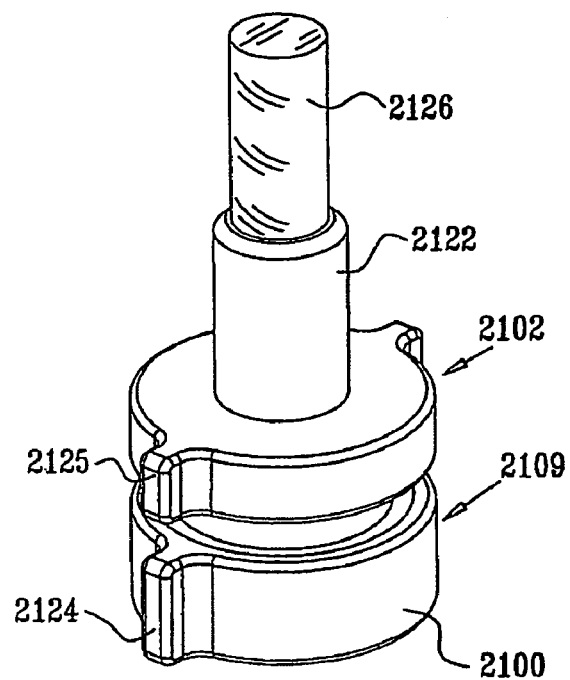
FIGS. 61A & 61B are oppositely facing simplified pictorial illustrations of the SEM compatible sample container of FIGS. 58A–60B in a fully assembled state.
Figure 61B:
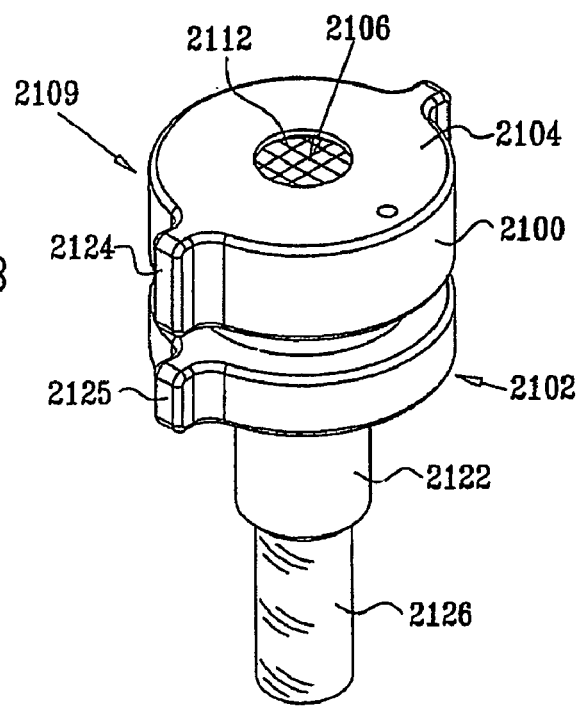

Enclosure elements 2100 and 2102 are preferably also provided with respective radially extending positioning and retaining protrusions 2124 and 2125, to enable the container to be readily seated in a suitable multi-container holder and also to assist users in threadably opening and closing the enclosure elements 2100 and 2102. Preferably, the mutual azimuthal positioning of the protrusions 2124 and 2125 on respective enclosure elements 2100 and 2102 is such that mutual azimuthal alignment therebetween indicates a desired degree of threaded closure therebetween, as shown in FIGS. 61A and 61B.

A light guide 2126 is provided to receive light from a sample in liquid sample enclosure 2116 during SEM inspection from a side of the sample not facing the electron beam permeable, fluid impermeable, membrane 2110.

The light guide 2126 is formed of a cylinder with a truncated conical tip 2128 and is inserted into bore 2123 of stub 2122. Light guide 2126 is preferably a plastic or glass clad light guide with a numerical aperture of 0.66, commercially available from Fiberoptics Technology, Inc. of 12 Fiber Rd., Pomfret, Conn., U.S.A. and is sealed to enclosure 2102 by any conventional means, such as by an adhesive.

The wall of conical tip 2128 is configured at an angle, such that the angle is smaller than a critical angle of reflection, so as to ensure that incident photons emitted from a sample are reflected in the light guide 2126.

Figure 63A:
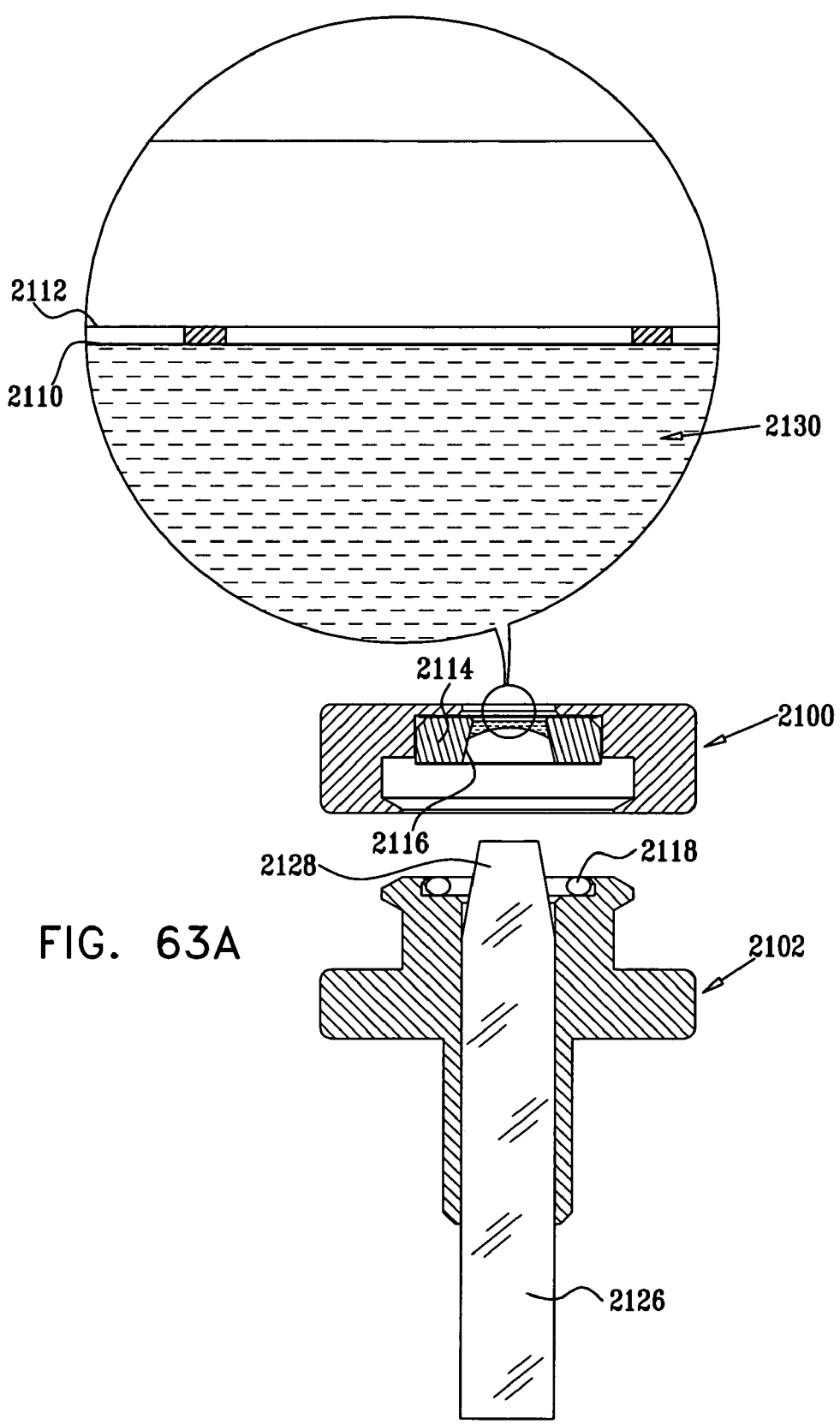
FIGS. 63A, 63B & 63C are three sectional illustrations showing the operative orientation of the SEM compatible sample container of FIGS. 58A–62B at three stages of operation.
Figure 63B:
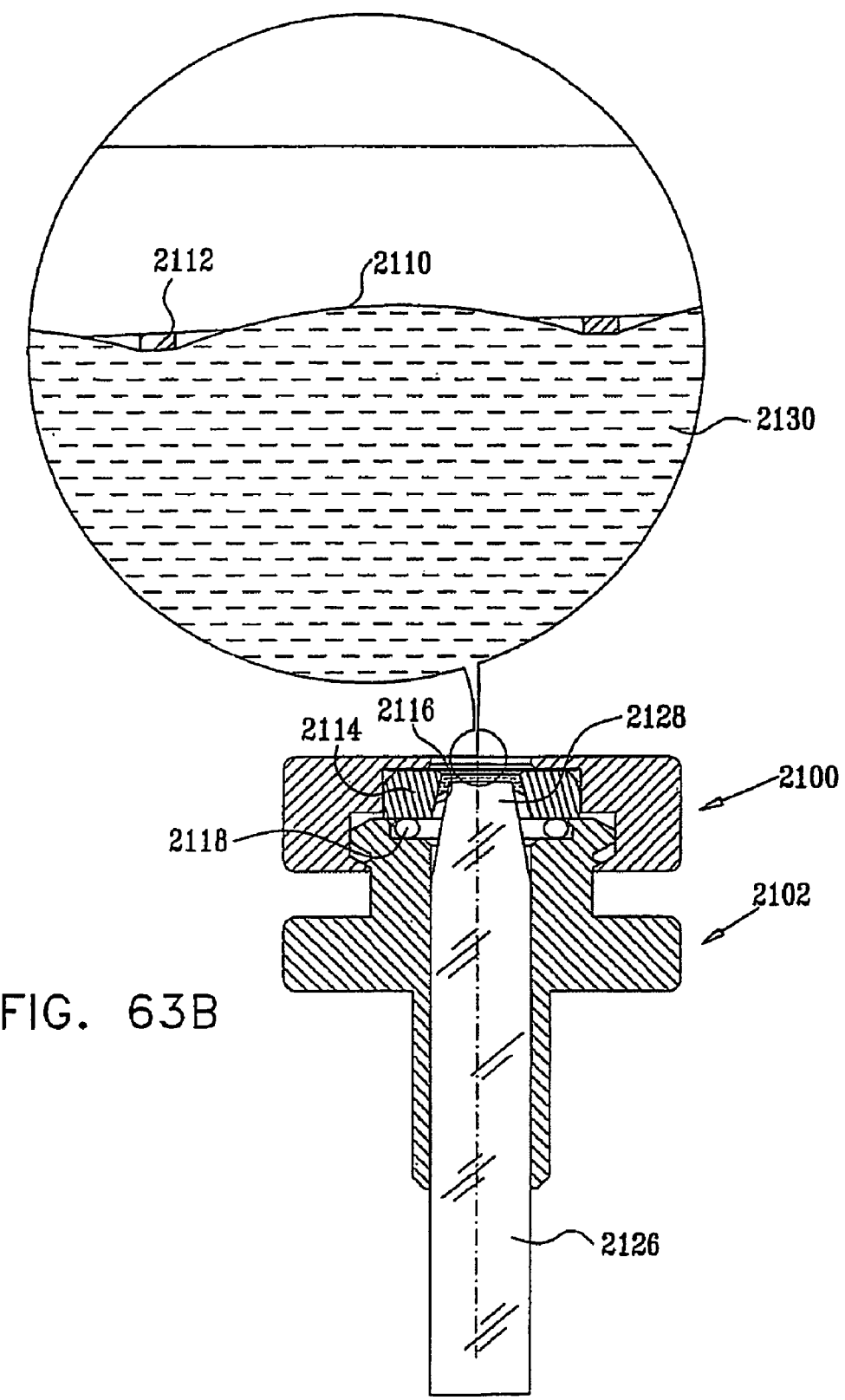
Figure 63C:
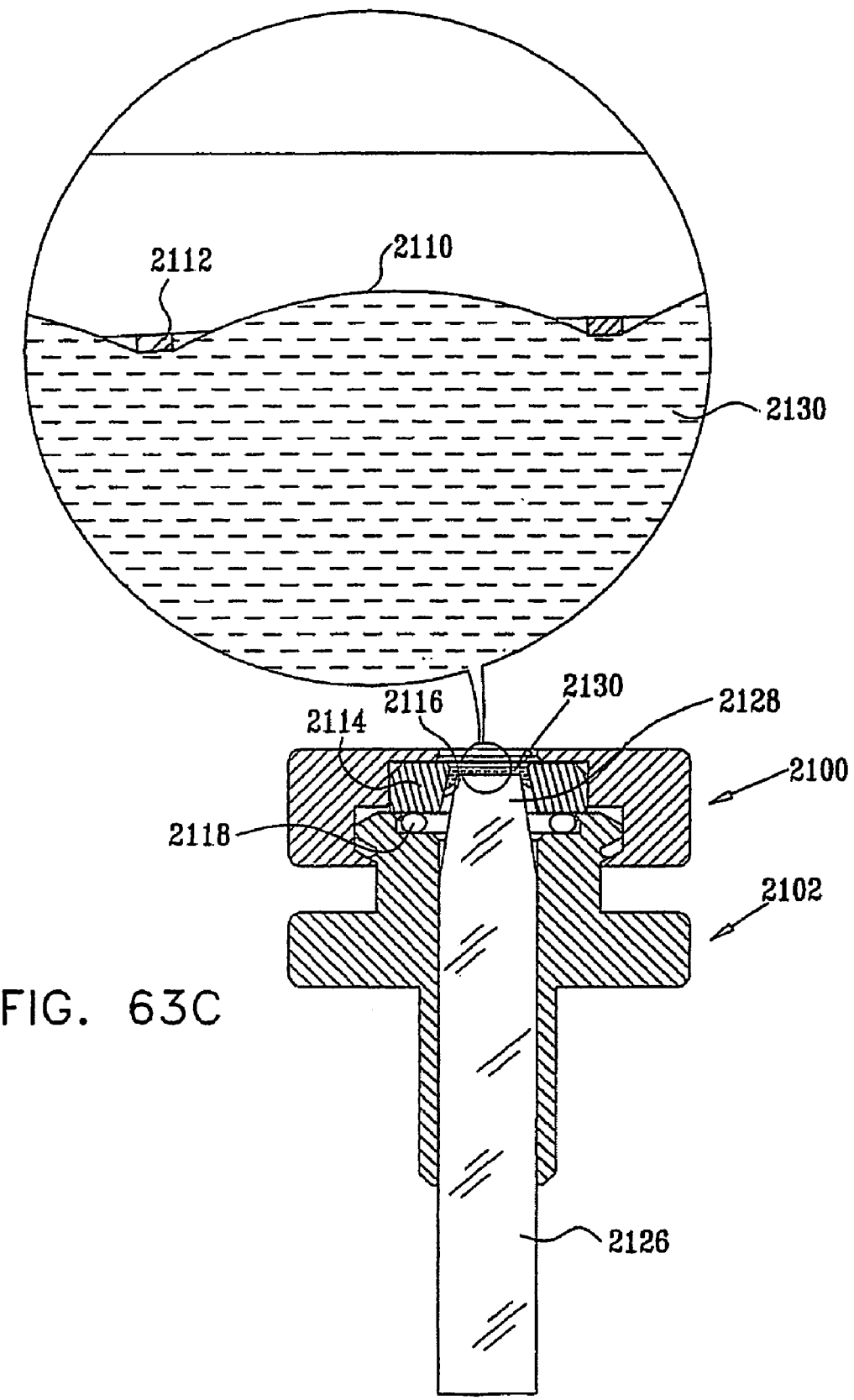

Reference is now made to FIGS. 63A, 63B & 63C, which are three sectional illustrations showing the operative orientation of the SEM compatible sample container of FIGS. 58A–62B at three stages of operation. FIG. 63A shows the container of FIGS. 58A–62B containing a liquid sample 2130 and arranged in the orientation shown in FIG. 58B, prior to threaded closure of enclosure elements 2100 and 2102. It is noted that the liquid sample does not flow out of the liquid sample enclosure 2116 due to surface tension. The electron beam permeable, fluid impermeable, membrane 2110 is seen in FIG. 63A to be generally planar.

FIG. 63B shows the container of FIG. 63A immediately following fill threaded engagement between enclosure elements 2100 and 2102, producing sealing of the liquid sample enclosure 2116 from the ambient The light guide tip 2128 is shown to be immersed in liquid sample 2130. It is seen that the electron beam permeable, fluid impermeable, membrane 2110 and its supporting grid 2112 bow outwardly due to pressure buildup in the liquid sample enclosure 2116 as the result of sealing thereof in this manner.

FIG. 63C illustrates the container of FIG. 63B, when placed in an evacuated environment of a SEM, typically at a vacuum of $10^{-2}$–$10^{-6}$ millibars. It is seen that in this environment, the electron beam permeable, fluid impermeable, membrane 2110 and support grid 2112 bow outwardly to a greater extent than in the ambient environment of FIG. 63B and further that the electron beam permeable, fluid impermeable, membrane 2110 tends to be forced into and through the interstices of grid 2112 to a greater extent than occurs in the ambient environment of FIG. 63B.

Figure 64A:
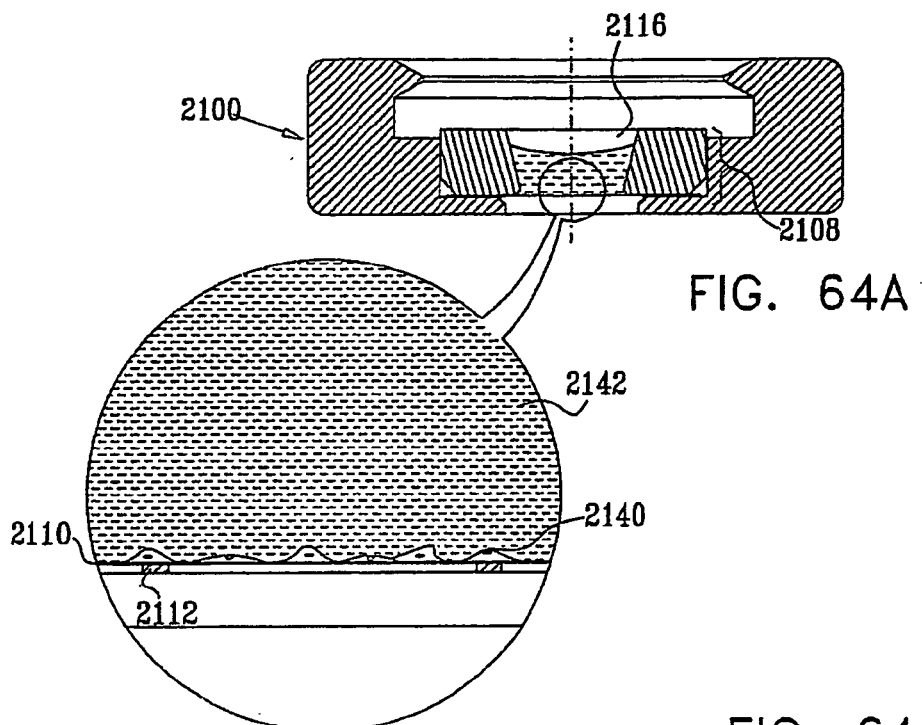

Reference is now made to FIGS. 64A, 64B, 64C, 64D and 64E, which are simplified sectional illustrations of cell growth, liquid removal, liquid addition, sealing and insertion into a SEM respectively using the SEM compatible sample container of FIGS. 58A–63C. Turning to FIG. 64A, which illustrates a typical cell culture situation, it is seen that the enclosure element 2100 having disposed therewithin subassembly 2108 is in the orientation shown in FIG. 58A and cells 2140 in a liquid medium 2142 are located within liquid sample enclosure 2116, the cells 2140 lying against the electron beam permeable, fluid impermeable, membrane 2110.

Figure 64B:
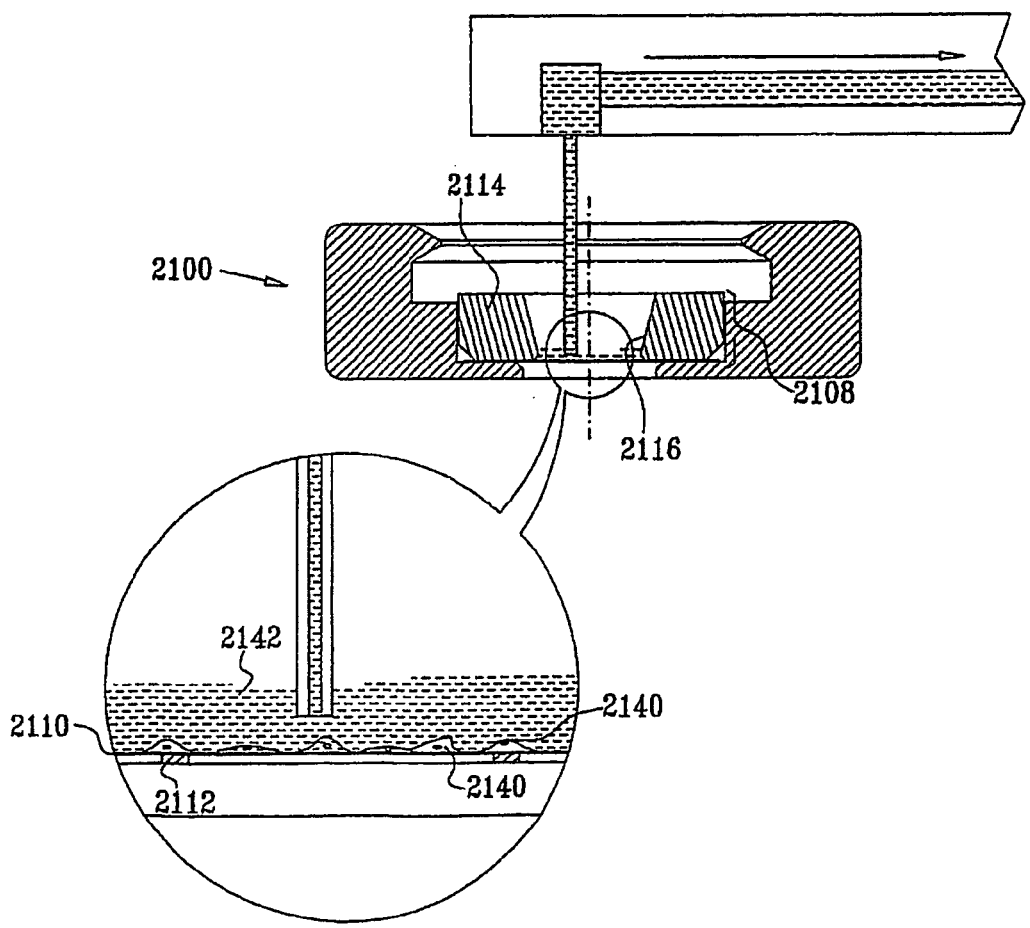
Figure 64C:
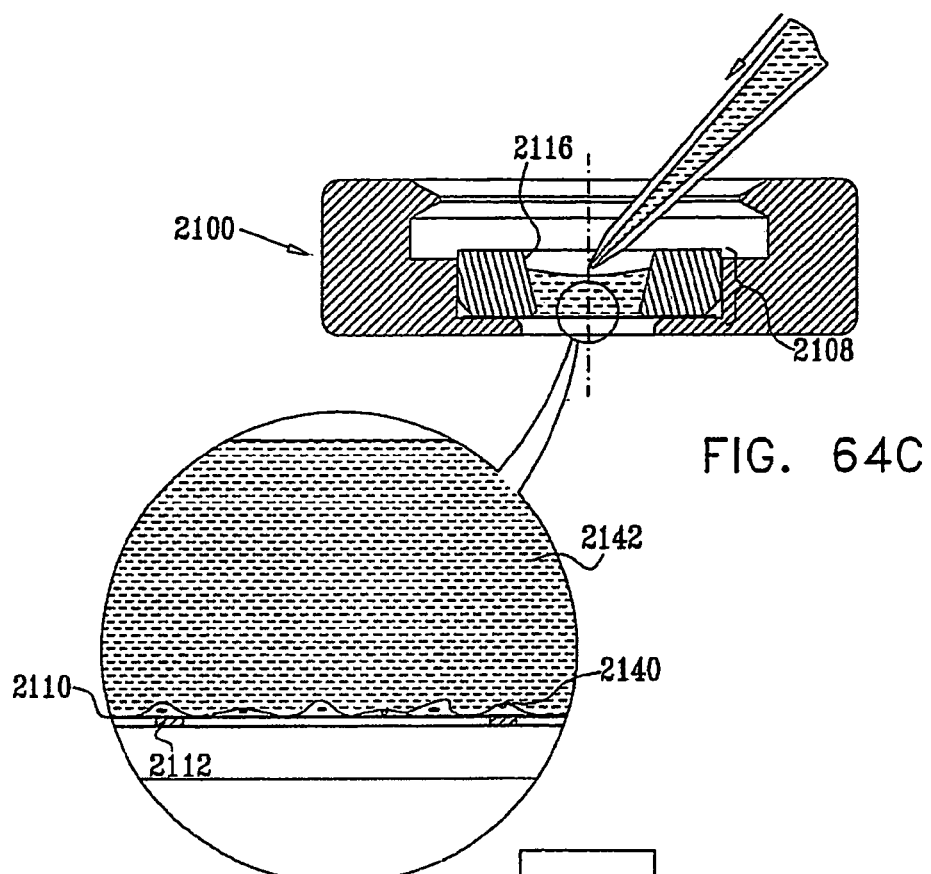

FIG. 64B shows removal of liquid from liquid sample enclosure 2116, typically by aspiration, and FIG. 64C shows addition of liquid to liquid sample enclosure 2116. It is appreciated that multiple occurrences of liquid removal and addition may take place with respect to a sample within liquid sample enclosure 2116. Preferably, the apparatus employed for liquid removal and addition is designed or equipped such as to prevent inadvertent rupture of the electron beam permeable, fluid impermeable, membrane 2110.

Figure 64D:
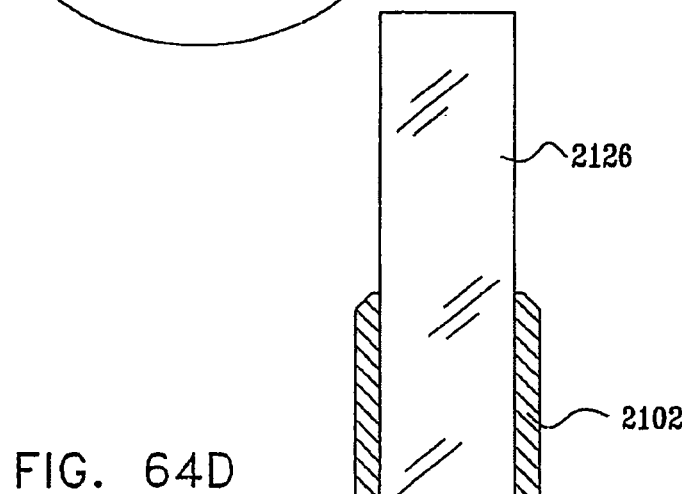

FIG. 64D illustrates closing of the container containing the cells 2140, seen in FIG. 64C, in a liquid medium 2142. The light guide tip 2128 is shown to be immersed in liquid medium.2142 of the liquid sample 2140. FIG. 64E shows the closed container, in the orientation of FIG. 58B being inserted onto a stage 2144 of a SEM 2146. It is appreciated that there exist SEMs wherein the orientation of the container is opposite to that shown in FIG. 64E.

FIGS. 64A–64D exemplify a situation wherein at least a portion of a liquid containing sample remains in contact with the electron beam permeable, fluid impermeable, membrane 2110 notwithstanding the addition or removal of liquid from liquid sample enclosure 2116. This situation may include situations wherein part of the sample is adsorbed or otherwise adhered to the electron beam permeable, fluid impermeable, membrane 2110. Examples of liquid containing samples may include cell cultures, blood, bacteria and acellular material.

Figure 65A:
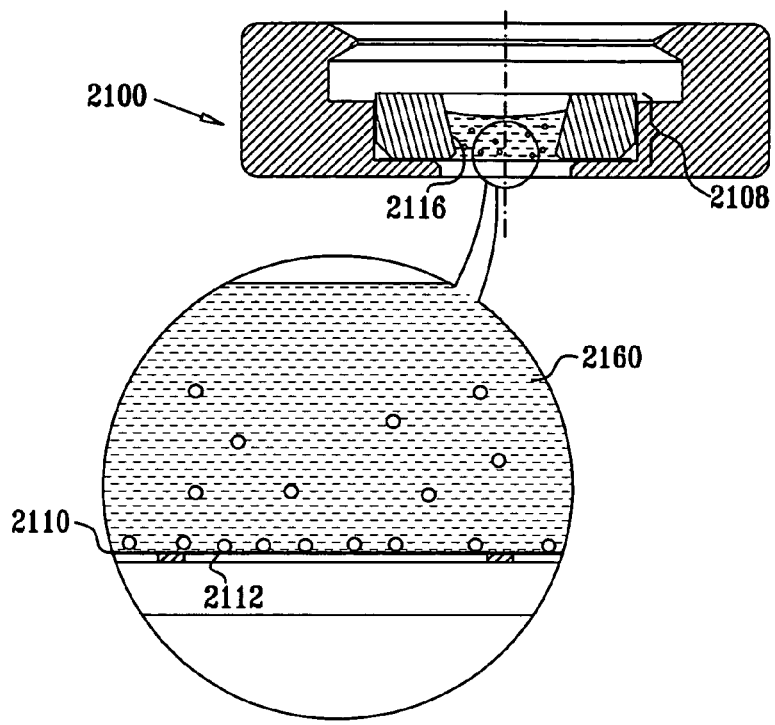
FIGS. 65A, 65B and 65C are simplified sectional illustrations of liquid containing samples, sealing and insertion into a SEM respectively using the SEM compatible sample container of FIGS. 58A–63C.
Figure 65B:
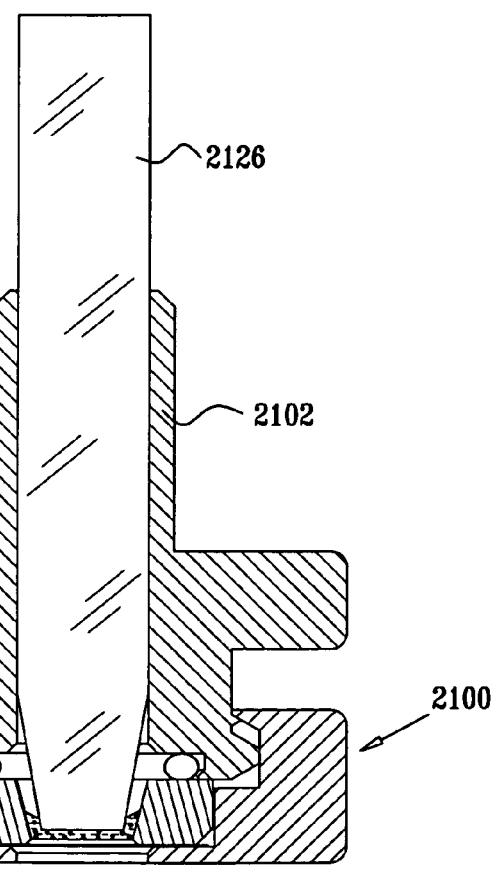
Figure 65C:
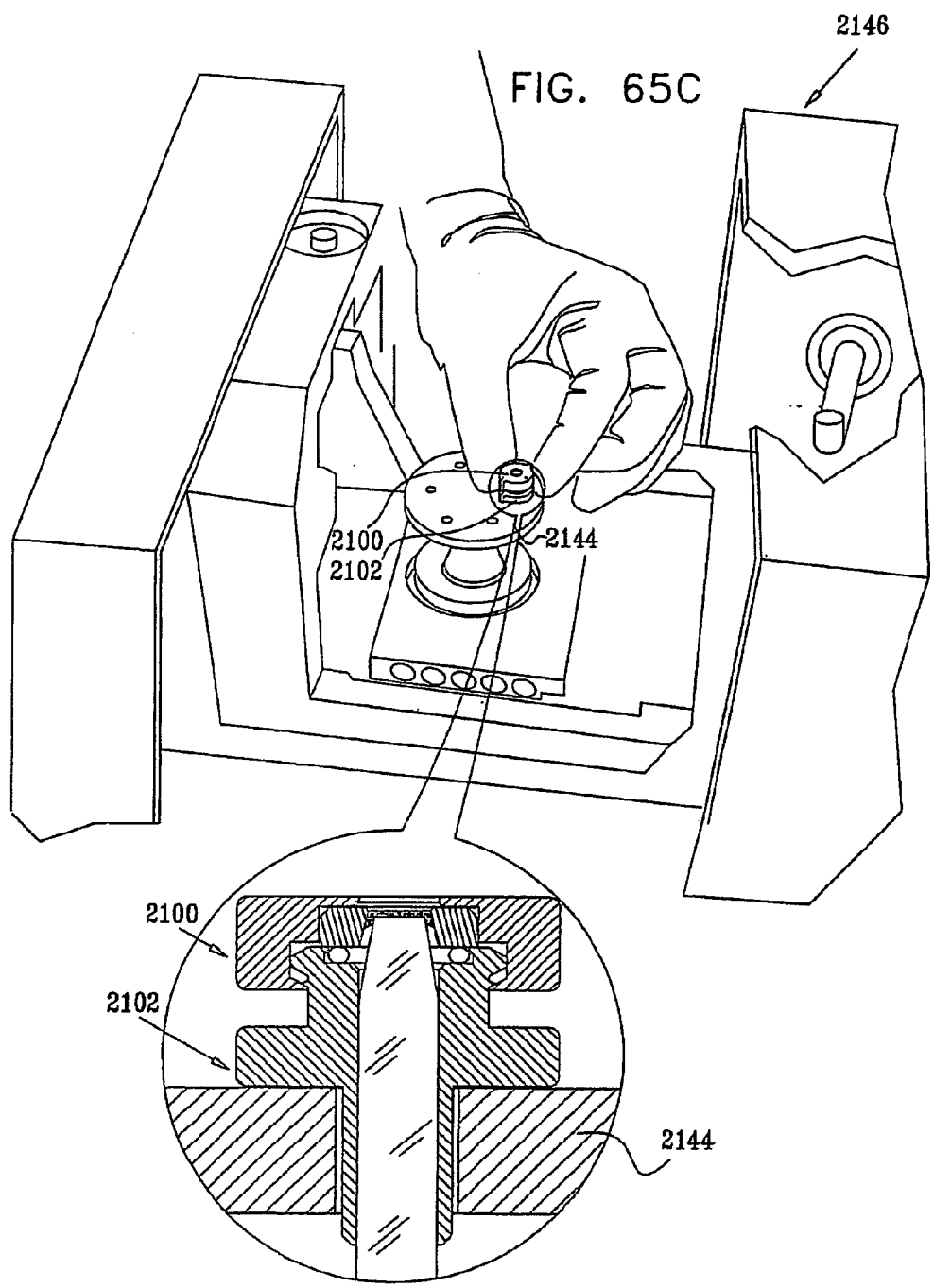

Reference is now made to FIGS. 65A, 65B and 65C which are simplified sectional illustrations of liquid containing samples in contact with the electron beam permeable, fluid impermeable, membrane 2110, sealing and insertion into a SEM respectively, using the SEM compatible sample container of FIGS. 58A–63C. FIGS. 65A–65C exemplify a situation wherein at least a portion of a liquid containing sample 2160 is in contact with the electron beam permeable, fluid impermeable, membrane 2110 but is not adhered thereto. Examples of liquid containing samples may include various emulsions and suspensions such as milk, cosmetic creams, paints, inks and pharmaceuticals in liquid form. It is seen that the enclosure element 2100 in FIGS. 65A and 65B, having disposed therewithin subassembly 2108, is in the orientation shown in FIG. 58A.

FIG. 65B illustrates closing of the container containing the sample 2160. FIG. 65C shows the closed container, in the orientation of FIG. 58B, being inserted onto stage 2144 of SEM 2146. It is appreciated that there exist SEMs wherein the orientation of the container is opposite to that shown in FIG. 65C.

Figure 66:
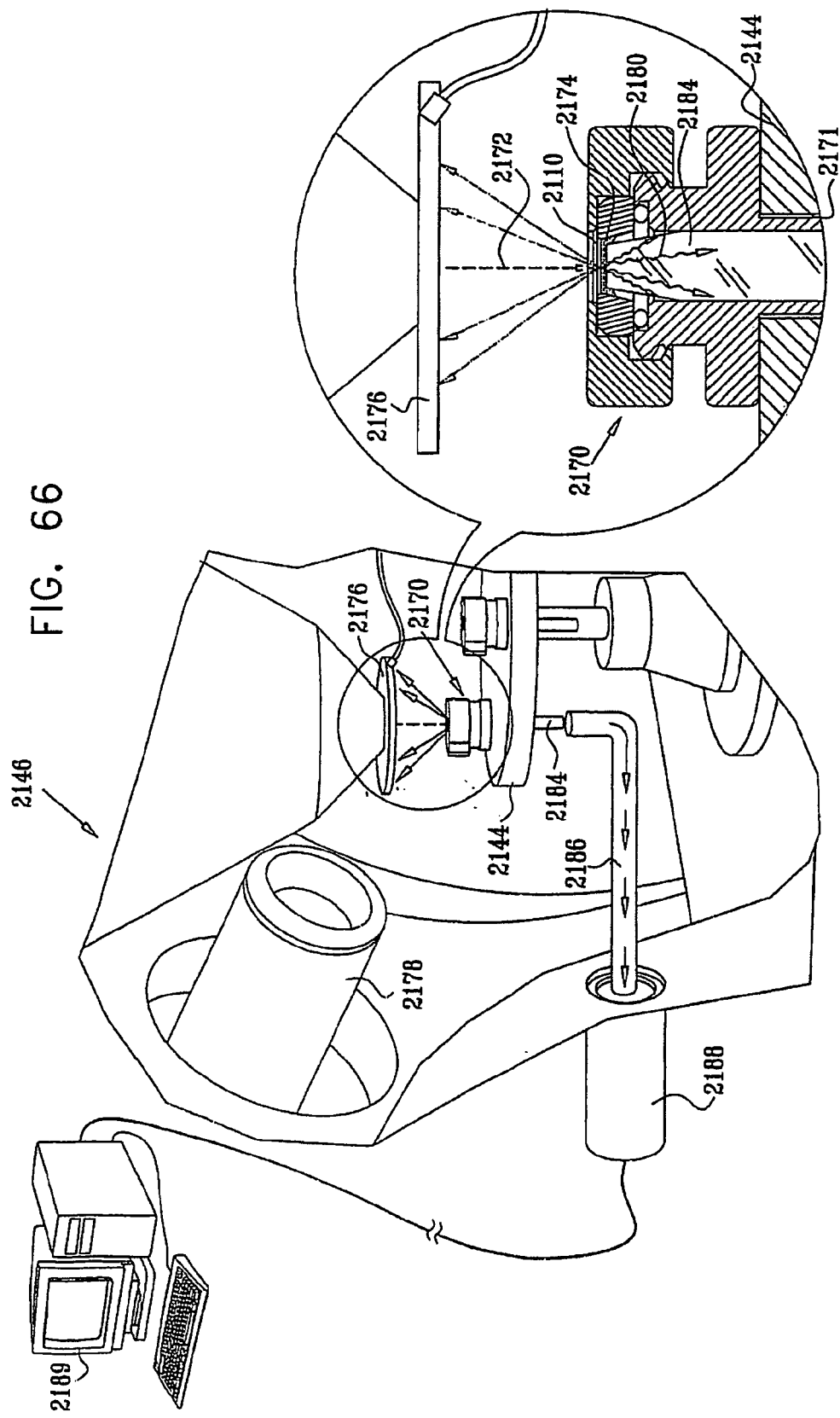
FIG. 66 is a simplified pictorial and sectional illustration of a SEM inspection of a sample using the SEM compatible sample container of FIGS. 58A–63C.

Reference is now made to FIG. 66, which is a simplified pictorial and sectional illustration of SEM inspection with light detection of a sample using the SEM compatible sample container of FIGS. 58A–63C. As seen in FIG. 66, the container, here designated by reference numeral 2170, is shown positioned on stage 2144 of SEM 2146 in a recess 2171. Stage 2144 is operative to rotate so as to enable positioning of container 2170 under an electron beam 2172 to inspect, during SEM inspection, regions of interest within a liquid containing sample 2174.

The electron beam 2172, generated by the SEM, passes through electron beam permeable, fluid impermeable, membrane 2110 and impinges on sample 2174 within container 2170. Backscattered electrons from sample 2174 pass through electron beam permeable, fluid impermeable, membrane 2110 and are detected by a detector 2176, forming part of the SEM. One or more additional detectors, such as a secondary electron detector 2178, may also be provided. An X-ray detector (not shown) may also be provided for detecting X-ray radiation emitted by the sample 2174 due to electron beam excitation thereof.

Photons 2180, emitted from liquid sample 2174 due to electron beam excitation, are transmitted through a first light guide, here designated by reference numeral 2184, which is the same as light guide 2126 of FIGS. 58A–63C, to a second light guide 2186. Second light guide 2186 is operative to transmit the photons 2180 to a light detector, such as a Photomultiplier Tube (PMT) 2188. Time dependent measurement of light intensity obtained from the light detector 2188, combined with information on the location of the scanning electron beam, are combined to produce an image of sample 2174 by methods known in the art, preferably as a digital image on a computer 2189.

Second light guide 2186, preferably, has a cross section with a diameter that is larger than the diameter of the cross section of the first light guide 2184 so as to minimize loss of photons in the passage between light guides 2184 and 2186 due to refraction or to imprecise relative alignment of the two light guides.

In the illustrated embodiment, second light guide 2186 is preferably formed in an L-shaped curve and preferably comprises a multiplicity of optic fibers disposed along the L-shaped light guide 2186 at an angle that ensures internal reflection of photons 2180 throughout the length of second light guide 2186.

It is appreciated that in the present invention photons 2180 may be transmitted vertically downward from first light guide 2184, via second light guide 2186 to a light detector located beneath the floor of the SEM 2146. Alternatively, photons 2180 may be transmitted from first light guide 2184 to a light detector, and that second light guide 2186 may be obviated.

In another embodiment of the present invention, the photons 2180 may be spectrally resolved prior to detection by light detector 2188 by conventional means, such as filters, diffraction gratings or prisms (not shown). This allows detection of photons with a wavelength within one or more specified ranges, yielding additional information on the composition and structure of the sample 2174 or features within sample 2174.

Additionally, a liquid, such as oil or a gel (not shown), with an index of refraction similar to the index of refraction of light guides 2184 and 2186, may be placed between light guides 2184 and 2186 to prevent the photons 2180 from scattering outside light guides 2184 and 2186.

Figure 67:
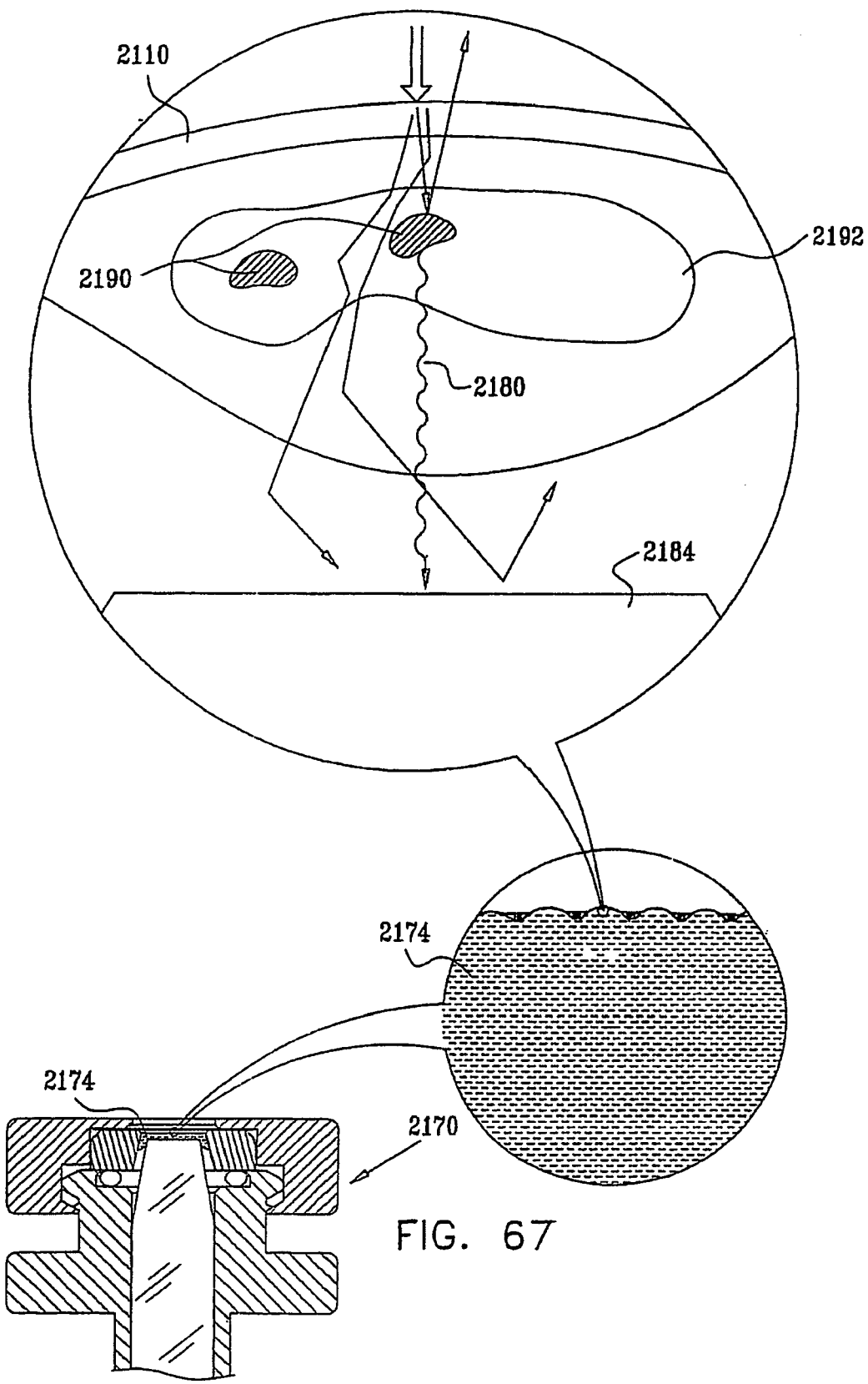
FIG. 67 is a greatly enlarged simplified schematic illustration of the SEM inspection of a sample in the context of FIG. 66.

Reference is now made additionally to FIG. 67, which schematically illustrates some details of the electron beam and photon interaction with the sample. 2174 in container 2170 in accordance with a preferred embodiment of the present invention. It is noted that the present invention enables high contrast imaging of features which are distinguished from each other by their average atomic number or, alternatively, by their average photon yield due to excitation by electrons, as illustrated in FIG. 67. In FIG. 67 it is seen that nucleoli 2190, having a relatively high average atomic number, backscatter electrons more than the surrounding nucleoplasm 2192.

Photons 2180 are shown to emit from the nucleoli 2190 and are transmitted to the light detector 2188 (shown in FIG. 66), via light guide 2184. It is noted that the contrast obtained by detection of backscattered electrons and the contrast obtained by photon detection are due to different physical processes and to different chemical properties of features within the sample, and therefore do not generally overlap.

It is also noted that in accordance with a preferred embodiment of the present invention, imaging of the interior of the sample to a depth of up to approximately 2 microns is achievable when employing electron beams having an energy level of less than 50 KeV, as seen in FIG. 67, wherein nucleoli 2190 disposed below electron beam permeable, fluid impermeable, membrane 2110 are imaged.

Reference is now made to FIGS. 68A–72B, which are oppositely facing simplified exploded view pictorial illustrations of a disassembled scanning electron microscope (SEM) compatible sample container constructed and operative in accordance with another preferred embodiment of the present invention As seen in FIGS. 68A & 68B, the SEM compatible sample container comprises first and second mutually threaded enclosure elements, respectively designated by reference numerals 2200 and 2202, arranged for enhanced ease and speed of closure. Enclosure elements 2200 and 2202 are preferably molded of plastic and coated with a conductive metal coating.

Figure 69A:
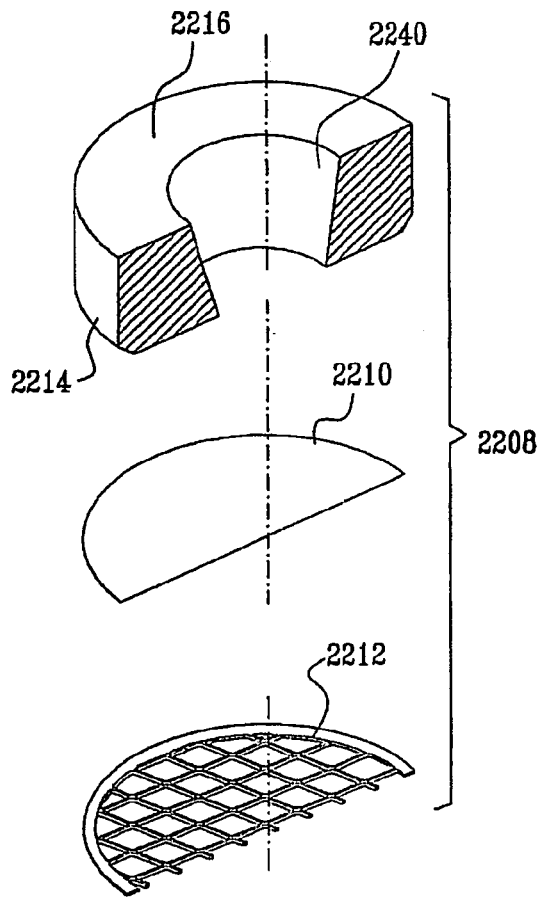
FIGS. 69A & 69B are oppositely facing simplified partially pictorial, partially sectional illustrations of a subassembly of the container of FIGS. 68A & 68B.
Figure 69B:
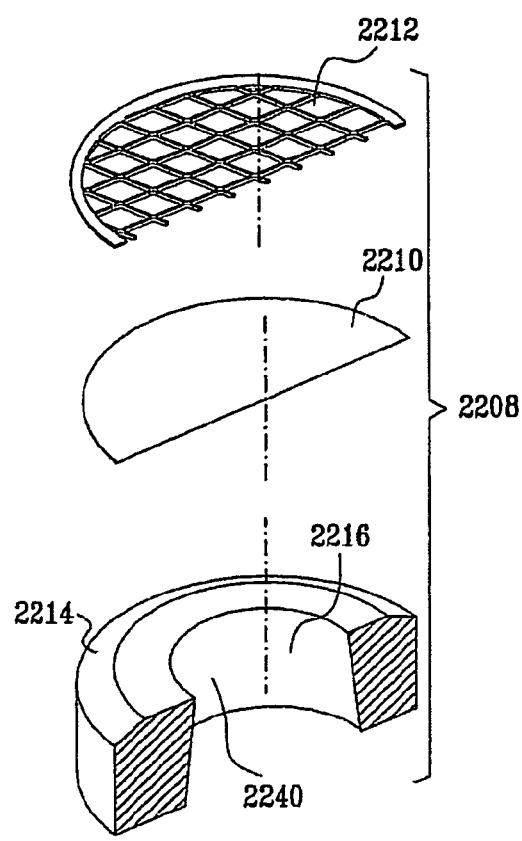

First enclosure element 2200 preferably defines a liquid sample enclosure and has a base surface 2204 having a generally central aperture 2206. An electron beam permeable, fluid impermeable, membrane subassembly 2208, shown in detail in FIGS. 69A and 69B, is seated inside enclosure element 2200 against and over aperture 2206, as shown in FIGS. 70A & 70B and 72A & 72B. A sample dish comprising subassembly 2208 suitably positioned in enclosure element 2200 is designated by reference numeral 2209, as shown in FIGS. 70A–72B.

Turning additionally to FIGS. 69A and 69B, it is seen that an electron beam permeable, fluid impermeable, membrane 2210, preferably a polyimide membrane, such as Catalog No. LWN00033, commercially available from Moxtek Inc. of Orem, Utah, U.S.A., is adhered, as by an adhesive, to a mechanically supporting grid 2212. Grid 2212, which is not shown to scale, is preferably Catalog No. BM 0090-01, commercially available from Buckbee-Mears of Cortland, N.Y., U.S.A., and the adhesive is preferably Catalog No. NOA61, commercially available from Norland Products Inc. of Cranbury, N.J., U.S.A. A liquid sample enclosure defining ring 2214 is adhered to electron beam permeable, fluid impermeable, membrane 2210, preferably by an adhesive, such as Catalog No. NOA61, commercially available from Norland Products Inc. of Cranbury, N.J., U.S.A. Ring 2214 is preferably formed of PMMA (polymethyl methacrylate), such as Catalog No. 692106001000, commercially available from Irpen of Barcelona, Spain, and preferably defines a liquid sample enclosure with a volume of approximately 20 microliters and a height of approximately 2 mm. Preferably ring 2214 is configured to define a liquid sample enclosure 2216 having inclined walls.

A diaphragm 2218 is preferably provided and is operative to provide dynamic and static pressure relief. Diaphragm 2218 is preferably integrally formed of an O-ring portion 2220 to which is sealed an expandable sheet portion 2221. The diaphragm 2218 is preferably molded of silicon rubber having a Shore hardness of about 50 and the sheet portion 2221 preferably has a thickness of 0.2–0.3 mm.

The diaphragm 2218 is inserted into a first aperture 2222 formed in an exterior surface of a wall of the second enclosure element 2202. A second aperture 2223, shown in FIGS. 72A&72B, is formed in an interior surface of a wall of the second enclosure element 2202. First aperture 2222 and second aperture 2223 enable diaphragm 2218 to provide pressure relief by defining a fluid communication channel between one side of the diaphragm 2218 and the environment in which the SEM compatible sample container is located. A plug 2224 is preferably provided to retain the diaphragm 2218 in aperture 2222. Plug 2224 is preferably formed of a ring 2225 having a generally central aperture 2226 and is attached to an internal surface of second enclosure element 2202 defined by aperture 2222 by any conventional means, such as by a tight fitting engagement.

An O-ring 2228 is preferably disposed between ring 2214 and an interior surface 2230 of second enclosure element 2202. O-ring 2228 is operative, when enclosure elements 2200 and 2202 are in tight threaded engagement, to obviate the need for the threaded engagement of elements 2200 and 2202 to be a sealed engagement.

Second Enclosure element 2202 preferably is formed with a generally central stub 2232, having a throughgoing bore 2233, which stub is arranged to be seated in a suitable recess (not shown) in a specimen stage of a scanning electron microscope.

Figure 71A:
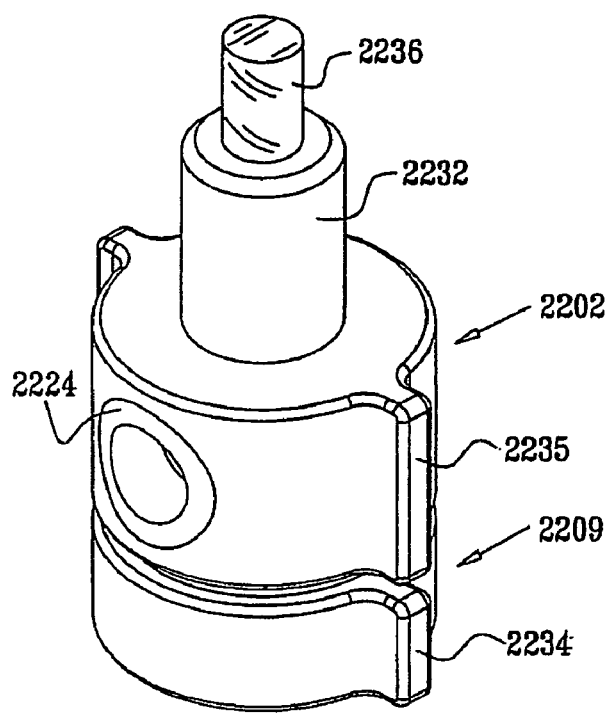
FIGS. 71A & 71B are oppositely facing simplified pictorial illustrations of the SEM compatible sample container of FIGS. 68A–70B in a fully assembled state.
Figure 71B:
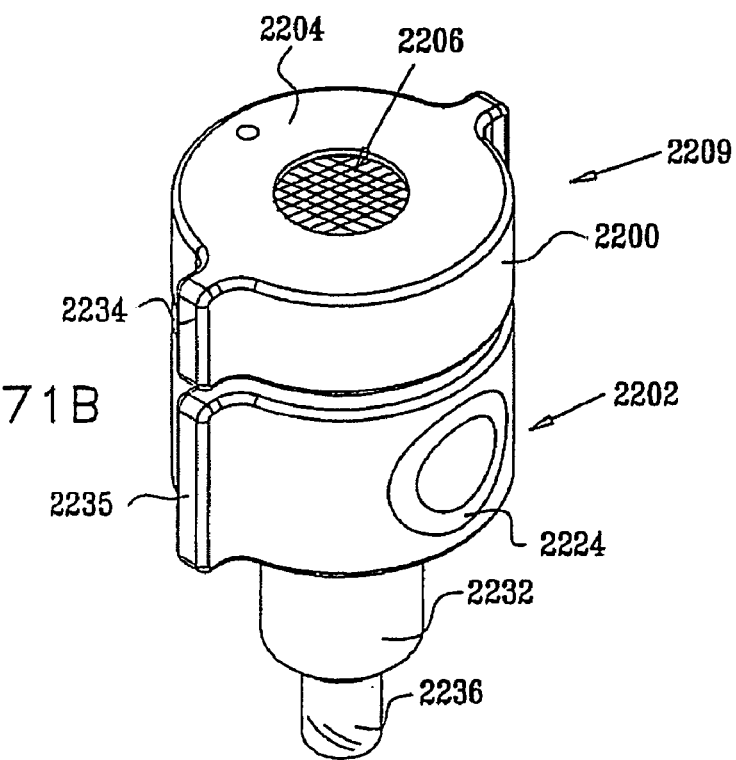

Enclosure elements 2200 and 2202 are preferably also provided with respective radially extending positioning and retaining protrusions 2234 and 2235, to enable the container to be readily seated in a suitable multi-container holder and also to assist users in threadably opening and closing the enclosure elements 2200 and 2202. Preferably, the mutual azimuthal positioning of the protrusions 2234 and 2235 on respective enclosure elements 2200 and 2202 is such that mutual azimuthal alignment therebetween indicates a desired degree of threaded closure therebetween, as shown in FIGS. 71A and 71B.

A light guide 2236 is provided to receive light from a sample in liquid sample enclosure 2216 during SEM inspection from a side of the sample not facing the electron beam permeable, fluid impermeable, membrane 2210.

Light guide 2236 is formed of a cylinder with a truncated conical tip 2238 and is inserted into bore 2233 of stub 2232. Light guide 2236 is preferably a plastic or glass clad light guide with a numerical aperture of 0.66, commercially available from Fiberoptics Technology, Inc. of 12 Fiber Rd., Pomfret, Conn., U.S.A and is sealed to enclosure 2202 by any conventional means, such as by an adhesive.

The wall of conical tip 2238 is configured at an angle, such that the angle is smaller than a critical angle of reflection, so as to ensure that incident photons emitted from a sample are reflected in the light guide 2236.

Figure 73A:
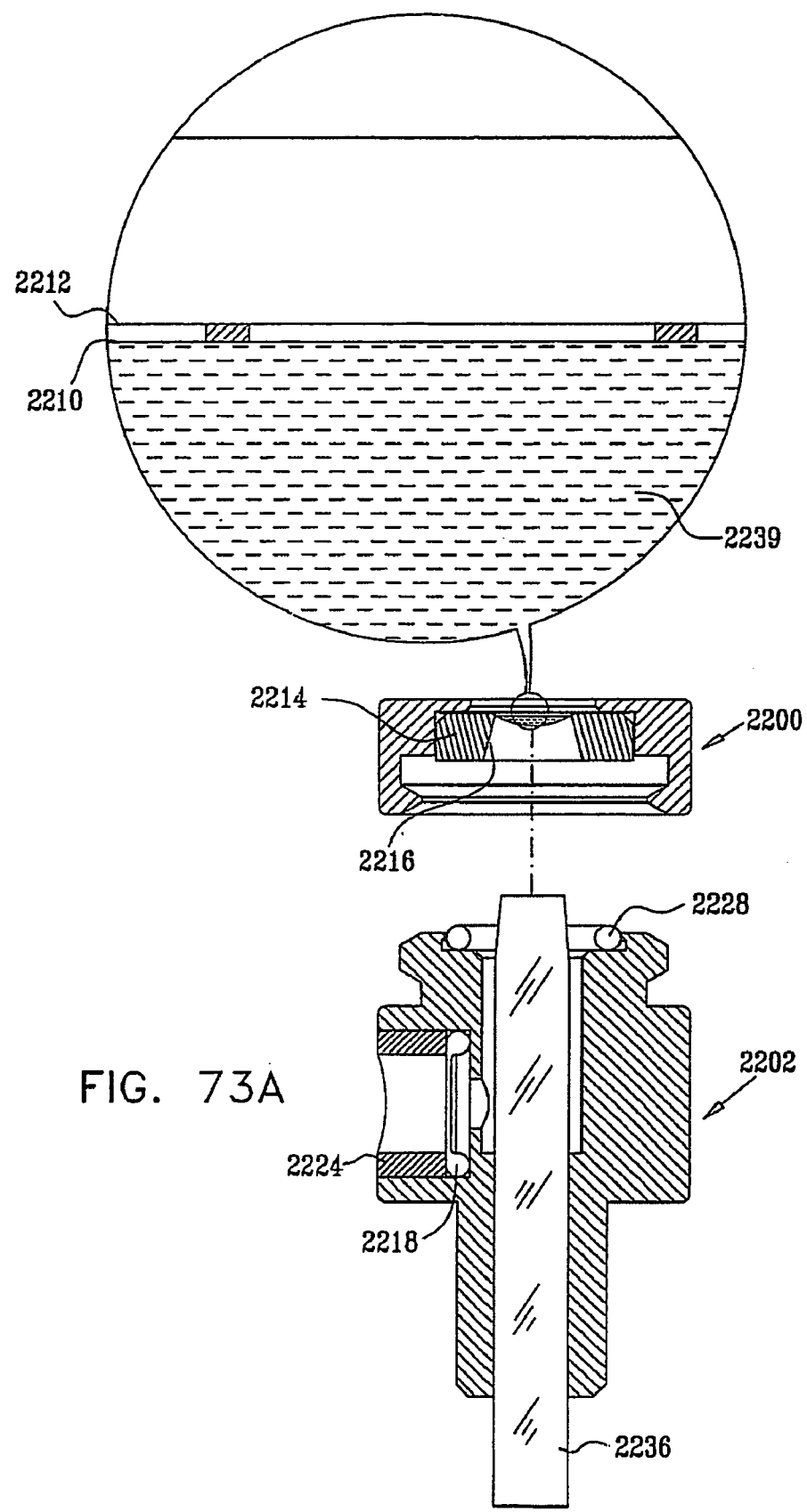
FIGS. 73A, 73B & 73C are three sectional illustrations showing the operative orientation of the SEM compatible sample container of FIGS. 68A–72B at three stages of operation.
Figure 73B:
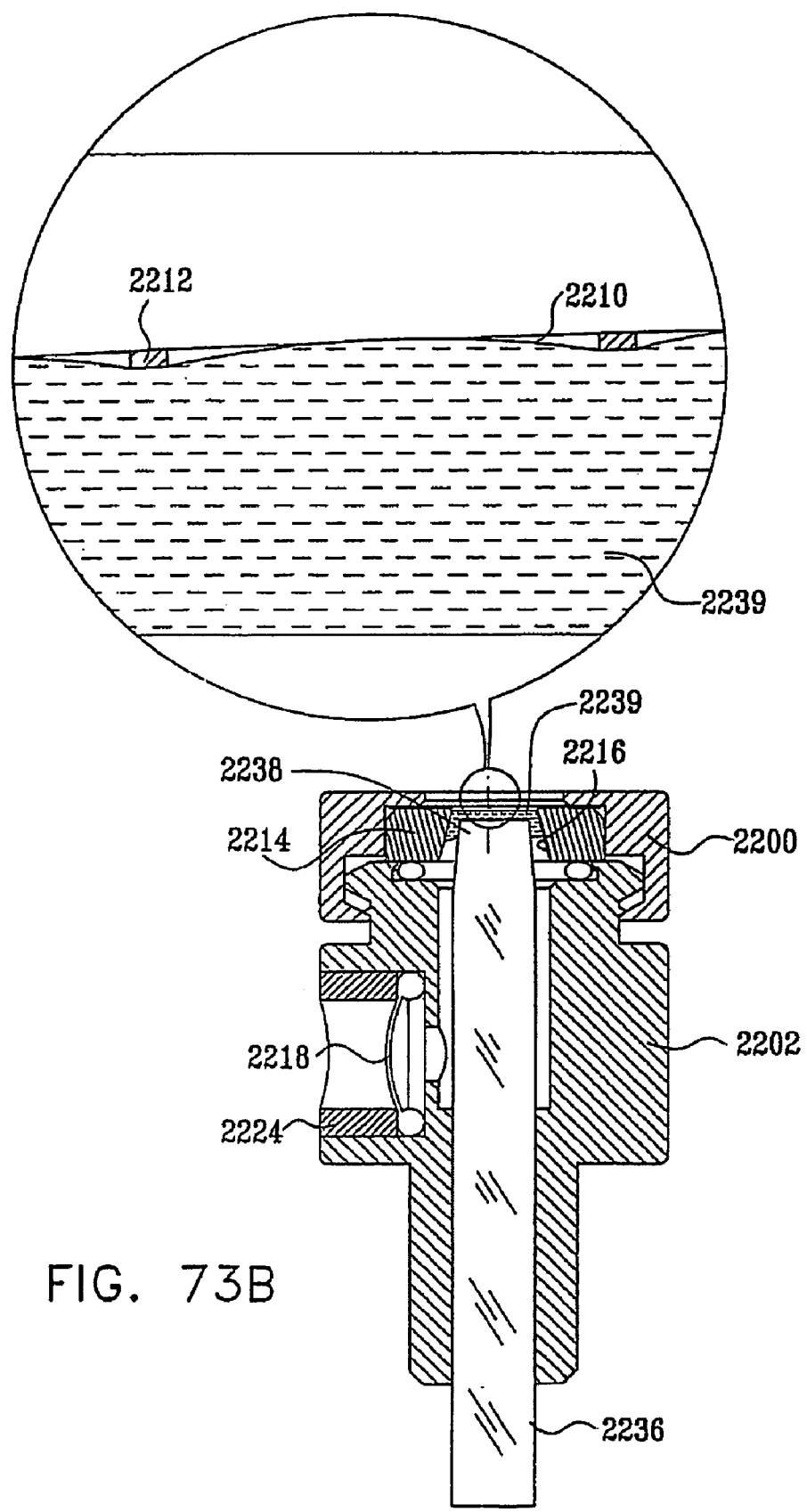
Figure 73C:
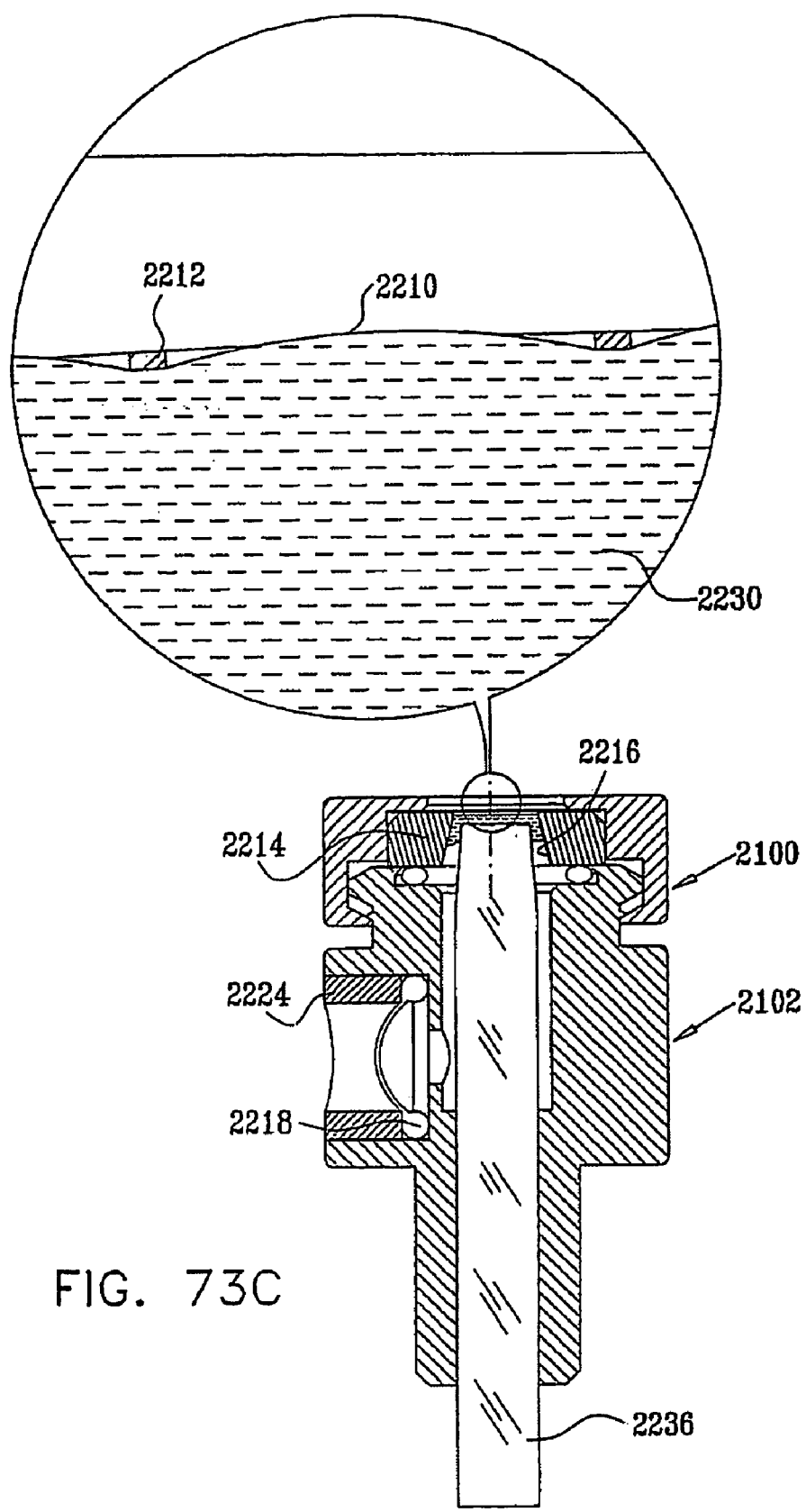

Reference is now made to FIGS. 73A, 73B & 73C, which are three sectional illustrations showing the operative orientation of the SEM compatible sample container of FIGS. 68A–72B at three stages of operation. FIG. 73A shows the container of FIGS. 68A–72B containing a liquid sample 2239 and arranged in the orientation shown in FIG. 68B, prior to threaded closure of enclosure elements 2200 and 2202. It is noted that the liquid sample does not flow out of the liquid sample enclosure 2216 due to surface tension. The electron beam permeable, fluid impermeable, membrane 2210 is seen in FIG. 73A to be generally planar.

FIG. 73B shows the container of FIG. 73A immediately following full threaded engagement between enclosure elements 2200 and 2202, producing sealing of the liquid sample enclosure 2216 from the ambient. The light guide tip 2238 is shown to be immersed in liquid sample 2239. It is seen that the diaphragm 2218 bows outwardly due to pressure buildup in the liquid sample enclosure 2216 as the result of sealing thereof in this manner. In this embodiment, electron beam permeable, fluid impermeable, membrane 2210 and its supporting grid 2212 also bow outwardly due to pressure buildup in the liquid sample enclosure 2216 as the result of sealing thereof in this manner, however to a significantly lesser extent than in the embodiment of FIG. 63B, due to the action of diaphragm 2218. This can be seen by comparing FIG. 73B with FIG. 63B.

FIG. 73C illustrates the container of FIG. 73B, when placed in an evacuated environment of a SEM, typically at a vacuum of $10^{-2}$–$10^{-6}$ millibars. It is seen that in this environment, the diaphragm 2218 bows outwardly to a greater extent than in the ambient environment of FIG. 73B and that electron beam permeable, fluid impermeable, membrane 2210 and support grid 2212 also bow outwardly to a greater extent than in the ambient environment of FIG. 73B, but to a significantly lesser extent than in the embodiment of FIG. 63C, due to the action of diaphragm 2218. This can be seen by comparing FIG. 73C with FIG. 63C.

It is also noted that the electron beam permeable, fluid impermeable, membrane 2210 tends to be forced into and through the interstices of grid 2212 to a greater extent than occurs in the ambient environment of FIG. 73B but to a significantly lesser extent than in the embodiment of FIG. 63C, due to the action of diaphragm 2218. This can also be seen by comparing FIG. 73C with FIG. 63C.

Figure 74A:
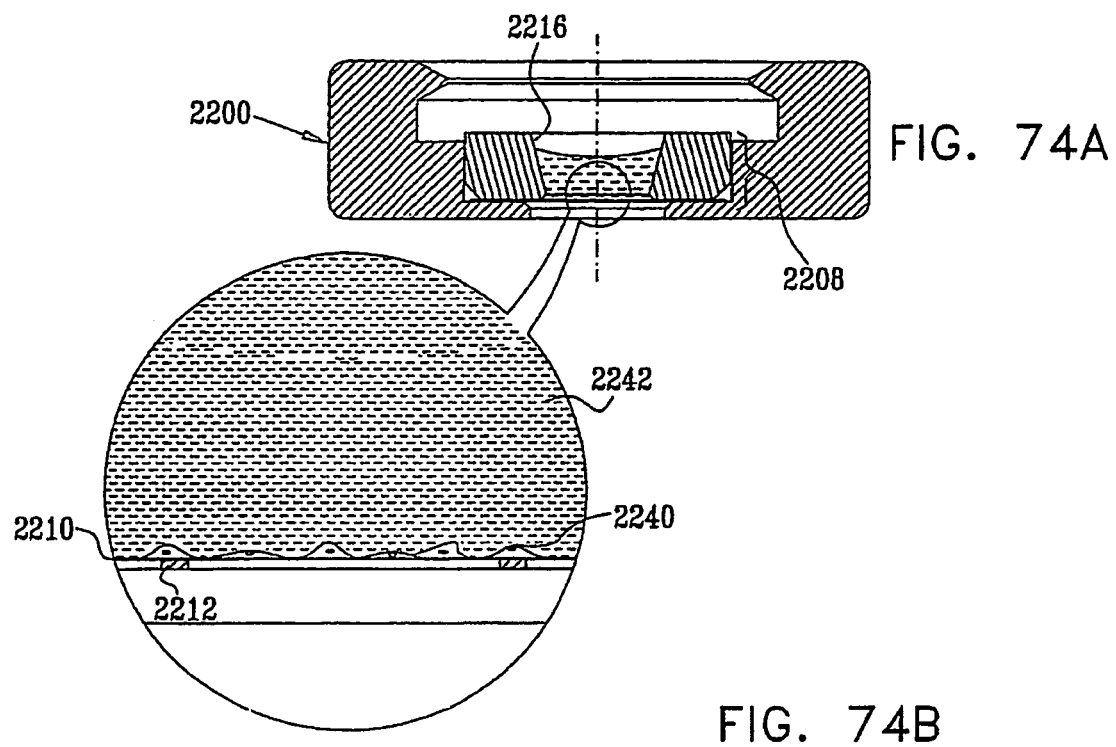
FIGS. 74A, 74B, 74C, 74D and 74E are simplified sectional illustrations of cell growth, liquid removal, liquid addition, sealing and insertion into a SEM respectively using the SEM compatible sample container of FIGS. 68A–73C.

Reference is now made to FIGS. 74A, 74B, 74C, 74D and 74E, which are simplified sectional illustrations of cell growth, liquid removal, liquid addition, sealing and insertion into a SEM, respectively, using the SEM compatible sample container of FIGS. 68A–73C. Turning to FIG. 74A, which is identical to FIG. 64A and illustrates a typical cell culture situation, it is seen that the enclosure element 2200 having disposed therewithin subassembly 2208 is in the orientation shown in FIG. 68A and cells 2240 in a liquid medium 2242 are located within liquid sample enclosure 2216, the cells 2240 lying against the electron beam permeable, fluid impermeable, membrane 2210.

Figure 74B:
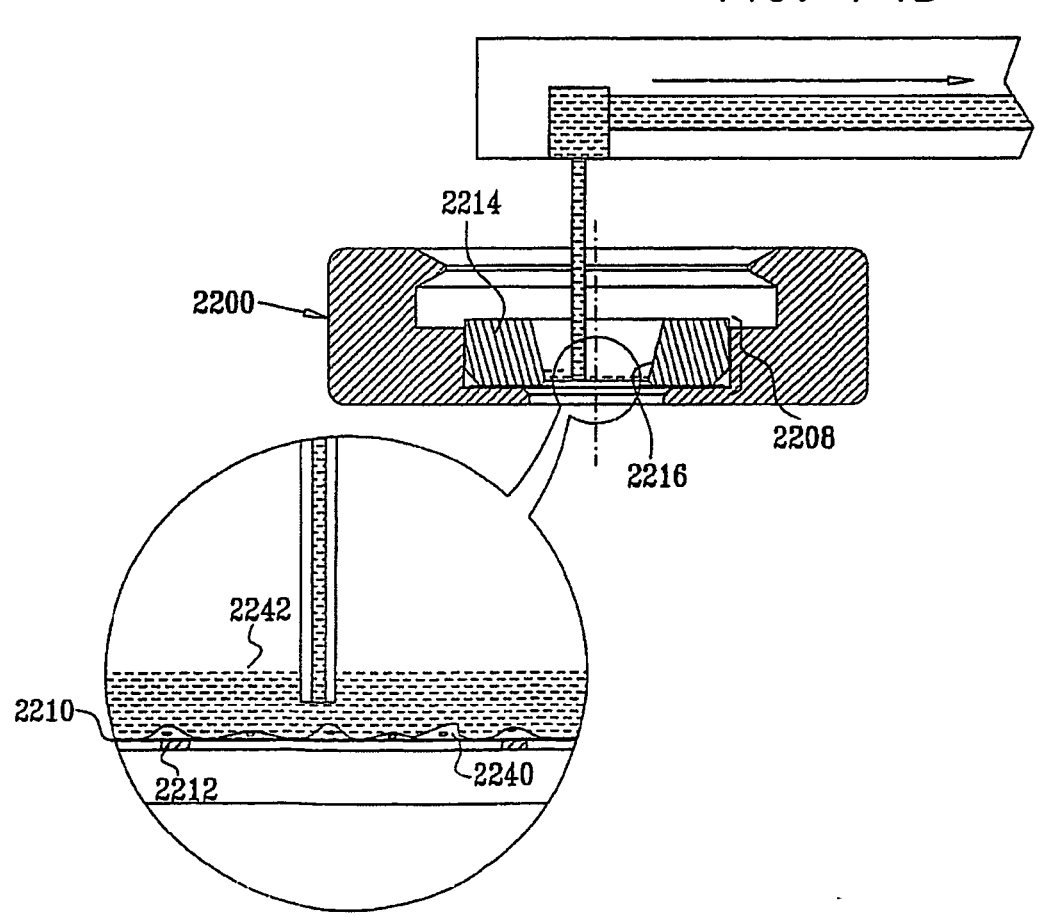
Figure 74C:
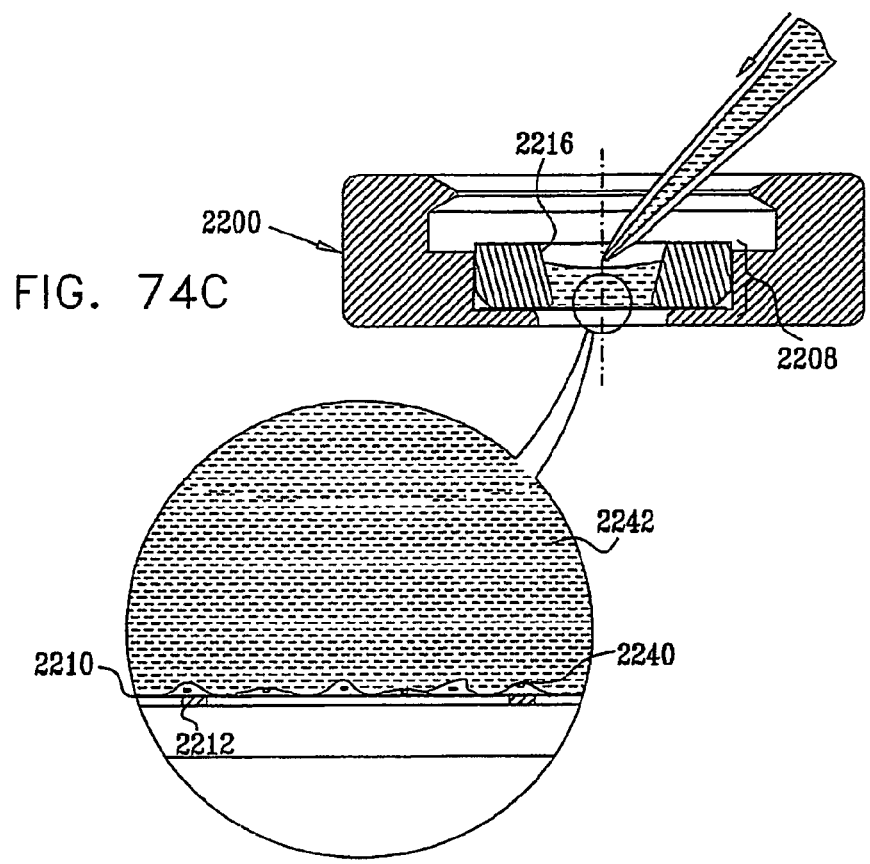

FIG. 74B, which is identical to FIG. 64B, shows removal of liquid from liquid sample enclosure 2216, typically by aspiration, and FIG. 74C, which is identical to FIG. 64C, shows addition of liquid to liquid sample enclosure 2216. It is appreciated that multiple occurrences of liquid removal and addition may take place with respect to a sample within liquid sample enclosure 2216. Preferably, the apparatus employed for liquid removal and addition is designed or equipped such as to prevent inadvertent rupture of the electron beam permeable, fluid impermeable, membrane 2210.

Figure 74D:
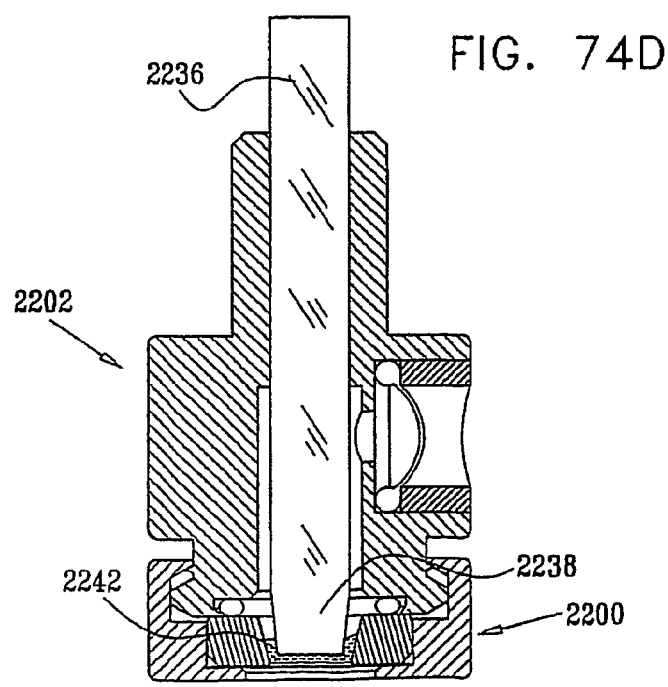
Figure 74E:
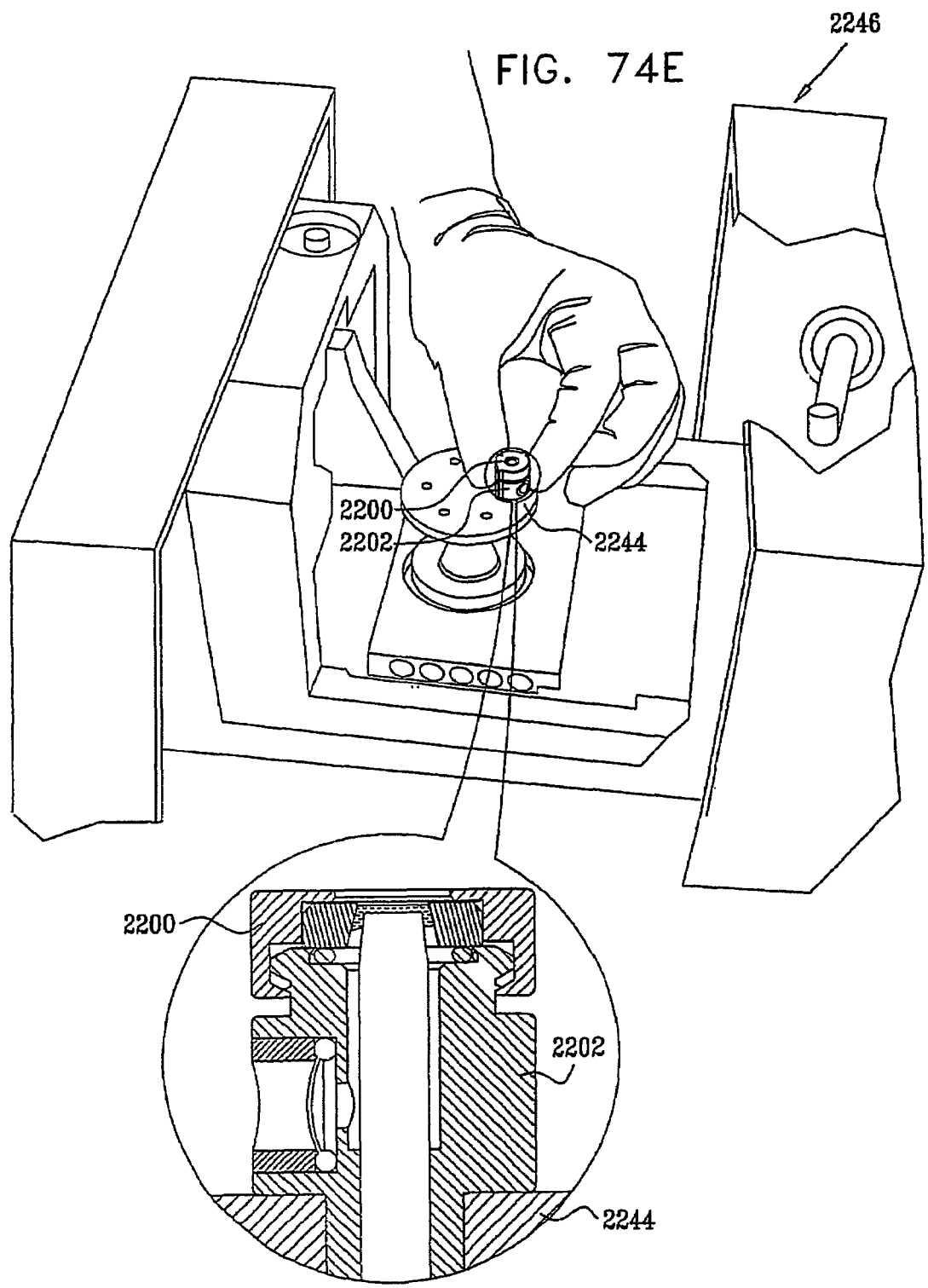

FIG. 74D illustrates closing of the container containing the cells 2240, seen in FIG. 74C, in a liquid medium 2242. The light guide tip 2238 is shown to be immersed in liquid medium 2242 of the liquid sample. FIG. 74E shows the closed container, in the orientation of FIG. 68B, being inserted onto a stage 2244 of a SEM 2246. It is appreciated that there exist SEMs wherein the orientation of the container is opposite to that shown in FIG. 74E.

FIGS. 74A–74D exemplify a situation wherein at least a portion of a liquid containing sample remains in contact with the electron beam permeable, fluid impermeable, membrane 2210 notwithstanding the addition or removal of liquid from liquid sample enclosure 2216. This situation may include situations wherein part of the sample is adsorbed or otherwise adhered to the electron beam permeable, fluid impermeable, membrane 2210. Examples of liquid containing samples may include cell cultures, blood, bacteria and acellular material.

Figure 75A:
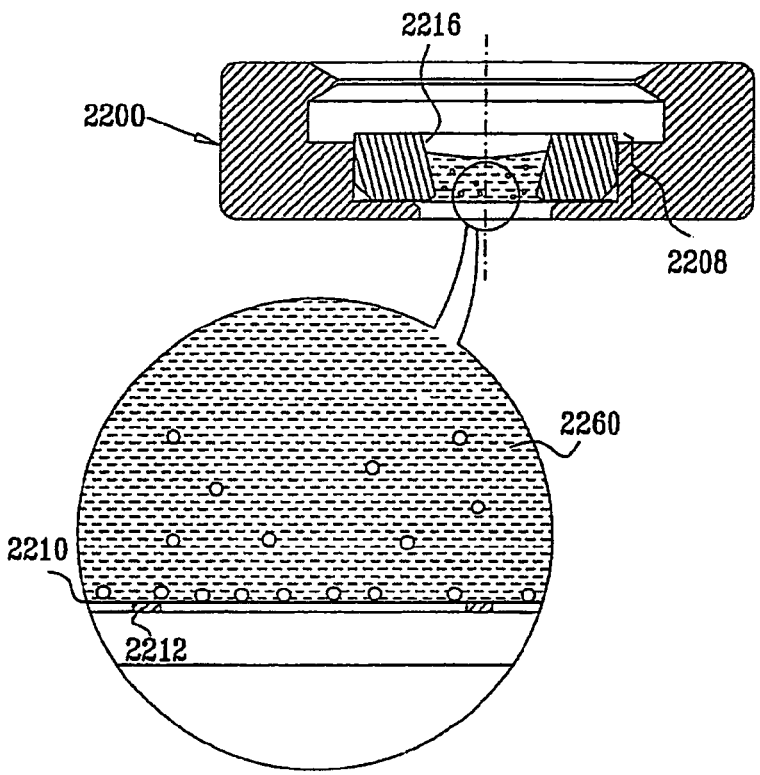
Figure 75B:
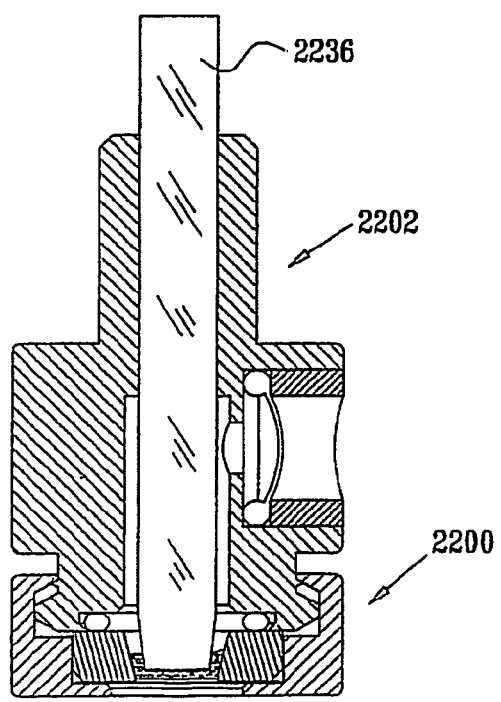

Reference is now made to FIGS. 75A, 75B and 75C which are simplified sectional illustrations of liquid containing samples in contact with the electron beam permeable, fluid impermeable, membrane 2210, sealing and insertion into a SEM, respectively, using the SEM compatible sample container of FIGS. 68A–73C. FIGS. 75A–75C exemplify a situation wherein at least a portion of a liquid containing sample 2260 is in contact with the electron beam permeable, fluid impermeable, membrane 2210 but is not adhered thereto. Examples of liquid containing samples may include various emulsions and suspensions such as milk, cosmetic creams, paints, inks and pharmaceuticals in liquid form It is seen that the enclosure element 2200 in FIGS. 75A and 75B, having disposed therewithin subassembly 2208, is in the orientation shown in FIG. 68A. FIG. 75A is identical to FIG. 65A.

FIG. 75B illustrates closing of the container containing the sample 2260. FIG. 75C shows the closed container, in the orientation of FIG. 68B, being inserted onto stage 2244 of SEM 2246. It is appreciated that there exist SEMs wherein the orientation of the container is opposite to that shown in FIG. 75C.

Figure 76:
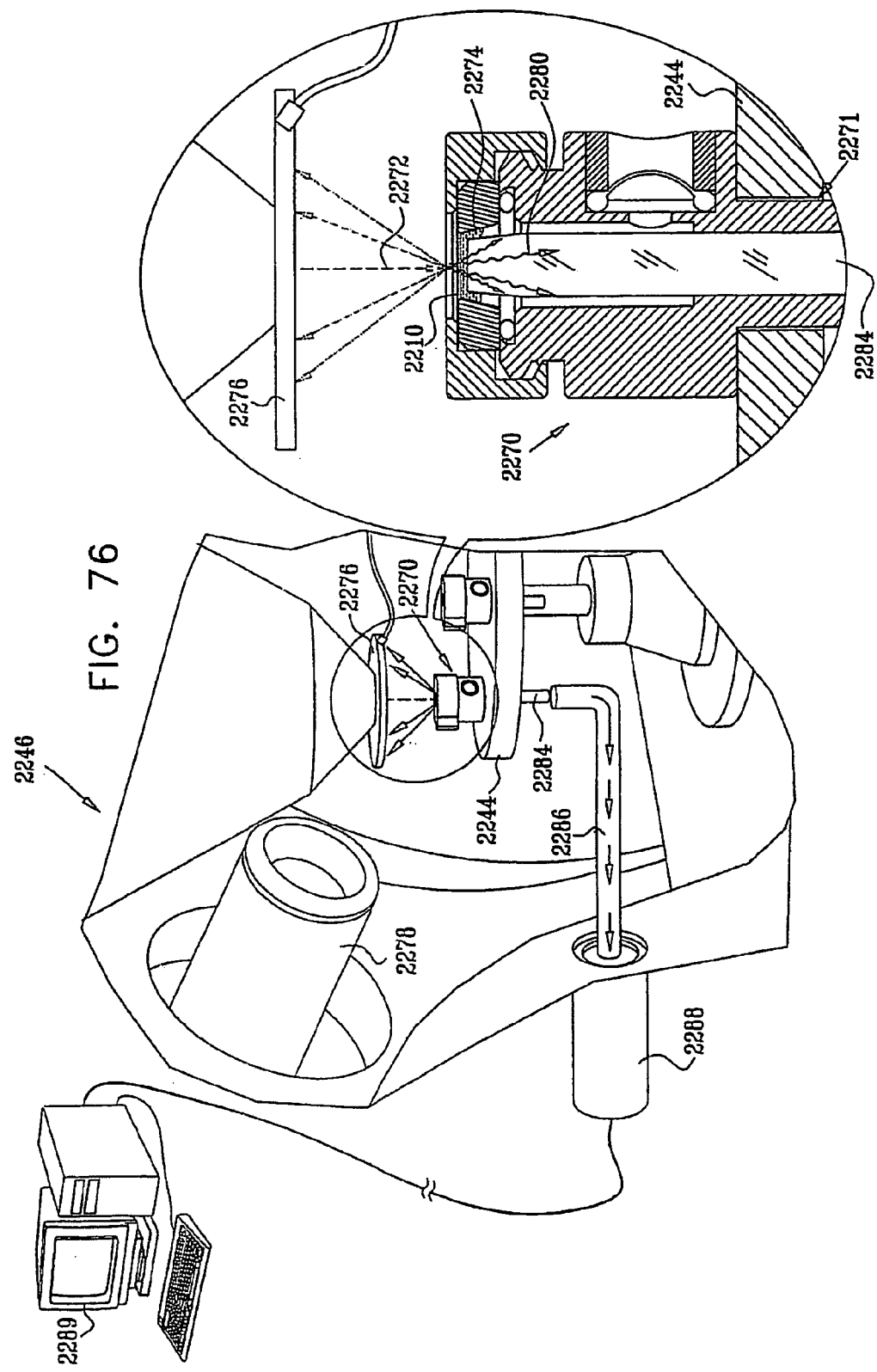
FIG. 76 is a simplified pictorial and sectional illustration of a SEM inspection of a sample using the SEM compatible sample container of FIGS. 68A–73C.

Reference is now made to FIG. 76, which is a simplified pictorial and sectional illustration of SEM inspection with light detection of a sample using the SEM compatible sample container of FIGS. 68A–73C. As seen in FIG. 76, the container, here designated by reference numeral 2270, is shown positioned on stage 2244 of SEM 2246 in a recess 2271. Stage 2244 is operative to rotate so as to enable positioning of container 2270 under an electron beam 2272 to inspect, during SEM inspection, regions of interest within a liquid containing sample 2274.

The electron beam 2272, generated by the SEM, passes through electron beam permeable, fluid impermeable, membrane 2210 and impinges on sample 2274 within container 2270. Backscattered electrons from sample 2274 pass through electron beam permeable, fluid impermeable, membrane 2210 and are detected by a detector 2276, forming part of the SEM. One or more additional detectors, such as a secondary electron detector 2278, may also be provided. An X-ray detector (not shown) may also be provided for detecting X-ray radiation emitted by the sample 2274 due to electron beam excitation thereof.

Photons 2280, emitted from liquid sample 2274 due to electron beam excitation, are transmitted through a first light guide, here designated by reference numeral 2284, which is identical to light guide 2226 of FIGS. 68A–73C, to a second light guide 2286. Second light guide 2286 is operative to transmit the photons 2280 to a light detector, such as a Photomultiplier Tube (PMT) 2288, such as Catalog No. H6180-01, commercially available at Hamamatsu Photonics of 325-6, Sunayama-cho, Hamamatsu City, Shizuoka Pref. Japan. Time dependent measurement of light intensity obtained from the light detector 2288, combined with information on the location of the scanning electron beam, are combined to produce an image of sample 2274 by methods known in the art, preferably as a digital image on a computer 2289.

Second light guide 2286, preferably, has a cross section with a diameter that is larger than the diameter of the cross section of the first light guide 2284, so as to minimize loss of photons in the passage between light guides 2284 and 2286 due to refraction or to imprecise relative alignment of the two light guides.

In the illustrated embodiment, second light guide 2286 is preferably formed in an L-shaped curve and preferably comprises a multiplicity of optic fibers disposed along the L-shaped light guide 2286 at an angle that ensures internal reflection of photons 2280 throughout the length of second light guide 2286.

It is appreciated that in the present invention photons 2280 may be transmitted vertically downward from first light guide 2284, via second light guide 2286 to a light detector located beneath the floor of the SEM 2246. Alternatively, photons 2280 may be transmitted from first light guide 2284 to a light detector, and that second light guide 2286 may be obviated.

In another embodiment of the present invention, the photons 2280 may be spectrally resolved prior to detection by light detector 2288 by conventional means, such as filters, diffraction gratings or prisms (not shown). This allows detection of photons with a wavelength within one or more specified ranges, yielding additional information on the composition and structure of the sample 2274 or features within sample 2274.

Additionally, a liquid, such as oil or a gel (not shown), with an index of refraction similar to the index of refraction of light guides 2284 and 2286, may be placed between light guides 2284 and 2286 to prevent the photons 2280 from scattering outside light guides 2284 and 2286.

Figure 77:
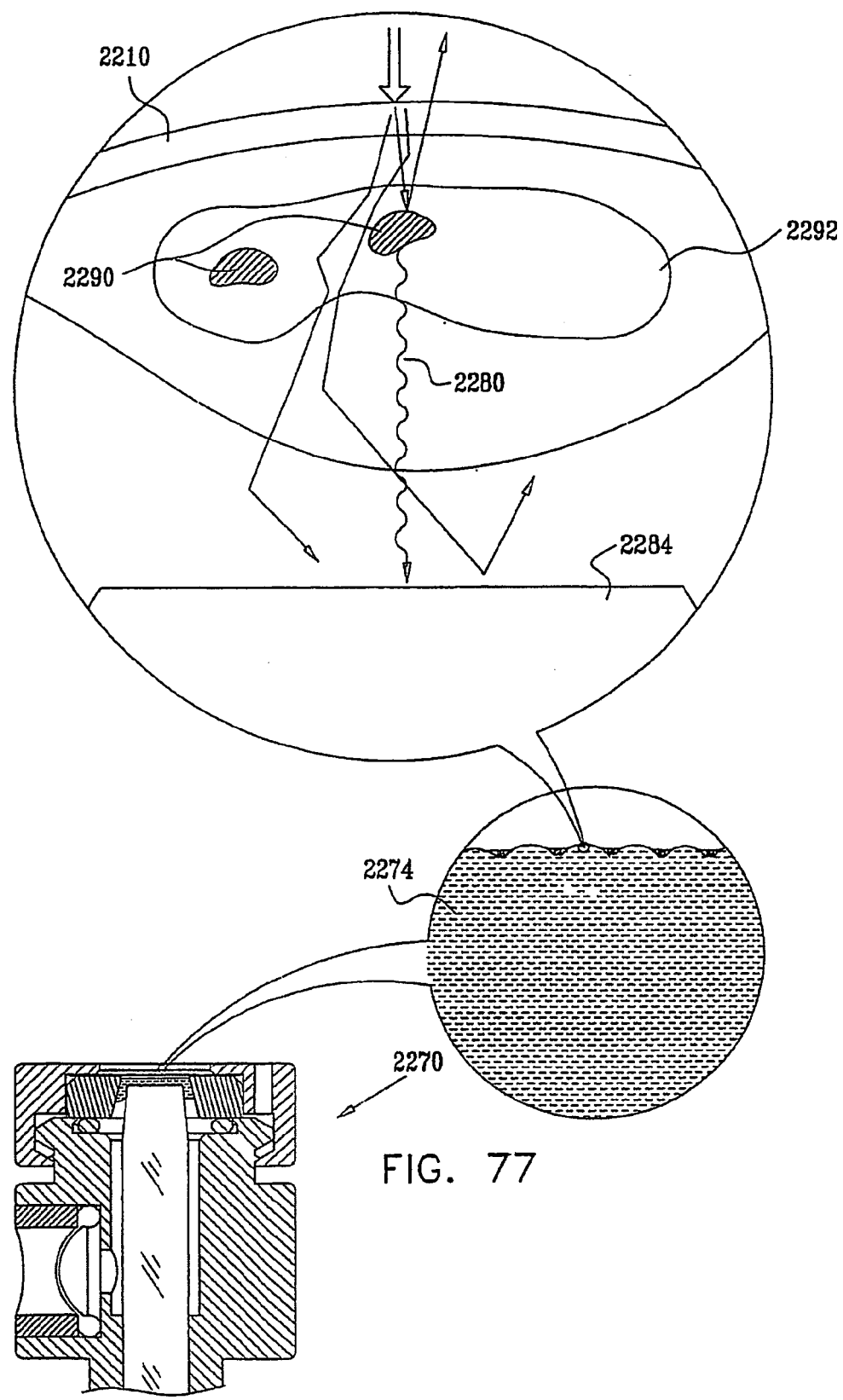
FIG. 77 is a greatly enlarged simplified schematic illustration of the SEM inspection of a sample in the context of FIG. 76.

Reference is now made additionally to FIG. 77, which schematically illustrates some details of the electron beam and photon interaction with the sample 2274 in container 2270 in accordance with a preferred embodiment of the present invention. It is noted that the present invention enables high contrast imaging of features which are distinguished from each other by their average atomic number, or, alternatively, by their average photon yield due to excitation by electrons, as illustrated in FIG. 77. In FIG. 77 it is seen that nucleoli 2290, having a relatively high average atomic number, backscatter electrons more than the surrounding nucleoplasm 2292.

Photons 2280 are shown to emit from the nucleoli 2290 and are transmitted to the light detector 2288 (shown in FIG. 76), via light guide 2284. It is noted that the contrast obtained by detection of backscattered electrons and the contrast obtained by photon detection are due to different physical processes and to different chemical properties of features within the sample, and therefore do not generally overlap.

It is also noted that in accordance with a preferred embodiment of the present invention, imaging of the interior of the sample to a depth of up to approximately 2 microns is achievable when employing electron beams having an energy level of less than 50 KeV, as seen in FIG. 77, wherein nucleoli 2290 disposed below electron beam permeable, fluid impermeable, membrane 2210 are imaged.

It is appreciated that the pre-microscopy multi-sample holder shown hereinabove in FIGS. 21A–22B may be provided for use with SEM compatible sample containers of the type shown in FIGS. 58A–77. Additionally, the pre-microscopy multi-sample holder may be associated with a suction device and pipettes shown hereinabove in FIGS. 23A, 23B and 23C.

Figure 78A:
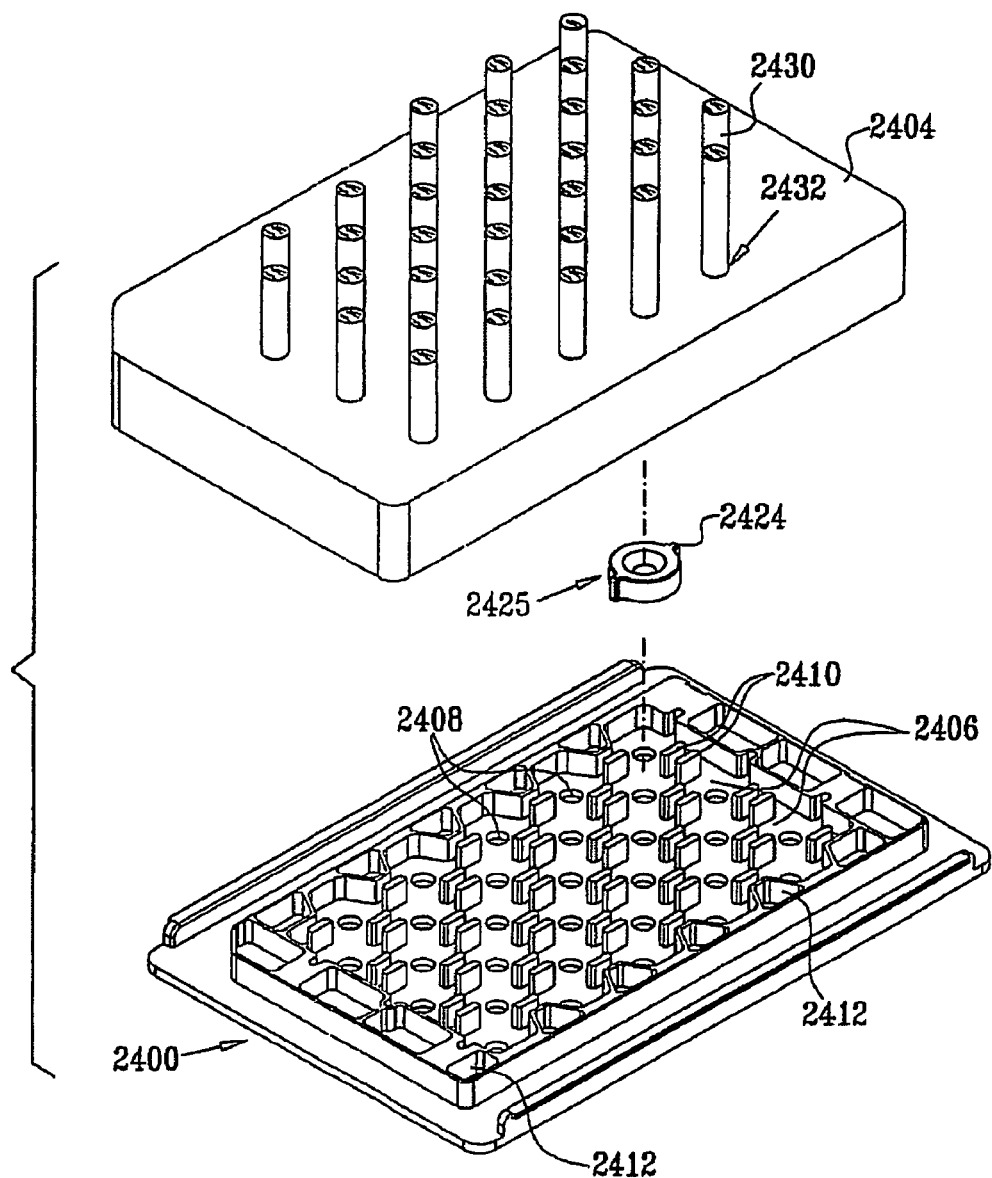
FIGS. 78A, 78B and 78C are simplified illustrations of a microscopy multi-sample holder in use with a SEM compatible sample dish of the type shown in FIGS. 58A–67.
Figure 78B:
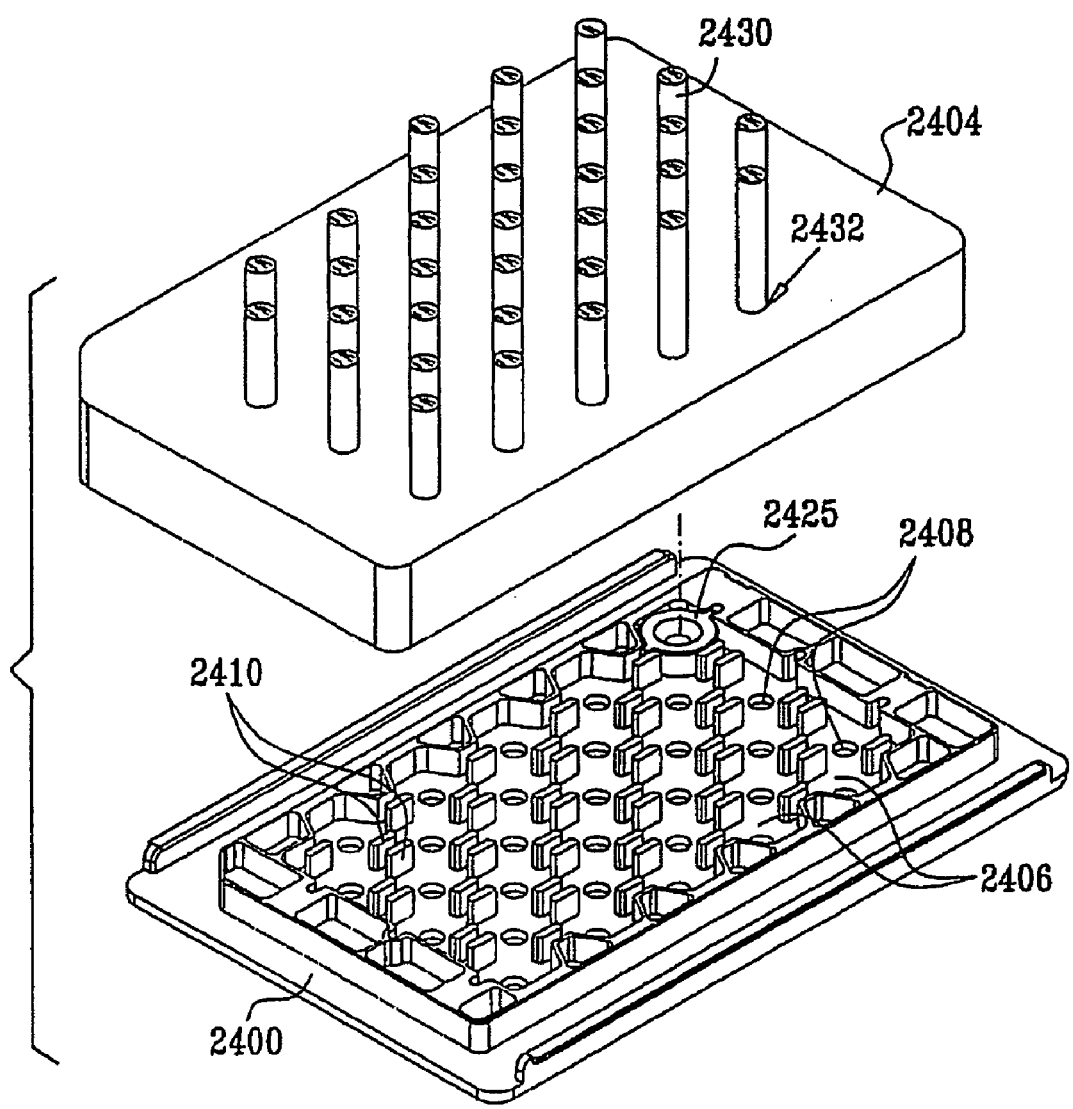
Figure 78C:
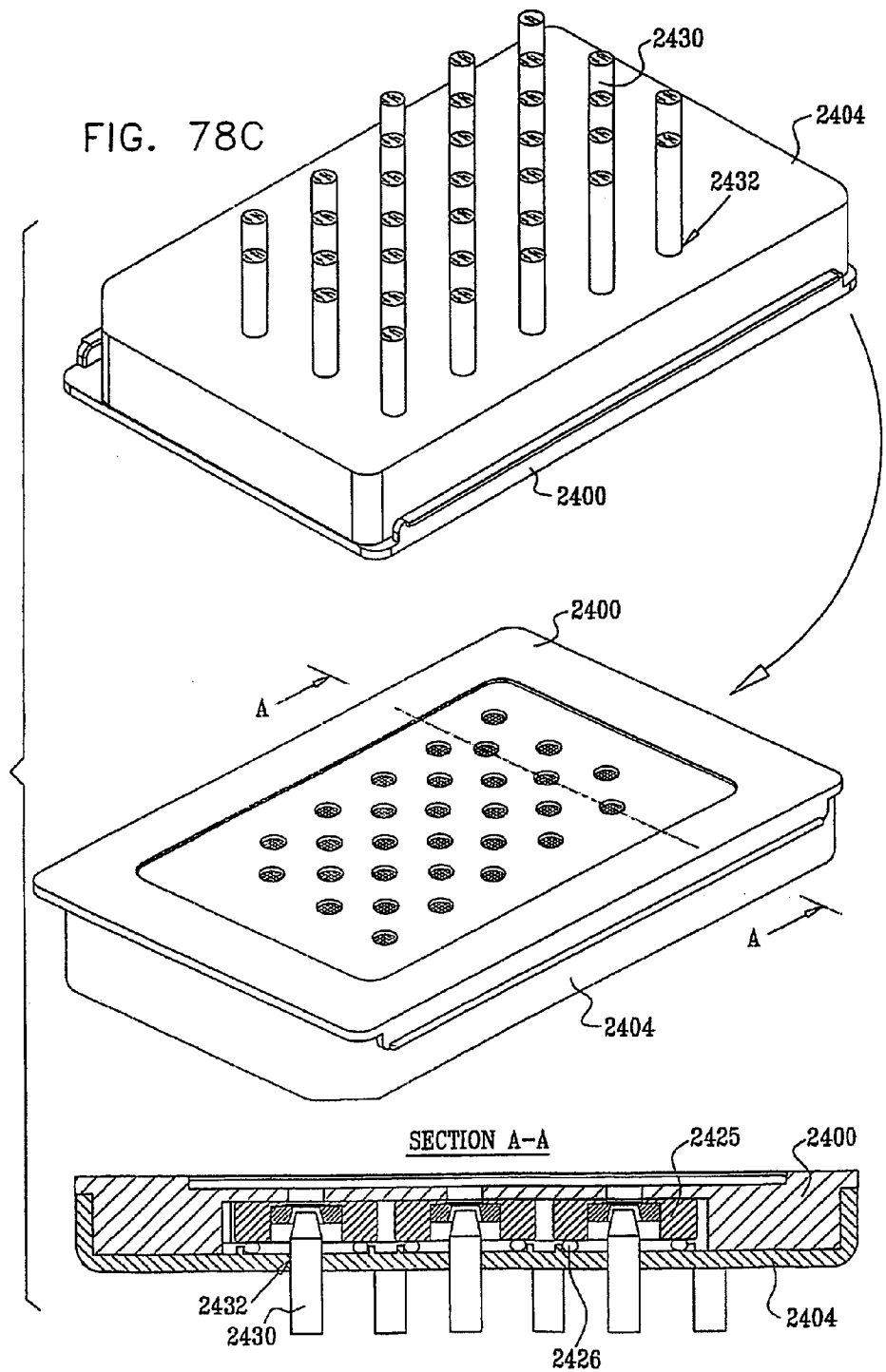

Reference is now made to FIGS. 78A, 78B and 78C, which are simplified illustrations of a microscopy multi-sample holder in use with a SEM compatible sample dish of the type shown in FIGS. 58A–67. As seen in FIG. 78A, the microscopy multi-sample holder preferably comprises a base 2400 and a sealing cover 2404. The base 2400 is preferably injection molded of a plastic material and defines an array of dish support locations 2406. Each dish support location 2406 is preferably defined by an aperture 2408 through which SEM microscopy may take place. Adjacent to each aperture 2408 there is preferably formed a pair of mutually aligned pairs of upstanding mutually spaced protrusions 2410 arranged to receive protrusions 2424 on sample dishes 2425. Sample dishes 2425 may be generally identical to sample dishes 2109, shown in FIGS. 60A–62B, but do not require any threading or other attachment mechanism.

Base 2400 preferably also defines a plurality of liquid reservoirs 2412 which are adapted to hold liquid used to maintain a desired level of humidity in the interior of the microscopy multi-sample holder.

Sealing cover 2404 is preferably arranged for individual sealing engagement with each of sample dishes 2425. Preferably sealing cover 2404 is provided on the underside thereof with an array of O-rings 2426, shown in FIG. 78C, sealed thereto and arranged so as to sealingly engage a top rim surface of each of sample dishes 2425, when the sealing cover 2404 is in place, preferably in removable snap-fit engagement with base 2400.

Sealing cover 2404 is preferably provided with an array of light guides 2430 arranged to receive light from a sample in sample dish 2425 during light detection. Light guides 2430 are inserted in apertures 2432 formed on sealing cover 2404.

FIG. 78B shows the apparatus of FIG. 78A with one sample dish 2425 positioned at a dish support location 2406 in base 2400. FIG. 78C shows sealing cover 2404 in snap fit engagement with base 2400, thereby providing individual sealing of each of sample dishes 2425 by means of O-ring 2426 and a portion of sealing cover 2404 circumscribed thereby.

Figure 79A:
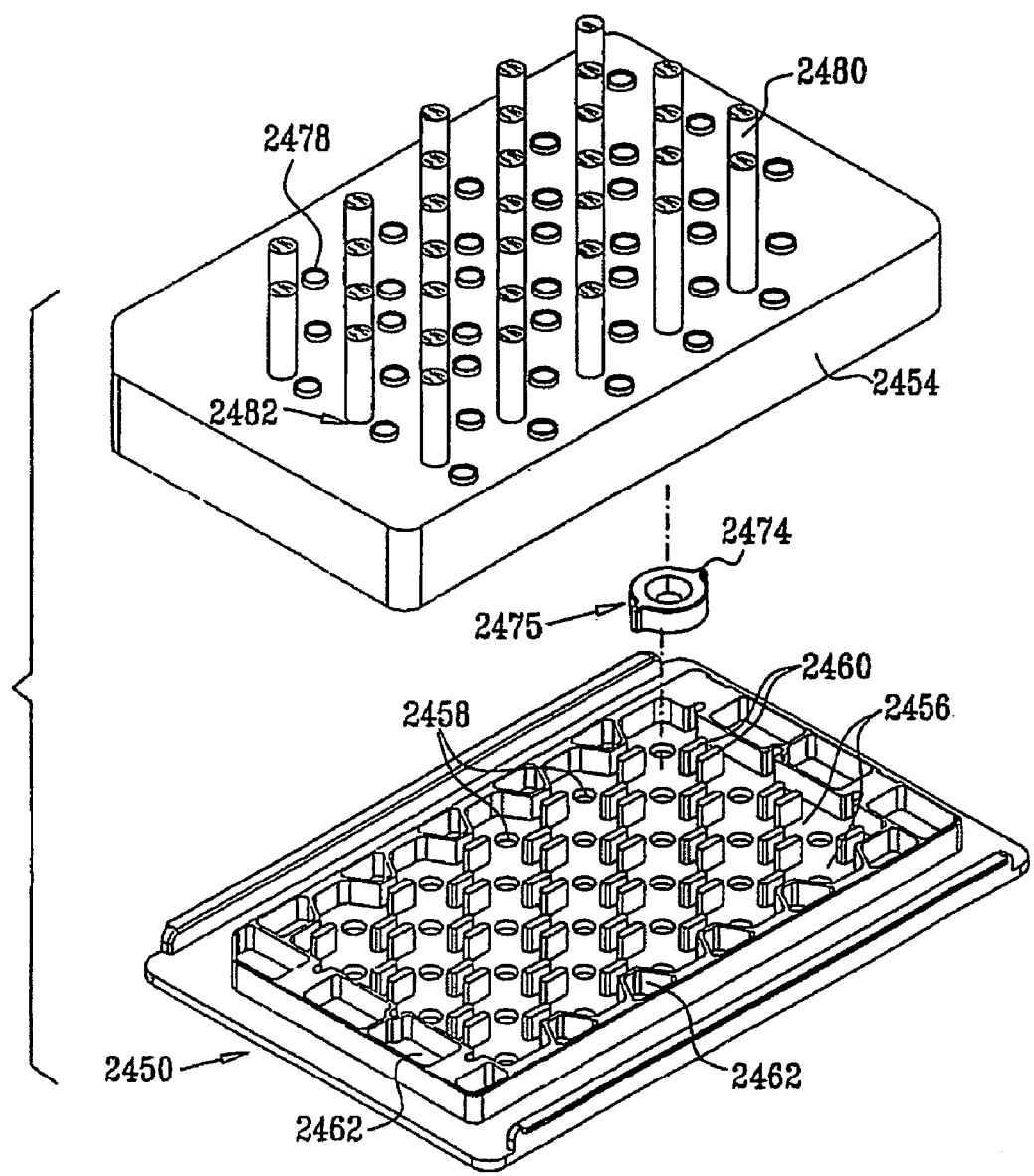
FIGS. 79A, 79B and 79C are simplified illustrations of a microscopy multi-sample holder in use with a SEM compatible sample dish of the type shown in FIGS. 68A–77.
Figure 79B:
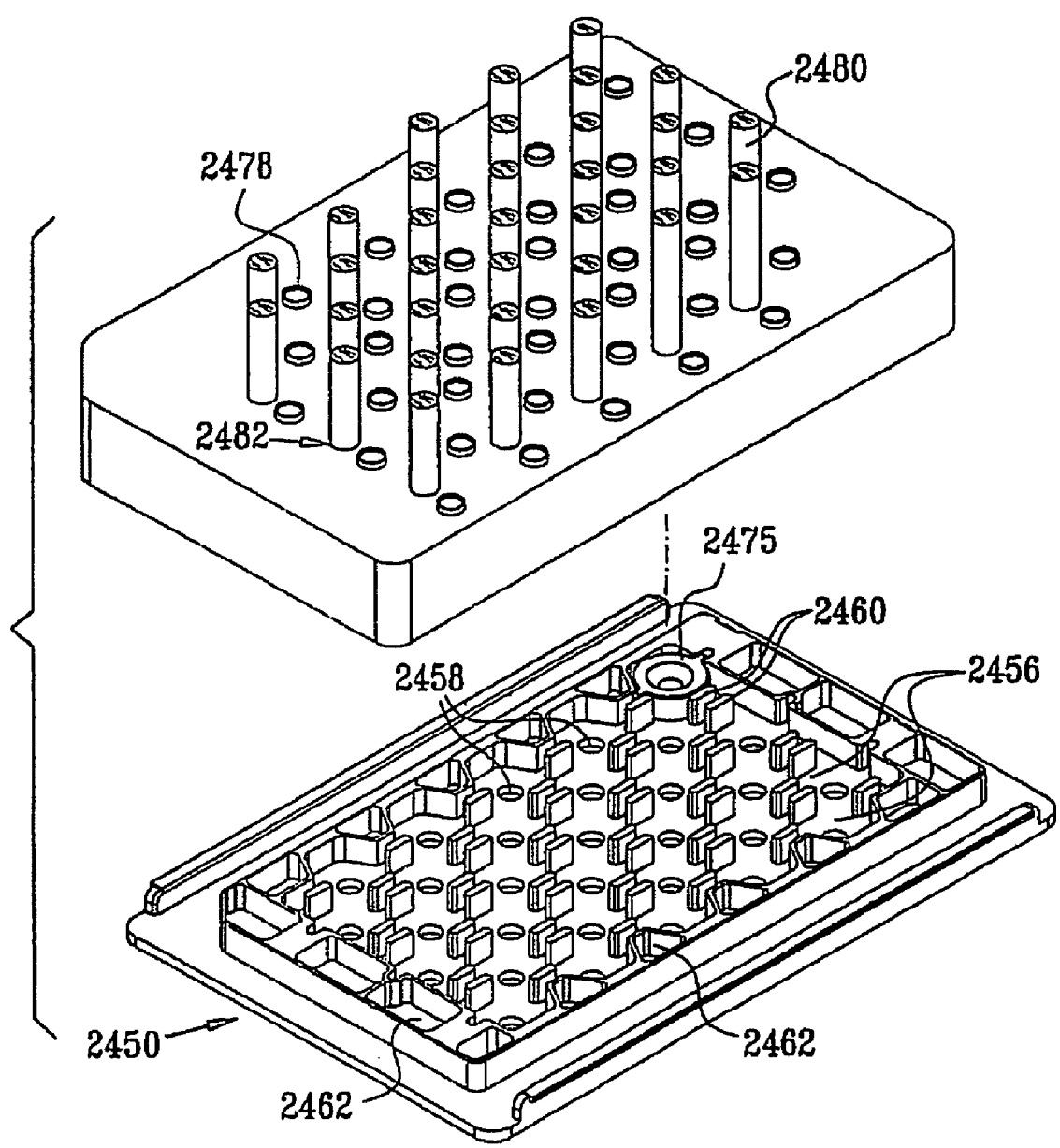
Figure 79C:
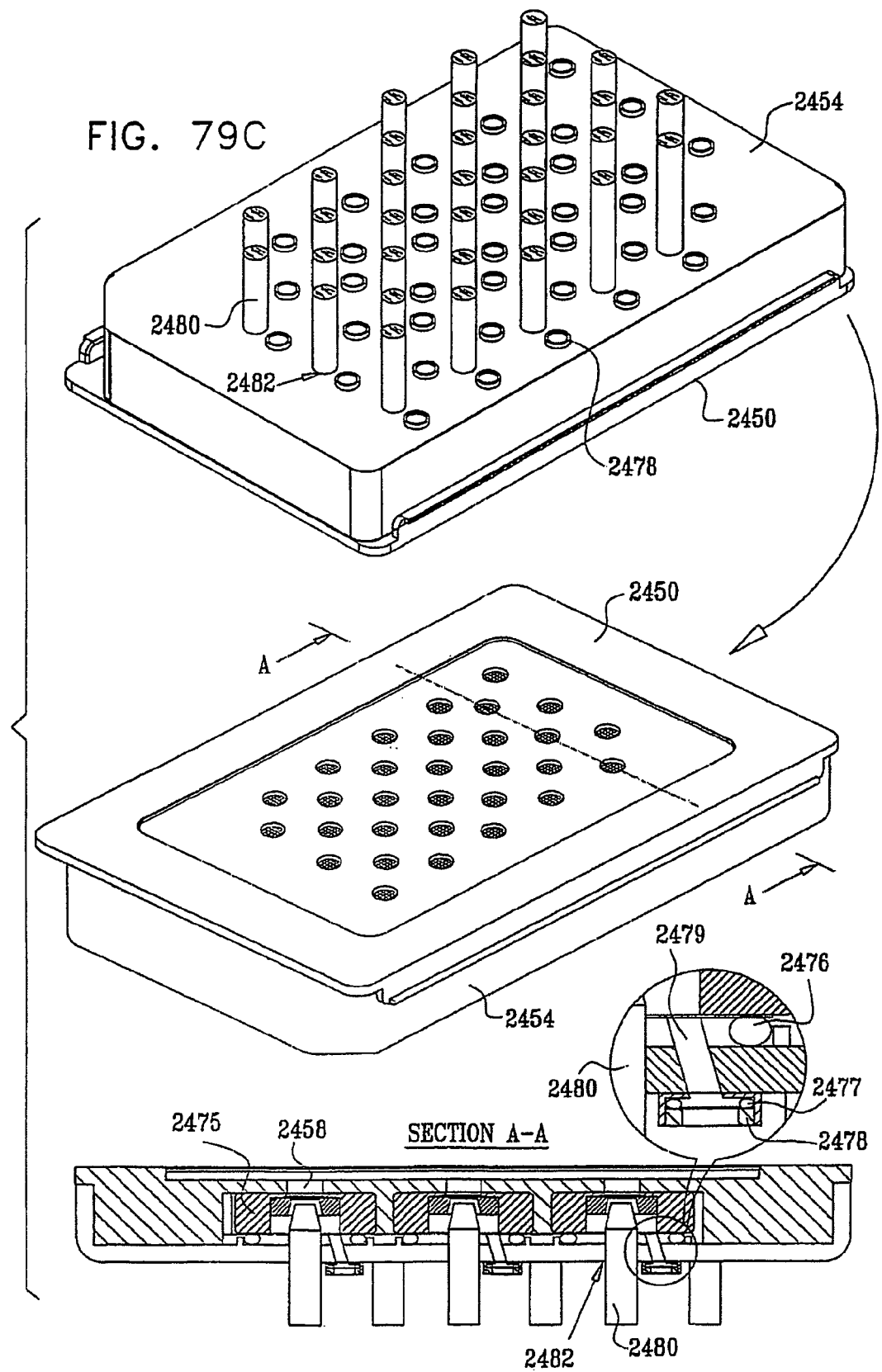

Reference is now made to FIGS. 79A, 79B and 79C, which are simplified illustrations of a microscopy multi-sample holder in use with a SEM compatible sample dish of the type shown in FIGS. 68A–77. As seen in FIG. 79A, the microscopy multi-sample holder preferably comprises a base 2450 and a sealing cover 2454. The base 2450 is preferably injection molded of a plastic material and defines an array of dish support locations 2456. Each dish support location 2456 is preferably defined by an aperture 2458 through which SEM microscopy may take place. Adjacent to each aperture 2458 there is preferably formed a pair of mutually aligned pairs of upstanding mutually spaced protrusions 2460 arranged to receive protrusions 2474 on sample dishes 2475. Sample dishes 2475 may be generally identical to sample dishes 2209, shown in FIGS. 70A–72B, but do not require any threading or other attachment mechanism.

Base 2450 preferably also defines a plurality of liquid reservoirs 2462 which are adapted to hold liquid used to maintain a desired level of humidity in the interior of the microscopy multi-sample holder.

Sealing cover 2454 is preferably arranged for individual sealing engagement of each of sample dishes 2475. Preferably sealing cover 2454 is provided on the underside thereof with an array of O-rings 2476, shown in FIG. 78C, sealed thereto and arranged so as to sealingly engage a top rim surface of each of sample dishes 2475, when the sealing cover 2454 is in place, preferably in removable snap-fit engagement with base 2450.

Preferably sealing cover 2454 is provided with an array of diaphragms 2477, shown in FIG. 79C, which may be identical to diaphragms 2218 described hereinabove with reference to FIGS. 68A–77. Individual diaphragms 2477 are seated in a ring 2478 mounted over an aperture 2479 formed in sealing cover 2454.

Sealing cover 2454 is preferably provided with an array of light guides 2480 arranged to receive light from a sample in sample dish 2475 during light detection. Light guides 2480 are inserted in apertures 2482 formed in sealing cover 2454. Individual light guides 2480 are provided to collect light from a sample in sample dish 2475 during SEM inspection.

FIG. 79B shows the apparatus of FIG. 79A with one sample dish 2475 positioned at a dish support location 2456 in base 2450. FIG. 79C shows sealing cover 2454 in snap fit engagement with base 2450, thereby providing individual sealing of each of sample dishes 2475 by means of O-ring 2476.

Figure 80A:
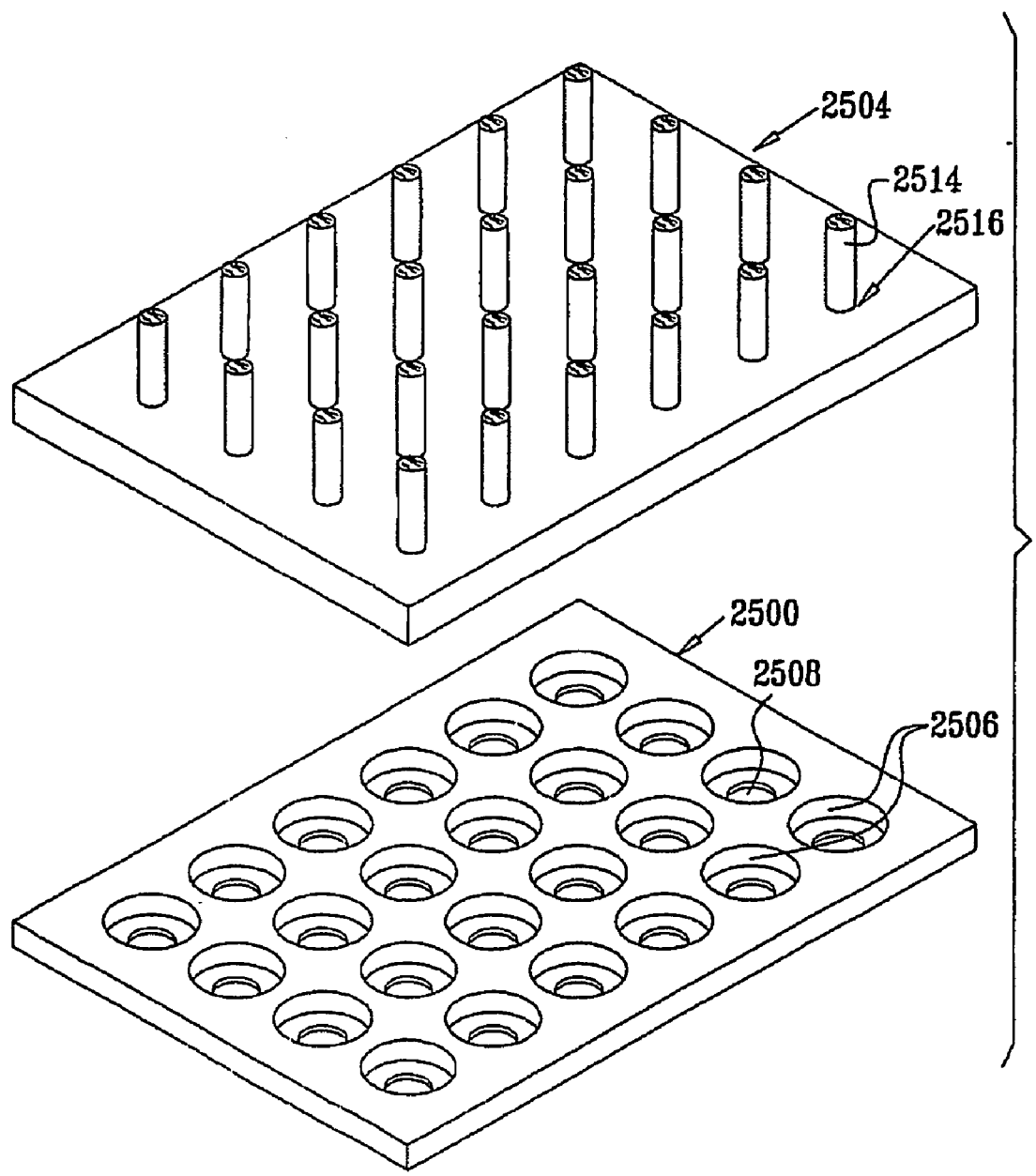

Reference is now made to FIGS. 80A and 80B, which are simplified illustrations of a microscopy multi-sample holder defining a plurality of SEM compatible sample containers in accordance with a preferred embodiment of the present invention. As seen in FIG. 80A, the microscopy multi-sample holder preferably comprises a base 2500 and a sealing cover 2504. The base 2500 is preferably injection molded of a plastic material and defines an array of sample containers 2506. Each sample container 2506 preferably includes an aperture 2508 through which SEM microscopy may take place. An electron beam permeable, fluid impermeable, membrane 2510, shown in FIG. 80B, is sealed over each aperture 2508. Membrane 2510 is preferably identical to membrane 2110 described hereinabove with reference to FIGS. 58A–67. Sealing cover 2504 preferably is arranged for individual sealing engagement with each of sample containers 2506.

Sealing cover 2504 is preferably provided with an array of light guides 2514 arranged to receive light from a sample in sample containers 2506 during light detection. Individual light guides 2514 are inserted into apertures 2516 formed in sealing cover 2504.

FIG. 80B shows the apparatus of FIG. 80A in sealed engagement, thereby providing individual sealing of each of sample containers 2506.

Figure 81A:
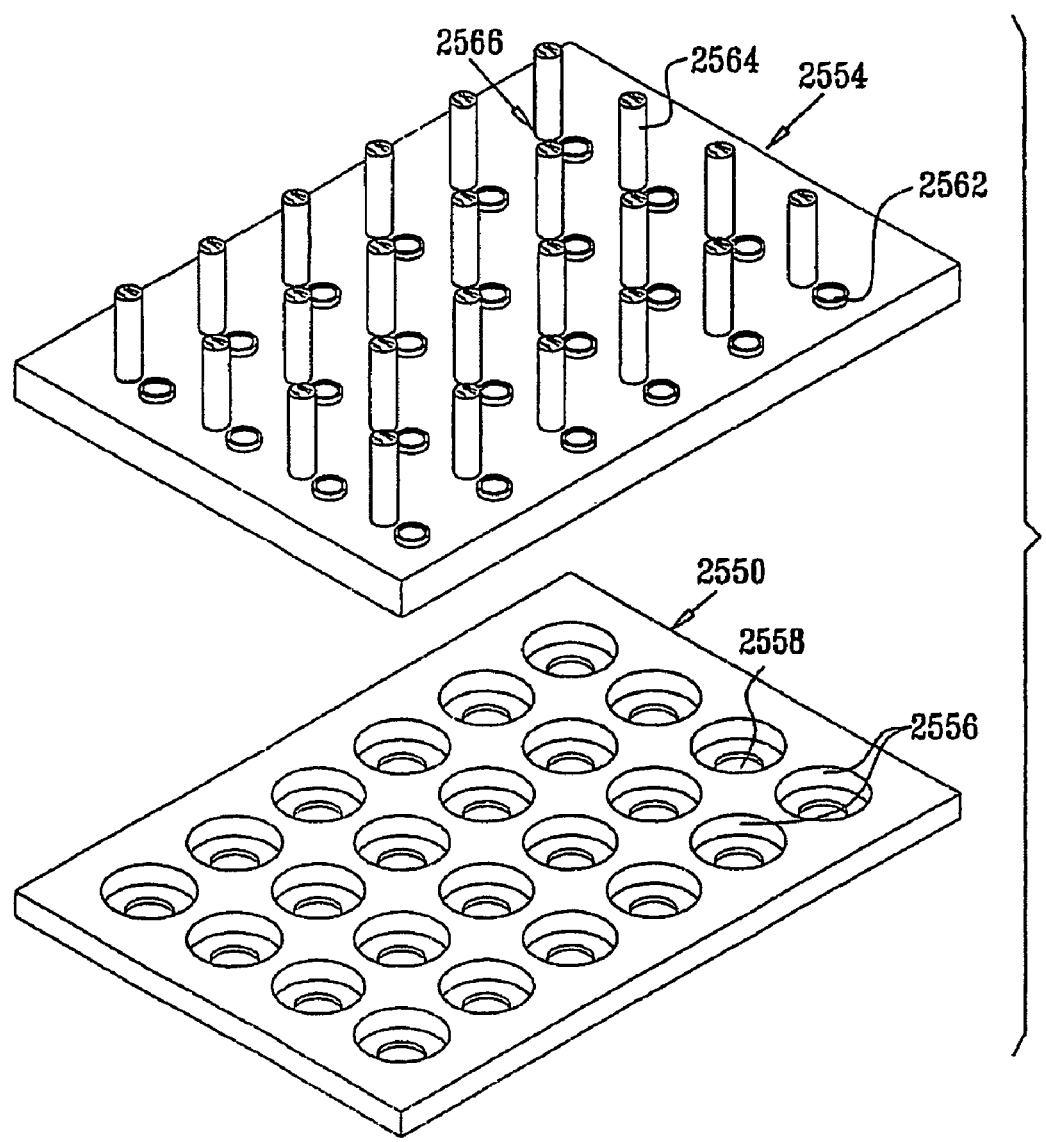

Reference is now made to FIGS. 81A and 81B, which are simplified illustrations of a microscopy multi-sample holder defining a plurality of SEM compatible sample containers in accordance with a preferred embodiment of the present invention. As seen in FIG. 81A, the microscopy multi-sample holder preferably comprises a base 2550 and a sealing cover 2554. The base 2550 is preferably injection molded of a plastic material and defines an array of sample containers 2556. Each sample container 2556 preferably includes an aperture 2558 through which SEM microscopy may take place.

An electron beam permeable, fluid impermeable, membrane 2560, shown in FIG. 81B, is sealed over each aperture 2558. Membrane 2560 is preferably identical to membrane 2210 described hereinabove with reference to FIGS. 68A–77.

Preferably sealing cover 2554 is provided with an array of diaphragms 2561, shown in FIG. 81B, which may be identical to diaphragms 2218 described hereinabove with reference to FIGS. 68A–77. Individual diaphragms 2561 are seated in a ring 2562 mounted over an aperture 2563 formed in sealing cover 2554.

Sealing cover 2554 is preferably provided with an array of light guides 2564 arranged to receive from a sample in sample containers 2556 during light detection. Individual light guides 2564 are inserted in apertures 2566 formed in sealing cover 2554.

FIG. 81B shows the apparatus of FIG. 81A in sealed engagement, thereby providing individual sealing of each of sample containers 2556.

Reference is now made to FIG. 82, which is a simplified illustration of a SEM based sample inspection system and a light detection system constructed and operative in accordance with a preferred embodiment of the present invention. As seen in FIG. 82, a plurality of pre-microscopy multi-sample holders 2600, each containing a multiplicity of SEM compatible sample containers 2602 of the type shown in FIGS. 58A–77, is shown in an incubator 2604. Preferably, light microscopy inspection of the samples in containers 2602 is carried out while the containers 2602 are mounted in holder 2600, as indicated at reference numeral 2606, in order to identify samples of interest Preferably an inverted light microscope 2608 is employed for this purpose.

Preferably automated positioning systems, such as robotic arms, as shown, are used for conveying the pre-microscopy multi-sample holders 2600 and the containers 2602 throughout the system, it being appreciated that manual intervention may be employed at one or more stages as appropriate.

Thereafter, individual containers 2602 are removed from holders 2600 and placed on a removable electron microscope specimen stage 2610, which is subsequently introduced into a scanning electron microscope 2612.

The resulting image from the SEM inspection may be inspected visually by an operator and/or analyzed by conventional image analysis functionality, typically embodied in a computer 2614.

Preferably, light inspection of the samples in containers 2602 is carried out while the containers 2602 are in the SEM 2612. Preferably a light guide 2620 is employed to receive light from a light guide (not shown) inserted in container 2602 and to transmit the light to a light detector, such as a PMT 2622.

The resulting image from the light inspection may be inspected visually by an operator and/or analyzed by conventional image analysis functionality, typically embodied in a computer 2624.

Figure 83:
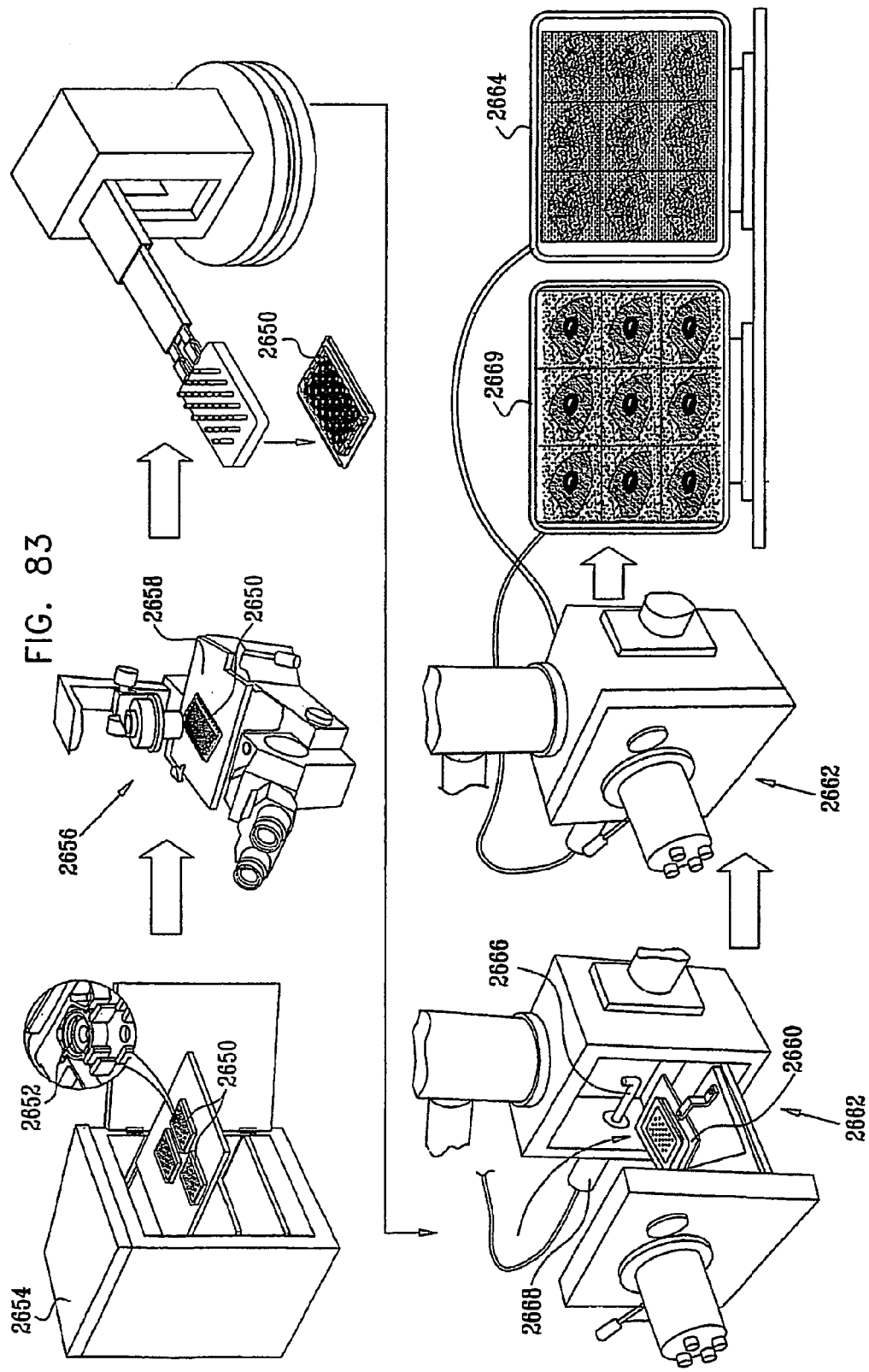
FIG. 83 is a simplified illustration of a SEM based sample inspection system constructed and operative in accordance with another preferred embodiment of the present invention.

Reference is now made to FIG. 83, which is a simplified illustration of a SEM based sample inspection system and a light detection system constructed and operative in accordance with another preferred embodiment of the present invention. As seen in FIG. 83, a plurality of microscopy multi-sample holders 2650, each containing a multiplicity of SEM compatible sample dishes 2652 of either of the types shown in FIGS. 78A–79C, is shown in an incubator 2654. Preferably, light microscopy inspection of the samples in sample dishes 2652 is carried out while the sample dishes are mounted in holder 2650, as indicated at reference numeral 2656, in order to identify samples of interest. Preferably an inverted light microscope 2658 is employed for this purpose.

Preferably automated positioning systems, such as robotic arms, as shown, are used for conveying the microscopy multi-sample holders 2650 containing sample dishes 2652 throughout the system, it being appreciated that manual intervention may be employed at one or more stages as appropriate.

Thereafter, holders 2650 are placed on an electron microscope specimen stage 2660, which is subsequently introduced into a scanning electron microscope 2662.

The resulting images may be inspected visually by an operator and/or analyzed by conventional image analysis functionality, typically embodied in a computer 2664.

Preferably, light inspection of the samples in sample dishes 2652 is carried out while the sample dishes 2652 are in the SEM 2662. Preferably a light guide 2666 is employed to receive light from a light guide (not shown) inserted in sample dishes 2652 and to transmit the light to a light detector, such as a PMT 2668.

The resulting image from the light inspection may be inspected visually by an operator and/or analyzed by conventional image analysis functionality, typically embodied in a computer 2669.

Figure 84:
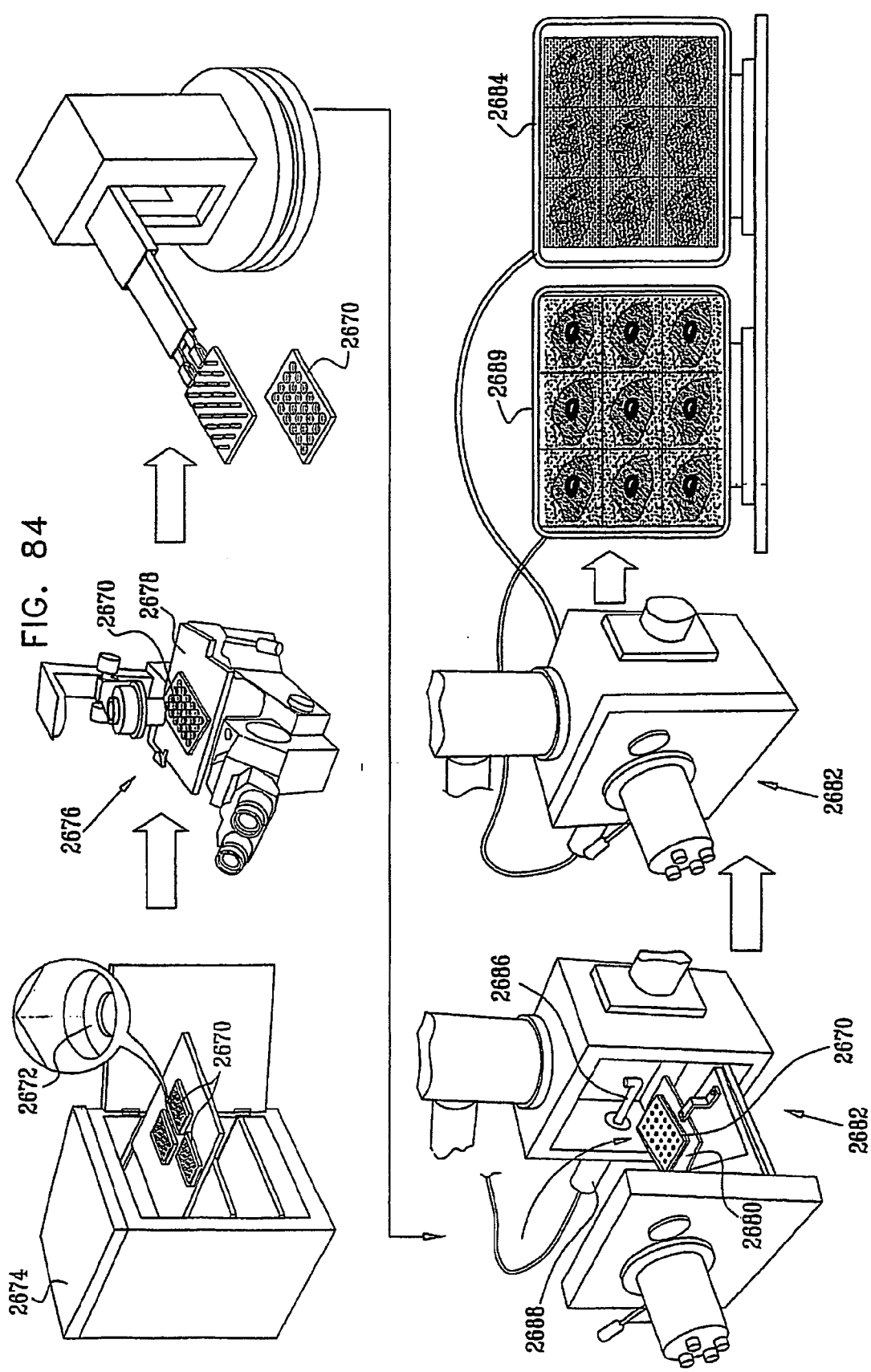
FIG. 84 is a simplified illustration of a SEM based sample inspection system constructed and operative in accordance with yet another preferred embodiment of the present invention.

Reference is now made to FIG. 84, which is a simplified illustration of a SEM based sample inspection system and a light detection system constructed and operative in accordance with yet another preferred embodiment of the present invention. As seen in FIG. 84, a plurality of microscopy multi-sample holders 2670, each defining a multiplicity of SEM compatible sample containers 2672, as shown in any of FIGS. 80A–81B, is seen in an incubator 2674. Preferably, light microscopy inspection of the samples in sample containers 2672 is carried out holder-wise, as indicated at reference numeral 2676, preferably in order to identify samples of interest. Preferably an inverted light microscope 2678 is employed for this purpose.

Preferably automated positioning systems, such as robotic arms, as shown, are used for conveying the microscopy multi-sample holders 2670 throughout the system, it being appreciated that manual intervention may be employed at one or more stages as appropriate.

Thereafter, holders 2670 are placed on an electron microscope specimen stage 2680, which is subsequently introduced into a scanning electron microscope 2682. The resulting images may be inspected visually by an operator and/or analyzed by conventional image analysis functionality, typically embodied in a computer 2684.

Preferably, light inspection of the samples in containers 2672 is carried out while the containers 2672 are in the SEM 2682. Preferably a light guide 2686 is employed to receive light from a light guide (not shown) inserted in containers 2672 and to transmit the light to a light detector, such as a PMT 2688.

The resulting image from the light inspection may be inspected visually by an operator and/or analyzed by conventional image analysis functionality, typically embodied in a computer 2689.

Figure 85:
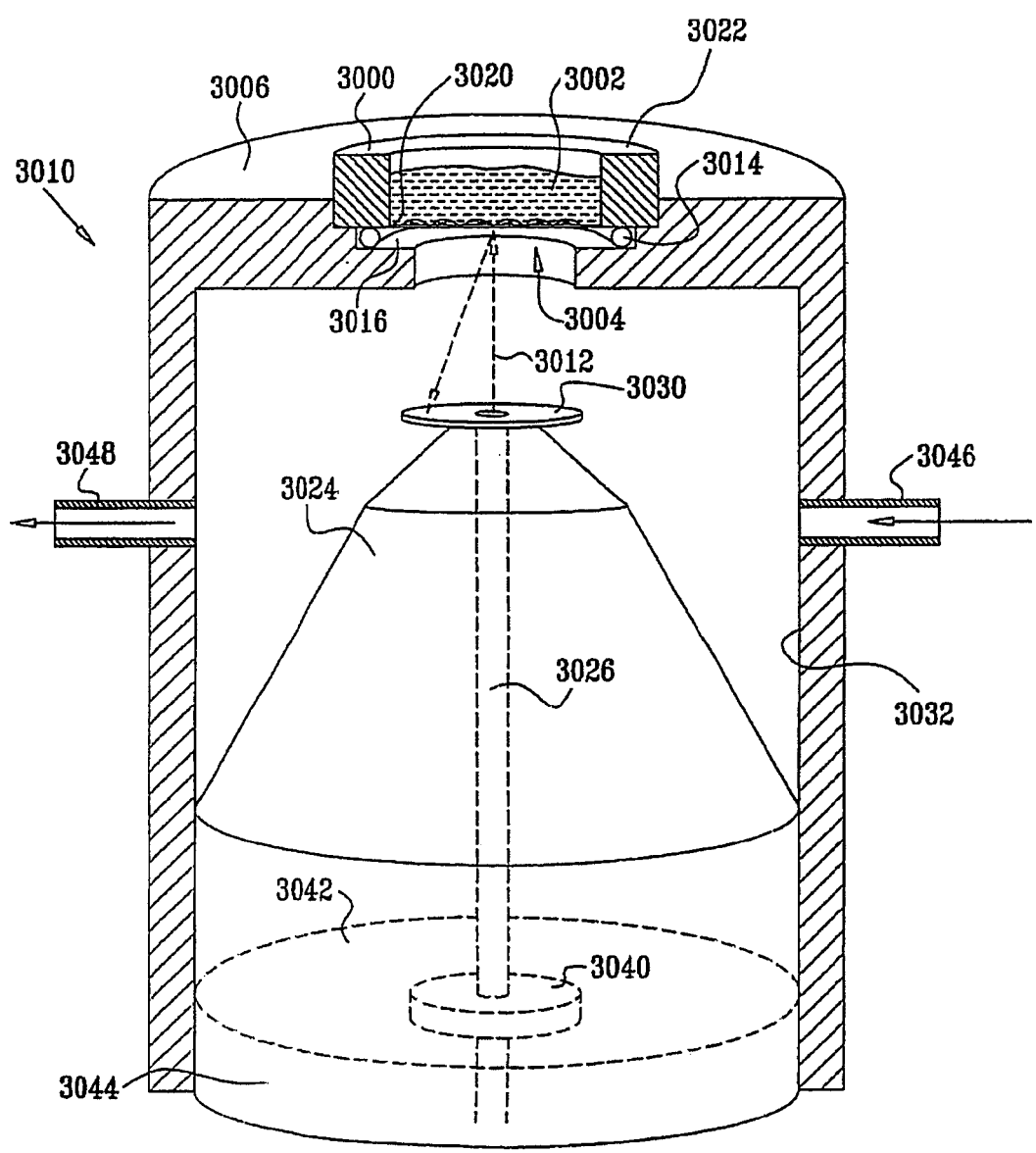
FIG. 85 is a simplified partially pictorial and partially sectional illustration of SEM inspection of a sample constructed and operative in accordance with another preferred embodiment of the present invention.

Reference is made to FIG. 85, which is a simplified partially pictorial and partially sectional illustration of SEM inspection of a sample constructed and operative in accordance with another preferred embodiment of the present invention As seen in FIG. 85, a sample container 3000 containing a sample 3002 is seated in a generally central aperture 3004 formed in a roof 3006 of an electron gun assembly 3010 and is positioned and sized so as to allow impingement of a focused electron beam 3012 on sample 3002 during SEM inspection.

Container 3000 is seated over an O-ring 3014 located in an interior surface 3016 of roof 3006. Container 3000 includes an electron-permeable, fluid impermeable, membrane 3020 adhered to the underside of a peripheral ring 3022 of sample container 3000. Sample 3002 lies over electron beam permeable, fluid impermeable membrane 3020.

Electron gun assembly 3010, which is part of a SEM inspection assembly, is provided with an electron gun (not shown) operative to provide electron beam 3012 emitted through a pole piece 3024 in a generally upward direction.

The electron beam 3012, generated by the electron gun, is shown to travel along a path 3026. The electron beam 3012 passes through electron beam permeable, fluid impermeable membrane 3020 and impinges on sample 3002 within sample container 3000. Electrons backscatter from sample 3002 and pass back through electron beam permeable, fluid impermeable membrane 3020 and are preferably detected by a backscattered electron detector 3030 in the electron gun assembly 3010.

It is a particular feature of the present invention that the electron beam 3020 impinges on sample 3002 on the underside thereof thereby inspecting a sample region lying against electron beam permeable, fluid impermeable membrane 3020.

The electron gun assembly 3010 defines an electron gun assembly internal volume 3032. Internal volume 3032 is sealed by walls of the electron gun assembly 3010 and the container 3000 so as to maintain an evacuated environment within internal volume 3032, typically at a vacuum of $10^{-2}$–$10^{-6}$ millibars, during SEM inspection.

Electron gun assembly 3010 also preferably includes a safety valve system comprising an airlock 3040 and a top wall 3042 defining a safety valve system internal volume 3044. Prior to removal of container 3000 the airlock 3040 is locked, so as to maintain an evacuated environment within internal volume 3044, typically at a vacuum of $10^{-2}$–$10^{-6}$ millibars, during container removal. After the airlock 3040 is locked, a gas, typically nitrogen, is introduced via an inlet tube 3046 into internal volume 3032 of electron gun assembly 3010. Container 3000 is then removed and preferably replaced. Alternatively, another container 3000 may then be placed in electron gun assembly 3010. After container 3000 or another container is introduced into the electron gun assembly 3010, the gas is pumped out, typically through an outlet tube 3048, by a pump (not shown) and airlock 3040 is unlocked.

Airlock 3040 also preferably is operative to rapidly isolate internal volume 3044 from fluid that may enter the electron gun assembly 3010 from the ambient, due to leakage through the sample container 3000 or aperture 3004, or through lesions in electron beam permeable, fluid impermeable membrane 3020.

In accordance with another preferred embodiment of the present invention, electron gun assembly 3010 includes an adjustable seat for sample container 3000. The adjustable seat allows high-magnification imaging of different regions within sample 3002.

Reference is made to FIG. 86A–87B, which are simplified partially pictorial and partially sectional illustrations of a tissue sample slicing assembly constructed and operative in accordance with a preferred embodiment of the present invention. As seen in FIG. 86A, a plurality of stacked removable rectangular shaped slabs 3050 are mounted on a stage 3052. Preferably, protrusions 3054 are provided to retain slabs 3050 on stage 3052. A generally central aperture 3056 is formed in each individual slab 3050 and defines part of a recess 3058. A conventional slicing instrument 3060, such as a razor blade 3062, is preferably provided and is operative to slice a tissue sample 3064 seated in recess 3058. The tissue sample 3064 is shown in FIG. 86A to extend beyond the top of the stack of slabs 3050.

Figure 86B:
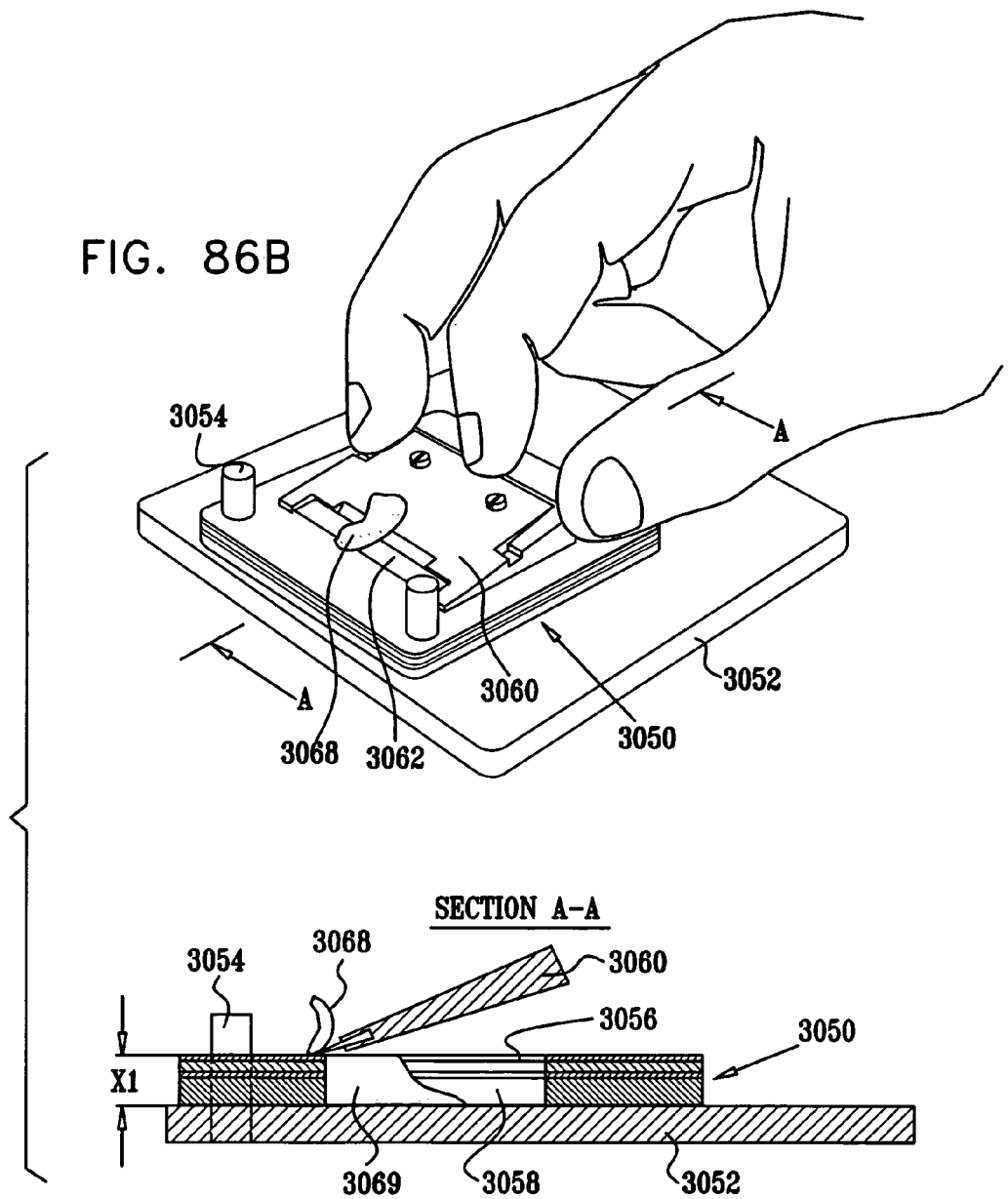

FIG. 86B shows a plurality of slabs 3050, including a top slab 3066, providing a tissue sample thickness of X1. The slicing instrument 3060 slices the tissue sample 3064 into two portions, top portion 3068 and bottom portion 3069, where resulting bottom portion 3069 has a thickness of X1.

Figure 87A:
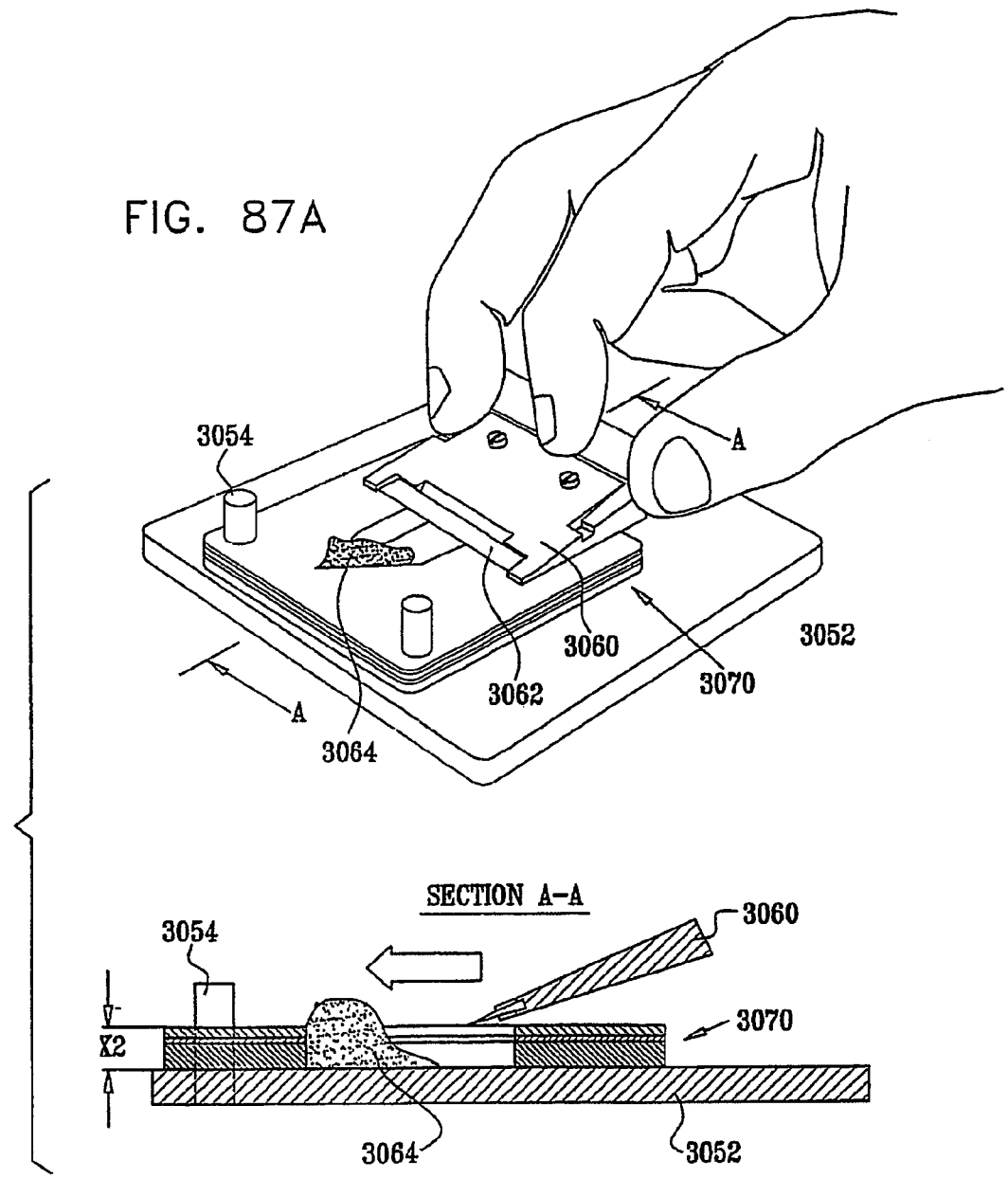
FIGS. 87A and 87B are simplified partially pictorial and partially sectional illustration of a tissue sample slicing assembly constructed and operative in accordance with a preferred embodiment of the present invention.
Figure 87B:
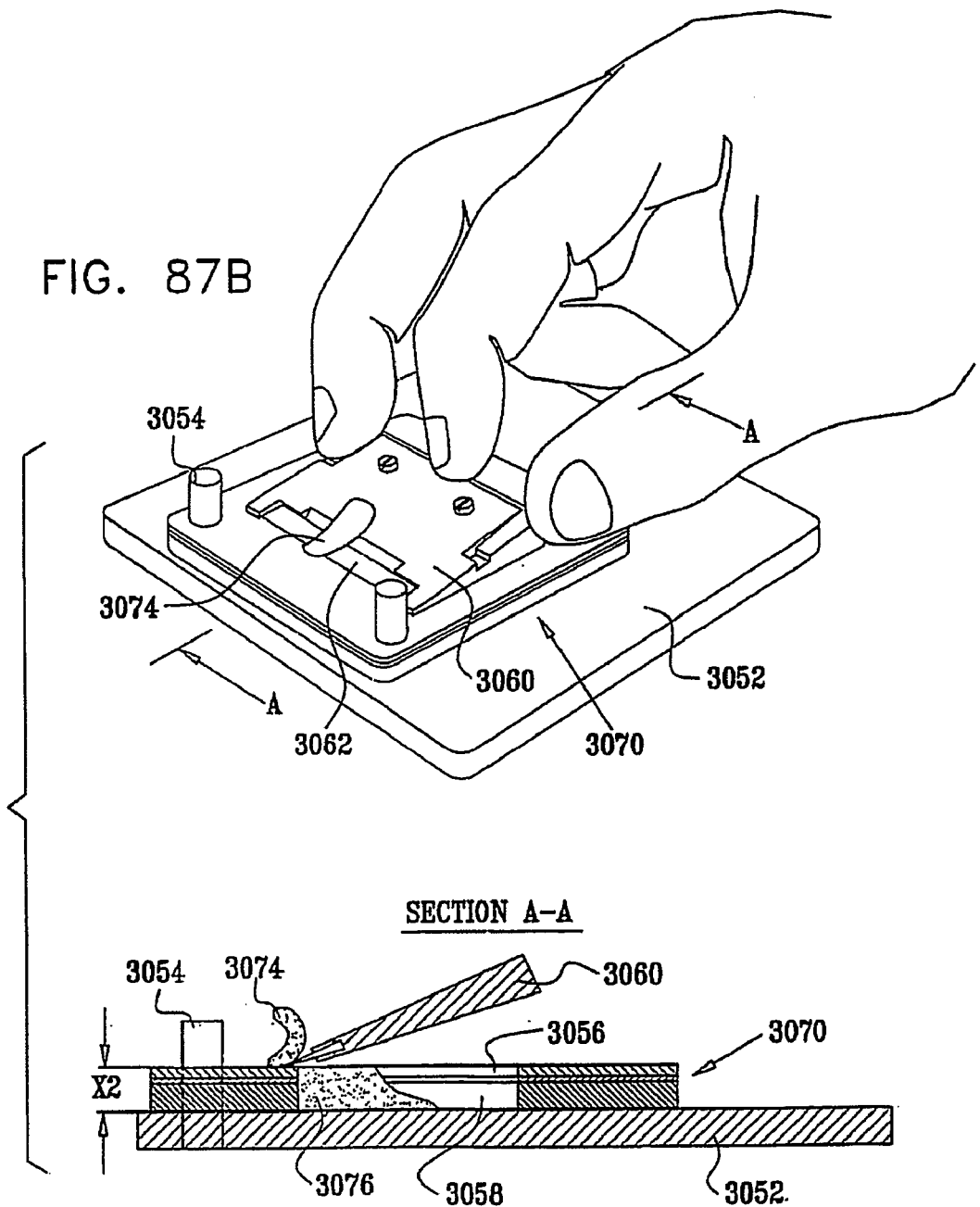

FIG. 87A illustrates the tissue sample slicing assembly of FIG. 86A with a plurality of slabs 3070, providing a tissue sample thickness of X2, where X2<X1 of FIGS. 86A and 86B. As seen in FIG. 87B, the slicing instrument 3060 slices the tissue sample 3064 into two portions, top portion 3074 and bottom portion 3076, where resulting bottom portion 3076 has a thickness of X2.

The present invention provides methods for imaging a wet sample in a scanning electron microscope, while maintaining the sample in a wet state, at near-atmospheric pressure and at any desired temperature, preferably temperatures in the range of 0–50° C. This is achieved by placing the sample in a SEM compatible sample container that seals the sample from the evacuated environment of the SEM. The sample is disposed in the SEM compatible sample container so that the sample, or a portion thereof, is positioned in close contact, preferably at a distance of less than 5 microns, with an electron-permeable partition membrane. Inspection of the sample in a SEM is then performed by placing the SEM compatible sample container containing the sample in a SEM, and directing a scanning electron beam at the sample through the electron permeable partition membrane.

In accordance with a preferred embodiment of the present invention, SEM inspection methods are provided for a wide variety of biological materials, such as cultured cells, tissue slices or fragments, organ slices, biopsied material, cells in a liquid suspension, fine needle aspirates and samples obtained by lavage of the respiratory system or the digestive system. Additionally, biological fluids, such as urine, cerebrospinal fluid, milk, saliva, blood plasma, tears, pus, sputum, mucous, interstitial fluid and semen, may also be inspected using the methods of the present invention. Also included in the present invention are SEM inspection of biological slurries, such as feces and vomit, soil samples, plant cells, plant tissue, and microorganisms, such as bacteria, fungi, algae, mycoplasma, and viruses. It is appreciated that the materials listed above are only representative of the biological materials that may be inspected using the method of the present invention. The materials to be inspected may be homogeneous samples or optionally heterogeneous mixtures of several different kinds of biological materials. Optionally, non-biological materials may also be included in the sample.

In accordance with another preferred embodiment of the present invention, cells are maintained under cell culture conditions, such as immersion in growth medium, for example, LB medium at 37° C. for bacteria or in Dulbecco's modified essential medium (DMEM) supplemented with 10% fetal bovine serum, at 37° C. in a humidified atmosphere including 5% $CO_2$, for cultured animal cells, in a SEM compatible sample container, or in a subassembly thereof, prior to imaging. In this embodiment, the SEM compatible sample container or subassembly serves as an experimental vessel, analogous to conventional vessels, such as Petri dishes, cell culture dishes, cell culture flasks, and/or multiwell plates, for growth and/or manipulation of cells. Additionally, samples including cells and other samples may be subjected to various treatments, including, but not limited to, addition of mitogens, drugs, hormones, cytokines, antibiotics, toxic materials, viruses, bacteria, vital stains or other staining solutions, mixing (co-culture) of different cell types, transfection of cells with DNA, irradiation with ultraviolet, X-ray or gamma radiation, replacement of the growth medium with other media, such as media lacking serum, while in the sample container or subassembly, in accordance with the objectives of an experiment or an analysis.

In accordance with yet another preferred embodiment of the present invention, methods for SEM visualization of non-biological samples and samples not directly derived from biological material, such as cosmetic creams, clays, used machine or motor oils, other emulsions and suspensions, processed food products, and pharmaceutical formulations, are provided.

In accordance with another preferred embodiment of the present invention methods are provided for imaging of samples without fixation. These samples include, but are not limited to, animal or human cells cultured in a SEM compatible sample container, animal, human, protozoan, fungal, plant or bacterial cells introduced into the sample container, segments of animal, human or plant tissue, or other liquid samples introduced into the sample container. Fixation processes are employed in microscopy to preserve structural integrity of a sample or of features within a sample during the time that elapses until observation and during preparative steps, such as permeabilization, dehydration, embedding, thin sectioning, and staining, between sample acquisition and imaging. The methods of the present invention allow imaging of samples without performing any of the aforementioned preparative steps.

In accordance with another preferred embodiment of the present invention, samples may be prepared using conventional fixation methods, such as addition of aldehydes, such as formaldehyde, glutaraldehyde or combinations thereof addition of methanol or addition of osmium tetroxide, prior to imaging.

In accordance with another preferred embodiment of the present invention, methods are provided for visualizing samples without heavy metal stains characteristic of electron microscopy. The efficiency of electron backscattering is a function of the material composition of the sample being scanned, varying, for example, with the atomic number or Z value of the different atoms that comprise the sample or its components. These quantitative differences in electron backscattering, stemming, for example, from differences in the Z value of different atoms, provide contrast even in the absence of heavy metal stains. Since the methods of the present invention disturb the molecular composition of a sample only nominally, if at all, components in a sample can be distinguished on the basis of differences in local concentrations of compounds that differ from one another in the average Z value. For example, subcellular organelles in a biological sample can be distinguished based on differences in their respective compositions and concentrations of lipids, phosphates, proteins, and salts. Similarly, the components of a complex mixture, such as those of milk or of sludge, may also be, distinguished on the basis of differences in their material composition, such as in their Z values.

Additionally, samples may be stained with conventional non-specific and/or specific stains. Non-specific stains, such as uranyl acetate, osmium tetroxide, potassium ferricyanide, lead citrate, and phosphotungstic acid, typically comprising a high Z value material, adhere to or otherwise associate with the features of a sample, thereby enhancing the contrast of features of the sample. Conventional specific stains bind or otherwise adhere selectively to specific targeted molecule or structures, on the surface of the sample or internally, if the sample is rendered permeable to the stain by conventional methods. The specific stain may comprise a molecule which has a high selective affinity to a targeted molecule or structure and thereby binds to, or otherwise associates with, the targeted molecule or structure. Examples of such targeting molecules are antibodies, receptor ligands, hormones, enzymes, enzyme substrates, avidin, streptavidin, lectins, and nucleic acids. At least one high Z-value, EM contrast providing atom may be linked by conventional methods to the high selective affinity molecule. Upon binding to or otherwise associating with the target molecule or structure, the target molecule or structure is identified when imaged in a scanning electron microscope by the presence of the at least one high Z-value atom linked to the high selective affinity molecule. This method is often referred to in the art as direct labeling.

Additionally, the at least one high Z-value, EM contrast providing atom need not be directly linked to the high selective affinity molecule, but may be attached through indirect labeling methods. The at least one EM contrast providing atom may be linked instead by conventional methods to a second high selective affinity molecule whose affinity is directed toward the first high selective affinity molecule. The first high selective affinity molecule is allowed to bind to, or otherwise associate with, the targeted molecule or structure and then the second high selective affinity molecule with the at least one linked EM contrast providing atom is allowed to bind to the first high selective affinity molecule, thereby identifying the target molecule or structure.

A conventional example of such first and second high selective affinity molecules are two different antibodies from two different organisms, wherein the first antibody from one organism is allowed to bind to the targeted molecule or structure, and then the second antibody, linked to at least one EM contrast providing atom, from the second organism is allowed to bind to the first antibody bound to the targeted molecule or structure. This method is known as indirect labeling. The major advantage of indirect labeling in the context of the present invention is that second high selective affinity reagent linked to at least one EM contrast providing agent are commercially available, eliminating the need to create de novo such linked molecules.

Another conventional example is where at least one molecule of biotin is linked by conventional methods to an antibody or other molecule with a high selective affinity to a targeted molecule or structure, and at least one EM contrast providing atom is linked either to the protein avidin or to the protein streptavidin. The biotin-linked antibody is allowed to bind to a targeted molecule or structure, and then either the protein avidin or to the protein streptavidin, linked to at least one EM contrast providing atom, is then allowed to bind to the biotin-linked antibody, thereby identifying the target molecule or structure bound by the biotin-linked molecule.

An additional conventional example is where a first antibody is allowed to bind to its target molecule or structure, and then either protein A or protein G, linked to at least one EM contrast providing atom, is allowed to bind specifically to the first antibody, thereby identifying the target molecule or structure.

In accordance with yet another preferred embodiment of the present invention a method for imaging of thick, "solid" samples, as opposed to cell cultures, cell suspensions, and liquid samples, is provided. In reference to this embodiment, the term "solid" denotes a range of consistencies including hard collagenous matrices, bone, and hard plant tissues, as well as soft tissues, such as thymus or pancreatic tissues, and gel-like materials, such as blood clots, agar gels and the like. These samples may include pieces of explanted tissues or tissue biopsies, natural and artificial gels and matrices, semisolid media, such as agarose, multicellular assemblies, or thin samples deposited on the surface of a thick, solid matrix.

In this embodiment, the method includes additional steps to provide close contact with the partition membrane. To maintain suitable contact with the partition membrane, a sample is provided with a fairly smooth surface. This surface may be the "natural" edge of the sample, such as an epithelial lining that is part of a tissue sample, or may be generated by cutting a tissue piece with a razor or a slicing instrument, preferably by the device and methods depicted in FIGS. 86A–87B, or in another preferred embodiment, with a mechanized instrument, such as a vibratome®. Additionally, in this embodiment, the tissue typically needs to be pushed against the partition membrane, such as by a positioning device, preferably, the device shown in FIGS. 31A–50.

The sample preparation and imaging are otherwise similar to those for cells, except as described hereinbelow. Tissues may be imaged without any treatment, following fixation, or following staining/labeling. Fixation, when used, is either performed by vascular perfusion with fixative or by immersing small tissue fragments in fixative. Staining and labeling are done using similar procedures to those described hereinbelow for cells. One important difference is that, whereas samples comprising cells adhered to the partition membrane of the sample container can be treated by exchanging the fluid in the container, samples comprising tissue fragments are preferably treated before introduction into the sample container. It will be appreciated by those skilled in the art that these procedures may have to be modified slightly for use with tissue fragments, in view of the empirical results.

In accordance with yet another preferred embodiment of the present invention, methods are also provided for visualizing a sample and/or specific structures on the sample. In addition to the detection of backscattered electrons, a SEM may be equipped with a photon detector, as shown in FIGS.

58A–84, to detect light produced as a result of the electron beam scanning. Two significant advantages are associated with the orientation of the photon detector disclosed in FIGS. 58A–84, which is different from the conventional orientation. First, the sample is completely isolated from the vacuum in the scanning chamber of the SEM, and can be maintained in a wet state at near-atmospheric pressure. Second, the light guide leading to the light detector is generally placed at an opposite side of the sample relative to the detectors of backscattered electrons, unlike conventional cathodoluminescence detectors, that are placed on the same general side of the sample. In the present invention the detectors used for the two modes of detection do not compete for the same space, allowing highly efficient and, preferably, concurrent collection of both light and backscattered electrons. The scanning electron beam excites, directly or indirectly, molecules in the sample, which then may emit visible light at characteristic wavelengths, a process variously known as cathodoluminescence or scintillation. The intensity and/or the spectral properties of the emitted light can then be used to construct an image of sample derived from the endogenous scintillating molecules in the sample. Just as inherent differences in the Z values of the different components or molecules that comprise the sample can be exploited to construct a micrograph on the basis of backscattered electrons, the inherent differences in the intensity and wavelength of the cathodoluminescence emitted by the different components or molecules that comprise the sample may also be used to construct a micrograph of the sample, by conventional methods.

Alternatively, exogenous cathodoluminescence labels known in the art can be contacted with the sample as a cathodoluminescence stain. Non-limiting examples of such cathodoluminescence labels are FLUOSPHERES, such as Catalog number F-8814, Molecular Probes, Eugene, Oreg., USA, and scintillation proximity assay (SPA) beads, such as Catalog no. RPNQ0006, Amersham Biosciences, Piscataway, N.J., USA. Preferably, the methods of the present invention also provide for specific cathodoluminescence stains. The specific cathodoluminescence stains are similar to the direct or indirect labeling techniques described above, wherein instead of the at least one high Z-value, EM contrast providing atom, at least one cathodoluminescence moiety is linked to the direct or indirect targeting molecules by methods known in the art A SEM image may be derived on the basis of cathodoluminescence alone or in conjunction with a SEM image constructed on the basis of the backscattered electrons. In another embodiment of the present invention, the cathodoluminescence detection system is equipped with conventional means for spectral resolution of the light emitted from the scanned sample. Non-limiting examples of such means for spectral resolution include filters, diffraction gratings, and prisms. Thus, this embodiment provides for measurement of light of a selected wavelength or of a wavelength within a selected range, enabling for example, to distinguish between light emitted by different materials in the sample, detecting a particular material or class of materials, or improving the signal to noise characteristics of the signal.

In accordance with still another preferred embodiment of the present invention, further information from the sample may be obtained by detection and spectroscopic analysis of X-rays emitted from the sample as a result of interaction with the electron beam, according to conventional methods. Such analysis provides specific and quantitative information on the elemental composition and distribution of the sample or of regions within the sample.

Additionally, for any given sample, different staining and labeling methods may be combined as dictated by the imaging and analytic needs. As non-limiting examples, backscattered electrons and cathodoluminescence can be detected during scanning of the same sample, yielding two images of the same region of a sample; in another example, backscattered electron detection can be combined with X-ray detection from either the whole scanned region or from a smaller region, using conventional methods.

In accordance with another preferred embodiment of the present invention, methods are provided for SEM imaging several microns below the surface of a sample. In conventional SEM the surface topology of a sample is imaged using a reflective mode, constructing an image from the detected secondary electrons dislodged from the surface of the sample by the scanning electron beam The present invention uses backscattered electron detection as the primary detection mode, and such backscattered electrons result from interaction of the scanning electron beam with components of the sample that can lay up to a few microns below the surface of the sample. Since the image is derived from the detected backscattered electrons, the actual thickness of the sample is in a sense arbitrary, limited only by the depth of the sample container of the invention. The contrast of the features of interest, both those on the surface of the sample and those below the surface, may be enhanced by employing any one or an appropriate combination of non-specific or specific stains.

In accordance with still another preferred embodiment of the present invention, methods are provided for a virtual serial sectioning of a sample. The sample is initially scanned with an electron beam at a low acceleration energy, producing an image of a region of the sample that is nearest to a partition membrane. Increasing the acceleration energy of the electron beam allows the beam to penetrate into the sample to a slightly greater depth and to derive an image of the interior of the sample at that depth from the resultant backscattered electrons. Subsequent images are obtained in a similar manner by increasing the acceleration energy in stepwise increments, thereby deriving an image at each level as the electron beam penetrates deeper into the sample, up to a depth of several microns. Acceleration energy values preferably range between approximately 8 keV and 30 keV. The series of images thus obtained serve to identify features lying at different depths within the sample, or may serve as raw data for reconstructing a three dimensional distribution of such features, using suitable algorithms.

In accordance with yet another preferred embodiment of the present invention, methods suitable for rapid histopathological analysis within the time frame of a surgical operation are provided. Surgical pathology, the analyses and results of which are used to determine the continuation and course of surgery, is currently built upon the light microscopic examination of frozen sections of the dissected tissue. While this technique can be accomplished in about 30 minutes, the crude freezing techniques used cause significant damage to the structure of the tissue, leading to loss of delicate details. The methods of the present invention permit a higher resolution SEM examination of the dissected tissue, within the required timeframe, in the absence of fixation or staining or drying and under atmospheric pressure, thereby preserving the delicate detail of the sample. Additionally, non-specific and specific stains, as well as gentler fixation techniques, may be included if additional, more detailed, analyses are required.

In accordance with another preferred embodiment, the methods of the present invention providing imaging capabilities may be used to replace or improve any process in research, diagnosis, therapy, industrial or regulatory inspection, that uses microscopic imaging.

As discussed hereinabove, conventional electron microscopy is used to examine a small proportion (3–8%) of specialized cases, such as kidney pathology or oncology, where the resolution of light microscopy is insufficient. The methods of the present invention permit a more widespread use of SEM for pathology in general and surgical pathology in particular. In addition, the methods of the present invention may be used instead of, or in addition to, histological or cytological examination that currently use light microscopy. The advantages provided by the methods of the present invention may relate to speed, to preservation of the sample in a state more closely resembling the native state, from obviating the need for thin sectioning, or from other features of the novel imaging mode. These advantages may be particularly important in medical areas in which current methods are insufficient, such as correct staging of brain tumors and of neural pathologies in general, cytological examination of dispersed cell specimens, such as fine needle aspirations of thyroid or breast tissue, and blood samples.

The method of the present invention is particularly suitable for use in the selected applications described hereinbelow. It is appreciated that these examples are used for illustrative purposes only, and are in no way intended as limiting.

Obesity and Diabetes: Lipid Droplets in Fat Cells, White and Brown Adipose Tissue Preparation of samples for conventional TEM involves complete removal of water, usually by replacement by organic solvents, such as alcohol or xylene. These solvents dissolve lipids, which are then lost from the sample. Fixation with osmium tetroxide, which cross-links lipid molecules, works to preserve lipids in thin structures such as lipid bilayer membranes. However, with larger lipid structures, such as lipid droplets or the lipid component of adipocytes (fat cells), the osmium reacts quickly with lipids on the surface, creating a "crust" that is less permeable to osmium tetroxide, the interior of the lipid structure is thus left unfixed, and may be destroyed or dissolved later.

The methods of the present invention provide a unique ability to observe lipid-rich components in biological samples, by avoiding the need for organic extraction and lipid fixation. This ability has utility in the medical areas of obesity and diabetes. Treatments for obesity and type II diabetes effect changes in one or more of the following parameters, which can be directly assessed using the methods of the present invention, the distribution of lipids in adipose cells (adipocytes), measurements of number and size of adipocytes, and the distinction between anatomically and metabolically different adipocytes, including brown adipose tissue (BAT) and white adipose tissue (WAT), adipose tissue from different anatomical locations, and adipose tissue from young vs. old individuals. Additionally, lipid distribution may be measured in adipocytes or pre-adipocytes derived from humans, experimental animals or in continuous cell lines, as means of diagnosis.

Fatty change in Kidney, Liver

Pathological states of the numerous tissue types, most prominently liver, kidney and muscle, are associated with rapid accumulation of lipid droplets inside and outside of cells, termed fatty change. The clinical observation of fatty change is an early sign of tissue damage due to alcohol and other hepatotoxins, of various kidney pathologies and of atherosclerosis. More rarely, but significantly, fatty change is also indicative of myocardial damage due to infarcts, ischemia, or degenerative diseases. Monitoring fatty change is also useful during the liver transplantation, to direct decisions on the course of operation and on the suitability of a liver for various patients.

Kidney Pathology

Kidney pathology is one of the major areas for which electron microscopy is presently used for clinical diagnosis. Electron microscopy (EM) is necessary for the diagnosis of many glomerular diseases, including minimal change disease, thin basement membrane nephropathy, hereditary nephritis (Alport's syndrome), and fibrillary glomerulonephritis. EM also permits precise localization of the immune complex deposits, the identification of tubulo-reticular inclusions in lupus nephritis and HIV-associated renal disease. The methods of the present invention allow rapid and easier performance of high-resolution imaging of kidney samples.

Toxicology

Toxicological studies are carried out in animals or in humans, the latter either in ethically controlled studies or in investigating the consequences of inadvertent exposure. Toxicological effects can often be assessed using microscopic analysis, many toxins affect primarily selected target organs, most often liver, kidney, lung and the digestive tract. The methods of the present invention provide means for sensitive and rapid analyses of samples derived from these and other tissues. Such analyses have applications, for example, in testing for environmental, occupational and nutritional toxins, as well as for toxic side effects of drugs. In another preferred embodiment of the present invention, such analysis is carried out using X-ray detection, which gives information on the distribution and concentration of various elements, this has utility, for example, in the detection of particulate contamination in the lung or in alveolar macrophages.

CNS: Myelin, MS, Nerve Trauma and Regeneration, and Tumors

The Myelin sheath of nerve processes are prominent lipid-rich structures, which are clearly visible in the methods of the present invention. Changes in the extent of nerve myelination and in the structure of the nerve fibers and the associated myelin sheaths accompany a wide variety of clinical neurodegenerative situations, such as autoimmune diseases such as Multiple Sclerosis, Guillain-BarréSyndrome, congenital storage diseases such as Neuronal Ceroid Lipofuscinoses (OMIM 256730, possibly the most common group of neurodegenerative diseases in children), complications of infectious diseases such as diphtheria, HIV, or prion diseases; and trauma. In these cases, the methods of the present invention can contribute to diagnosis based on rapid, high resolution imaging of small samples, such as biopsies or cerebrospinal fluid, to histopathological analysis in either patients or in animals. Additionally, the ability to observe the organization of neural tissue at high resolution can be employed in the analysis of suspected tumors in the nervous system.

Extracellular Matrix

The extracellular matrix (ECM), which is composed mostly of protein, glycoproteins, oligosaccharide and polysaccharide chains, is the structural foundation of tissues and organs. The ECM plays crucial roles in diverse processes, including morphogenesis and organogenesis, regulation of cell growth, migration and polar extension, such as axonal growth. Several genetic and degenerative diseases are associated with alterations in the structure of the extracellular matrix, such as scurvy due to vitamin C deficiency, which leads to incomplete modification of collagen and general dissolution of connective tissues; collagen modification in aging, resulting in changes in connective tissue; genetic diseases due to mutations in collagen genes, such as Osteogenesis imperfecta (Collagen I mutations), The Helers-Danlos Syndrome, and various arthritic conditions. Additionally, cancer cells may have specialized interactions with the surrounding extracellular matrix, for example, cancer cells produce and secrete enzymes that change the structure of the surrounding matrix. Such production and secretion of enzymes may be associated with specific properties of the cancer cells, including metastatic activity, which may have important implications for prognosis and treatment.

The methods of the present invention allow a unique imaging capability for the structure and composition of the extracellular matrix. Such imaging can provide means of diagnosis, or analysis of drug action in patients and in experimental animals. In the context of cancer, analysis of extracellular matrix in samples derived directly from tumors, or from incubation of cancer cells in vitro, can be carried out in accordance with methods of the present invention; such analysis may provide data for characterization of the tumor, for designating a treatment protocol and for assessing the progress of the treatment.

Epithelia

The methods of the present invention provide a direct and effective means of viewing epithelia. An epithelial cell layer is placed directly in a sample container so that it is in contact or in close proximity to a partition membrane, the container is sealed and placed in a SEM, and imaged by scanning electron microscopy according to an embodiment of the present invention. The epithelial layer may be imaged while attached to an underlying tissue, or may be removed from such tissues before imaging. Additionally, the epithelial layer may occur without such attachment in its natural position in the body prior to removal for imaging. Applications include the diagnosis of many diseases that affect the structure of epithelia, such as diseases of the digestive system, the respiratory system, endocrine and exocrine glands, vascular diseases, skin diseases, eye diseases.

Hematology and Immunology

The methods of the present invention provide means of analysis of cells of the hematopoietic system, both in the context of a tissue, such as in a biopsy of thymus, lymph nodes or bone marrow, within capillaries in a tissue biopsy, or outside blood vessels, especially in sites of inflammation, or in fluid samples, such as blood or fine-needle aspirates. Information on the abundance or the arrangement of hematopoietic cells in tissues can be used to derive diagnosis and to direct decisions on treatment protocols in a variety of pathological situations, including inflammatory diseases, such as rheumatoid arthritis, lupus, other autoimmune diseases, atherosclerosis, and wound healing. Another application of unique importance is the early and accurate detection of rejection of transplanted tissues, such as a heart. Recipients of such transplanted tissues are generally placed under immuno-suppressive treatment for extended periods to prevent rejection of the transplant. However, the transplant must be frequently monitored for early signs of rejection, which must be met with immediate adjustment of treatment Such monitoring is currently achieved by microscopic examination of tissue biopsies taken, for example, at weekly intervals. The methods of the present invention may provide a more sensitive or accurate means of assessing the state of the transplant from such biopsies.

Cancer

Microscopic imaging of tumors, biopsies, needle aspirations, or cell suspensions from suspected tumors, of portions of surgically removed tumors, and of cells derived from tumors and maintained in vitro have an important role in diagnosis, typing, and grading of tumors, as well as in determining the prognosis and course of patient treatment. The methods provided in the present invention provide new capabilities for microscopic imaging, such as high resolution, easy and rapid sample preparation, reduction of artifacts due to sample preparation, and unique contrast mechanisms, which may be used for improvements or as unique tools in diagnosis, typing, and grading of tumors, as well as in determining the prognosis and course of patient treatment Microbiological Entities In accordance with another preferred embodiment of the present invention, the method provides for imaging of microbiological entities, including, but not limited to, bacteria, archea, fungi, protozoa, *Giardia, Pneumocystis carinii*, bacterial and fungal colonies, mycelia, bacterial and fungal biofilms, and viruses. Microbiological entities may be imaged in several types of samples, such as blood, sweat, tears, stool, sputum, stool, urine, pus, cerebrospinal fluid, tissue specimens, lavages of the lungs; bronchia, or digestive system, environmental samples, soil samples, and plant samples. Such inspection may be of use for detecting microbiological contamination in patients, animals or plants, or on medical, industrial or household devices.

Additionally, SEM inspection of microbiological entities may be used for detection of the presence of such entities in a sample, for identification of the entities, as for example distinguishing bacteria from fungi or viruses, or determining a broad or unique classification of a microbiological entity. Additionally, SEM inspection may be used to characterize some property of a microbiological entity. For example, the sensitivity or resistance of a bacterium to one or more antibiotic substances may be rapidly examined by incubating small numbers of such bacteria with the antibiotics, preferably using different concentrations of antibody in each of several parallel experiments, and after a period sufficient to detect an effect on individual cells, typically less than one hour for penicillin, inspecting the bacteria by SEM according to the methods of the present invention. Antibiotics may induce morphological changes or lysis of susceptible bacteria, while the same antibiotic may not induce such changes in resistant bacteria, thus establishing a criterion for rapid assessment of antibiotic susceptibility or resistance in the bacteria.

Cell-coated Devices, Implants, Stents

Another aspect of the present invention provides for imaging of samples derived from devices or formulations used as biomedical implants or as cell carriers for biotechnology, or other medical or industrial devices or formulations that may come in contact with biological materials during operation or storage. A common feature for these samples is that cells, including human, animal, protozoa or microbial cells, are adhered or grown on a surface of the device or formulation. The device or formulation may be of such thickness or material composition that is generally impermeable to electrons or to light, thus precluding direct imaging in a transmission electron microscope or by transmitted light microscopy. Using methods of the present invention, such samples can be placed in a sample container so than the surface of interest is proximal to the electron-transparent partition membrane. As discussed, the reflective mode of imaging of the present invention allows to image the surface layer of the sample, including any cells present on the surface. Examples of such samples include cardiovascular implants such as stents, covered stents, valves, bypass or replacement arteries. These devices are typically made of metal, synthetic or natural polymers or tissues, or combinations thereof. Major concerns with the use of such devices include the presence of cells, especially fungi and microbes, before implantation, the coverage by normal endothelial, and the prevention of unwanted reactions leading to clot formation. Implants may be examined before implantation, in experimental or quality control conditions, after incubation with cells or bacteria in vitro, after implantation in animals, or after implantation in humans, conceivably after the implant is no longer required or after its failure.

Implants such as the cardiovascular implants or, prostheses, sutures, hard or soft tissue implants may additionally be examined by methods of the present invention as part of the manufacturing process to derive information on the material and structural properties, or on any other functional aspect of the implants, such as response to a variety of treatments in vitro or in vivo. The examination may occur during development of the implants or of materials and parts used in the manufacture of the implants. In other embodiments, the examination may be performed on a sample of part of a manufacturing batch or of every manufactured implant.

Medical devices which may suffer deposition of unwanted materials on surfaces, including various catheters, kidney dialysis devices, infusion tubing, endoscopy devices, and any containers or tubings that may contact materials that are to be used medically or nutritionally may also be examined by methods of the present invention. Examples of materials that may be deposited on the devices include bacteria, bacterial biofilms, fungi, protozoa, mycoplasma, organic or inorganic precipitates or adhered phases, blood cells such as platelets, macrophages, leukocytes.

Additionally, materials and formulations used in tissue engineering, typically including a synthetic or biologically derived matrix and, optionally, cells deposited within or on the surface of such a matrix may also be examined by methods of the present invention. Vessels, tubings, filters, substrata for cell attachment or growth including microcarriers, fiber beds, hollow fibers and stacked plate modules, used in biotechnology and bioengineering applications may also be examined by methods of the present invention. Non-limiting examples of cell growth microcarriers include CYTOLINE® and CYTODEX® from Amersham Bioscience and CULTISPHER® from Hyclone of Logan, Utah, USA, hollow fibers include FiberCells® from Fibercell systems of Frederick, Md., USA The vessels, tubings and substrata come in contact with cultured cells, with cell growth media, and/or with cleaning solutions. The arrangement, density, integrity and structures of cultured cells and of layers and aggregates of such cells may have important consequences in the biotechnological applications of such cells, and can be monitored and analyzed using methods of the present invention. Deposition or growth of undesired substances and organisms on the vessels, tubings and substrata, including aberrant cells or cell assemblies, microbes, microbial biofilms, fungi, protozoa, mycoplasma, organic or inorganic precipitates or adhered phases, can also be monitored and analyzed using the methods of the current invention.

Quantitative Pattern Analysis of Biomolecules

In another aspect of the present invention, methods are provided for determining the quantity and spatial distribution of specific molecules in a sample. The need for such analysis arises in a multitude of situations, some of which are detailed hereinbelow.

Quantitation of biomolecules in biological samples is currently done by a variety of means, including:

1. Biochemical and immunological assays in which the total amount of a biomolecule in multiple cells is measured; for example, radioligand binding assays, radioimmunoassay, fluorescence-based binding assays, assays of enzyme activity, immunoblotting, etc. While yielding accurate measures of the total quantity of biomolecules in the sample, such methods do not give any information on the spatial distribution, on differential concentration in different cells in the sample, etc. Furthermore, two issues of sensitivity arise: first, limits on sensitivity of detection may necessitate the use of a large number of cells or a large amount of tissue for measurement. Second, biomolecules that are highly concentrated in a limited region of the cells, such as a subcellular organelle, or of the tissue sample are diluted with an excess of material from regions of the sample that do not contain the biomolecules, thus limiting the sensitivity of detection.

2. Antibody, ligand or enzyme-based staining of cytological or histological samples, and detection by light microscopy. Typically, a sample is incubated with a solution containing antibodies that bind specifically to a biomolecule of interest. The antibodies are linked, either directly or indirectly, to a labeling moiety that is visible by light microscopy. Such labeling moieties may include fluorophores, chromophores, particles that are either opaque to light or scatter light, or enzymes that generate localized concentration of fluorophores, chromophores, opaque or highly scattering materials. Such methods, coupled to imaging and image analysis with light microscopy, yield information on both the amount and distribution of the target biomolecules. Limitations of such techniques include resolution (limited by light diffraction to approximately 250 nm), signal to noise ratio, especially when analyzing biomolecules with a diffuse distribution, sensitivity, bleaching of fluorescent dyes, limited dynamic range and non-linear response.

3. Antibody or ligand-based staining of cytological or histological samples, and detection by electron microscopy (EM). Similar in general principle to light-microscopy based methods, the detection here is based on electron-dense or electron-scattering substances, including for example colloidal gold particles, ferritin, precipitates such as lead phosphate, and polymerized diaminobenzidine stained with heavy metals or osmium tetroxide. EM-based detection, quantitation and pattern analysis of biomolecules can reach very high resolutions (better than 1 nm in transmission EM, 5–10 nm in scanning Ed. A comparative analysis of EM based relative to fluorescence based quantitation of biomolecules (Levit-Binnun N, Lindner AB, Zik O, Eshhar Z, Moses E., 2003. Quantitative detection of protein arrays. *Anal. Chem.* 75(6): 143641; and patent application WO02/14830-PCT/IL01/00764) documents a significant advantage of EM-based detection of gold colloids in sensitivity, signal to noise ratio, and dynamic range.

Current methods for EM-based quantitation and pattern analysis of biomolecules in biological samples such as cells or tissues require sample preparation procedures typical of electron microscopy. For transmission EM, these require embedding or rapid freezing followed by ultrathin sectioning. One resulting limitation is that only a small, and often arbitrary, portion of the cell or tissue is present in the thin section. For example, when attempting to detect and quantify proteins associated with the cell membrane, a thin section will include only a very small portion of the entire cell membrane. Labeling and imaging intact or permeabilized cells, is made possible when scanning EM is used for detection, where the samples do not need to be thin sectioned for imaging. Standard SEM, in which the sample needs to be dried by methods such as critical point drying, suffer from artifacts due to the drying process, as well as problem in clear identification of the labeling particles when the samples are coated and imaged by secondary electron detection.

The methods of the present invention provide a mode of detection and quantitation of biomolecules that uniquely overcomes many limitations of existing techniques. The EM-based detection provides for high sensitivity, dynamic range, and signal to noise ratio; the high resolution imaging and the optional use of discreet labeling moieties such as colloidal gold particles, allow to map with high precision the spatial distribution of biomolecules; the ability to observe intact, or permeabilized but otherwise intact, cells, yields a global view of the distribution of biomolecules throughout the cell or the cell surface or the tissue examined; and the ability to observe cell and tissues without dehydration, drying and embedding results in the elimination of potential artifacts associated with these processes.

Non-limiting examples of applications in which the quantity and spatial distribution of biomolecules are important parameters include:

Distribution of receptors on the cell surface. Cell surface receptors for signaling molecules such as hormones, cytokines, chemokines, growth factors, extracellular matrix, cell: cell interactions, cell adhesion molecules, and cell: pathogen interactions are often distributed on the cell surface in a non-uniform distribution, and both the quantity and distribution of such receptors may affect the reactivity to, signals and may be modulated in response to signals. Thus, the quantity and distribution of receptors on the cell surface in cells and in tissues are important predictors of the properties, of potential responsiveness to external stimuli, and of the cells and tissues. Additionally, changes in the quantity and distribution of receptors upon application of signals may yield unique information on the response to the signals. Extensively studied cases include the dimerization and multimerization of growth factor receptors such as the Epidermal Growth Factor (EGF) receptor. The EGF receptor, which may be in monomeric form prior to binding of EGF, rapidly aggregates into dimers and larger multimers upon binding of EGF. This aggregation is a necessary and sufficient step in at least part of the signal transduction process. After the initial aggregation, receptors may undergo additional processes that change the quantity and surface distribution, namely further aggregation, and internalization into intracellular compartments not accessible from outside the cell. These processes also have important roles in signal transduction, in modulating the duration of the activated state, and in modulating the sensitivity to subsequent signals.

Association of biomolecules with identical or distinct biomolecules.

Biomolecules such as proteins often function as dimers or larger oligomers, in which the subunits may be identical (homodimers, homo-oligomers) or different (heterodimers and hetero-oligomers). For example, the EGF receptor, also designated HER1, can form dimers with an other HER1 molecule, or with any of a group of similar receptor molecules termed HER2, HER3 and HER4; in fact, the HER1–4 proteins can associate in a variety of homodimers and heterodimers. The formation of each such dimer may be differentially influenced by binding of any of several EGF-like ligands, with different biological consequences. Finally, the HER family of receptors are differentially expressed in some types of cancer; a much-discussed example is the high prevalence of HER-2 in some breast cancers. Indeed, high prevalence of HER2 in a cancer is liked to a poor prognosis, and drugs such as Herceptin® target this receptor specifically. The association of receptors and other proteins into dimers and larger oligomers has been investigated using bulk techniques, in which (for example) a general crosslinking molecule is used to covalently link molecules that are in close proximity, or by distance-dependent energy transfer between fluorescent molecules and chromophores attached to different proteins. The methods of the present invention uniquely allow to measure the extent of association of similar or different biomolecules, by using labeling each of the biomolecules with a label that can be distinguished from each other by SEM inspection according to the methods of the present invention. Non-limiting examples of such distinguishable labels are colloidal gold particles of different sizes (e.g. 10 nm and 20 nm, 15 nm, 25 nm and 35 nm, etc.), and combination of electron-dense labels with cathodoluminescence labels, visualized in the same sample by simultaneous detection of backscattered electrons and light.

Emulsions and Suspensions

Emulsions, comprising a fine mixture of immiscible phases such as oil and water, and suspensions, which are fine mixtures of solid particles in a liquid, are very difficult to analyze using current electron microscopy techniques. Nearly any method for fixation or freezing, may damage or significantly alter the microscopic structure of the sample. Observation of such samples using environmental SEM is also unreliable due to the difficulty in maintaining the composition of the unfixed sample.

The methods of the present invention provide a unique means of imaging such samples such as dairy products, other food products including butter, margarines and substitutes, cosmetic creams, sunscreen creams, machine and motor oils and lubricants, clays, and pharmaceutical formulations, biological fluids such as milk, blood, plasma and serum, feces, and environmental samples.

Automated SEM

It is another objective of the present invention to provide means for automated electron microscopy of wet samples, and specifically of biological samples. Such automated microscopy has been widely applied in the semiconductor industry. The main barrier to the application of automated electron microscopy to wet samples is the need to employ sample preparation procedures such as drying, embedding, sectioning or coating, which are highly complex and not amenable to automation. The present invention provides means for direct imaging of wet samples in a scanning electron microscope, thus obviating the need for the aforementioned preparative procedures. In fact, the introduction of biological or other wet samples into the sample container and the preparation for imaging involve, at most, a series of additions and removals of liquids to a dish. Such manipulations, carried out by appropriately designed pipettors and fluid aspirators, are easy to automate, as is done on a massive scale in applications such as drug screening and genomic sequencing. Automated sample preparation provided by the methods of the present invention, which may be coupled to other automated steps known in the art such as automated introduction into a SEM, automated positioning, registration of location markers, selection of area of interest for observation, and image analysis, can provide for essentially any level of automation required. A non-limiting example of the utility of such automated systems include drug screening using parameters measured at high resolution and disclosed in the preceding sections, such as drug-induced structural changes in cells or drug-induced changes in abundance or distribution of cell surface receptors; and quality assurance applications, for example in the drug or other chemical industries.

GENERAL PROTOCOLS OF THE PRESENT INVENTION

A general outline of the protocols used in the methods of the present invention is disclosed hereinbelow. It will be appreciated by those skilled in the art of electron microscopy that these protocols are general in scope and may be adapted or modified to suit the circumstances of the particular sample being examined and the desired analyses.

Figure 88:
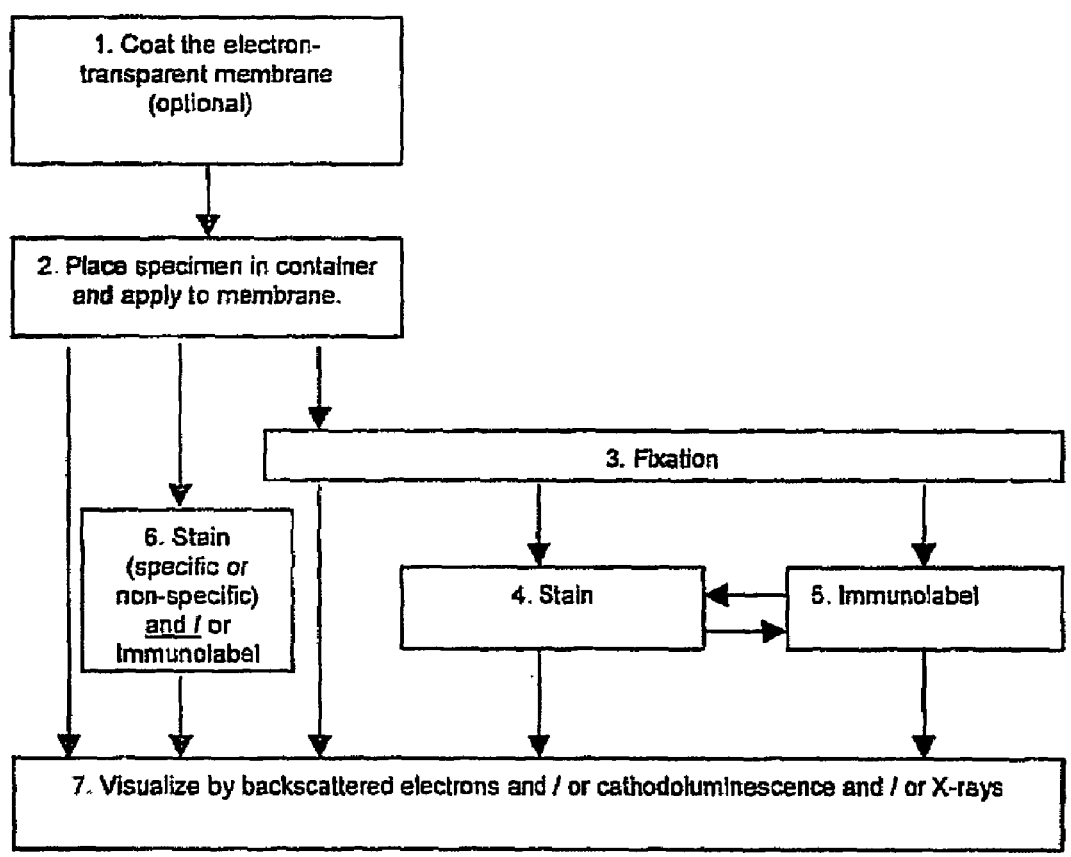
FIG. 88 is a schematic depiction of the main steps that comprise a method for electron microscopic inspections of wet biological and environmental samples at a non-vacuum environment in accordance with a preferred embodiment of the present invention.

Reference is now made to FIG. 88, which depicts schematically the main protocol steps that comprise the method of the present invention. It is appreciated that not all embodiments will comprise all of the steps enumerated hereinbelow. It is appreciated that the methods herein disclosed provide for a desirable degree of flexibility in preparing and visualizing the sample.

The individual steps comprising the protocol are now explained in greater detail. In all protocols, unless specified otherwise, all operations are performed at room temperature; and a "wash" means removing the liquid from the sample container, adding the appropriate washing liquid, then incubating for approximately 5 minutes.

1. Coating the Electron-transparent Partition Membrane

The sample to be imaged must be held in close proximity to, and preferably contacting, the electron-transparent partition membrane. Some samples may adhere directly to the partition membrane without special treatment. Other samples adhere better if the membrane is coated with an adhesion agent before sample is placed into the container and applied to the partition membrane. A non-limiting example of a general adhesion agent is poly-L-lysine. Poly-L-lysine can be used with a variety of samples, including non-adherent animal cells (eg. blood cells), bacteria, protozoa, and a-cellular particles (e.g. particulate matter in a suspension). Other non-limiting examples of adhesion agents known in the art are extracellular matrix components, such as fibronectin, collagen, gelatin, laminin, or Matrigel® (Invitrogen). Extracellular matrix components are typically used as adhesion agents when cultured or primary animal cells are to be maintained on the partition membrane for some duration (several hours or days) under culture conditions. The particular adhesion agent is then selected on the basis of the sample's particular growth requirements and the nature of the biological experiment performed, if any, on the partition membrane.

The following are non-limiting examples of methods of the invention that may be used to coat the electron-transparent partition membrane.

(a) Fibronectin Coating

Materials

Fibronectin 0.1% w/v (e.g. Catalog No. F-1141, Sigma Chemical Co.).

PBS (Phosphate-buffered saline, e.g. catalog No. 14040, Invitrogen)

Procedure

Dilute fibronectin 1:10 with PBS (final concentration of fibronectin, 0.01%).

Apply 15 µl of the diluted solution onto the partition membrane and incubate for 30 min at room temperature.

Remove the solution and wash 5 times with PBS.

Wash twice with the appropriate growth medium (e.g alpha-Minimal Essential Medium, α-MEM with 10% fetal bovine serum).

(b) Poly-L-lysine Coating

Materials

Poly-L-lysine 0.1% w/v in water (e.g. cat no. P8920 from Sigma Chemical Co.)

PBS

Procedure

Apply 15 µl of poly-L-lysine 0.1% solution on partition membrane and incubate for 1 hour at room temperature.

Remove the solution and wash 5 times with distilled water.

Wash twice with PBS or appropriate medium.

2. Placing Sample in Container and Applying to Partition Membrane

Liquid samples or cell suspensions are placed in the container and applied to the partition membrane by pipetting the liquid or cell suspension directly into the container on to the membrane. Cells and particles will usually reach the membrane by gravity or by random motion and will adhere. Adhesion may be a passive process, mediated for example by electrostatic interactions; in the case of animal cells, adhesion is often a specific process mediated by receptors which may depend on metabolic energy, and is often followed by cell spreading on the partition membrane. If the cell concentration is low or the cells are not easily adsorbed on to the membrane, the cells may be centrifuged gently in the sample container (e.g., 5 minutes, 500×g), thereby concentrating the cells onto the partition membrane.

Additionally, cells may be grown on the optionally coated partition membrane under conditions identical or very similar to growth on standard polystyrene tissue culture dishes. The cells will spread, multiply, interact with neighboring cells and respond to exogenous or endogenous signals. Typically, the cells are maintained in growth medium such as α-MEM, Dulbecco's Modified Essential Medium (DMEM) or Ham's F-12, supplemented with 10% fetal bovine serum, in a humidified atmosphere with 5% $CO_2$, at 37° C. In addition, it is possible to transfect the cells with DNA or to infect the cells with viruses or recombinant viral vectors.

As depicted in FIG. 88, the sample may be imaged without any additional processing (see step 7 below), or optionally processed fierier so to enhance the sample's contrast or to label specific components, as described hereinbelow.

3. Fixation

Although it is possible to optionally stain the sample both non-specifically and specifically without prior fixation, the sample is usually fixed prior to optional staining. Fixation preserves the cellular structures as close to the living state as possible and protects the sample from morphological alteration and damage during the subsequent treatments. Additionally, fixation can permanently stabilize ("freeze") the sample in a particular state for subsequent observation, and is particularly useful if transient states are to be visualized.

A wide range of fixation methods known in the art for cytological, immunostaining and electron microscopy may be used. No one fixative preserves all the cellular structures, thus correct choice of fixative will depend on the sample, and on the particular features to be visualized. If the sample is to undergo specific staining such as immunostaining subsequent to fixation, the nature of antigen and antibody will also affect the selection of a fixation procedure.

Fixation typically involves washing off the culture medium, incubating the sample with a fixative solution for the appropriate time interval, and then removal of the fixative.

The following are non-limiting examples of fixation protocols that may be used with the methods of the invention. Optionally other fixation procedures known in the art may also be used as dictated by the particulars of the sample, staining, labeling, and visualization objectives.

Unless otherwise specified, all methods described henceforth are performed at room temperature.

(a) Mild ormaldehyde fixation (optionally used before specific staining, to minimize the damage to targeted sites):

Materials
Paraformaldehyde, EM grade (for example 16% solution, electron microscopy sciences, cat no. 15710)
PBS Procedure
Prepare paraformaldehyde 4% solution in PBS.
Wash the sample several times with PBS.
Fix with paraformaldehyde 4% at room temperature for 15 min.
Wash five times with PBS.

(b) Glutaraldehyde/formaldehyde fixation (optionally used prior to aggressive staining procedures, such as uranyl acetate).

Materials
PBS
Wash solution: 0.1 M sodium cacodylate, pH 7.4, 1% sucrose, 5 mM $CaCl_2$.
Fixative solution: 2% glutaraldehyde, 3% formaldehyde in wash solution.

Procedure
Wash the sample 5 times in PBS
Incubate in fixative solution for 1 hour at room temperature
Wash 5 times with wash solution
Wash 5 times with water.

(c) Cold methanol fixation (optionally used before specific labeling, when treatment with formaldehyde may interfere with such labeling)

Materials
Methanol cooled to –20° C.
PBS

Procedure
Wash the sample 5 times with PBS at room temperature.
Place the sample container on ice, taking care to avoid direct contact of the partition membrane with the ice.
Remove the PBS and add pre-cooled (–20° C.) methanol. Transfer to –20° C. for 5 min.
Wash 5 times with PBS at room temperature.
Proceed to staining or labeling reaction.

4. Non-Specific Staining.

The overall electron microscopic contrast of the sample may be enhanced by use of non-specific stains and staining procedures known in the art. What is common to these procedures is that they result in the adsorption or concentration of high atomic number (Z-value) atoms on the sample or on to structures in the sample.

The following are non-limiting examples of staining procedures known in the art Optionally other staining procedures known in the art may be used as dictated by the sample, labeling, and visualization objectives.

(a) Uranyl Acetate (UA) Staining.

Materials:
Tannic acid, 1% (w/v) solution in water (prepared from e.g. cat. No. Sigma Chemical Co.).
Acidic uranyl acetate (UA) concentrate: 5% (w/v) UA in water, adjusted to pH 3.5 with HCl.
UA staining solution: 0.1% UA, prepared freshly by dilution from 5% UA concentrate in water.

Procedure:
Fix sample as described in the glutaraldehyde/formaldehyde procedure.
Wash 5 times in distilled water.
Add tannic acid solution, incubate 5 minutes.
Wash 5 times in water
Add UA staining solution, incubate 20 minutes.
Wash 5 times in water. Leave in water for imaging.

Osmium Tetroxide ($OsO_4$) Staining.

Material:
$OsO_4$ staining solution: 1% (w/v) osmium tetroxide in water, diluted from commercial 4% stock solution.

Procedure:
Fix sample as described in the glutaraldehyde/formaldehyde procedure.
Wash 5 times in distilled water.
Add $OsO_4$ staining solution, incubate 30 min.
Wash 5 times in water. Leave in water for imaging.

5. Specific Labeling

The location and quantity of particular molecules and/or structures in a sample may be measured by the use of specific targeting molecules that bind or otherwise associate with the targeted molecules and/or structures. At least one high Z-value atom directly or indirectly linked to the specific targeting molecule provide the contrast enhancement for the targeted molecules and/or structures. Alternatively, the specific targeting molecules may lead to the localized accumulation of substances that generate measurable contrast in the vicinity of the targeted molecules and/or structures when visualized by the methods of the present invention.

Non-limiting examples of commercially available molecules that can be used as specific targeting molecules that bind or otherwise associate with the targeted molecules and/or structures include antibodies, protein A, and streptavidin; antibodies, protein A and streptavidin to which colloidal gold particles have been linked; and antibodies, protein A and streptavidin to which horseradish peroxidase has been linked.

It will be appreciated by those skilled in the art, that the labeling moiety need not be limited to high Z value atoms. If the SEM instrument is equipped with a photon detector and/or an X-ray detector, the specific targeting molecules may be linked moieties that emit light or X-rays in response to the electron beam instead of the high Z value atoms.

Generically, specific labeling procedures consist of four or five main steps, depending on whether the at least one high Z value atom is directly or indirectly linked to the targeting molecule: optional sample preparation, optional fixation, optional blocking of non-specific binding, binding of the targeted molecule or structure by the targeting molecule, and optional removal of excess, unbound targeting molecules. If the targeting molecule is already linked to at least one high Z-value atom, then the labeling process is complete and the sample is ready for visualization. If the targeting molecule is not so labeled, then one or more added steps are needed prior to visualization in which high Z-value atoms are bound to the first targeting molecule by a second targeting molecule.

Surface molecules or structures can be labeled on live or fixed cells. Intracellular antigens can be labeled on fixed, permeabilized cells. It will be appreciated by those skilled in the art that fixation procedures can mask or change some epitopes, and thus optimal fixation procedure for each targeting molecule should be determined experimentally. It will also be appreciated by those skilled in the art that, optimal blocking for non-specific background, concentration of the targeting molecule, and incubation time, are parameters that depend on the targeted molecule and/or structure and targeting molecule in question. In some cases specific incubation and wash buffers are required to avoid non-specific binding. Thus, there is no standard procedure that works for all labeling reactions. Optimal conditions may be established based on prior experience with the particular targeting molecules and targets, or by conducting preliminary experiments using fluorescent labels and visualization in a fluorescence microscope.

The following are non-limiting examples of specific labeling procedures known in the art. Optionally other specific labeling procedures known in the art may be used as dictated by the sample, staining, and visualization objectives.

(a) Specific Labeling of Cell Surface Receptors

Materials
PBS
Blocking agent: bovine serum albumin, (BSA) or normal serum.
Primary or first antibody targeted to desired receptor
  Gold particle conjugate capable of binding to or otherwise associating with the primary or first antibody
Distilled H$_2$O
Silver enhancement kit, (e.g., AURION R-GENT SE-EM® cat no. 500.033)

Procedure
Fix cells with the mild formaldehyde procedure.
Incubate cells with protein containing solution, such as 3% BSA (bovine serum albumin) or, if indirect labeling via a secondary antibody is to be used, 1–5% normal serum from the species of the secondary antibody, in PBS, for 30 min. Incubate cells with primary antibody in the same blocking solution as above (typically 30–60 minutes). For some antibodies labeling can be improved by incubating at 37° C. or by longer incubation (several hours to overnight) at 4° C. Perform control reaction as above but without primary antibody.
Wash cells several times with PBS.
Incubate with the gold labeled conjugate (e.g., gold conjugated secondary antibody targeted against primary antibody, or gold conjugated protein A or G; if primary antibody is biotinylated, gold-conjugated streptavidin or avidin can be used) in protein containing solution, such as 1–3% BSA or 1–5% normal serum. Wash extensively with PBS to remove unbound antibodies.
If the colloidal gold particles are too small to be effectively viewed in the SEM (typically less than 30 nm in an SEM with a thermal electron gun, or less than 10 nm in an SEM with a field emission electron gun), silver enhancement can be used to increase the size of the high-Z particles. Silver enhancement can be done using commercially available kits such as AURION R-GENT SE-EM® cat no. 500.033.
Wash several times with distilled water.

(b) Specific Labeling of Intracellular Molecules or Structures:

The procedure for specific labeling of internal molecules or structures is essentially the same as for surface molecules except that the cells must be permeablized after fixation.

Additional Materials
0.2% Triton X-100 in PBS
1% Triton X-100 in PBS

Procedure
For paraformaldehyde or glutaraldehyde fixed cells, permeabilize the cells by incubating with 0.2% TritonX-100/ PBS for 5–15 min. (When methanol fixation is used, no additional permeabilization is required).
Wash five times with PBS.
Peform specific labeling procedure as described above. If subsequent visualization reveals problems with excessive background signal, add a mild detergent such as Triton X-100/NP40 (1% v/v) to the wash buffer used after incubation with primary antibody.
It is preferable to use small gold particles (e.g. 0.8 nm colloidal gold particles) or other contrast-generating materials (e.g. peroxidase/diaminobenzidine/osmium tetroxide) that penetrate the fixed, permeabilized cells more readily than large (e.g. 20–40 nm) colloidal gold particles.

(c) Specific Labeling Using Enzyme-Linked Targeting Molecules.

In another method of the present invention, specific labeling is achieved without having the high-Z contrast generating agent directly linked to targeting molecules. Rather, the targeting molecule causes the local accumulation of contrast-generating molecules in its vicinity. As a non-limiting example, this can be achieved by an enzymatic or other chemical reaction that causes precipitation of a material containing high Z number atoms. An example known in the art is a labeling procedure that uses the enzymatic activity of horseradish peroxidase (HRP) that is covalently linked to an antibody. The enzyme catalyzes the polymerization and insolubilization of diaminobenzidine (DAB); the polymerized DAB binds and accumulates high-Z reagents such as osmium tetroxide or metallic compounds with a much higher affinity than surrounding material in the sample, yielding high contrast The following is a non-limiting example of a specific labeling procedure using HRP.

Materials:
All reagents for fixation and immunostaining as described above; the second antibody is conjugated to HRP (e.g. cat. No. Amersham)
Diaminobenzidine staining kit (e.g. cat. No. SK-4100, Vector Laboratories) 0.05% osmium tetroxide in water (diluted from 4% concentrate)

Procedure
Fix sample with mild formaldehyde procedure, stain with first antibody as described above.
Incubate with secondary antibody, anti-mouse peroxidase (1:100 dilution, 1 h).
Wash 5 times with PBS.
Wash 3 times with distilled water.

Perform DAB staining (Vector laboratories, cat no. SK-4100) according to the kit protocol
Wash with water ×3
Incubate with 0.05% Osmium tetroxide for 1 min.
Wash 5 times with distilled water, retain in water until imaging.

6. Specific Labeling Without Fixation (Limited to Extracellular Molecules or Structures).

It is often possible to specifically label surface proteins or structures without fixation using the above procedure, assuming the targeted surface proteins or structures do not redistribute or internalize into the cell while the procedure is being carried out. Performing the incubations at 0°–4° C. may inhibit the target redistribution or internalization processes. Incubation times may then have to be increased accordingly.

7. Imaging

After sample preparation is complete, and the sample is disposed within the sample container, the sample container is sealed, for example by engaging a bottom and a part of the container, and is placed on a sample stage in an SEM. Imaging is done either at high vacuum or at "low vacuum" modes, as the degree of vacuum outside the sample container does not substantially affect the imaging or the stability of the samples. However, as a precaution, the SEM imaging may be perform at low vacuum conditions to prevent possible contamination of the microscope in the rare cases in which the partition membrane is ruptured.

Imaging is done with an electron beam, generally set from 10 to 30 KeV. Imaging parameters (beam energy, current, spot size, scan rate, contrast and brightness settings, etc.) are used that are optimal for the sample, as determined by a skilled SEM operator.

Alternatively, the sample may be fixed, stained and/or specifically labeled before introduction into the sample container. This option is implicitly depicted in the leftmost arrow in FIG. 88, whereby a sample thus treated is also considered a "sample". Such treatment of the sample prior to introduction into the sample container may be applicable in particular for tissue samples, for which treatments are difficult to perform after introduction into the sample container, but also for cellular or other liquid samples.

The following protocols exemplifies preparation and immunostaining of non-adherent cellular samples prior to introduction into the sample container and onto the partition membrane.

The present invention provides methods for imaging thick solid samples. SEM inspection of such samples according to the methods of the present invention minimally entails placing the surface of the sample to be imaged in close contact with an partition membrane of the sample container of the present invention, sealing the sample container, placing the sample container in a scanning electron microscope, and scanning the sample with an electron beam.

Preferably, the imaged surface of the sample should be such that can be made to contact the partition membrane over a substantial area In practice, this means that the imaged surface should be generally flat, or of moderate curvature or irregularity, either before the sample is placed in the sample container, or after application of pressure to abut the sample against the partition membrane.

A solid sample may have such a surface, for example a natural edge of a tissue or organ, or an epithelial layer that lines a tissue. In other cases, for example when internal regions of a solid tissue are to be visualized, the image surface is generated by cutting the sample. This cutting can be achieved manually with a scalpel or razor blade; using razor blades supported by supporting spacers that provide better control of the flatness and position of the cut surface. Such supporting spacers are exemplified in FIGS. 86A–87B. Alternatively, mechanized devices such as a Vibratome® or a tissue slicer (EMS Sciences) can be used to generate flat, undamaged surfaces from a wide variety of samples. Note that preparation of solid samples for the methods of the present invention is different from most other imaging modes, in that a thin section is not required. Thin sectioning (to slices of several microns for LM, or less than 0.1 micron for TEM) requires that the sample be hardened, which is achieved either by embedding in solid media such as paraffin and epoxy resins, or by rapid freezing and sectioning at low temperatures. In most aspects of the present invention, such hardening measures are not required, obviating the need for dehydration or freezing and shortening sample preparation times.

If the sample is larger that the size of the internal volume of the sample container, some additional trimming of the sample (on sides other than the imaged surface) may be performed. As a non-limiting example, a sample container may have internal volume shaped as a cylinder with diameter of 3 mm and height of 3 mm, and solid samples must be segmented or trimmed to these dimensions or less to be introduced in the sample container. Sample containers of various sizes and shapes may be used if imaging larger, continuous samples is desired.

As described for cellular samples in the preceding protocols, the methods of the present invention provide for SEM inspection of solid, thick samples without any treatment other than the (optional) cutting and trimming; contrast due to material distribution in such untreated samples may reveal significant information Optionally, the samples may be fixed to preserve structural features and to allow some staining procedures that depend on prior fixation. Optionally, the samples may be stained using methods known in the art to enhance contrast and to allow identification and quantification of structural components. Three protocols described below exemplify protocols used in tissue imaging.

Imaging of Untreated Heart Tissue.

Materials:
PBS

Procedure:
Obtain heart of experimental animal (e.g. from a mouse sacrificed by asphyxiation). Maintain in PBS on ice until ready for processing (preferably less than 1 hour). Cut with scalpel a tissue fragment no larger than 2 mm in any dimension. Place in a sample container of such as described in FIGS. 31A–50 with the desired surface facing the partition membrane. Seal the container while applying pressure by the sample positioner 1128 of FIG. 30A, as shown for example in FIGS. 36A–36C. Examine in a SEM, as shown for example in FIGS. 37 and 3940.

Fixation with Formaldehyde by Immersion

Materials:
PBS
Concentrated formaldehyde solution (16% or 37%): preferably prepared from paraformaldehyde and used either fresh or preserved frozen in tightly sealed aliquots. Alternatively, formalin solutions of similar concentrations may be used, although generally of lesser purity.
Working formaldehyde solution: 4% formaldehyde in PBS (freshly diluted).

Procedure:

Obtain tissue from animal or human source. Wash briefly with PBS to remove excess blood.

Cut tissue to pieces of thickness of no more than 2 mm (in one dimension), Place in a large volume (at least 20 fold, v/w) of formaldehyde working solution.

Fix for at least one hour.

Store in fresh formaldehyde working solution.

Process for imaging as described above or proceed to staining.

Fixation by Vascular Perfusion.

Materials:
Flushing Solution
    1 ml Heparin solution (1000 units/ml)
    1 ml Sodium nitrite
    1000 ml deionized water
    8.5 g Sodium chloride
    Adjust pH to 7.2–7.4
Perfusion solution (McDowell's and Trump's 4F:1G fixative)
    Add the following sequentially with stirring:
    71 ml distilled water
    25 ml 16% PFA (EM grade)
    4 ml 25% glutaraldehyde (EM grade)
    1.16 g $NaH_2PO_4.H_2O$
    ~0.27 g NaOH (check pH and adjust to 7.2–7.4 with 1N NaOH)
PBS Procedure:

Anesthetize a rat

Dissect to reveal the heart Insert a needle to the left ventricle. Puncture the right atrium to allow fluid expulsion.

Perfuse the animal with at least 250 ml of flushing solution pre-warmed to 37° C., until the liver is homogenously pale.

Perfuse with 250 ml of perfusion solution pre-warmed to 37° C.

Dissect animal, remove organs or tissues of interest (e.g. kidney). Dissect the organs further, if required, and store fragments in perfusion solution at 4° C.

Uranyl Acetate Staining of Fixed Tissues.

Staining solutions permeate samples by diffusion, so best staining in reasonable times is achieved close to the surface. It is, therefore, preferable to expose the surface to be imaged directly to the staining solutions: if this surface is not the original edge of the sample, then it is preferable to cut the tissue and expose the desired internal surface.

Materials:
Fixative solution (e.g. formaldehyde working solution or Trump's fixative)
PBS
Water
1% tannic acid solution
0.1% uranyl acetate solution (diluted freshly from 5% w/v stock, pH 3.5).

Procedure:

Fix the tissue by immersion or vascular perfusion.

Cut tissue to fragments of desired size, expose surfaces to be imaged.

Wash extensively in water to remove all fixative and phosphate ions.

Incubate in 1% tannic acid for 5 minutes.

Wash 3 times in water, 5 minutes each wash.

Immerse in uranyl acetate solution for 10 minutes.

Wash 5 times in water.

Immunostaining of Tissues.

Materials:
Fixative: 4% paraformaldehyde in PBS
PBS
Blocking solution: PBS including 1% BSA, pH 8.2
1° antibody
Wash solution
2° antibody/gold
silver enhancement kit Procedure:

mix, fix, block, blotch, wash, watch.

EXAMPLES OF THE PRESENT INVENTION

The following examples of the present invention are given as illustrations and are not meant to limit the invention to the specific examples herein disclosed. Those skilled in the art will appreciate that the methods herein disclosed may be modified or adapted to the particulars of additional samples not described herein.

Figure 89:
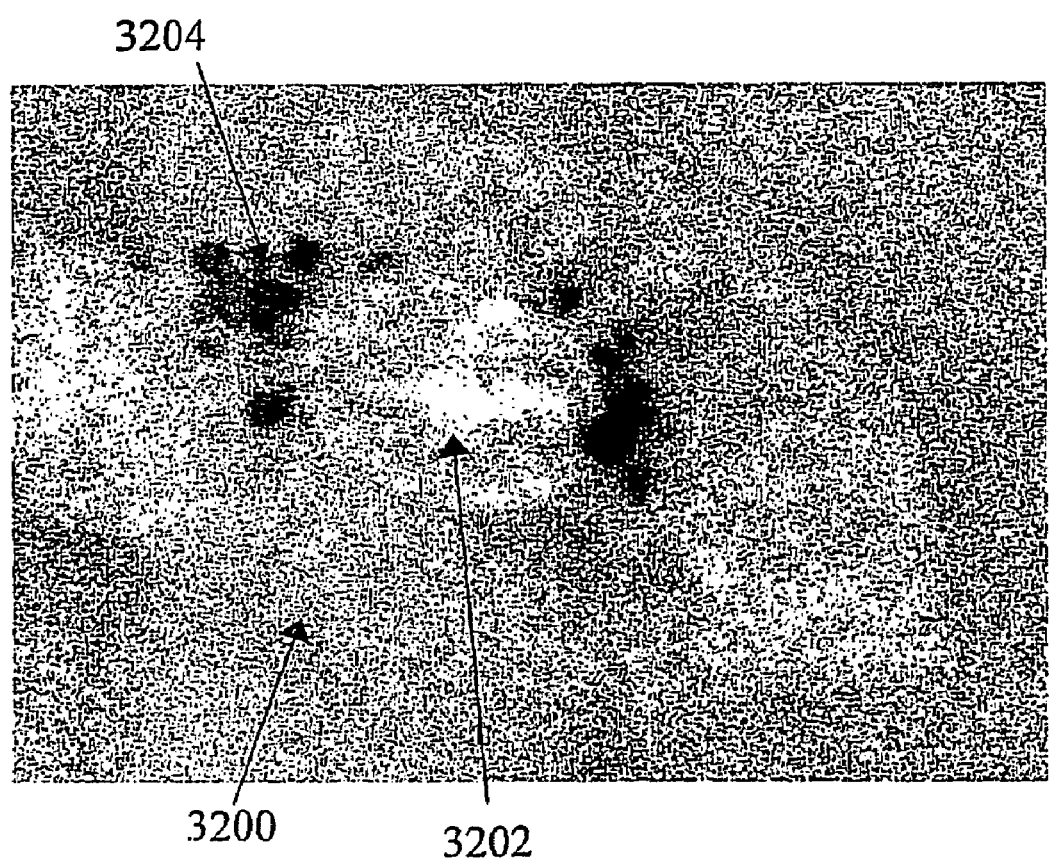
FIG. 89 is a SEM micrograph of a cultured Chinese Hamster Ovary (CHO) cell prepared and imaged in accordance with a preferred embodiment of the present invention.

Reference is now made to FIG. 89, which shows a SEM micrograph of a cultured Chinese Hamster Ovary (CHO) cell. A sample container, such as the container shown in FIGS. 11A–20, is treated with a solution of fibronectin, then washed with phosphate-buffered saline (PBS) and CHO cells are plated in normal growth medium (DMEM supplemented with 10% fetal bovine serum). During overnight incubation the cells adhere to the electron permeable, fluid impermeable membrane 210, and spread on the membrane. The sample container is then sealed and placed in a SEM. Although the interior of the SEM is evacuated and maintained in a vacuum, the fluid inside the sample container is fully retained and the cells remain in a medium that maintains its composition. The SEM micrograph thus obtained exemplifies that material contrast due to constituents of the cells is sufficient to visualize the outline of the cell 3200 as well as distinguish internal structures in the cell, including the nucleus 3202 and lipid droplets 3204. FIG. 89 further exemplifies that lipid rich structures, such as lipid droplets 3204, can be vividly seem against an aqueous surrounding without addition of extraneous substances, such as stains or fixatives.

Figure 90:
FIGS. 90A and 90B are SEM micrographs of HeLa cells prepared and imaged in accordance with a preferred embodiment of the present invention.
Figure 90:

Reference is now made to FIGS. 90A and 90B, which are SEM micrographs of HeLa cells. A sample container, preferably such as described in FIGS. 11A–20, is treated with a solution of fibronectin, then washed with phosphate-buffered saline (PBS) and HeLa cells are plated in normal growth medium (α-MEM supplemented with 10% fetal bovine serum). During overnight incubation the cells adhere to the partition membrane 210 and spread on the membrane. The medium is then removed by aspiration, preferably as shown in FIG. 17B, and the cells, which remain adhered to the membrane 210, are subjected to uranyl acetate staining, as detailed above.

FIGS. 90A and 90B show a high level of detail, including cell nuclei 3210, nucleoli 3212, actin stress fibers 3214 and cortical actin 3216. FIGS. 90A and 90B exemplify that contrast and resolution can be enhanced, and specific biological structures can be identified, by general contrast-enhancing agents, such as uranyl compounds.

Figure 91:
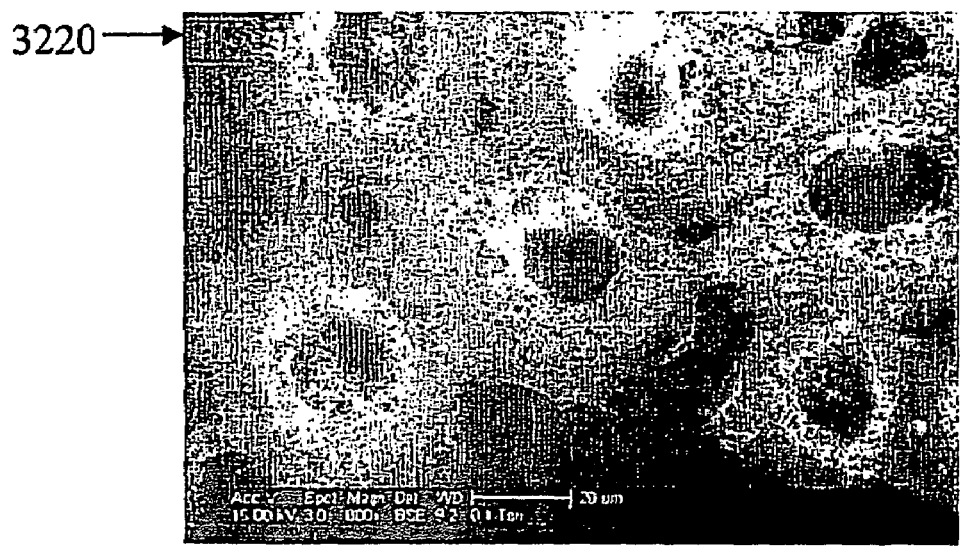
FIGS. 91A and 91B are SEM micrographs, at two different magnifications, of A431 cells prepared and imaged in accordance with a preferred embodiment of the present invention.
Figure 91:
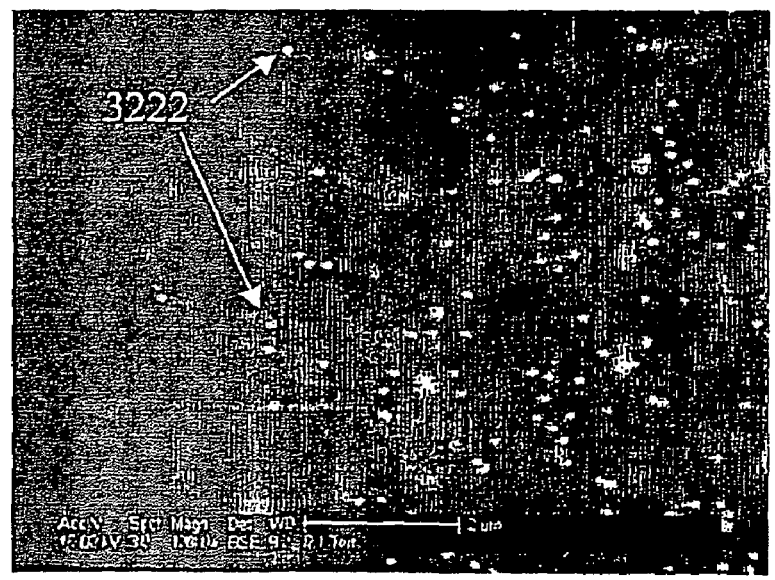

Reference is now made to FIGS. 91A and 91B, which are SEM micrographs of A431 cells, fixed and stained with anti Epidermal Growth Factor Receptor (EGFR) antibody, followed by second antibody linked to 20-nm colloidal gold particles, in accordance with a preferred embodiment of the present invention, at two different magnifications. FIG. 91B depicts a magnified view of the region marked by a dark rectangle 3220 in FIG. 91A. The 20-nm gold particles are visible as bright dots 3222 in FIG. 91B; at the lower magnification employed in FIG. 91A the gold particles are not resolved, but the distribution of the gold colloids is seen as a changes in intensity of electron backscattering.

Figure 92:
FIG. 92 is a SEM micrograph of HeLa cells prepared and imaged in accordance with a preferred embodiment of the present invention.

Reference is now made to FIG. 92, which is a SEM micrograph of HeLa cells transiently transfected with a gene encoding the human interleukin-2 receptor CD25, labeled with anti-CD25 antibodies and imaged in a wet state in accordance with a preferred embodiment of the present invention. HeLa cells, which do not express the CD25 protein, are transfected with a plasmid encoding the human CD25 gene in polystyrene culture dishes using the FUGENE-6 reagent (Cat. No. 1 814 443, Roche Diagnostics, Basel, Switzerland). After two days, the cells are detached from the dish using trypsin and plated in a sample container, preferably such as described in FIGS. 11A–20, with a fibronectin-coated partition membrane 220. After an additional 24 hours of incubation, the cells are fixed with formaldehyde and stained with anti-CD25 antibody followed by secondary antibody linked to 30 nm colloidal gold particles; finally, the sample was treated by silver enhancement.

As known in the art, the transfection procedure results in uptake and expression of the transfected DNA in a fraction of the cell population, whereas other cells do not take up or express any of the transfected gene. This is clearly seen in FIG. 92, where, for example, one cell 3230 whose nucleus 3232 is clearly visible as a bright oval, is heavily stained with the gold-linked antibody, as seen in bright patches 3234, whereas a neighboring cell is not stained by the antibody, its nucleus 3236 being visible due to its inherent material contrast from the cytoplasm. This image exemplifies the excellent signal to noise characteristics achievable with the methods of the present invention.

Figure 93A:
FIGS. 93A, 93B and 93C are SEM micrographs of HeLa cells prepared and imaged in accordance with another preferred embodiment of the present invention.
Figure 93B:
Figure 93C:
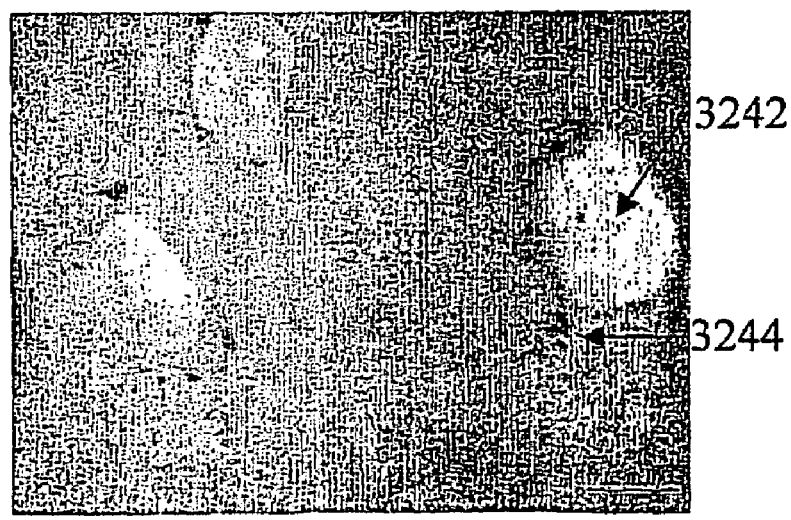

Reference is now made to FIGS. 93A, 93B and 93C, which show SEM micrographs of HeLa cells, permeabilized and labeled with anti-biotin antibodies and imaged in a wet state according to a preferred embodiment of the present invention. Cells grown on fibronectin-coated partition membranes as described in FIG. 90A, are washed 4 times in PBS, then fixed by adding a solution of 4% (w/v) formaldehyde in PBS for 15 minutes. The solution is then removed, the cells are washed 4 times with PBS, and then permeabilized by incubating for 5 minutes with a solution of 0.1% triton X-100 in PBS. The cells are then treated for 30 minutes in a blocking solution: PBS containing 1% bovine serum albumin (BSA) and 5% (v/v) normal goat serum. The cells are then incubated for one hour with anti-biotin antibody in blocking solution, followed by four washes in PBS. The cells are then incubated for 1 hour with secondary antibody linked to 0.8-nm gold colloids, such as catalog number 25371, Electron Microscopy Sciences, Ft. Washington, Pa., USA, in blocking solution, washed 4 times in PBS, then fixed with 2% glutaraldehyde in PBS for 5 minutes. The cells are then washed six times in distilled water, and the subjected to silver enhancement using a commercially available kit (Aurion R-GENT SE-EM). Anti biotin antibodies used in this experiment detect proteins (enzymes) that contain covalently attached biotin moieties; such enzymes are predominantly located in the inner matrix of mitochondria, and are therefore good markers of this organelle (reference: Hollinshead M, et al. 1997). FIGS. 93A and 93B show two different magnifications of HeLa cells labeled as described. FIG. 93C shows a control experiment, identically conducted except that the anti-biotin antibody is omitted. FIGS. 93A–93C clearly demonstrate specific labeling of mitochondria (3240), seen as bright string-like structures. The structures such as nuclei 3242 and lipid droplets 3244 which are seen both in FIG. 93A and in FIG. 93C do not result from specific labeling with the antibody; rather, they result from the natural contrast demonstrated in the discussion of FIG. 89 and from some contribution from general staining with the silver enhancement reagents. Note the significant differences between the method elaborated for FIGS. 93A–93C and that used in FIGS. 91A–92. In FIGS. 93A–93C special steps are taken to allow efficient labeling by the antibodies of molecules within cells: first, the cells are permeabilized with detergent (triton X-100), allowing entry of antibodies. Second, the colloidal gold particles used for visualizing the bound antibodies are very small (0.8 nm), not larger than a typical antibody molecule, allowing facile entry and equilibration of the gold colloids with intracellular sites. Finally, silver enhancement is used to allow visualization of the gold colloids in the SEM. The extent of silver enhancement (which, in effect, enlarges the gold colloids) is controlled so as to maintain the desired resolution.

FIGS. 91A–93C illustrate the capability of the present invention to measure the location and quantity of specific target molecules, by utilizing specific antibodies, or other ligands, with a resolution and precision that far exceed those of light microscopy. The method of the present invention also avoids the lengthy and potentially harmful steps usually associated with sample preparation required to obtain EM images.

Figure 106:
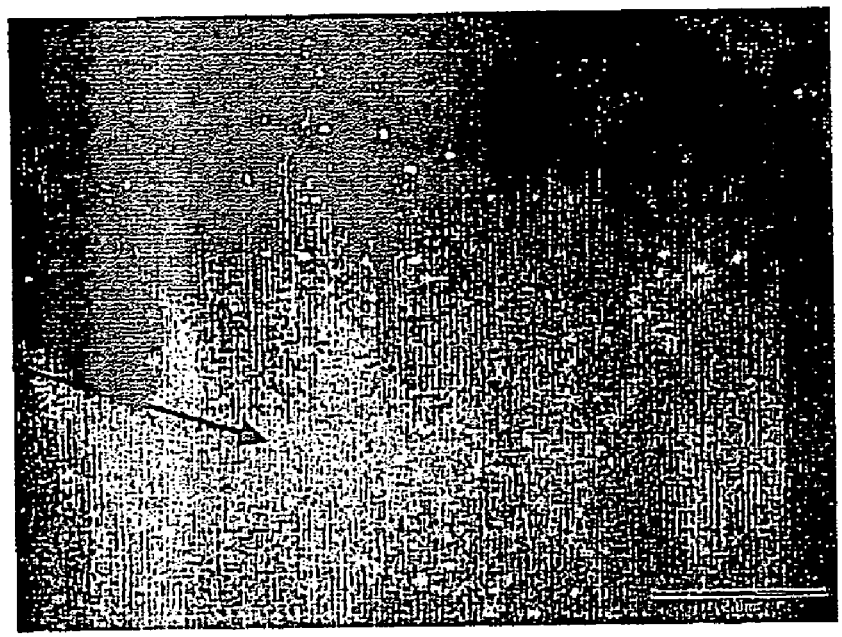
FIGS. 106A and 106B are SEM micrographs of immunolabeled rat kidney prepared and imaged in accordance with yet another preferred embodiment of the present invention.
Figure 106:
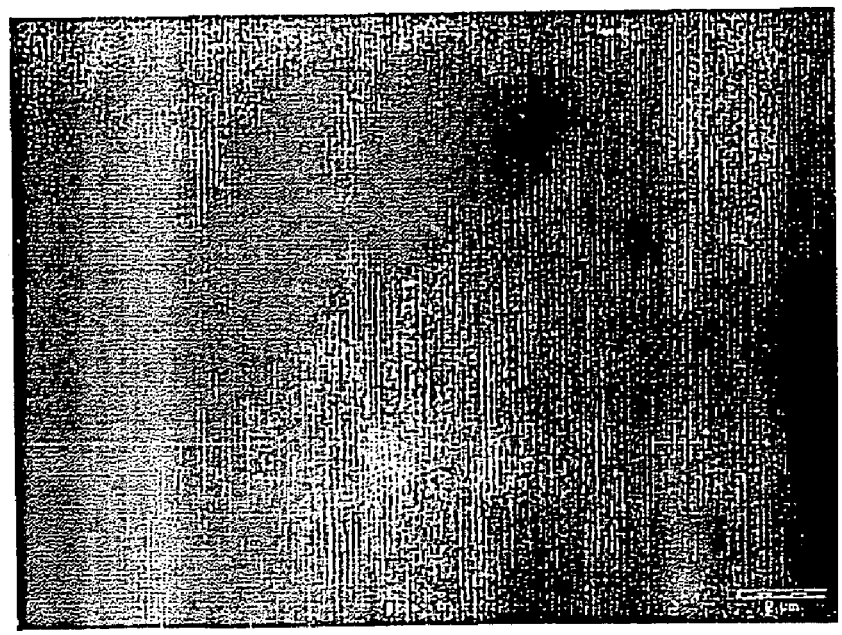

This capability extends to cell surface molecules, to intracellular molecules, and, as shown in FIG. 106 hereinbelow, extracellular structures.

Figure 94:
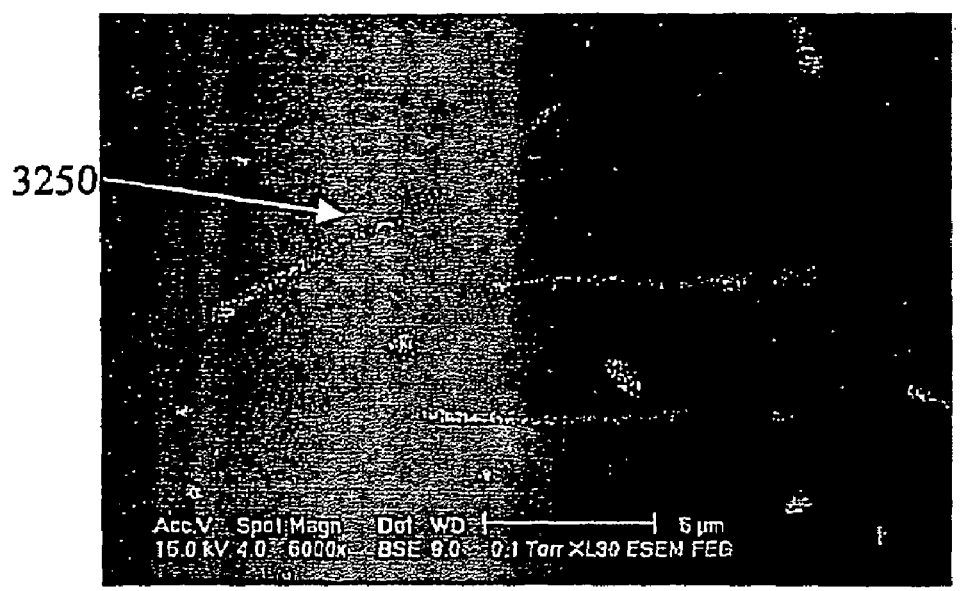
FIGS. 94A and 94B are SEM micrographs of *Escherichia coli* bacteria and *Bacillus subtillis* bacteria, respectively, prepared and imaged in accordance with yet another preferred embodiment of the present invention.
Figure 94:
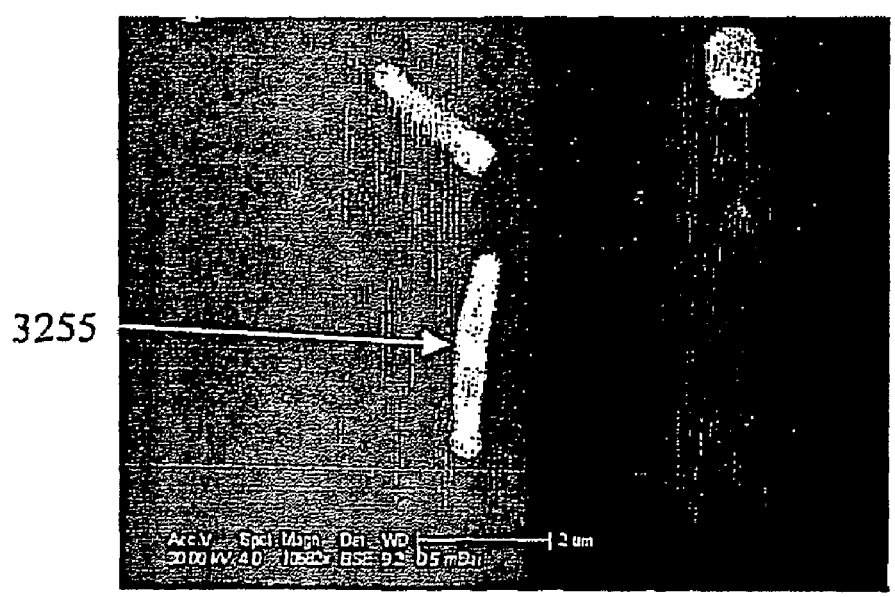

Reference is now made to FIGS. 94A and 94B, which are SEM micrographs of bacteria (*Escherichia coli* and *Bacillus subtillis*, respectively) adhered to a polylysine-coated membrane and imaged in a wet state in accordance with a preferred embodiment of the present invention. Bacterial cells in growth medium (LB, DIFCO) are applied to a sample container, preferably such as described in FIGS. 11A–20, in which partition membrane 210 has been previously coated with poly L-lysine as described. After 30 minutes, the medium was removed and the cells were fixed with 4% formaldehyde in PBS. The cells in FIG. 94A were imaged in a SEM without further treatment, while the cells in FIG. 94B were washed with water and stained with uranyl acetate as described hereinabove, then imaged in a SEM. The Escherichia coli cells 3250 in FIG. 94A are not stained, and the structural details are visible due to natural material contrast, as in FIG. 89. The Bacillus subtillis cells 3255 in FIG. 94B are stained with uranyl acetate, and the contrast derived mostly from the uranyl. FIGS. 94A–94B demonstrate the ability of the method to image microbiological entities, and the general ability to attach cells that are not normally adherent to the electron-permeable partition membrane of the sample container of the present invention.

Figure 95A:
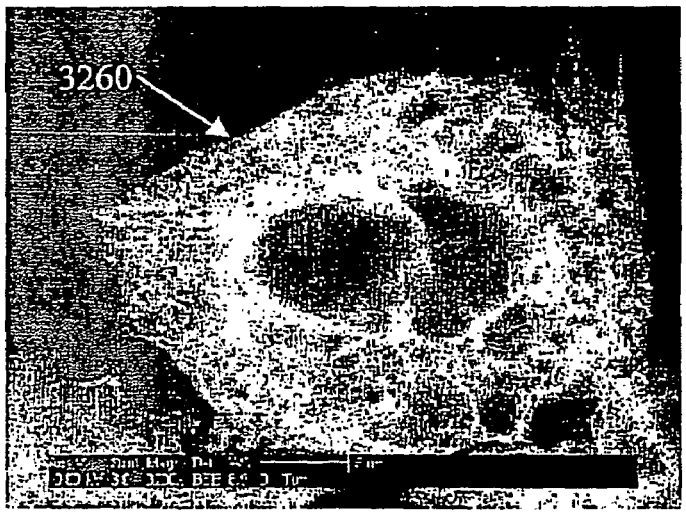
FIGS. 95A, 95B and 95C are SEM micrographs, taken at different energy levels of a scanning electron beam, of a CHO cell prepared and imaged in accordance with still another preferred embodiment of the present invention.
Figure 95B:
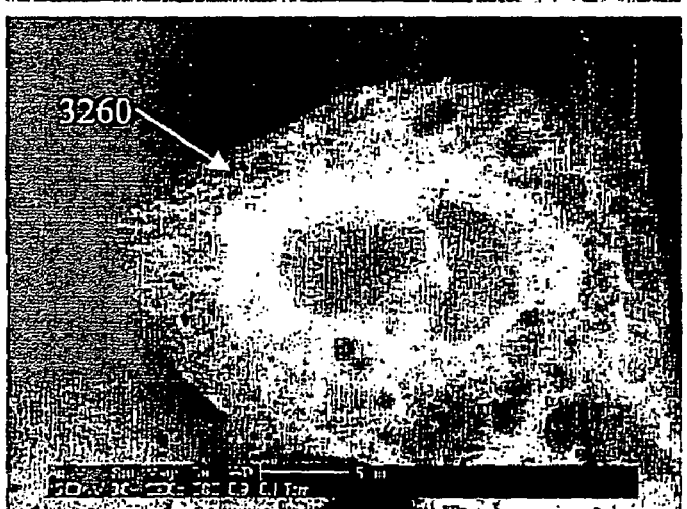
Figure 95C:
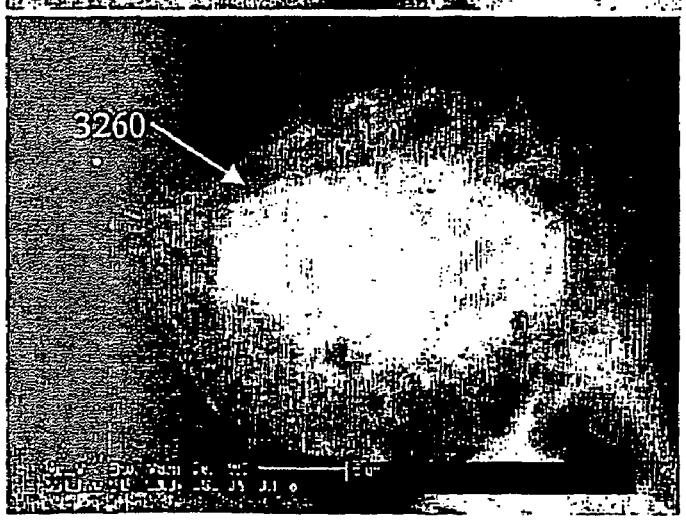

Reference is now made to FIGS. 95A, 95B and 95C, which are SEM micrographs of a CHO cell, fixed and stained with uranyl acetate and imaged in a wet state, preferably as described in FIGS. 11A–20, in accordance with a preferred embodiment of the present invention, at different energies of the scanning electron beam: 12 keV, 15 keV, and 25 keV, respectively. FIG. 95A shows exclusively the layer of the cell 3260 that is closest to the partition membrane 210, which is significantly thinner than the entire thickness of the cell in a direction perpendicular to the partition membrane. FIGS. 95B and 95C include contributions to the image from layers of the cell at progressively larger distances from the partition membrane. FIGS. 95A–95C thus exemplify the ability provided by the methods of the present invention to view "virtual sections" representing different depths of imaging, which may also be the basis for subsequent 3-dimensional reconstruction.

Figure 96A:
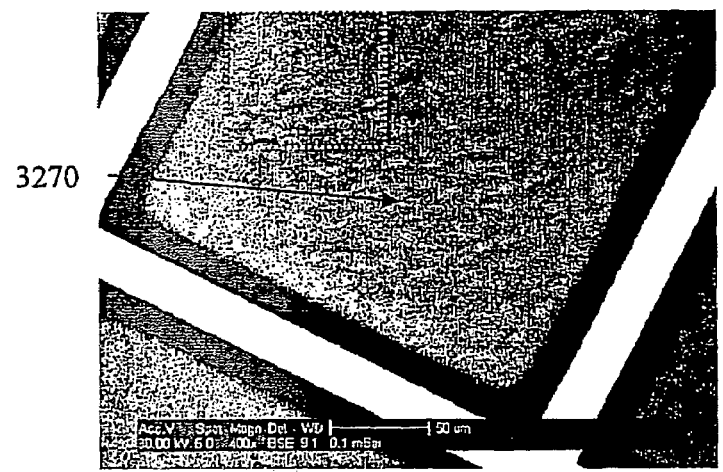
FIGS. 96A and 96B and 96C are SEM micrographs, at three different magnifications, of a fragment of murine heart prepared and imaged in accordance with a preferred embodiment of the present invention.
Figure 96B:
Figure 96C:
Figure 97A:
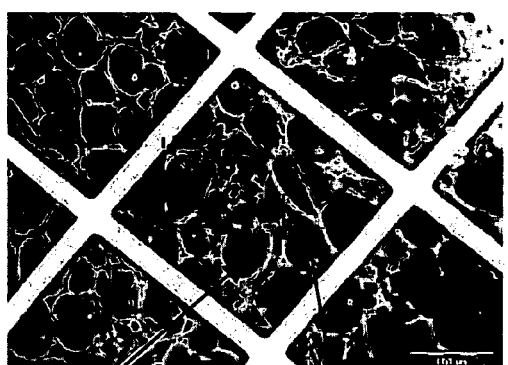
FIGS. 97A, 97B, 97C and 97D are SEM micrographs of a fragment of porcine adipose tissue, prepared and imaged in accordance with another preferred embodiment of the present invention.
Figure 97B:
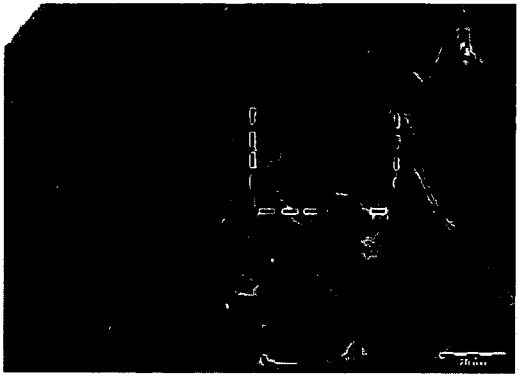
Figure 97C:
Figure 97D:
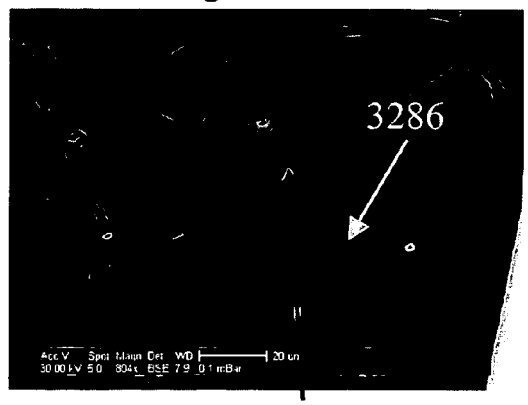

Reference is now made to FIGS. 96A and 96B and 96C, which are SEM micrographs of a fragment of murine heart inserted without treatment into a sample container and imaged in a wet state in accordance with a preferred embodiment of the present invention, preferably according to the description in FIGS. 41A–50, at three different magnifications. Note the general arrangement of cells 3270 seen in at lower magnification in FIGS. 96A–96B, and the intracellular details (nucleus 3272 and the bright organelles 3274, probably mitochondria) seen at higher magnification in FIG. 96C. Membrane supporting grid, shown for example FIGS. 96A–96C demonstrate again the ability provided by methods of the present invention to generate imaging contrast from natural material distribution in the sample, but more importantly, the ability to generate an image in a very short time (5–10 minutes) after obtaining the tissue, which may be a biopsy or a sample taken during surgery.

Reference is now made to FIGS. 97A, 97B, 97C and 97D, which are SEM micrographs of a fragment of porcine adipose tissue, fixed in glutaraldehyde imaged in a wet state without further staining (97A–97C) or following uranyl acetate staining (FIG. 97D) according to a preferred embodiment of the present invention, preferably according to the description of FIGS. 41A–50. Adipocytes (fat cells) are seen as large (50–100 µm) dark ovals 3280. The dark areas are the lipid-rich regions within the adipocytes (winch are large lipid droplets), surrounded by aqueous material 3282 (cytoplasm and nuclei of the cells as well as extracellular material) visible as bright areas surrounding the dark lipid-rich regions. Lipids are lost during most conventional sample preparation procedures, so the methods of the present invention provide unique imaging capabilities for lipids. Natural contrast differentiates well between lipids and other regions in the tissue; further differentiation can be achieved using staining, as in FIG. 97D, where uranyl acetate staining marks the nuclei 3284 and cytoplasm 3286.

Figure 98A:
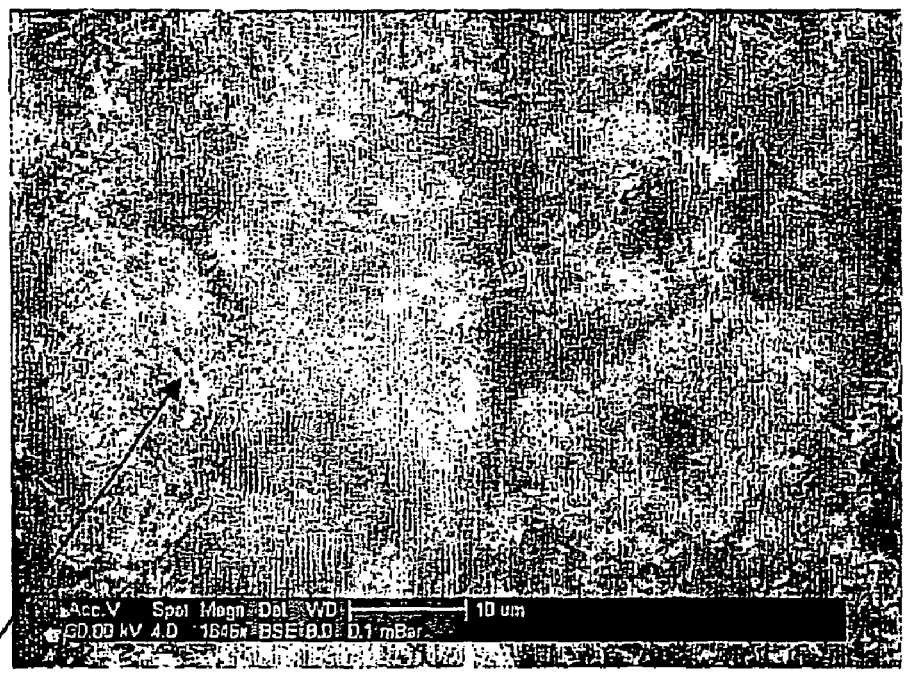
FIGS. 98A and 98B are SEM micrographs at two different magnifications of retinal pigment epithelium (RPE) of a rabbit's eye, prepared and imaged in accordance with yet another preferred embodiment of the present invention.
Figure 98B:

Reference is now made to FIGS. 98A and 98B, which are SEM micrographs at two different magnifications of retinal pigment epithelium (RPE) of a rabbit's eye, fixed with formalin, inserted into an SEM without staining, and imaged in a wet state in accordance with a preferred embodiment of the present invention, preferably according to the description of FIGS. 41A–50. In this unstained sample, the most prominent features seen are melanosomes 3290, which appear as bright cigar-shaped objects. The outline of the epithelium is generally seen in FIG. 98A, as approximately polygonal clusters of melanosomes, which reside in microvilli on the surface of the cells in this epithelial tissue. FIGS. 98A and 98B again demonstrate the natural contrast obtained using methods of the present invention from material distribution in the sample: in this case, the melanosomes (melanin-rich bodies in cells) in the villi of the RPE.

Figure 99A:
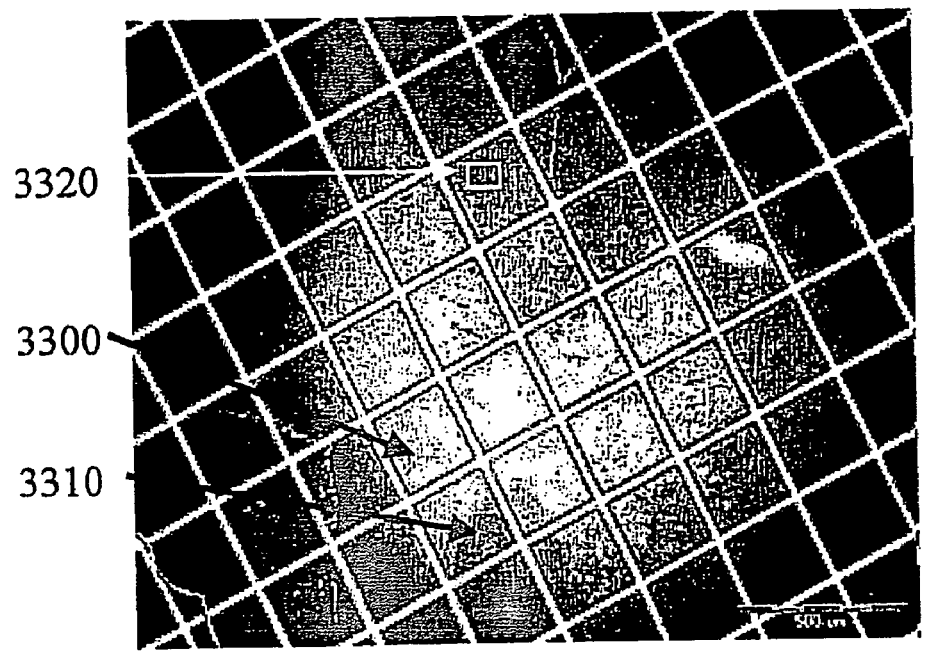
FIGS. 99A and 99B are SEM micrographs at two different magnifications of a spinal chord of a rat, prepared and imaged in accordance with still another preferred embodiment of the present invention.
Figure 99B:

Reference is now made to FIGS. 99A and 99B, which are SEM micrographs at two different magnifications of a spinal chord of a rat, fixed with glutaraldehyde, inserted into an SEM without staining, and imaged in a wet state in accordance with a preferred embodiment of the present invention, preferably according to the description of FIGS. 41A–50. FIG. 99A showing a low-magnification view encompassing the entire cross section of the spinal chord, differentiates brighter areas 3300 and darker areas 3310; the brighter areas are rich in cells bodies of neurons and glial cells, whereas the darker areas are rich in myelinated nerve fibers and are distinguished from the brighter areas due to the higher lipid content. This is apparent in more detail in FIG. 99B, which is a higher magnification of a region shown in rectangle 3320 in FIG. 99A. Here the axons are seen as bright areas 3330 surrounded by dark, lipid-rich myelin sheath 3340. FIGS. 99A and 99B exemplify again the capability provided by methods of the present invention to resolve different components in unstained samples based on contrast derived from material differences between the components. Furthermore, the unique image of neural tissues, which generally include a juxtaposition of lipid-rich and aqueous phases, may yield important capabilities in research, diagnosis and treatment of neural disorders including demyelination, trauma and regeneration, inflammation and cancer.

Figure 100A:
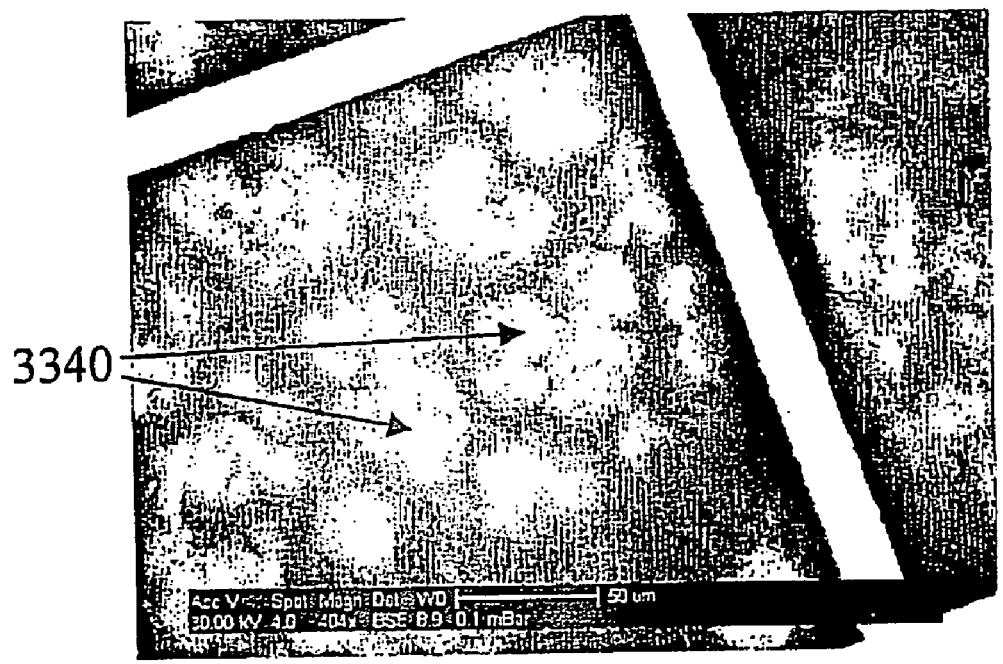
FIGS. 100A and 100B are SEM micrographs, at different energy levels of the scanning electron beam of a fragment of murine pancreas, prepared and imaged in accordance with a preferred embodiment of the present invention.
Figure 100B:
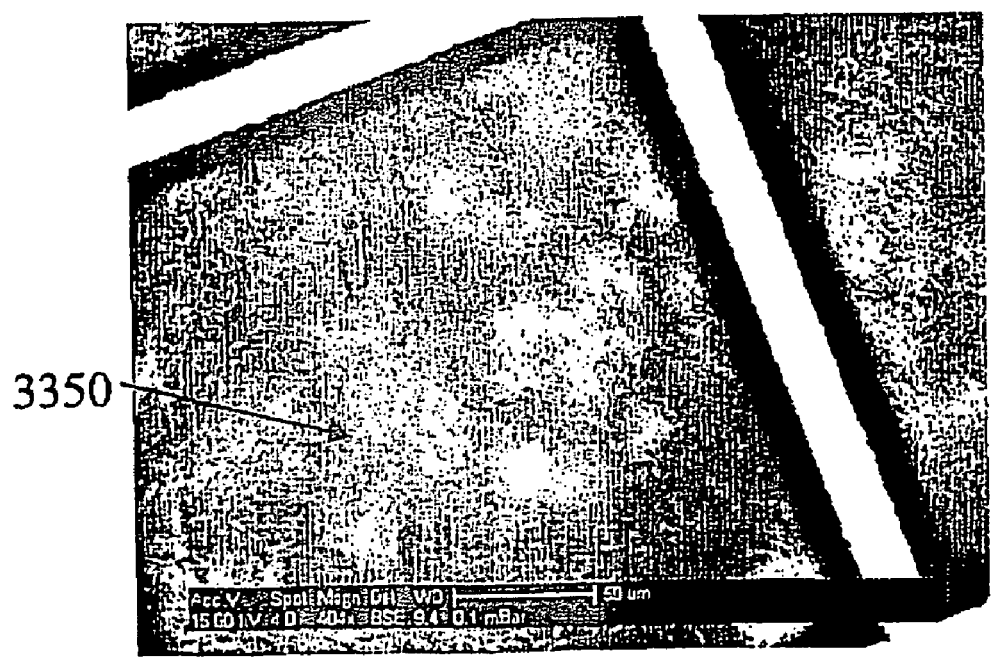

Reference is now made to FIGS. 100A and 100B, which are SEM micrographs of a fragment of murine pancreas, fixed with formaldehyde, stained with uranyl acetate and imaged in a wet state at different energies of the scanning electron beam in accordance with a preferred embodiment of the present invention, preferably according to the description of FIGS. 41A–50. FIG. 100A, which is a micrograph taken at an electron beam energy of 30 kV, shows the organization of several acini 3340 of the exocrine pancreas; the edges of the cells are generally visible. FIG. 100B, taken at an electron beam energy of 15 kV, shows only fibers of the extracellular matrix 3350 laying close to the partition membrane (1210 of FIG. 41), due to the more limited penetration of the lower-energy electrons. FIGS. 100A–100B demonstrate the ability provided by methods of the present invention for obtaining three-dimensional information of a sample imaged in a wet state; furthermore, FIG. 100B demonstrates the ability to image structures of the extracellular matrix in the wet state.

Figure 101:
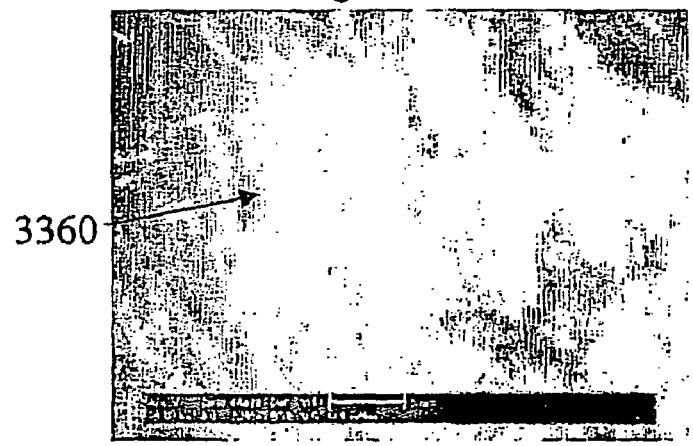
FIGS. 101A, 101B and 101C are SEM micrographs of fragments of murine pancreas, rat tail, and mouse duodenum, respectively, prepared and imaged in accordance with another preferred embodiment of the present invention.
Figure 101:
Figure 101:
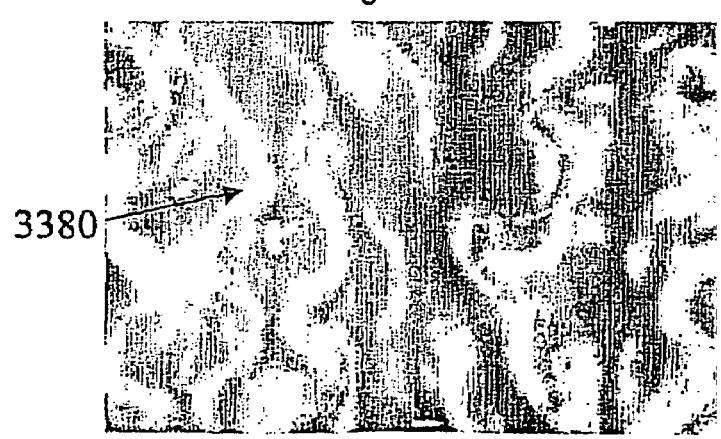

Reference is now made to FIGS. 101A, 101B and 101C, which are SEM micrographs of fragments of murine pancreas, rat tail, and mouse duodenum, respectively, fixed with formaldehyde, stained with uranyl acetate and imaged in a wet state, in accordance with a preferred embodiment of the present invention, preferably according to the description of FIGS. 41A–50. The images in FIGS. 101A, 101B and 101C, as well as in FIG. 10B, show fibers of the extracellular matrix (ECM) of pancreas (3360), tail (3370) and duodenum (3380). The methods of the present invention thus provide a unique view of the ECM, which is radically different in structure in different tissues and pathological states; this structure is probably destroyed when samples are dehydrated or frozen, as commonly done for other methods for microscopic examination.

Figure 102A:
FIGS. 102A, 102B, 102C and 102D are SEM micrographs of fragments of murine kidney, prepared and imaged in accordance with yet another preferred embodiment of the present invention.
Figure 102B:
Figure 102C:
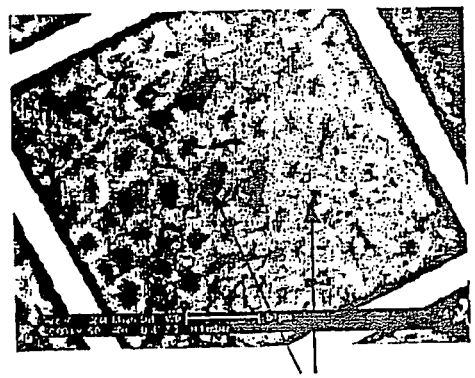
Figure 102D:

Reference is now made to FIGS. 102A, 102B, 102C and 102D, which are SEM micrographs of fragments of murine kidney, fixed by vascular perfusion, stained with uranyl acetate and imaged in a wet state, in accordance with a preferred embodiment of the present invention, preferably according to the description of FIGS. 41A–50. FIG. 102A, taken from the cortex, shows part of a glomerulus, and FIG. 102B is an image of the same at higher magnification. Clearly visible are cell nuclei 3390 and basement membrane 3392. FIG. 102C is a micrograph of a region of the medulla, and FIG. 102D is a higher magnification of the same. Here, renal tubules 3394 are seen, as well as epithelial cells 3396 and basement membrane 3398. FIGS. 102A–102D demonstrate a general capability provided by methods of the present invention to obtain images at high magnification and resolution of tissue fragments without drying, freezing, embedding or thin sectioning, yielding detailed view of features of medical and diagnostic significance, such as the glomerular and tubular basement membranes of the kidney.

Figure 103:
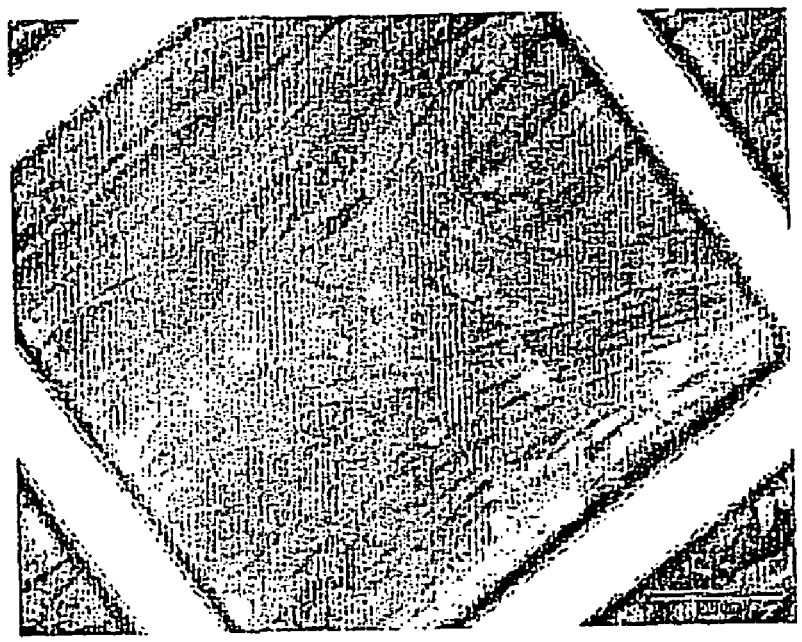
FIGS. 103A and 103B are SEM micrographs, at two different magnifications, of rat cardiac muscle, prepared and imaged in accordance with still another preferred embodiment of the present invention.
Figure 103:
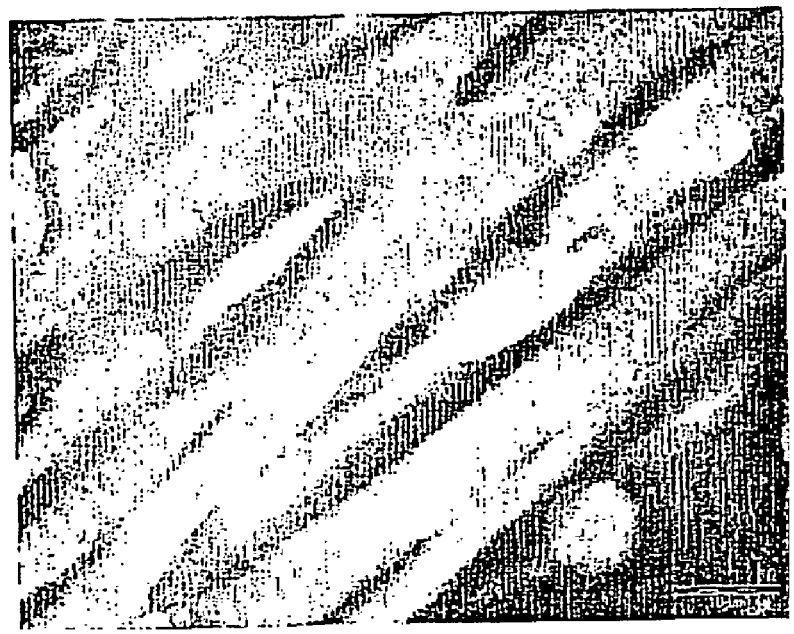

Reference is now made to FIGS. 103A and 103B, which are SEM micrographs of rat cardiac muscle, fixed in formaldehyde, stained with uranyl acetate and imaged in a wet state at two different magnifications, in accordance with a preferred embodiment of the present invention, preferably according to the description of FIGS. 41A–50. The cellular organization of the tissue is clearly seen in FIG. 103A; the higher magnification used in FIG. 103B reveals subcellular features such as the striated structure of the cardiac muscle cells. FIGS. 103A–103B further demonstrate the capability provided by methods of the present invention to image a variety of structures at high resolution; the particular ability to image cardiac and other striated muscles may be useful in research, diagnosis and treatment for abnormalities of heart and skeletal muscles, including cardiac myopathies and myodegenerative diseases.

Figure 104:
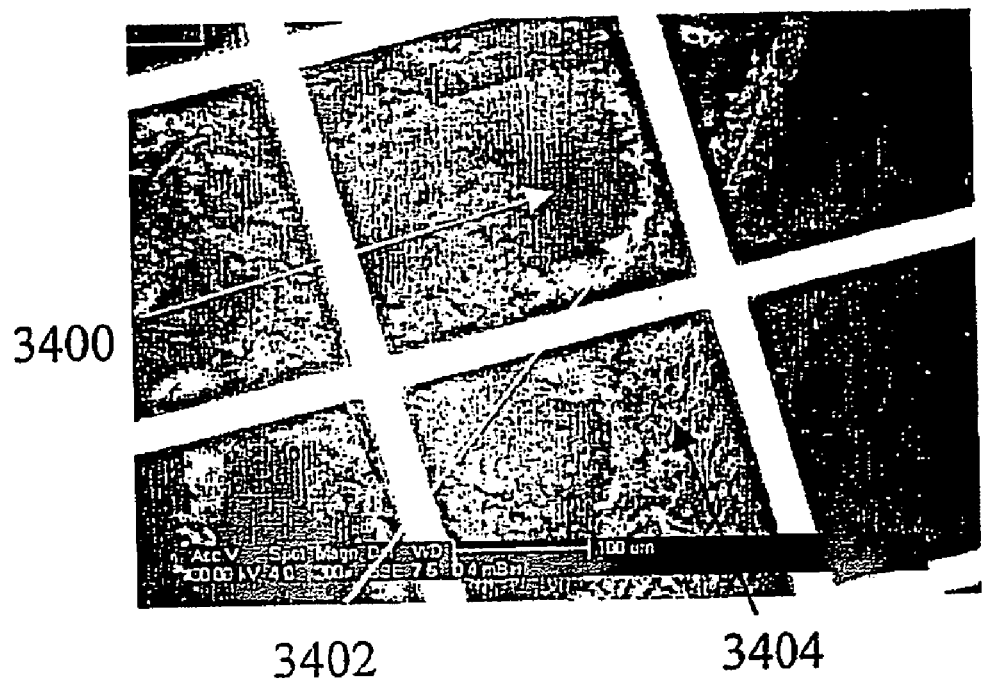
FIGS. 104A and 104B are SEM micrographs, at two different magnifications, of human thyroid, prepared and imaged in accordance with a preferred embodiment of the present invention.
Figure 104:

Reference is now made to FIGS. 104A and 104B, which are SEM micrographs at two different magnifications of human thyroid fixed with formaldehyde, stained with uranyl acetate and imaged in a wet state, in accordance with a preferred embodiment of the present invention, preferably according to the description of FIGS. 41A–50. FIG. 104A shows the lumen of thyroid follicles 3400, surrounded by an epithelium of follicular cells 3402 and a region of connective tissue 3404 surrounding the follicles. FIG. 104B shows a higher magnification of a region of a follicle 3400 with follicular cells 3402. The junctions 3406 between the follicular cells are clearly seen as brightly stained thin lines in a nearly polygonal arrangement FIGS. 104A and 104B demonstrate the capability provided by methods of the present invention.

Figure 105:
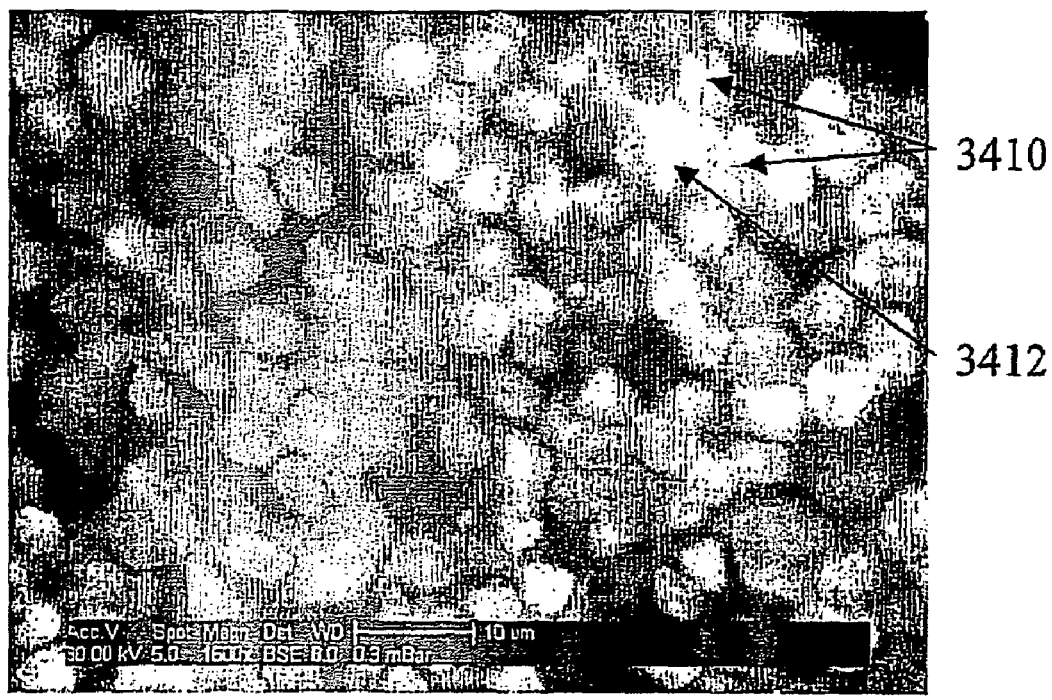
FIG. 105 is a SEM micrograph of rat thymus, prepared and imaged in accordance with another preferred embodiment of the present invention.

Reference is now made to FIG. 105, which is a SEM micrograph of rat thymus, fixed with formaldehyde, stained with uranyl acetate and imaged in a wet state, in accordance with a preferred embodiment of the present invention, preferably according to the description of FIGS. 41A–50. Different cell types are seen (lymphocytes 3410 and macrophages 3412) as is their mutual arrangement. Imaging and identification of hematopoietic cells, such as lymphocytes and macrophages may have utility in research, diagnosis and treatment of various diseases including, but not limited to, inflammatory diseases, autoimmune diseases, atherosclerosis, wound healing and cancer.

Reference is now made to FIGS. 106A and 106B, which are SEM micrographs of immunolabeled rat kidney imaged in a wet state, in accordance with a preferred embodiment of the present invention, preferably according to the description of FIGS. 41A–50. A male rat is treated with D-limonene, leading to accumulation of alpha-2 microglobulin, especially in the cortical tubules of the kidney (Kristiansen and Madsen, 1995). The rat is then sacrificed, the kidneys fixed by vascular perfusion, cut into fragments, and the fragments are treated with anti-alpha-2 microglobulin antibodies followed by secondary antibody linked to 0.8-nm gold colloids, and finally treated by silver enhancement, according to a preferred embodiment of the present invention. FIG. 106A shows an image of a fragment of kidney thus labeled and imaged; FIG. 106B shows another fragment from the same general region of the kidney, identically treated except that the anti-alpha-2 microglobulin antibodies were omitted. The immune label is seen is FIG. 106A as bright spots 3420, representing silver-enhanced gold colloids; such immunolabels are absent in FIG. 106B, demonstrating the specificity of labeling. FIGS. 106A and 106B demonstrate the capability provided by methods of the present invention to label and visualize specific biomolecules at high resolution in wet, unsliced tissue samples. Such capability may be important in research, diagnosis and treatment of diseases.

Figure 107A:
FIGS. 107A and 107B are SEM micrographs, at two different magnifications, of commercial 1.5% fat cow's milk, prepared and imaged in accordance with still another preferred embodiment of the present invention.
Figure 107B:

Reference is now made to FIGS. 107A and 107B, which are SEM micrographs of commercial cow's milk (1.5% fat), inserted directly into a SEM and imaged at two different magnifications in accordance with a preferred embodiment of the present invention, preferably as shown in FIGS. 18A–20. Milk, being an emulsion, comprises lipid droplets in an aqueous medium. FIGS. 107A–107B show lipid droplets 3430 of various sizes as dark areas on a bright background 3432, which is the aqueous medium of milk. FIG. 107B, at higher magnification, shows lipid droplets as small as 120 nm (3434), defining the approximate resolution of the image.

Figure 108:
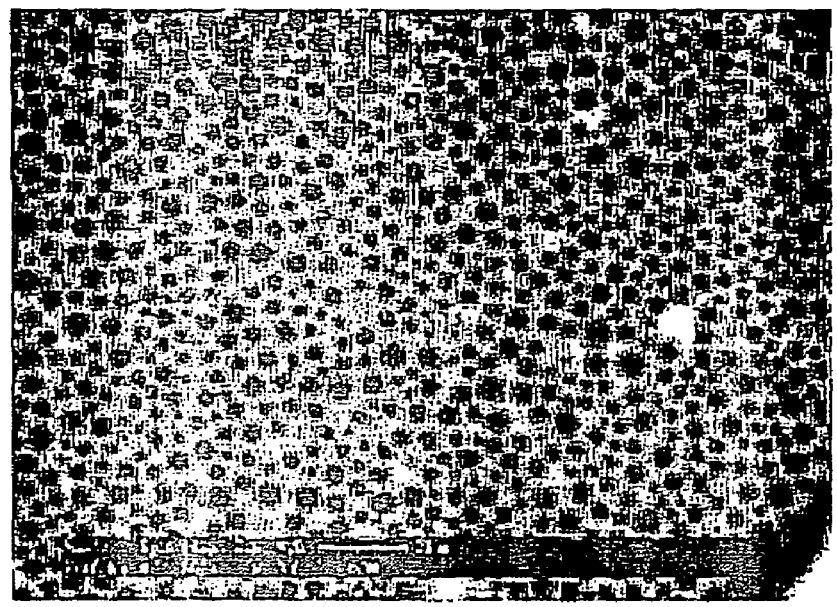
FIGS. 108A and 108B are SEM micrographs, at two different magnifications, of fresh human milk, prepared and imaged in accordance with a preferred embodiment of the present invention.
Figure 108:

Reference is now made to FIGS. 108A and 108B, which are SEM micrographs of fresh human milk inserted directly into a SEM and imaged at two different magnifications in accordance with a preferred embodiment of the present invention, preferably as shown in FIGS. 18A–20. Lipid droplets 3436 are seen as in FIGS. 107A–B as dark spots, with a different overall shape and size distribution than lipid droplets 3432 in FIGS. 107A–107B. FIGS. 107A–108B demonstrate the capability provided by methods of the present invention to image emulsions without any treatment whatsoever in a scanning electron microscope, such capability having uses in research, analysis and quality assurance of various samples including biological fluids, food products, cosmetics, and pharmaceutical preparations.

Figure 109:
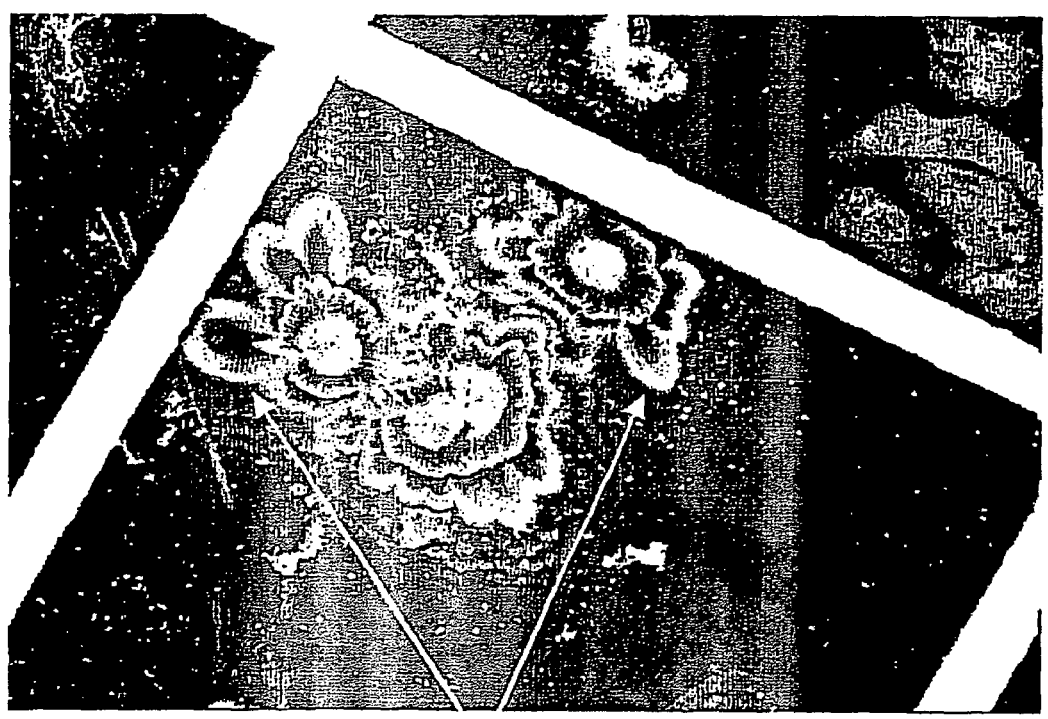
FIG. 109 is a SEM micrograph of crystals of pyroantimonate salts prepared and imaged in accordance with another preferred embodiment of the present invention.

Reference is now made to FIG. 109, which is a SEM micrograph of crystals of pyroantimonate salts formed in a SEM-compatible sample enclosure and imaged in a wet state in accordance with a preferred embodiment of the present invention. HeLa cells are grown in a sample container as described in the reference to FIGS. 90A and 90B. The cells are fixed in a solution of 2% (w/v) potassium pyroantimonate and 4% glutaraldehyde. During incubation, crystals of pyroantimonate are nucleated mostly at the cells, and are visible as multiple ridges 3438. FIG. 109 demonstrates the capability provided by methods of the present invention to image crystallization processes, such capability having uses in research, analysis and quality assurance of various samples including pharmaceutical preparations and other industrial preparations.

Figure 110:
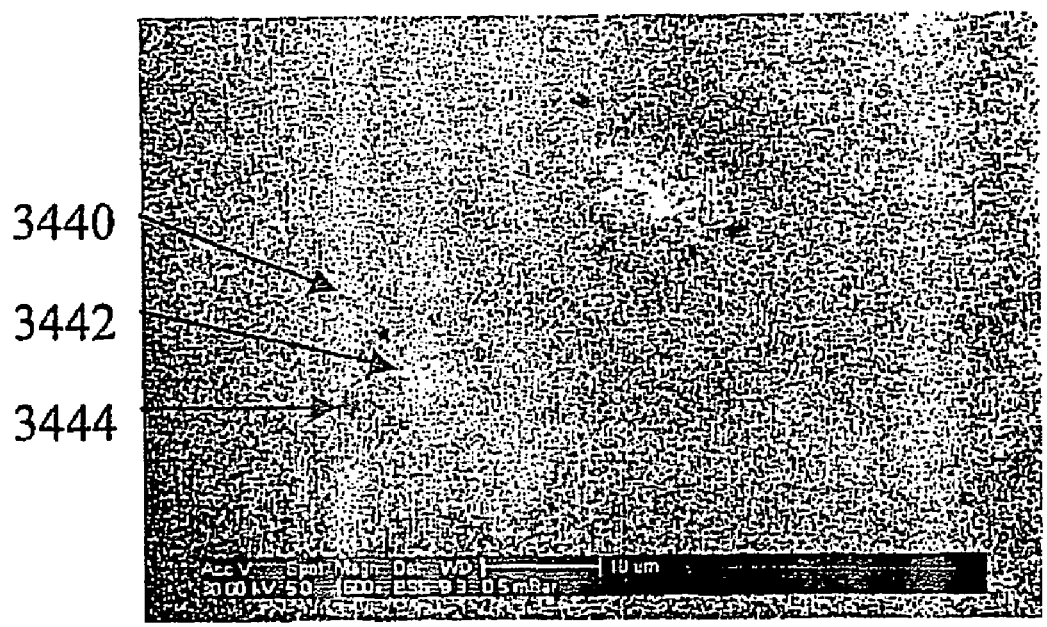
FIGS. 110A and 110B are micrographs of CHO cells obtained by backscattered electron detection and light detection, respectively, in a scanning electron microscope, in accordance with yet another preferred embodiment of the present invention.
Figure 110:
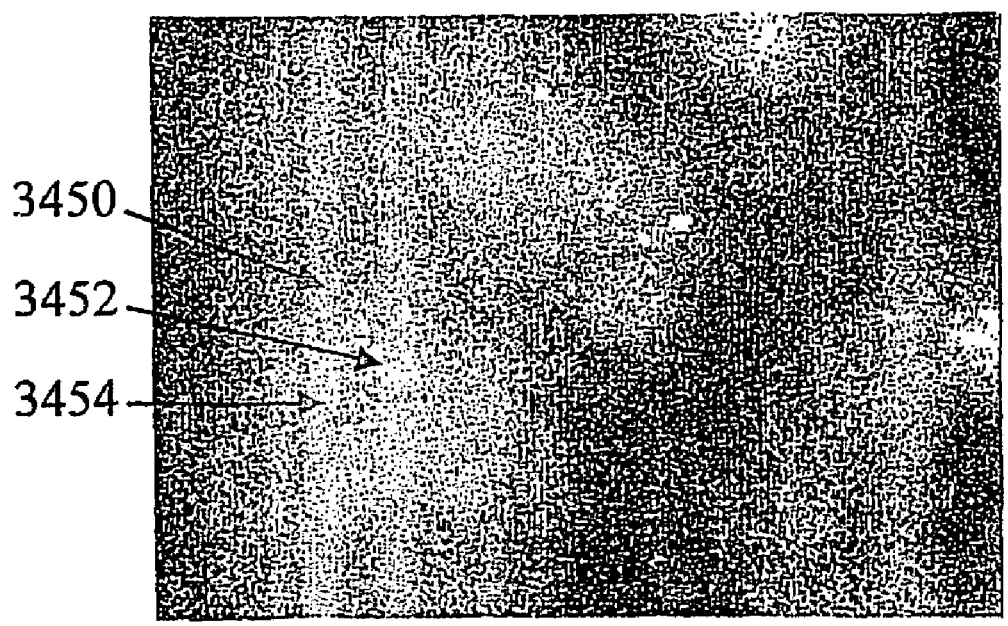

Reference is now made to FIGS. 110A and 110B, which are micrographs of CHO cells obtained by backscattered electron detection and light detection, respectively, in a scanning electron microscope, in accordance with a preferred embodiment of the present invention, preferably according to FIGS. 58A–77. The cells are grown on the partition membrane 2110 and imaged directly without treatments such as fixation or staining. FIG. 110A shows an image generally similar to that seen in FIG. 89, whereby the general outline 3440 of a cell, a bright region 3442 indicating a nucleus, and dark spots 3444 indicating lipid droplets. The contrast in this image is due to material differences reflected in efficiency of electron backscattering. FIG. 110B is an image obtained concurrently, derived from photons emitted from the sample during SEM scanning. In this image, the outline 3450 of the cell, a bright region 3452 indicating the nucleus, and bright spots 3454 indicating lipid droplets. The contrast in FIG. 110B is derived from totally distinct mechanisms than the contrast in FIG. 110A, namely from efficiency of cathodoluminescence. In this case, the cathodoluminescence image may yield unique information on material distribution within the specimen.

Figure 111:
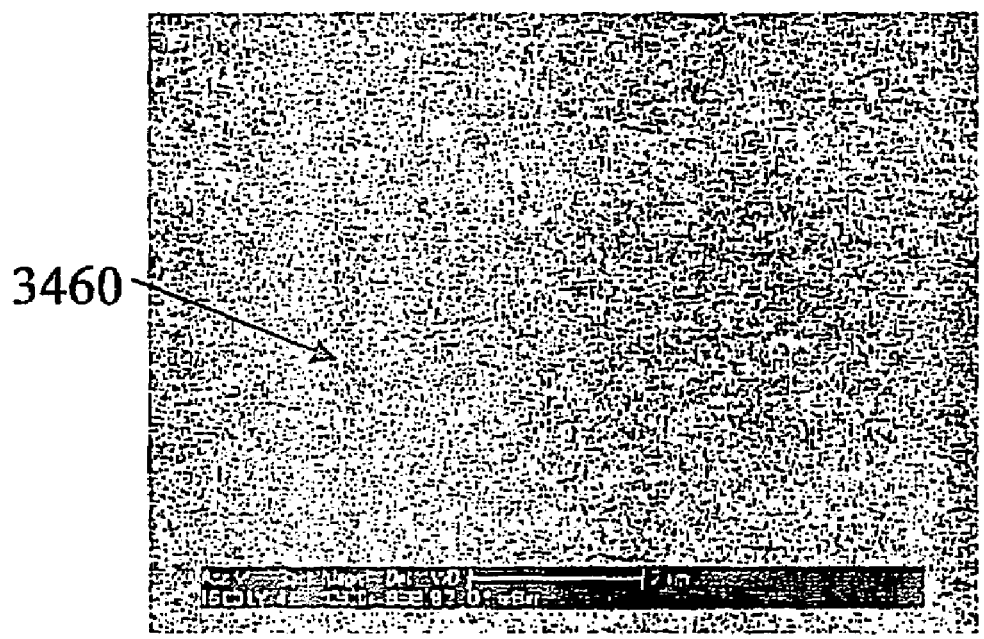
FIGS. 111A and 111B are micrographs of Fluorescent beads obtained by backscattered electron detection and light detection, respectively, in a scanning electron microscope, in accordance with still another preferred embodiment of the present invention.
Figure 111:
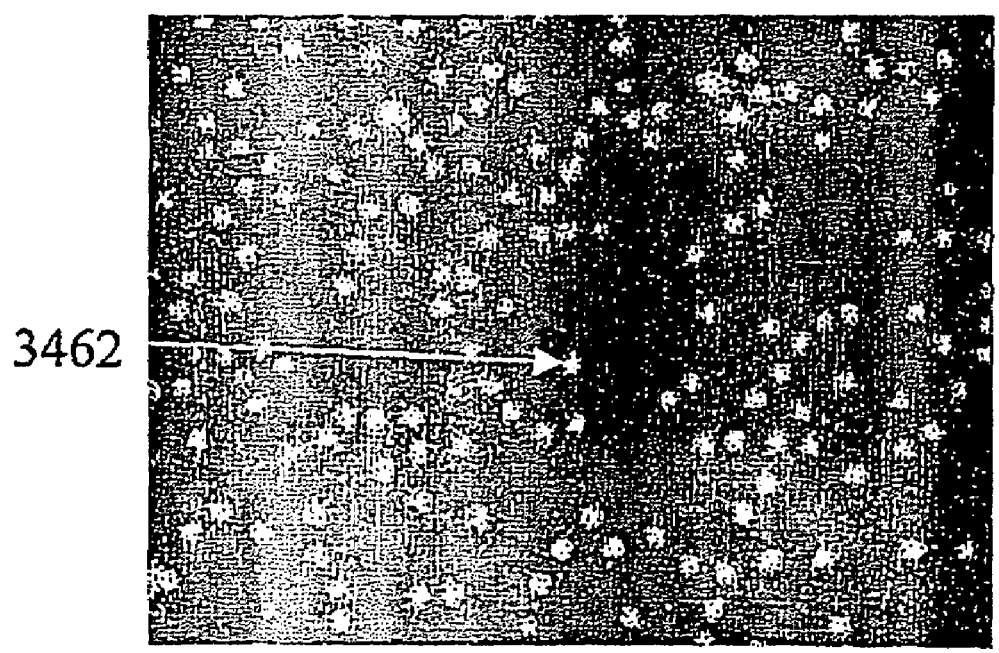

Reference is now made to FIGS. 111A and 111B, which are micrographs of Fluorescent beads of 200 nm diameter (Polystyrene beads with Surf-Green fluorescent dye, from BLI, Indiana, USA) obtained by backscattered electron detection and light detection, respectively, in a scanning electron microscope, in accordance with a preferred embodiment of the present invention, preferably according to FIGS. 58A–77. The beads 3460, which are barely discernable in the backscattered electron image in FIG. 111A, are seen as brightly cathodoluminescent spheres 3462 in FIG. 111B. FIGS. 111A–111B demonstrate the ability provided by methods of the present invention to image light emission at a resolution exceeding that available with light microscopes.

Reference is now made to FIGS. 112A–112B, which depict SEM inspection of samples using X-ray detection in accordance to a preferred embodiment of the present invention. FIG. 112A shows a SEM inspection of an aqueous sample of HeLa cells in water in a sample container such as shown in FIGS. 11A–20, using X-ray spectroscopy. The analysis identifies oxygen 3474 as the major component, with carbon 3472 at a lesser amount; these are the expected results from analysis of cells in water. FIG. 112B shows a similar analysis of a vacuum grease; here carbon 3476, oxygen 3477 and fluorine 3478 are the predominant elements.

Figure 113:
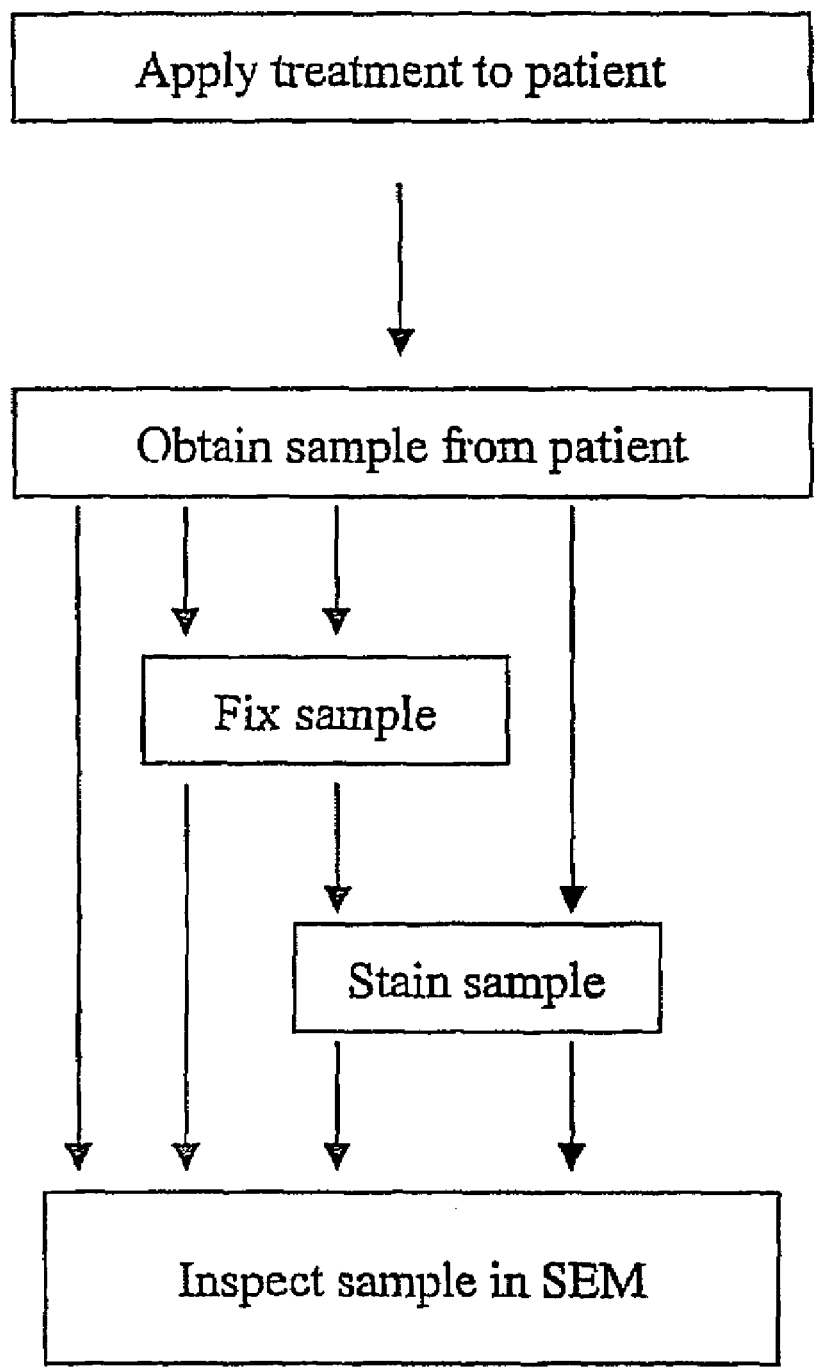
FIG. 113 is a schematic depiction of a method for examining patients in accordance with a preferred embodiment of the present invention.

Reference is now made to FIG. 113, which is a schematic depiction of a method for examining patients in accordance with a preferred embodiment of the present invention. At least one sample is obtained from a patient, which may be optionally subjected to a treatment prior to obtaining the sample. The at least one sample may be obtained by methods known in the art, such as drawing a blood sample, oral swabbing, drawing cerebrospinal fluid, obtaining urine, sputum or feces, lavage, tissue biopsy, surgical dissection, or post-mortem dissection.

The at least one sample is then inspected in a SEM according to the methods of the present invention. Optionally, samples may be inspected without sample preparation steps prior to imaging, or after optional fixation or staining or combination thereof. In another embodiment of the present invention, separate samples from the patient, or separate portions of a sample of the patient, may be prepared for SEM inspection or inspected, each using a different protocol, so as to obtain additional information.

Figure 114:
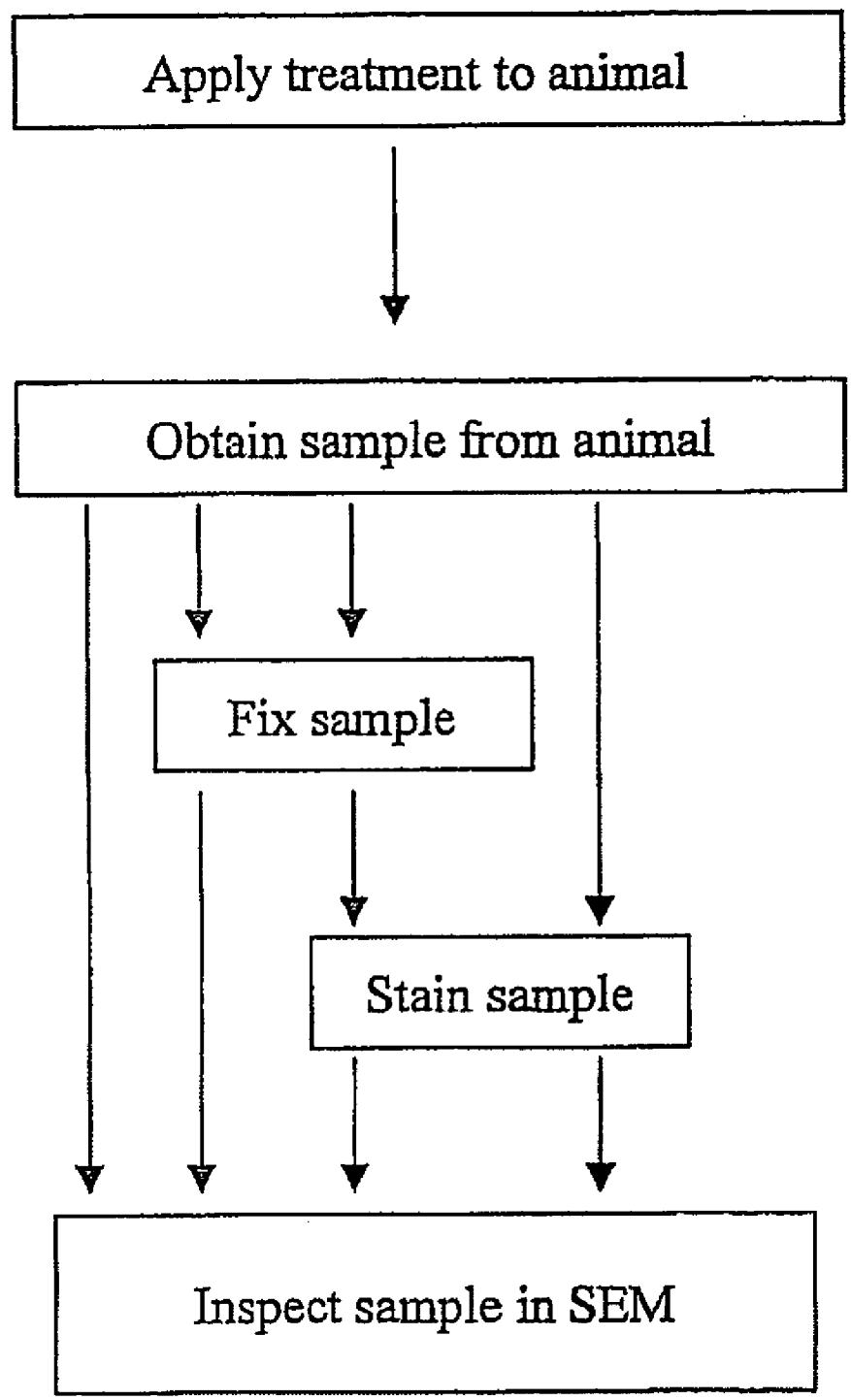
FIG. 114 is a schematic depiction of a method for testing the effects of a treatment on experimental animals in accordance with another preferred embodiment of the present invention.

Reference is now made to FIG. 114, which is a schematic depiction of a method for testing the effects of a treatment on experimental animals. Such testing may be used for example as a step in drug discovery or development, in testing toxicity or suspected toxicity of pharmaceutical, environmental, nutritional or occupational conditions. At least one sample is obtained from at least one animal, which may be optionally subjected to a treatment prior to obtaining the sample. The at least one sample may be obtained by methods known in the art, such as drawing a blood sample, oral swabbing, drawing cerebrospinal fluid, obtaining urine, sputum or feces, lavage, tissue biopsy, or dissection of live or dead animal.

The at least one sample is then inspected in a SEM according to the methods of the present invention Optionally, samples may be inspected without sample preparation steps prior to imaging, or after optional fixation or staining or combination thereof. In another embodiment of the present invention, separate samples from the animal, or separate portions of a sample of the animal, may be prepared for SEM inspection or inspected, each using a different protocol, so as to obtain additional information.

Figure 115:
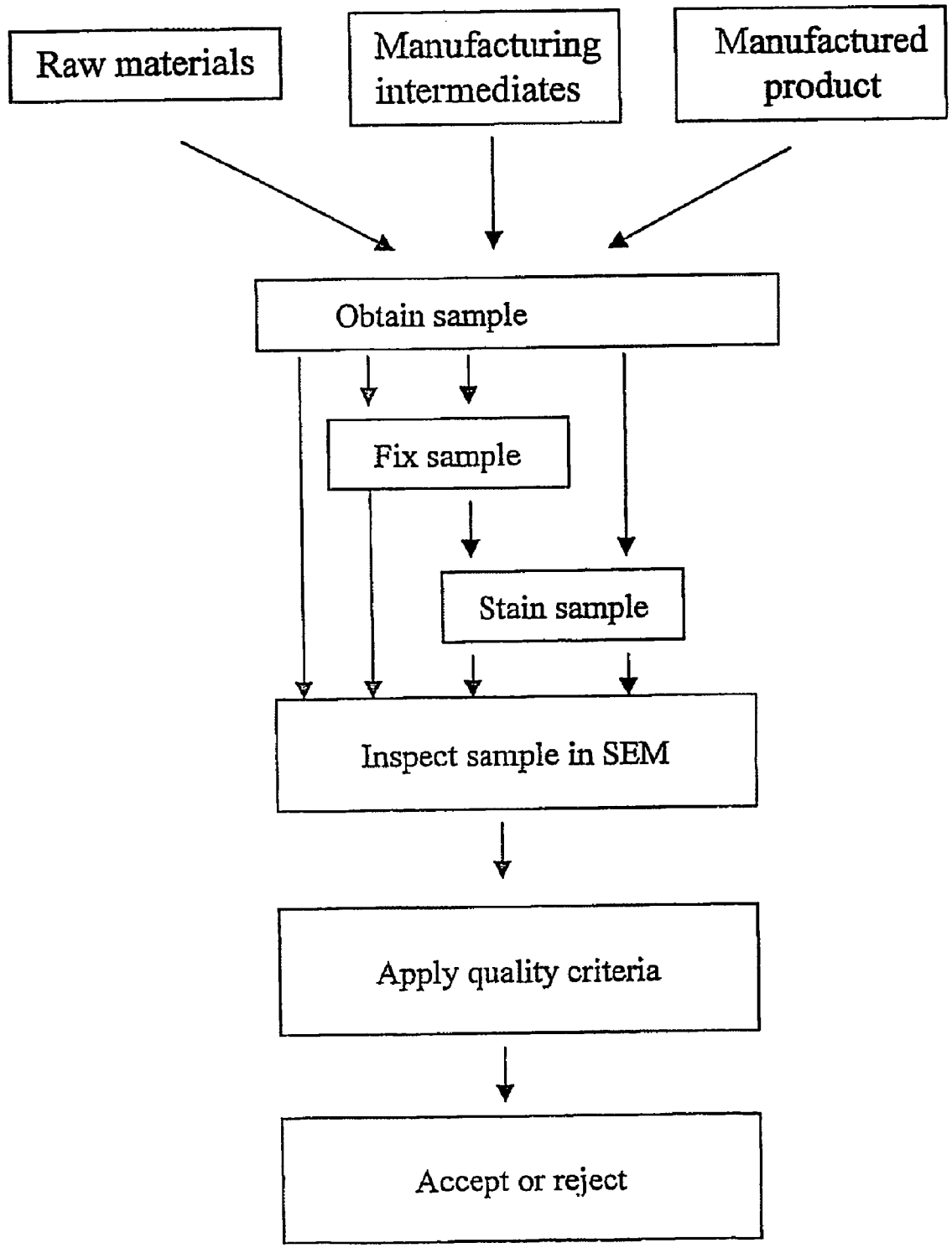
FIG. 115 is a schematic depiction of manufacturing process that includes SEM inspection in accordance with yet another preferred embodiment of the present invention.

Reference is now made to FIG. 115, which is a schematic depiction of manufacturing process that includes SEM inspection in accordance with methods of the present invention. Samples of entities derived from any stage of the manufacturing process may be thus inspected, including raw materials, intermediates of the manufacturing process, and the manufactured product Samples of the entities are obtained and inspected in a SEM according to the methods of the present invention. Optionally, samples may be inspected without sample preparation steps prior to imaging, or after optional fixation or staining or combination thereof. In another embodiment of the present invention, separate samples from the entity, or separate portions of a sample of the entity, may be prepared for SEM inspection or inspected, each using a different protocol, so as to obtain additional information. The results of SEM inspection are then evaluated based on quality criteria, and a decision to accept or reject an individual or a batch of raw materials, intermediates of the manufacturing process, or manufactured product.

Reference is now made to FIG. 116, which is a schematic depiction of a method for bioassaying pharmaceutical entities or suspected or known toxic entities. Cells are introduced into one or more sample enclosures, such as described in any of FIGS. 1A–84, and the pharmaceutical entity or suspected or known toxic entity is applied to the cells. The cells are then inspected in a SEM according to the methods of the present invention. Optionally, cells may be inspected without sample preparation steps prior to imaging, or after optional fixation or staining or combination thereof. In another embodiment of the present invention, cells in separate sample containers may be prepared for SEM inspection or inspected, each using a different protocol, so as to obtain additional information. The results of SEM inspection are then analyzed and the results of the analysis applied to evaluate the effects of the pharmaceutical entity or suspected or known toxic entity.

It will be appreciated by persons skilled in the art that the present invention is not limited by what has been particularly shown and described herein above. Rather the scope of the present invention includes both combinations and sub-combinations of the various features described hereinabove as well as variations and modifications which would occur to persons skilled in the art upon reading the specifications and which are not in the prior art.

The invention claimed is:

1. A SEM compatible sample container comprising:
   a sample enclosure including:
      an electron beam permeable, fluid impermeable membrane; and
      a peripheral enclosure sealed to said membrane and defining with said membrane said sample enclosure; and
   a sample enclosure closure for sealing said sample enclosure.

2. A SEM compatible sample container according to claim 1 and wherein said sample enclosure closure comprises quick-connect attachment functionality for sealing engagement with said sample enclosure.

3. A SEM compatible sample container according to claim 2 and wherein said quick-connect attachment functionality comprises a threaded connection.

4. A SEM compatible sample container according to claim 2 and wherein said sample enclosure is preassembled and ready to receive a sample therein, following which said sample enclosure closure may be readily sealingly joined thereto by means of said quick-connect attachment functionality.

5. A SEM compatible sample container according to claim 1 and wherein said peripheral enclosure is at least partially electrically conductive.

6. A SEM compatible sample container according to claim 1 and also comprising a pressure relief diaphragm associated with said sample enclosure.

7. A SEM compatible sample container according to claim 1 and also comprising at least one membrane support grid supporting said membrane.

8. A SEM compatible sample container according to claim 1 and wherein said membrane is formed from a material selected from the group comprising polyimide, polyamide, polyamide-imide, polyethylene, polypyrrole, PARLODION, COLLODION, KAPTON, FORMVAR, VINYLEC, BUTVAR, PIOLOFORM, PARYLENE, silicon dioxide, silicon monoxide and carbon.

9. A SEM compatible sample container according to claim 1 and wherein said sample enclosure is configured for containing a sample at a depth which is not permeable by electrons having an energy level of less than 50 KeV.

10. A SEM compatible sample container according to claim 1 and wherein said sample enclosure comprises an outer enclosure arranged about said peripheral enclosure and defining an aperture for electron communication through said membrane with the interior of said sample enclosure.

11. A SEM compatible sample container according to claim 1 and also including a sample positioner arranged to position a sample adjacent to said membrane.

12. A SEM compatible sample container according to claim 11 and wherein said sample positioner comprises a spring.

13. A SEM compatible sample container according to claim 1 and also including at least one portion of a light guide.

14. A SEM compatible sample container according to claim 13 and wherein said light guide is arranged to receive light from a sample in said sample enclosure during SEM inspection, said light guide being arranged with respect to said sample enclosure for collecting light from said sample.

15. A method for performing scanning electron microscopy comprising:
  placing a sample in a sample enclosure comprising:
    an electron beam permeable, fluid impermeable membrane;
    a peripheral enclosure sealed to said membrane and defining with said membrane said sample enclosure; and
    a sample enclosure closure including quick-connect attachment functionality for sealing engagement with said sample enclosure;
  sealing said sample enclosure with said sample enclosure closure;
  placing said sample enclosure in a beam of electrons; and
  analyzing results of interactions of said beam of electrons with said sample.

16. A method for performing scanning electron microscopy according to claim 15 and also comprising removal of liquid from said sample enclosure prior to said sealing.

17. A method for performing scanning electron microscopy according to claim 15 and also comprising addition of liquid to said sample enclosure prior to said sealing.

18. A method for performing scanning electron microscopy according to claim 15 and also comprising incubation of said sample in said sample enclosure.

19. A method for performing scanning electron microscopy according to claim 15 and also comprising positioning a sample positioner arranged to position said sample adjacent to said membrane.

20. A method for performing scanning electron microscopy according to claim 15 and wherein said analyzing results of interactions of said beam of electrons with said sample is performed by at least one of:
  detection of X-rays;
  detection of light in the ultraviolet to infrared range;
  detection of backscattered electrons; and
  detection of secondary electrons.

21. A method for performing scanning electron microscopy according to claim 15 and wherein said analyzing results of interactions of said beam of electrons with said sample comprises displaying an image of at least one portion of said sample.

22. A method for performing scanning electron microscopy according to claim 15 and wherein said sample is a biological sample.

* * * * *